(12) United States Patent
Hall et al.

(10) Patent No.: US 11,479,464 B2
(45) Date of Patent: Oct. 25, 2022

(54) SYSTEMS AND METHODS FOR GENERATING NITRIC OXIDE

(71) Applicant: Third Pole, Inc., Waltham, MA (US)

(72) Inventors: Gregory W. Hall, Belmont, MA (US); Benjamin J. Apollonio, Lunenburg, MA (US); Ian J. Gillerman, Somerville, MA (US)

(73) Assignee: Third Pole, Inc., Waltham, MA (US)

( * ) Notice: Subject to any disclaimer, the term of this patent is extended or adjusted under 35 U.S.C. 154(b) by 0 days.

(21) Appl. No.: 16/875,971

(22) Filed: May 15, 2020

(65) Prior Publication Data

US 2020/0361772 A1 Nov. 19, 2020

Related U.S. Application Data

(60) Provisional application No. 62/959,937, filed on Jan. 11, 2020, provisional application No. 62/959,942, (Continued)

(51) Int. Cl.
*C01B 21/20* (2006.01)
*A61M 16/06* (2006.01)
(Continued)

(52) U.S. Cl.
CPC ......... *C01B 21/203* (2013.01); *A61M 16/024* (2017.08); *A61M 16/0666* (2013.01); (Continued)

(58) Field of Classification Search
CPC . C01B 21/203; A61M 16/0666; A61M 16/10; A61M 2202/0208;
(Continued)

(56) References Cited

U.S. PATENT DOCUMENTS

| | | |
|---|---|---|
| 709,867 A | 9/1902 | Bradley et al. |
| 2,485,478 A | 10/1949 | Cotton |
| | (Continued) | |

FOREIGN PATENT DOCUMENTS

| | | |
|---|---|---|
| CA | 2413834 A1 | 6/2004 |
| CN | 1099997 | 3/1995 |
| | (Continued) | |

OTHER PUBLICATIONS

Arjunan Thesis—Plasma Produced Reactive Oxygen and Nitrogen Species in Angiogenesis—May 2011—Krishna Priya Arjunan.
(Continued)

*Primary Examiner* — Xiuyu Tai
(74) *Attorney, Agent, or Firm* — Greenberg Traurig, LLP; David J. Dykeman; Jaime L. Burke

(57) ABSTRACT

Systems and methods for generating nitric oxide are disclosed. A nitric oxide (NO) generation system includes at least one pair of electrodes configured to generate a product gas containing NO from a flow of a reactant gas; and a controller configured to regulate the amount of nitric oxide in the product gas produced by the at least one pair of electrodes by utilizing duty cycle values of plasma pulses selected from a plurality of discrete duty cycles to produce a target rate of NO production based on an average of discrete production rates associated with each of the plurality of discrete duty cycles.

5 Claims, 83 Drawing Sheets

Related U.S. Application Data filed on Jan. 11, 2020, provisional application No. 62/959,933, filed on Jan. 11, 2020, provisional application No. 62/848,530, filed on May 15, 2019.

(51) Int. Cl.
  *A61M 16/10* (2006.01)
  *H01J 37/32* (2006.01)
  *H01J 37/04* (2006.01)
  *A61M 16/12* (2006.01)
  *A61M 16/00* (2006.01)

(52) U.S. Cl.
  CPC .......... *A61M 16/10* (2013.01); *A61M 16/122* (2014.02); *H01J 37/04* (2013.01); *H01J 37/32146* (2013.01); *A61M 2016/102* (2013.01); *A61M 2202/0208* (2013.01); *A61M 2202/0275* (2013.01)

(58) Field of Classification Search
  CPC ............. A61M 2202/0275; H01J 37/04; H01J 37/32146; H05H 1/42; H05H 1/34; H05H 1/3452; A61B 18/042
  See application file for complete search history.

(56) References Cited

U.S. PATENT DOCUMENTS

| | | | |
|---|---|---|---|
| 2,485,481 A | 10/1949 | Cotton | |
| 2,525,938 A | 10/1950 | Peck | |
| 2,684,448 A | 7/1954 | Nilles | |
| 3,047,370 A | 7/1962 | Aviges et al. | |
| 3,225,309 A | 10/1965 | Phelps | |
| 4,287,040 A | 9/1981 | Alamaro | |
| 4,500,563 A | 2/1985 | Ellenberger et al. | |
| 4,505,795 A | 3/1985 | Alamaro | |
| 4,680,694 A | 7/1987 | Huynh et al. | |
| 4,695,358 A | 9/1987 | Mizuno et al. | |
| 4,705,670 A | 11/1987 | O'Hare | |
| 4,816,229 A | 3/1989 | Jensen et al. | |
| 4,877,589 A | 10/1989 | Conrad | |
| 5,285,372 A | 2/1994 | Huynh et al. | |
| 5,378,436 A | 1/1995 | Endoh et al. | |
| 5,396,882 A | 3/1995 | Zapol | |
| 5,413,097 A | 5/1995 | Birenheide et al. | |
| 5,471,977 A | 12/1995 | Olsson et al. | |
| 5,485,827 A | 1/1996 | Zapol et al. | |
| 5,531,218 A | 7/1996 | Krebs | |
| 5,546,935 A | 8/1996 | Champeau | |
| 5,558,083 A | 9/1996 | Bathe et al. | |
| 5,573,733 A | 11/1996 | Salama | |
| 5,674,381 A | 10/1997 | Dekker | |
| 5,692,495 A | 12/1997 | Sheu | |
| 5,732,693 A | 3/1998 | Bathe et al. | |
| 5,749,937 A | 5/1998 | Detering et al. | |
| 5,752,504 A | 5/1998 | Bathe | |
| 5,827,420 A | 10/1998 | Shirazi et al. | |
| 5,839,433 A | 11/1998 | Higenbottam | |
| 5,845,633 A | 12/1998 | Psaros | |
| 6,089,229 A | 7/2000 | Bathe et al. | |
| 6,109,260 A | 8/2000 | Bathe | |
| 6,125,846 A | 10/2000 | Bathe et al. | |
| 6,164,276 A | 12/2000 | Bathe et al. | |
| 6,186,140 B1 | 2/2001 | Hoague | |
| 6,186,142 B1 | 2/2001 | Schmidt et al. | |
| 6,197,091 B1 | 3/2001 | Ji et al. | |
| 6,224,653 B1 | 5/2001 | Shvedchikov et al. | |
| 6,250,302 B1 | 6/2001 | Rantala | |
| 6,290,683 B1 | 9/2001 | Erez et al. | |
| 6,296,827 B1 | 10/2001 | Castor et al. | |
| 6,365,868 B1 | 4/2002 | Borowy et al. | |
| 6,432,077 B1 | 8/2002 | Stenzler | |
| 6,532,956 B2 | 3/2003 | Hill | |
| 6,536,429 B1 | 3/2003 | Pavlov et al. | |
| 6,581,599 B1 | 6/2003 | Stenzler | |
| 6,668,828 B1 | 12/2003 | Figley et al. | |
| 6,758,214 B2 | 7/2004 | Fine et al. | |
| 6,920,876 B2 | 7/2005 | Miller et al. | |
| 6,955,171 B1 | 10/2005 | Figley et al. | |
| 6,955,790 B2 | 10/2005 | Castor et al. | |
| 6,984,256 B2 | 1/2006 | Lamprecht et al. | |
| 6,986,351 B2 | 1/2006 | Figley et al. | |
| 7,025,869 B2 | 4/2006 | Fine et al. | |
| 7,040,313 B2 | 5/2006 | Fine et al. | |
| 7,122,018 B2 | 10/2006 | Stenzler et al. | |
| 7,220,393 B2 | 5/2007 | Miller et al. | |
| 7,255,105 B2 | 8/2007 | Figley et al. | |
| 7,299,785 B1 | 11/2007 | Lee | |
| 7,312,584 B2 | 12/2007 | Tamita et al. | |
| 7,335,181 B2 | 2/2008 | Miller et al. | |
| 7,520,866 B2 | 1/2009 | Stenzler et al. | |
| 7,485,324 B2 | 2/2009 | Miller et al. | |
| 7,498,000 B2 | 3/2009 | Pekshev et al. | |
| 7,516,742 B2 | 4/2009 | Stenzler et al. | |
| 7,523,752 B2 | 4/2009 | Montgomery et al. | |
| 7,531,133 B2 | 5/2009 | Hole et al. | |
| 7,560,076 B2 | 7/2009 | Rounbehler et al. | |
| 7,589,473 B2 | 9/2009 | Suslov | |
| 7,597,731 B2 | 10/2009 | Palmerton et al. | |
| 7,618,594 B2 | 11/2009 | Rounbehler et al. | |
| 7,744,812 B2 | 6/2010 | Witherspoon et al. | |
| 7,861,516 B2 | 1/2011 | Allanson et al. | |
| 7,861,717 B1 | 1/2011 | Krebs | |
| 7,914,743 B2 | 3/2011 | Fine et al. | |
| 7,947,227 B2 | 5/2011 | Fine et al. | |
| 7,955,294 B2 | 6/2011 | Stenzler et al. | |
| 8,030,849 B2 | 10/2011 | Suslov | |
| 8,043,252 B2 | 10/2011 | Miller et al. | |
| 8,057,742 B2 | 11/2011 | Rounbehler et al. | |
| 8,066,904 B2 | 11/2011 | Fine et al. | |
| 8,079,998 B2 | 12/2011 | Hole et al. | |
| 8,083,997 B2 | 12/2011 | Rounbehler et al. | |
| 8,091,549 B2 | 1/2012 | Montgomery et al. | |
| 8,151,791 B2 | 4/2012 | Arlow et al. | |
| 8,173,072 B2 | 5/2012 | Fine et al. | |
| 8,187,544 B2 | 5/2012 | Fine et al. | |
| 8,211,368 B2 | 7/2012 | Fine et al. | |
| 8,221,800 B2 | 7/2012 | Fine et al. | |
| 8,226,916 B2 | 7/2012 | Rounbehler et al. | |
| 8,246,725 B2 | 8/2012 | Rounbehler et al. | |
| 8,267,884 B1 | 9/2012 | Hicks | |
| 8,268,252 B2 | 9/2012 | Fuller et al. | |
| 8,277,399 B2 | 10/2012 | Hamilton et al. | |
| 8,282,966 B2 | 10/2012 | Baldassarre et al. | |
| 8,291,904 B2 | 10/2012 | Bathe et al. | |
| 8,293,284 B2 | 10/2012 | Baldassarre et al. | |
| 8,328,998 B2 | 12/2012 | Wada et al. | |
| 8,344,627 B1 | 1/2013 | Hooke et al. | |
| 8,371,296 B2 | 2/2013 | Fine et al. | |
| 8,377,462 B2 | 2/2013 | DesNoyer et al. | |
| 8,397,721 B2 | 3/2013 | Montgomery et al. | |
| D679,366 S | 4/2013 | Fuller | |
| 8,408,206 B2 | 4/2013 | Montgomery et al. | |
| 8,431,163 B2 | 4/2013 | Baldassarre et al. | |
| D688,352 S | 8/2013 | Fuller | |
| 8,517,015 B2 | 8/2013 | Montgomery et al. | |
| 8,518,457 B2 | 8/2013 | Miller et al. | |
| 8,573,209 B2 | 11/2013 | Bathe et al. | |
| 8,573,210 B2 | 11/2013 | Bathe et al. | |
| 8,574,531 B2 | 11/2013 | Miller et al. | |
| 8,580,109 B2 | 11/2013 | Kruckenberg et al. | |
| 8,607,785 B2 | 12/2013 | Fine et al. | |
| 8,607,792 B2 | 12/2013 | Montgomery et al. | |
| 8,609,026 B2 | 12/2013 | Fine et al. | |
| 8,609,028 B2 | 12/2013 | Rounbehler et al. | |
| 8,613,958 B2 | 12/2013 | Fine | |
| 8,616,204 B2 | 12/2013 | Montgomery et al. | |
| 8,646,445 B2 | 2/2014 | Fine et al. | |
| D701,963 S | 4/2014 | Abarbanel et al. | |
| 8,685,467 B2 | 4/2014 | Miller et al. | |
| 8,701,657 B2 | 4/2014 | Fine et al. | |
| 8,715,577 B2 | 5/2014 | Fine et al. | |
| 8,717,733 B2 | 5/2014 | Gefter et al. | |

(56) References Cited

U.S. PATENT DOCUMENTS

| | | |
|---|---|---|
| 8,720,440 B2 | 5/2014 | Montgomery et al. |
| 8,741,222 B2 | 6/2014 | Fine et al. |
| 8,757,148 B2 | 6/2014 | Montgomery et al. |
| 8,770,199 B2 | 7/2014 | Flanagan et al. |
| 8,776,794 B2 | 7/2014 | Bathe et al. |
| 8,776,795 B2 | 7/2014 | Bathe et al. |
| 8,790,715 B2 | 7/2014 | Montgomery et al. |
| 8,795,222 B2 | 8/2014 | Stenzler et al. |
| 8,795,741 B2 | 8/2014 | Baldassarre |
| 8,808,655 B2 | 8/2014 | Solovyov et al. |
| 8,821,801 B2 | 9/2014 | Rounbehler et al. |
| 8,821,828 B2 | 9/2014 | Hilbig et al. |
| 8,846,112 B2 | 9/2014 | Baldassarre |
| 8,887,720 B2 | 11/2014 | Fine et al. |
| 8,893,717 B2 | 11/2014 | Montgomery et al. |
| 8,944,049 B2 | 2/2015 | Fine et al. |
| 9,067,788 B1 | 6/2015 | Spielman et al. |
| 9,095,534 B2 | 8/2015 | Stenzler et al. |
| 9,108,016 B2 | 8/2015 | Acker et al. |
| 9,180,217 B2 | 11/2015 | Arnold et al. |
| 9,192,718 B2 | 11/2015 | Fine |
| 9,265,911 B2 | 2/2016 | Bathe et al. |
| 9,279,794 B2 | 3/2016 | Tolmie et al. |
| 9,295,802 B2 | 3/2016 | Bathe et al. |
| 9,351,994 B2 | 5/2016 | Montgomery et al. |
| 9,408,994 B2 | 5/2016 | Fine et al. |
| 9,408,993 B2 | 8/2016 | Bathe et al. |
| 9,522,249 B2 | 12/2016 | Rounbehler et al. |
| 9,550,039 B2 | 1/2017 | Flanagan et al. |
| 9,550,040 B2 | 1/2017 | Acker et al. |
| 9,573,110 B2 | 2/2017 | Montgomery et al. |
| 9,604,028 B2 | 3/2017 | Fine et al. |
| 9,701,538 B2 | 7/2017 | Fine et al. |
| 9,713,244 B2 | 7/2017 | Tabata et al. |
| 9,770,570 B2 | 9/2017 | Schnictman et al. |
| 9,795,756 B2 | 10/2017 | Flanagan et al. |
| 9,895,199 B2 | 2/2018 | Montgomery et al. |
| 9,896,337 B2 | 2/2018 | Montgomery et al. |
| 9,956,373 B2 | 5/2018 | Rounbehler et al. |
| 9,982,354 B2 | 5/2018 | Kim |
| 10,081,544 B2 | 9/2018 | Fine et al. |
| 10,086,352 B2 | 10/2018 | Fine et al. |
| 10,099,029 B2 | 10/2018 | Montgomery et al. |
| 10,124,142 B2 | 11/2018 | Rounbehler et al. |
| 10,179,222 B2 | 1/2019 | Fine et al. |
| 10,213,572 B2 | 2/2019 | Gellman et al. |
| 10,226,592 B2 | 3/2019 | Acker et al. |
| 10,232,138 B2 | 3/2019 | Acker et al. |
| 10,239,038 B2 | 3/2019 | Zapol et al. |
| 10,279,139 B2 | 5/2019 | Zapol et al. |
| 10,286,176 B2 | 5/2019 | Zapol et al. |
| 10,293,133 B2 | 5/2019 | Zapol et al. |
| 10,328,228 B2 | 6/2019 | Zapol et al. |
| 10,398,820 B2 | 9/2019 | Potenziano et al. |
| 10,426,913 B2 | 10/2019 | Tolmie et al. |
| 10,434,276 B2 | 10/2019 | Zapol et al. |
| 10,532,176 B2 | 1/2020 | Zapol et al. |
| 10,548,920 B2 | 2/2020 | Montgomery et al. |
| 10,556,082 B2 | 2/2020 | Flanagan et al. |
| 10,556,086 B2 | 2/2020 | Goldstein et al. |
| 10,576,239 B2 | 3/2020 | Zapol et al. |
| 10,646,682 B2 | 5/2020 | Zapol et al. |
| 10,682,486 B1 | 6/2020 | Moon et al. |
| 10,695,523 B2 | 6/2020 | Zapol et al. |
| 10,737,051 B2 | 8/2020 | Gellman et al. |
| 10,758,703 B2 | 9/2020 | Kohlmann et al. |
| 10,773,046 B2 | 9/2020 | Schnitman et al. |
| 10,773,047 B2 | 9/2020 | Zapol et al. |
| 10,780,241 B2 | 9/2020 | Fine et al. |
| 10,814,092 B2 | 10/2020 | Rounbehler et al. |
| 10,946,163 B2 | 3/2021 | Gillerman et al. |
| 11,007,503 B2 | 5/2021 | Zapol et al. |
| 11,033,705 B2 | 6/2021 | Zapol et al. |
| 11,045,620 B2 | 6/2021 | Hall et al. |
| 11,376,390 B2 | 7/2022 | Gillerman et al. |
| 2001/0031230 A1 | 10/2001 | Castor et al. |
| 2001/0035186 A1 | 11/2001 | Hill |
| 2002/0111748 A1 | 8/2002 | Kobayashi et al. |
| 2002/0185126 A1 | 12/2002 | Krebs |
| 2004/0019274 A1 | 1/2004 | Galloway, Jr. et al. |
| 2004/0028753 A1 | 2/2004 | Hedenstierna et al. |
| 2004/0031248 A1 | 2/2004 | Lindsay |
| 2004/0050387 A1 | 3/2004 | Younes |
| 2004/0181149 A1 | 9/2004 | Langlotz et al. |
| 2005/0172971 A1 | 8/2005 | Kolobow et al. |
| 2005/0218007 A1 | 10/2005 | Pekshev et al. |
| 2005/0263150 A1 | 12/2005 | Chathampally et al. |
| 2005/0274381 A1 | 12/2005 | Deane et al. |
| 2005/0281465 A1 | 12/2005 | Marquart et al. |
| 2006/0025700 A1 | 2/2006 | Fallik |
| 2006/0090759 A1 | 5/2006 | Howes et al. |
| 2006/0172018 A1 | 8/2006 | Fine et al. |
| 2006/0173396 A1 | 8/2006 | Hatamian et al. |
| 2006/0207594 A1 | 9/2006 | Stenzler et al. |
| 2006/0276844 A1 | 12/2006 | Alon et al. |
| 2007/0051712 A1 | 3/2007 | Kooken et al. |
| 2007/0113851 A1 | 5/2007 | Delisle et al. |
| 2007/0151561 A1 | 7/2007 | Laurila |
| 2007/0181126 A1 | 8/2007 | Tolmie et al. |
| 2007/0190184 A1 | 8/2007 | Montgomery et al. |
| 2008/0017030 A1 | 1/2008 | Fleck |
| 2008/0078382 A1 | 4/2008 | LeMahieu et al. |
| 2008/0135044 A1 | 6/2008 | Freitag et al. |
| 2008/0176335 A1 | 7/2008 | Alberti et al. |
| 2008/0202509 A1 | 8/2008 | Dillon et al. |
| 2009/0039790 A1* | 2/2009 | Suslov .............. H05H 1/34 315/111.21 |
| 2010/0030091 A1 | 2/2010 | Fine |
| 2010/0043789 A1 | 2/2010 | Fine et al. |
| 2010/0089392 A1 | 4/2010 | Fine et al. |
| 2010/0189808 A1 | 7/2010 | Gupta et al. |
| 2010/0275911 A1 | 11/2010 | Arlow et al. |
| 2010/0330193 A1 | 12/2010 | Baldassarre et al. |
| 2011/0140607 A1 | 6/2011 | Moore et al. |
| 2011/0240019 A1 | 10/2011 | Fine et al. |
| 2012/0093948 A1 | 4/2012 | Fine et al. |
| 2012/0279500 A1 | 11/2012 | Singvogel et al. |
| 2012/0285449 A1 | 11/2012 | Fine et al. |
| 2012/0296265 A1 | 11/2012 | Dobrynin et al. |
| 2013/0123801 A1 | 5/2013 | Umasuthan et al. |
| 2013/0150863 A1 | 6/2013 | Baumgartner |
| 2013/0239963 A1 | 9/2013 | Goldstein et al. |
| 2013/0309328 A1 | 11/2013 | Watts et al. |
| 2014/0020685 A1 | 1/2014 | Szabo |
| 2014/0031668 A1 | 1/2014 | Mobasser et al. |
| 2014/0127081 A1 | 5/2014 | Fine et al. |
| 2014/0127330 A1 | 5/2014 | Fine et al. |
| 2014/0144436 A1 | 5/2014 | Fine et al. |
| 2014/0144444 A1 | 5/2014 | Fine et al. |
| 2014/0158121 A1 | 6/2014 | Flanagan et al. |
| 2014/0166009 A1 | 6/2014 | Flanagan et al. |
| 2014/0216452 A1 | 8/2014 | Miller et al. |
| 2014/0251787 A1 | 9/2014 | Montgomery et al. |
| 2014/0363525 A1 | 12/2014 | Montgomery et al. |
| 2014/0377378 A1 | 12/2014 | Baldassarre |
| 2015/0000659 A1 | 1/2015 | Martin |
| 2015/0004248 A1 | 1/2015 | Morfill et al. |
| 2015/0034084 A1 | 2/2015 | Av-Gay et al. |
| 2015/0044305 A1 | 2/2015 | Av-Gay et al. |
| 2015/0072023 A1 | 3/2015 | Greenberg et al. |
| 2015/0090261 A1 | 4/2015 | Crosbie |
| 2015/0101604 A1 | 4/2015 | Crosbie |
| 2015/0174158 A1 | 6/2015 | Av-Gay et al. |
| 2015/0272988 A1 | 10/2015 | Av-Gay et al. |
| 2015/0328430 A1 | 11/2015 | Miller et al. |
| 2016/0022731 A1 | 1/2016 | Av-Gay et al. |
| 2016/0030699 A1 | 2/2016 | Zapol et al. |
| 2016/0038710 A1 | 2/2016 | Zapol et al. |
| 2016/0106949 A1 | 4/2016 | Kohlmann et al. |
| 2016/0121071 A1 | 5/2016 | Moon et al. |
| 2016/0151598 A1 | 6/2016 | Fine |
| 2016/0183841 A1 | 6/2016 | Duindam et al. |
| 2016/0191887 A1 | 6/2016 | Casas |
| 2016/0228670 A1 | 8/2016 | Av-Gay et al. |

(56) References Cited

U.S. PATENT DOCUMENTS

| | | |
|---|---|---|
| 2016/0243328 A1 | 8/2016 | Tolmie et al. |
| 2016/0271169 A1 | 9/2016 | Potenziano et al. |
| 2016/0279165 A1 | 9/2016 | Av-Gay et al. |
| 2016/0324580 A1 | 11/2016 | Esterberg |
| 2016/0367775 A1 | 12/2016 | Tolmie et al. |
| 2017/0014571 A1 | 1/2017 | Deem et al. |
| 2017/0014591 A1 | 1/2017 | Tolmie et al. |
| 2017/0014592 A1 | 1/2017 | Tolmie et al. |
| 2017/0021124 A1 | 1/2017 | Tolmie et al. |
| 2017/0065631 A1 | 3/2017 | Av-Gay et al. |
| 2017/0112871 A1 | 4/2017 | Nelson et al. |
| 2017/0128694 A1 | 5/2017 | Acker et al. |
| 2017/0143758 A1 | 5/2017 | Greenberg et al. |
| 2017/0165294 A1 | 6/2017 | Dasse et al. |
| 2017/0182088 A1 | 6/2017 | Dasse et al. |
| 2017/0232166 A1 | 8/2017 | Potenziano et al. |
| 2017/0239289 A1 | 8/2017 | Av-Gay et al. |
| 2017/0259025 A1 | 9/2017 | Fine et al. |
| 2017/0296463 A1 | 10/2017 | Minton et al. |
| 2017/0348503 A1 | 12/2017 | Westermark |
| 2018/0049622 A1 | 2/2018 | Ryan et al. |
| 2018/0104432 A1 | 4/2018 | Flanagan et al. |
| 2018/0125883 A1 | 5/2018 | Av-Gay et al. |
| 2018/0126111 A1 | 5/2018 | Moon et al. |
| 2018/0133246 A1 | 5/2018 | Av-Gay et al. |
| 2018/0169370 A1 | 6/2018 | Montgomery et al. |
| 2018/0243527 A1 | 8/2018 | Zapol et al. |
| 2018/0243528 A1 | 8/2018 | Zapol et al. |
| 2018/0280920 A1 | 10/2018 | Zapol et al. |
| 2018/0296790 A1 | 10/2018 | Zapol et al. |
| 2018/0311460 A1 | 11/2018 | Rounbehler et al. |
| 2018/0328842 A1 | 11/2018 | Kjaer |
| 2019/0038864 A1 | 2/2019 | Montgomery et al. |
| 2019/0092639 A1 | 3/2019 | Fine et al. |
| 2019/0127223 A1 | 5/2019 | Montgomery et al. |
| 2019/0135633 A1 | 5/2019 | Montgomery et al. |
| 2019/0143068 A1 | 5/2019 | Rounbehler et al. |
| 2019/0184116 A1 | 6/2019 | Acker et al. |
| 2019/0209993 A1 | 7/2019 | Fine et al. |
| 2019/0217042 A1 | 7/2019 | Zapol et al. |
| 2019/0217043 A1 | 7/2019 | Fine et al. |
| 2019/0233288 A1 | 8/2019 | Montgomery et al. |
| 2019/0233289 A1 | 8/2019 | Montgomery et al. |
| 2019/0276313 A1 | 9/2019 | Montgomery et al. |
| 2019/0314596 A1 | 10/2019 | Zapol et al. |
| 2019/0374739 A1 | 12/2019 | Tolmie et al. |
| 2020/0094011 A1 | 3/2020 | Zapol et al. |
| 2020/0139071 A1 | 5/2020 | Fine et al. |
| 2020/0139072 A1 | 5/2020 | Zapol et al. |
| 2020/0139073 A1 | 5/2020 | Tector et al. |
| 2020/0163989 A1 | 5/2020 | Montgomery et al. |
| 2020/0171259 A1 | 6/2020 | Flanagan et al. |
| 2020/0171264 A1 | 6/2020 | Goldstein et al. |
| 2020/0180958 A1 | 6/2020 | Fine et al. |
| 2020/0282375 A1 | 9/2020 | Fine et al. |
| 2020/0360649 A1 | 11/2020 | Hall et al. |
| 2020/0361773 A1 | 11/2020 | Gillerman et al. |
| 2020/0390994 A1 | 12/2020 | Gillerman et al. |
| 2021/0214222 A1 | 7/2021 | Kondiboyia et al. |
| 2021/0220586 A1 | 7/2021 | Shah et al. |
| 2021/0268221 A1 | 9/2021 | Gillerman et al. |
| 2021/0353898 A1 | 11/2021 | Hall et al. |
| 2021/0386954 A1 | 12/2021 | Tamiya et al. |
| 2021/0395905 A1 | 12/2021 | Silkoff et al. |
| 2022/0047837 A1 | 2/2022 | Zapol et al. |
| 2022/0135406 A1 | 5/2022 | Apollonio et al. |
| 2022/0162070 A1 | 5/2022 | Silkoff et al. |
| 2022/0211967 A1 | 7/2022 | Hall et al. |

FOREIGN PATENT DOCUMENTS

| | | |
|---|---|---|
| CN | 1730115 | 2/2006 |
| CN | 201037113 Y | 3/2008 |
| CN | 100404083 C | 7/2008 |
| CN | 101036482 B | 12/2010 |
| CN | 110872714 A | 3/2020 |
| DE | 101 51 270 | 10/2006 |
| EP | 621051 | 10/1994 |
| EP | 03763500 A2 | 3/1997 |
| EP | 1036758 | 9/2000 |
| EP | 2151554 | 2/2010 |
| EP | 1854494 | 6/2012 |
| EP | 2565157 B1 | 10/2017 |
| EP | 3372267 A1 | 12/2018 |
| JP | H04132560 | 5/1992 |
| JP | 2000102616 | 4/2000 |
| JP | 2004065636 | 3/2004 |
| JP | 2006273677 | 10/2006 |
| KR | 20100087977 | 8/2010 |
| RU | 2199167 C1 | 2/2003 |
| WO | WO199507610 | 3/1995 |
| WO | WO2004032719 | 4/2004 |
| WO | 2005094138 A1 | 10/2005 |
| WO | 2005110441 A2 | 11/2005 |
| WO | 2008019102 A2 | 2/2008 |
| WO | 2008112143 A1 | 9/2008 |
| WO | WO2009018837 | 2/2009 |
| WO | WO2010021944 | 2/2010 |
| WO | WO2011/002606 | 1/2011 |
| WO | 2012014805 A1 | 2/2012 |
| WO | WO2012/034089 | 3/2012 |
| WO | WO2012/094008 | 7/2012 |
| WO | 2012155213 A1 | 11/2012 |
| WO | WO2013/052548 | 4/2013 |
| WO | WO2013/070712 | 5/2013 |
| WO | WO2013/181179 | 12/2013 |
| WO | WO2014/085719 | 6/2014 |
| WO | WO2014/143842 | 9/2014 |
| WO | WO2014/144151 | 9/2014 |
| WO | 2015049783 A1 | 4/2015 |
| WO | WO2015/066278 | 5/2015 |
| WO | WO2015/127085 | 8/2015 |
| WO | WO2016/064863 | 4/2016 |
| WO | WO2018/157172 | 8/2018 |
| WO | WO2018/157175 | 8/2018 |
| WO | 2019046415 A1 | 3/2019 |
| WO | WO2019/046413 | 3/2019 |
| WO | WO2019/133776 | 7/2019 |
| WO | WO2019/133777 | 7/2019 |
| WO | 2019222640 A1 | 11/2019 |
| WO | 2020033768 A1 | 2/2020 |
| WO | 2020142658 A1 | 7/2020 |
| WO | 2020148155 A1 | 7/2020 |
| WO | 2020150195 A1 | 7/2020 |
| WO | 2020232414 A1 | 11/2020 |
| WO | 2020232419 A1 | 11/2020 |
| WO | 2021087382 A1 | 5/2021 |
| WO | 2021142472 A1 | 7/2021 |
| WO | 2021258025 A1 | 12/2021 |

OTHER PUBLICATIONS

Arora et al., Nitric Oxide Regulation of Bacterial Biofilms, Biochemistry, vol. 54, pp. 3717-3728, May 21, 2015.

Barraud et al., Involvement of Nitric Oxide n Biofilm Dispersal of Pseudomonas Aeruginosa, Journal of Bacteriology, vol. 188, No. 21, pp. 7344-7353, Nov. 2006.

Bentur et al., Pilot Study to Test Inhaled Nitric Oxide in Cystic Fibrosis Patients with Refractory Mycobacterium Abscessus Lung Infection, Journal of Cystic Fibrosis, vol. 19, pp. 225-231, May 23, 2019.

Bogdonovski et al., Anti-Mycobacterial Activity of High-Dose Nitric Oxide Against Mycobacterium Abscessus In Vitro, National Institutes of Health Poster, Jul. 8, 2018.

Deppisch et al., Gaseous Nitric Oxide to Treat Antibiotic Resistant Bacterial and Fungal Lung Infections in Patients with Cystic Fibrosis: A Phase I Clinical Study, Infection, vol. 44, pp. 513-520, Feb. 9, 2016.

Dobrynin et al. "Direct and Controllable Nitric Oxide Delivery into Biological Media and Living Cells by a Pin-to-Hole Spark Discharge (PHD) Plasma" Journal of Physics D: Applied Physics, vol. 44, pp. 1-10, Jan. 28, 2011.

(56) References Cited

OTHER PUBLICATIONS

Howlin et al., Low-Dose Nitric Oxide as Targeted Anti-Biofilm Adjunctive Therapy to Treat Chronic Pseudomonas Aeruginosa Infection in Cystic Fibrosis, Molecular Therapy, vol. 25, No. 9, pp. 2104-2116, Sep. 2017.

Hu et al., "Study on Production of Inhaled Nitric Oxide for Medical Applications by Pulsed Discharge" IEEE Transactions on Plasma Science, vol. 35, No. 3, pp. 619-625, Jun. 2007.

Kuo, Spencer P. "Air Plasma for Medical Applications" J. Biomedical Science and Engineering, vol. 5, pp. 481-495, Sep. 2012.

McMullin et al., The Antimicrobial Effect of Nitric Oxide on the Bacteria That Cause Nosocomial Pneumonia in Mechanically Ventilated Patients in the Intensive Care Unit, Respiratory Care, vol. 50, No. 11, pp. 1451-1456, Nov. 2005.

Miller et al., Gaseous Nitric Oxide Bactericidal Activity Retained During Intermittent High-Dose Short Duialion Exposure, Nitric Oxide, vol. 20, Issue 1, pp. 16-23, Feb. 2009.

Miller et al., Inhaled Nitric Oxide Decreases the Bacterial Load in a Rat Model of Pseudomonas Aeruginosa Pneumonia, Journal of Cystic Fibrosis, vol. 12, pp. 817-820, Mar. 6, 2013.

Miller et al., Nitric Oxide is a Potential Antimicrobial Against Slow and Fast Growing Mycobacteria, Online Abstracts Bsue, American Journal Respiratory Care Medicine, vol. 193, A7498, May 18, 2016.

Miller et al., A Phase I Clinical Study of Inhaled Nitric Oxide in Healthy Adults, Journal of Cystic Fibrosis, vol. 11, pp. 324-331, Apr. 18, 2012.

Namihira et al., "Temperature and Nitric Oxide Generation in a Pulsed Arc Discharge Plasma" Plasma Science and Technology, vol. 9, No. 6, pp. 747-751, Dec. 2007.

Navarro-Gonzalez et al., "The Physical Mechanism of Nitric Oxide Formation in Simulated Liyl lining" Geophysical Research Letters, vol. 28, No. 20, pp. 3867-3870, Oct. 15, 2001.

Olivier et al., Treatment of Refractory Mycobacterium Abscessus Lung Infection with Inhaled Intermittent Nitric Oxide, Poster, Jul. 8, 2018.

Sakai et al., "Nitric Oxide Generator Based on Pulsed Arc Discharge" Acta Physica Polonica A, vol. 115, No. 6, pp. 1104-1106, Jun. 2009.

Tal et al., Nitric Oxide Inhalations in Bronchiolitis: A Pilot, Randomized, Double-Blinded, Controlled Trial, Pediatric Pulmonology, vol. 53, Issue 1, pp. 95-102, Jan. 2018.

Yaacoby-Bianu et al., Compassionate Nitric Oxide Adjuvant Treatment of Persistent Mycobacterium Infection in Cystic Fibrosis Patients, The Pediatric Infectious Disease Journal, vol. 37, No. 4, Apr. 2018.

Bellerophon, "A Dose Escalation Study to Assess the Safety and Efficacy of Pulsed iNO in Subjects With Pulmonary Fibrosis", Aug. 30, 2017, https://clinicaltrials.gov/ct2/show/NCT03267108.

Fowler, "Exercise Intolerance in Pulmonary Arterial Hypertension", Pulmonary Medicine, vol. 2012, Article ID 39204, 11 pages, (2012).

Keshav, Saurabh. "Using Plasmas for High-speed Flow Control and Combustion Control" Diss. The Ohio State University, 2008.

Li et al., Production of Medically Useful Nitric Monoxide Using AC Arc Discharge, Nitric Oxide, Feb. 28, 2018, vol. 73, pp. 89-95.

Mok et al. "Application of Positive Pulsed Corona Discharge to Removal of SO2 and NOx," Proceedings, ICESP VII, Sep. 20-25, 1998, Kyongiu, Korea.

Namihira et al., Production of Nitric Oxide Using a Pulsed Arc Discharge, IEEE Transactions on Plasma Science, 2002, 30(5):1993-1998.

Namihira et al., Production of Nitric Monoxide Using Pulsed Discharges for a Medical Application, IEEE Transactions on Plasma Science, vol. 29, No. 1, pp. 109-114, Feb. 2000.

Schilz, "Treatment of Pulmonary Hypertension Related to Disorders of Hypoxia" Advances in Pulmonary Hypertension, vol. 4, No. 2, pp. 14-22, May 2005.

Birkeland, K., "On the Oxidation of Atmospheric Nitrogen in Electric Arcs", A Paper read before the Faraday Society on Monday, Jul. 2, 1906, Published on Jan. 1, 1906.

Feigerle, C., et al., "Multiphoton Ionization of Vibrationally Hot Nitric Oxide Produced in a Pulsed Supersonic Glow Discharge", Journal of Chemical Physics, vol. 90, Issue 6, pp. 2900-2908, Mar. 15, 1989.

Hu, Hui et al., "Study on Pulsed Arc Discharge Conditions on Production of Nitric Oxide for Medical Application", High Voltage Apparatus, Issue 3, Mar. 2005.

Hu, Hui et al., "Study on Production of Nitric Monoxide for Respiratory Distress by Pulsed Discharge", Proceedings of the CSEE, vol. 23, No. 2, Jan. 2005.

Hu, Hui et al., "The Effect of Flow Distribution on the Concentration of NO Produced by Pulsed Arc Discharge", Plasma Science and Technology, vol. 9, No. 6, pp. 766-769, Dec. 2007.

Johns Hopkins University—"American Chemical Journal vol. XXXV"—No. 4, Reports Chapter, pp. 358-368, Apr. 1906.

Kornev, J., et al., "Generation of Active Oxidant Species by Pulsed Dielectric Barrier Discharge in Water-Air Mixtures", Ozone: Science & Engineering, vol. 28, Issue 4, pp. 207-215, Jul. 2006.

Li, Z. et al., "Development of Miniature Pulsed Power Generator," 2005 IEEE Pulsed Power Conference, Monterey, CA, pp. 1053-1056, Jul. 2005.

Matsuo, K. et al., "Nitric Oxide Generated by Atmospheric Pressure Air Microplasma," 2009 IEEE Pulsed Power Conference, Washington, DC, Jun. 28-Jul. 2, 2009, pp. 999-1003, Jan. 19, 2010.

Namihara et al., "Production of NO Using Pulsed Arc Discharges and Its Medical Applications", Journal of Plasma and Fusion Research, vol. 79, No. 1 pp. 35-38, Jun. 25, 2002.

Namihira et al., "Production of Nitric Monoxide in Dry Air Using Pulsed Ddischarge," Digest of Technical Papers. 12th IEEE International Pulsed Power Conference. (Cat. No. 99CH36358), Monterey, CA, pp. 1313-1316 vol. 2, Aug. 6, 2002.

Overzet, et al. "Why and How to Pulse a Plasma"—slide show presentation, Oct. 1997.

Pontiga, F., et al., "Nitrogen Oxides Generation Induced by Negative Corona Discharge in N2 + 02 Mixtures," 2006 IEEE Conference on Electrical Insulation and Dielectric Phenomena, Kansas City, MO, pp. 264-267, Oct. 2006.

Sakai, et al., "A Compact Nitric Oxide Supply for Medical Application," 2007 16th IEEE International Pulsed Power Conference, Albuquerque, NM, pp. 752-755, Oct. 14, 2008.

International Search Report in PCT/US2020/033300 dated Aug. 6, 2020.

Charles, et al., "SiO2 Deposition from Oxygen/Silane Pulsed Helicon Diffusion Plasmas" Applied Physics Letters, vol. 57, No. 1, pp. 40-42, Jul. 3, 1995.

Patil et al., Plasma Assisted Nitrogen Oxide Production from Air, AiChE Journal, vol. 64, Issue 2, Aug. 14, 2017.

Pawlat et al., Evaluation of Oxidative Species in Gaseous, Plasma Chemistry and Plasma Processing, vol. 39, pp. 527-642, Mar. 28, 2019.

Wang et al., Gliding Arc Plasma for CO2 Conversion, Chemical Engineering Journal, vol. 330, pp. 11-25, 2017.

Heli, Study on the Removal of Byproduct Nitrogen Dioxide from the Mixture of Inhaled Nitric Oxide Produced by Pulsed Arc Discharge, Thesis for Degree of Master of Engineering, Huazhong University of Science & Technology, China, Apr. 2006, 78 pages (Includes English Language Translation of Title Page and Abstract).

Hui, Research on the Production of Nitric Oxide by Pulsed Arc Discharge and the Curing of Respiratory Distress Instrument, Dissertation for Degree of Doctor of Philosophy in Engineering, Huazhong University of Science and Technology, China, Apr. 2005, 138 pages (Includes English Language Translation of Title Page and Abstract).

Donohoe et al., "Production of 03, NO and N2O in a Pulsed Discharge at 1 Atm", Ind. Eng. Chem., Fundam., vol. 16, No. 2, pp. 208-215, May 1977.

Encyclopaedia Britannica, "Soda Lime" published Nov. 12, 2018, https://www.britannica.com/science/soda-lime.

Habib, Bassam Hanna, "A Simple Model of Spark Gap Discharge Phase", Eng. & Tech. Journal, vol. 31, Part (A), No. 9, pp. 1692-1704, 2013.

Hanning et al., "Pulse Oximetry: A Practical Review", British Medical Journal, vol. 311, pp. 367-370, Aug. 5, 1995.

(56) References Cited

OTHER PUBLICATIONS

Higenbottam et al., "The Direct and Indirect Action of Inhaled Agents on the Lung and Its Circulation: Lessons from Clinical Science," Environmental Health Perspectives, vol. 109, Supplement 4, pp. 559-562, Aug. 2001.
Intersurgical Complete Respiratory Systems, Carbon Dioxide Absorbents Catalogue, www.intersurgical.com/distributors, Issue 5, Oct. 17, 2021.
Lorente L., "Respiratory Filters and Ventilator-Associated Pneumonia: Composition, Efficacy Tests and Advantages and Disadvantages", Humidification in the Intensive Care Unit, pp. 171-177, Springer, Berlin, Heidelberg 2012.
Takaki, et al., "Resistance of Pulsed Arc Discharge in Air and SF/sub 6", Pulsed Power Plasma Science, vol. 2, pp. 1758-1761, Jun. 2001.
Tsukahara et al., "Gas-Phase Oxidation of Nitric Oxide: Chemical Kinetics and Rate Constant," Nitric Oxide Biology and Chemistry, vol. 3, No. 3, pp. 191-198, Jun. 1999.
Yu, et al., "Detection and Removal of Impurities in Nitric Oxide Generated from Air by Pulsed Electrical Discharge", Nitric Oxide, vol. 60, pp. 16-23, Nov. 30, 2016.
Yu, et al. "Development of a Portable Mini-Generator to Safely Produce Nitric Oxide for the Treatment of Infants with Pulmonary Hypertension", Nitric Oxide, vol. 75, pp. 7-76, May 1, 2018.

\* cited by examiner

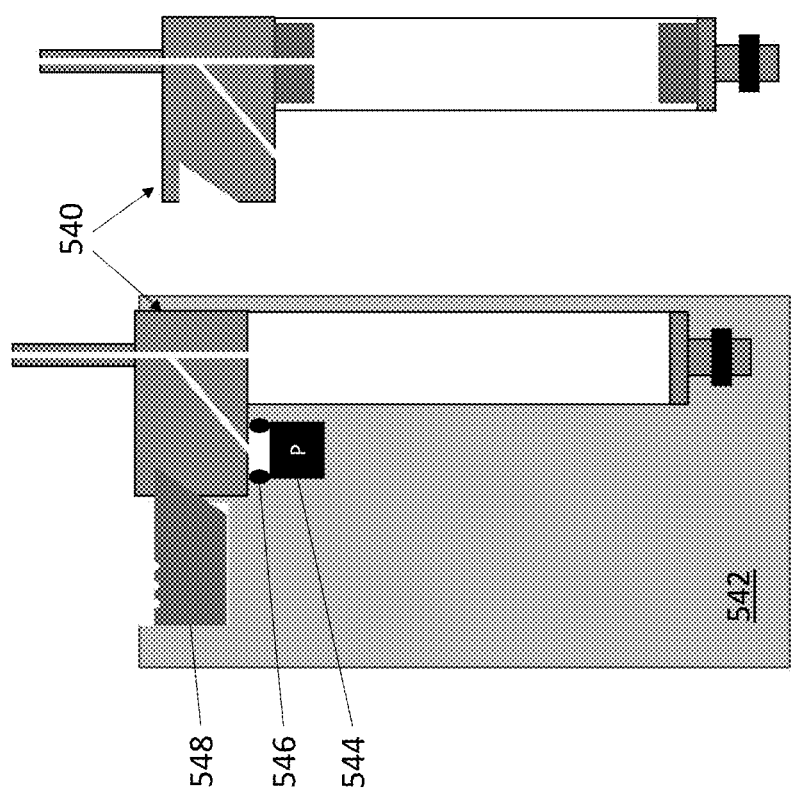

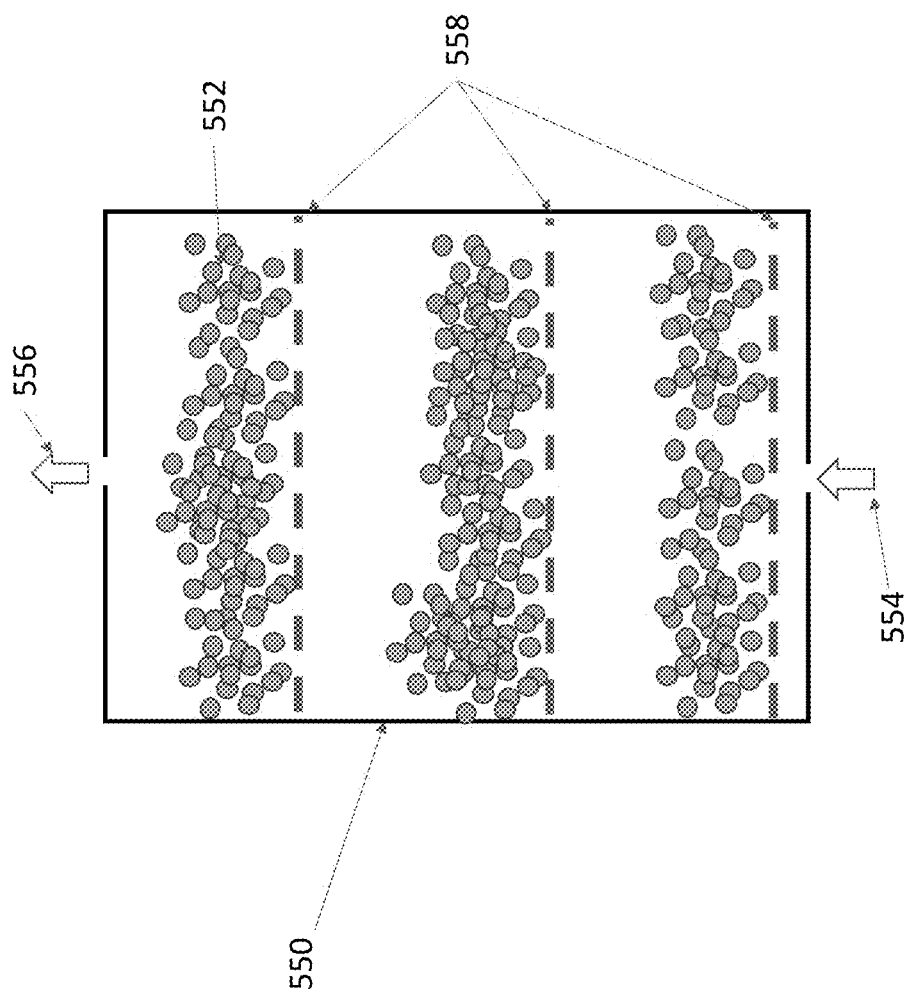

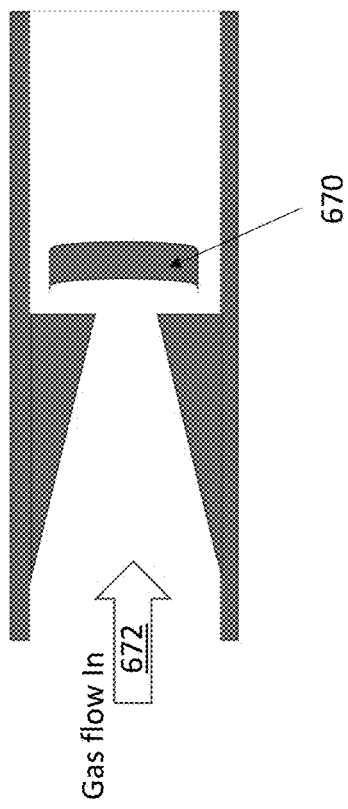
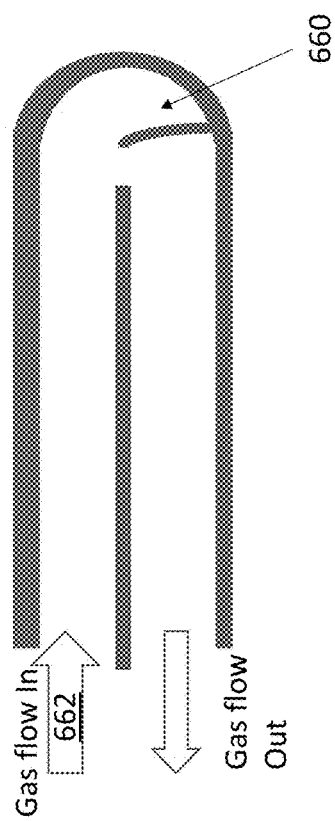
FIG. 38B
FIG. 38A

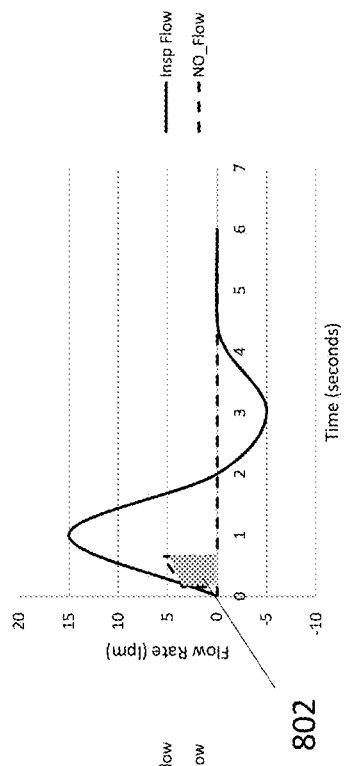
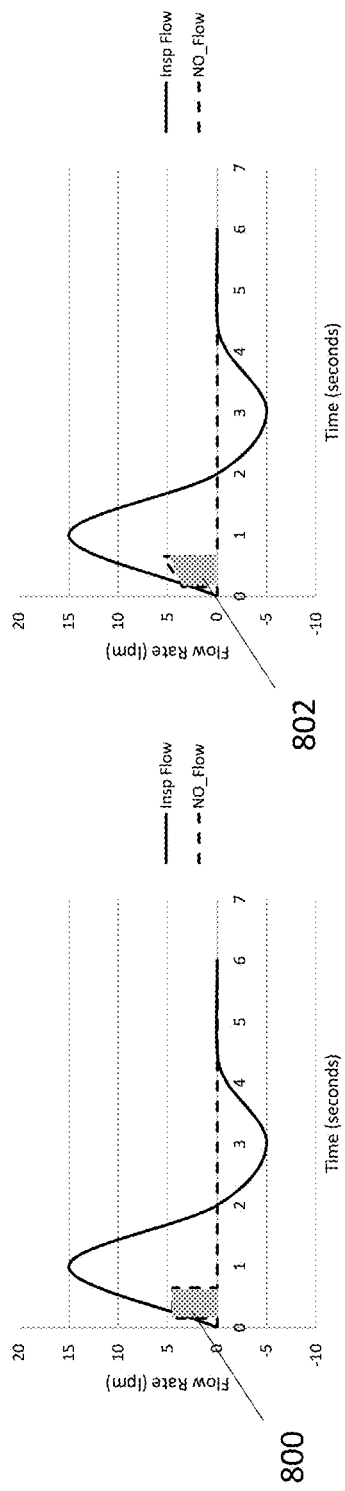
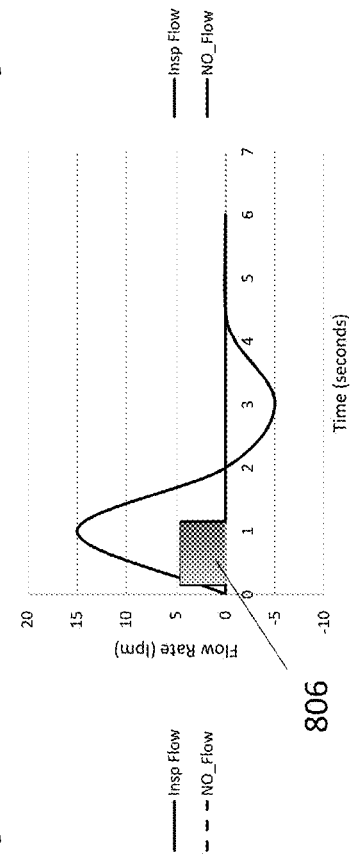
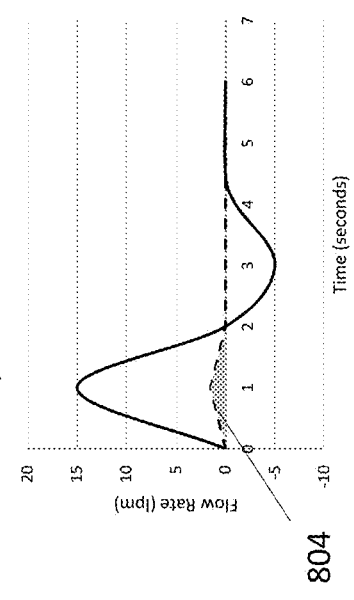
FIG. 48A — Flat NO Pulse Profile and Timing
FIG. 48B — Ramped NO Pulse Profile and Timing
FIG. 48C — Proportional NO Pulse Profile and Timing
FIG. 48D — Varied Concentration NO Pulse Profile and Timing

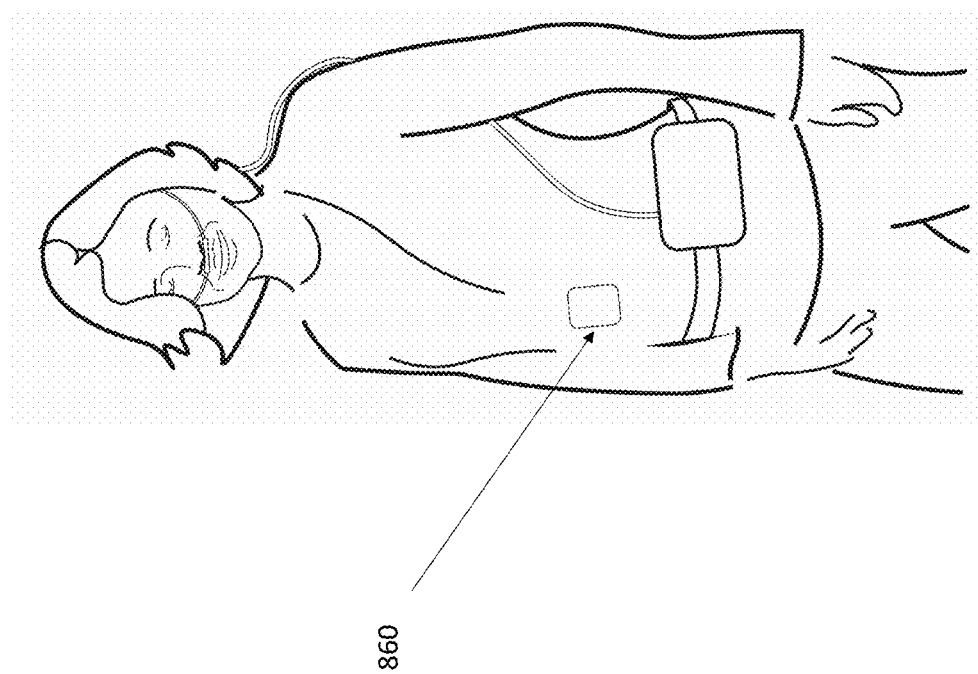

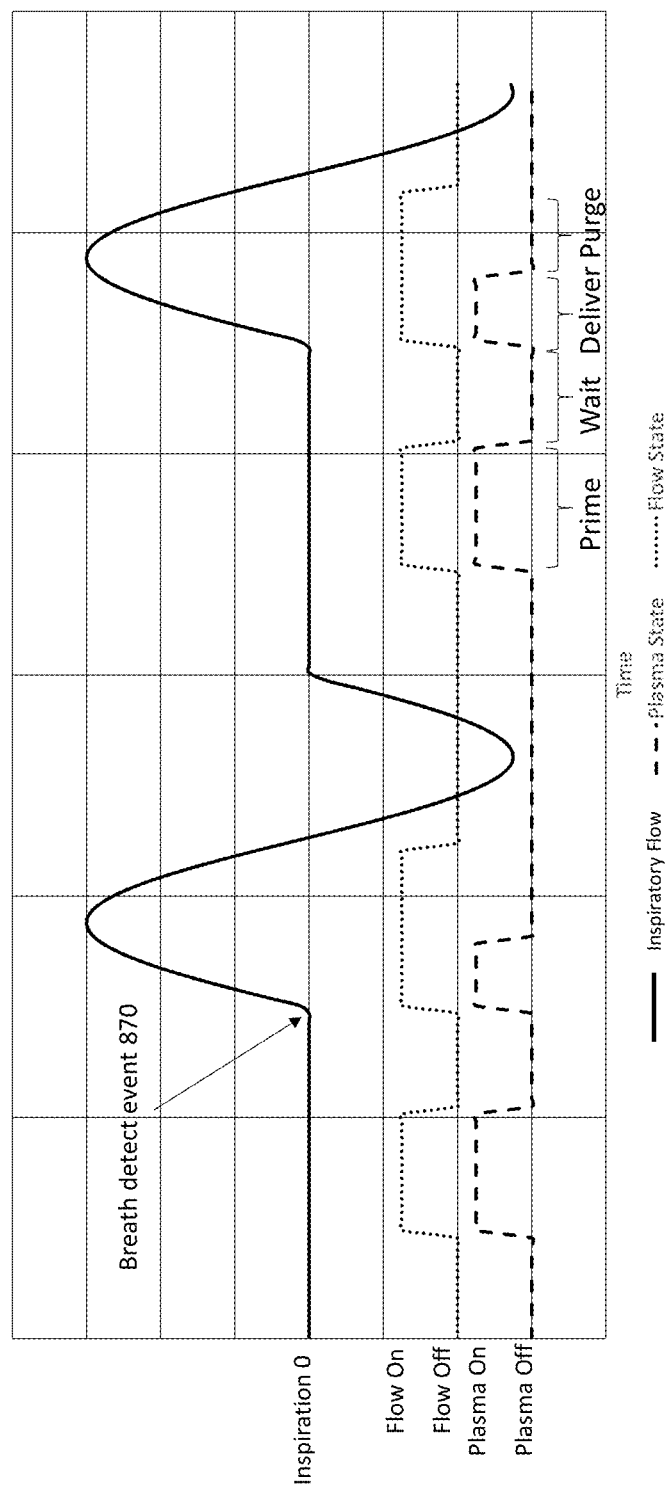
FIG. 54A
FIG. 54B

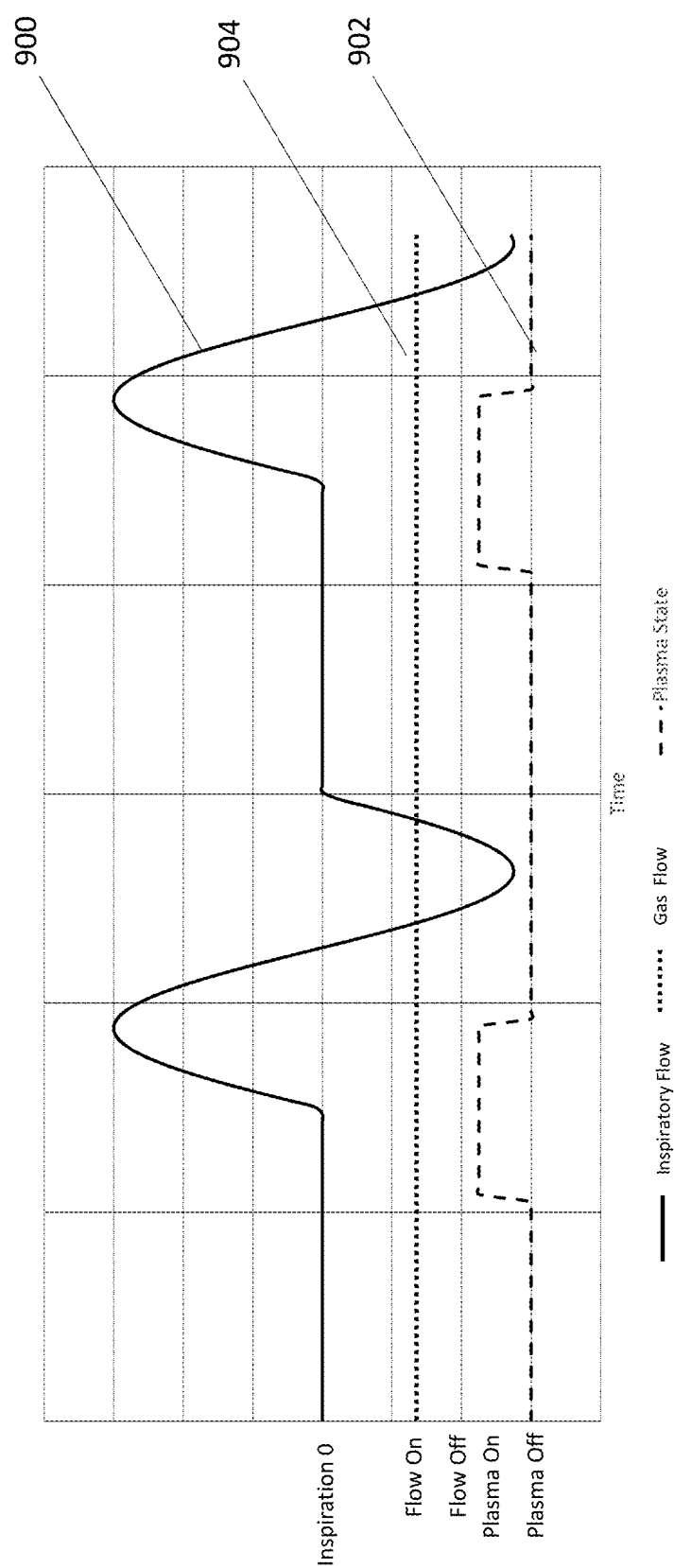

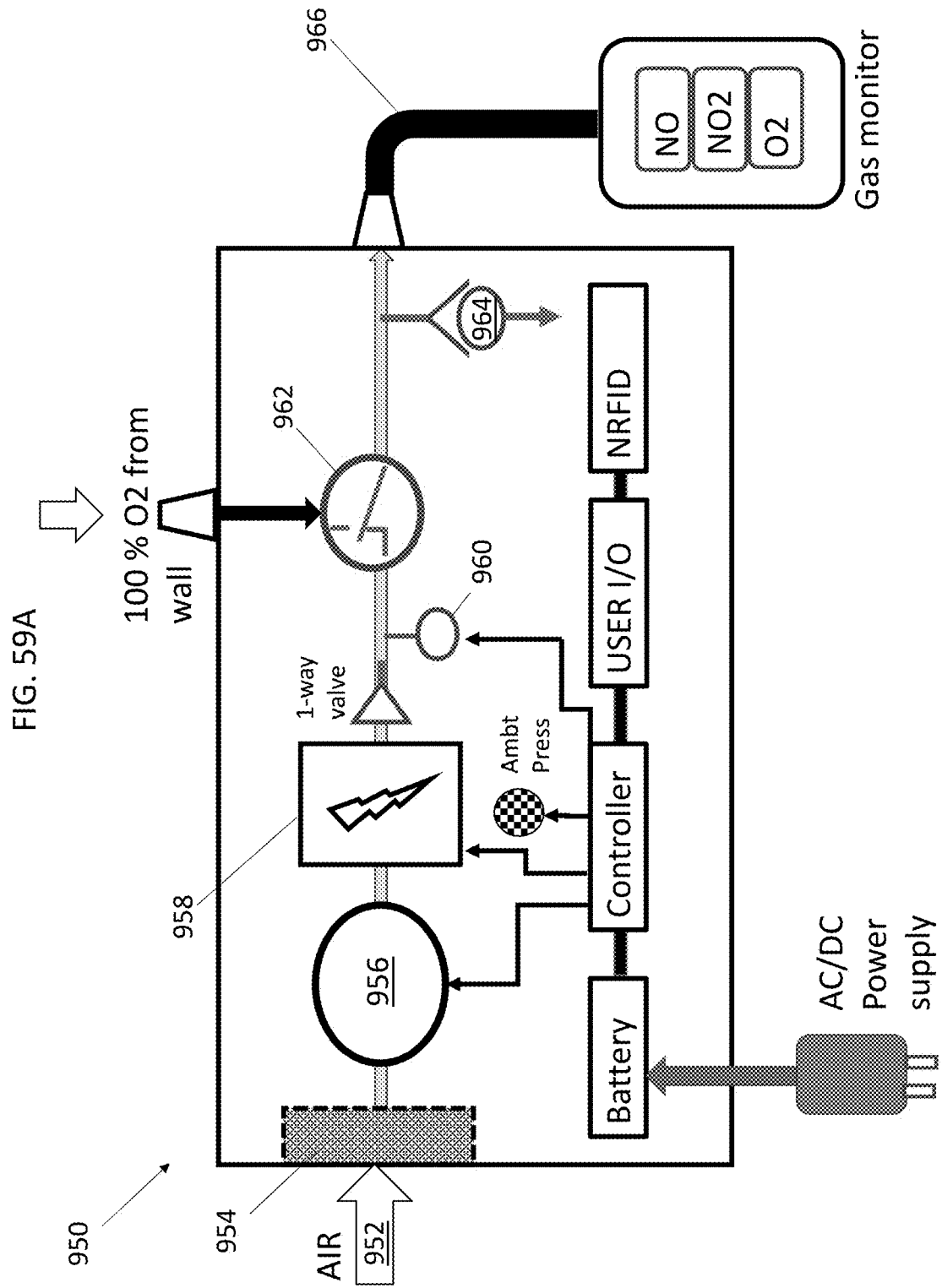

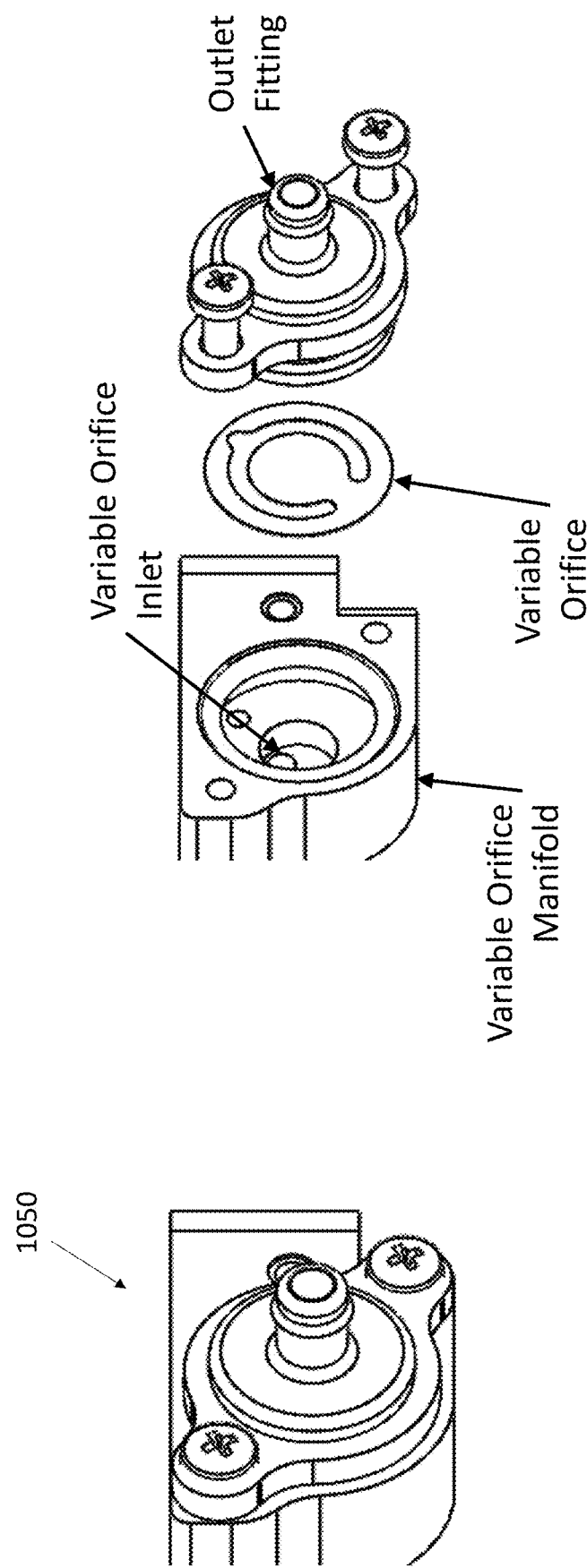

SYSTEMS AND METHODS FOR GENERATING NITRIC OXIDE

RELATED APPLICATIONS

This application claims the benefit of and priority to U.S. Provisional Application No. 62/959,942 filed Jan. 11, 2020, U.S. Provisional Application No. 62/959,933 filed Jan. 11, 2020, U.S. Provisional Application No. 62/959,937 filed Jan. 11, 2020, and U.S. Provisional Application No. 62/848,530 filed May 15, 2019, and the contents of each of these applications are hereby incorporated herein by reference in their entireties.

FEDERALLY SPONSORED RESEARCH OR DEVELOPMENT

This invention was made with government support under Grant No. R44 HL134429 and Grant No. R44 TR001704, both awarded by the National Institutes of Health (NIH). The government has certain rights in the invention.

FIELD

The present disclosure relates to systems and methods for generating nitric oxide for use with various ventilation devices.

BACKGROUND

Nitric oxide (NO) has been found to be useful in a number of ways for treatment of disease, particularly cardiac and respiratory ailments. Previous systems for producing NO and delivering the NO gas to a patient have a number of disadvantages. For example, tank-based systems required large tanks of NO gas at a high concentration and are required to purge with NO when treatment is resumed. Synthesizing NO from $NO_2$ or $N_2O_4$ requires the handling of toxic chemicals. Prior electric generation systems involve generating plasma in the main flow of air to be delivered to patients, or pumped through a delivery tube.

Calibration of current systems can also be difficult, as a user is required to connect high pressure gas canisters containing calibration gas to the system. Calibration gases typically include NO, $NO_2$, and $O_2$. For one concentration and one gas at a time, gas is flowed through the sensor chamber to provide a known input. This manual calibration can take roughly 15 minutes or more of respiratory therapist time. When current systems flow, they release NO into the system at all times. When treatment with a current system is paused, NO in the manual circuit stalls and converts into $NO_2$, requiring the user to purge the manual ventilation device circuit before resuming manual ventilation.

SUMMARY

The present disclosure is directed to systems, methods and devices for nitric oxide generation for use with various ventilation devices. In some embodiments, an NO generation system can include a controller and disposable cartridge that can provide nitric oxide for one treatment, two treatments or at least two different treatments at the same time. The disposable cartridge can have many purposes including preparing incoming gas for exposure to the NO generation process, removing and/or reducing undesirable gases, characterizing the patient inspiratory flow, and removing and/or reducing moisture from gases. Plasma can be generated within the cartridge or within the controller. In some embodiments, the system can calibrate the NO and $NO_2$ gas analysis sensors without the use of a calibration gas.

The presently disclosed embodiments disclose a nitric oxide (NO) generation system including at least one pair of electrodes configured to generate a product gas containing NO from a flow of a reactant gas; a controller configured to regulate the amount of nitric oxide in the product gas produced by the at least one pair of electrodes by utilizing duty cycle values of plasma pulses selected from a plurality of discrete duty cycles to produce a target rate of NO production based on an average of discrete production rates associated with each of the plurality of discrete duty cycles.

In some embodiments, the average of discrete production rates used for each iteration of discrete duty cycle improves a resolution such that the average of the discrete production rates approaches the target rate of NO production over time. In some embodiments, for each pulse sent to the at least one pair of electrodes, the controller utilizes a higher duty cycle if the target NO production exceeds the actual production from a previous pulse. In some embodiments, for each pulse sent to the at least one pair of electrodes, the controller utilizes a lower duty cycle if the target NO production is less than the actual production from a previous pulse.

In some embodiments, a frequency in the system is constant. In some embodiments the duty cycle can range from 0% to 100%.

The presently disclosed embodiments disclose a nitric oxide (NO) generation system including at least one pair of electrodes configured to generate a product gas containing NO from a flow of a reactant gas; a controller configured to regulate the amount of nitric oxide in the product gas produced by the at least one pair of electrodes by varying current to the electrodes with respect to time during a plasma pulse associated with the electrodes.

In some embodiments, wherein the current variation is tied to a duty cycle of the plasma pulse. In some embodiments, the current is configured to increase with to respect to time during the plasma pulse such that the current is an initial current at a start of a duty cycle of the electrical discharge and increases along the duty cycle. In some embodiments, a longer duty cycle results in a higher current at the end of the duty cycle. In some embodiments, a lower current is configured to be associated with a small gap between the electrodes to protect the electrodes from erosion in a small gap region. In some embodiments, the current is configured to increase over time to increase production at a large electrode gap between the pairs of electrodes.

The presently disclosed embodiments disclose methods of generating nitric oxide (NO) including identifying a target amount of NO production; controlling the amount of NO production to generate an actual amount of NO over a plurality of plasma pulses by varying at least one of a current to the electrodes with respect to time during each plasma pulse associated with the electrodes and duty cycle values of the plasma pulses selected from a plurality of discrete duty cycles to produce a target rate of NO production based on an average of discrete production rates associated with each of the plurality of the discrete duty cycles; and adjusting a subsequent plasma pulse based on a comparison of the actual and the target amount of NO production.

In some embodiments, for each subsequent plasma pulse sent to the at least one pair of electrodes, the controller utilizes a higher duty cycle if the target amount of NO production exceeds the actual amount of NO from a previous plasma pulse. In some embodiments, for each subsequent plasma pulse sent to the at least one pair of electrodes, the controller utilizes a lower duty cycle if the target amount of NO production is less than the actual amount of NO from a previous plasma pulse. In some embodiments, the current variation is a function of a duty cycle of each plasma pulse. In some embodiments, a frequency is constant. In some embodiments, varying both the current and the duty cycle allows for the generation of low doses of NO production. In some embodiments, the current variation is a function of the elapsed time within a duty cycle of each plasma pulse.

BRIEF DESCRIPTION OF THE DRAWINGS

The present disclosure is further described in the detailed description which follows, in reference to the noted plurality of drawings by way of non-limiting examples of exemplary embodiments, in which like reference numerals represent similar parts throughout the several views of the drawings, and wherein:

FIG. 28A and FIG. 28B illustrate an embodiment of a removable scrubber cartridge that includes a port for breath detection;

FIG. 29 illustrates an embodiment of a fluidized bed chamber including scrubber material;

FIG. 38A illustrates an embodiment of a particulate trap;

FIG. 38B illustrates an embodiment of a particulate trap;

FIG. 48A, FIG. 48B, FIG. 48C, and FIG. 48D illustrate exemplary graphs depicting constant concentration of NO within the inspired gas of a breath using an NO generation device;

FIG. 53 illustrates an embodiment of a system that is configured to sense diaphragm activity using an EMG signal;

FIG. 54A and FIG. 54B illustrate a method of priming and purging a cannula;

FIG. 55A, FIG. 55B, FIG. 55C, and FIG. 55D illustrate exemplary graphs showing timing a pump ahead of a pulse;

FIG. 59A illustrates an embodiment of an $NO/NO_2$ calibration device;

FIG. 67A, FIG. 67B, FIG. 67C, and FIG. 67D illustrate an embodiment of a variable orifice flow controller to prevent plasma noise;

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It will be understood that various changes may be made in the function and arrangement of elements without departing from the spirit and scope of the presently disclosed embodiments.

The present disclosure relates to systems and methods of nitric oxide (NO) delivery for use in various applications, for example, inside a hospital room, in an emergency room, in a doctor's office, in a clinic, and outside a hospital setting as a portable or ambulatory device. An NO generation and/or delivery system can take many forms, including but not limited to a device configured to work with an existing medical device that utilizes a product gas, a stand-alone (ambulatory) device, a module that can be integrated with an existing medical device, one or more types of cartridges that can perform various functions of the NO system, and an electronic NO tank. The NO generation system uses a reactant gas, including but not limited to ambient air, to produce a product gas that is enriched with NO.

An NO generation device can be used with any device that can utilize NO, including but not limited to a ventilator, an anaesthesia device, a defibrillator, a ventricular assist device (VAD), a Continuous Positive Airway Pressure (CPAP) machine, a Bilevel Positive Airway Pressure (BiPAP) machine, a non-invasive positive pressure ventilator (NIPPV), a nasal cannula application, a nebulizer, an extracorporeal membrane oxygenation (ECMO), a bypass system, an automated CPR system, an oxygen delivery system, an oxygen concentrator, an oxygen generation system, and an automated external defibrillator AED, MM, and a patient monitor. In addition, the destination for nitric oxide produced can be any type of delivery device associated with any medical device, including but not limited to a nasal cannula, a manual ventilation device, a face mask, inhaler, or any other delivery circuit. The NO generation capabilities can be integrated into any of these devices, or the devices can be used with an NO generation device as described herein.

Figure 1:
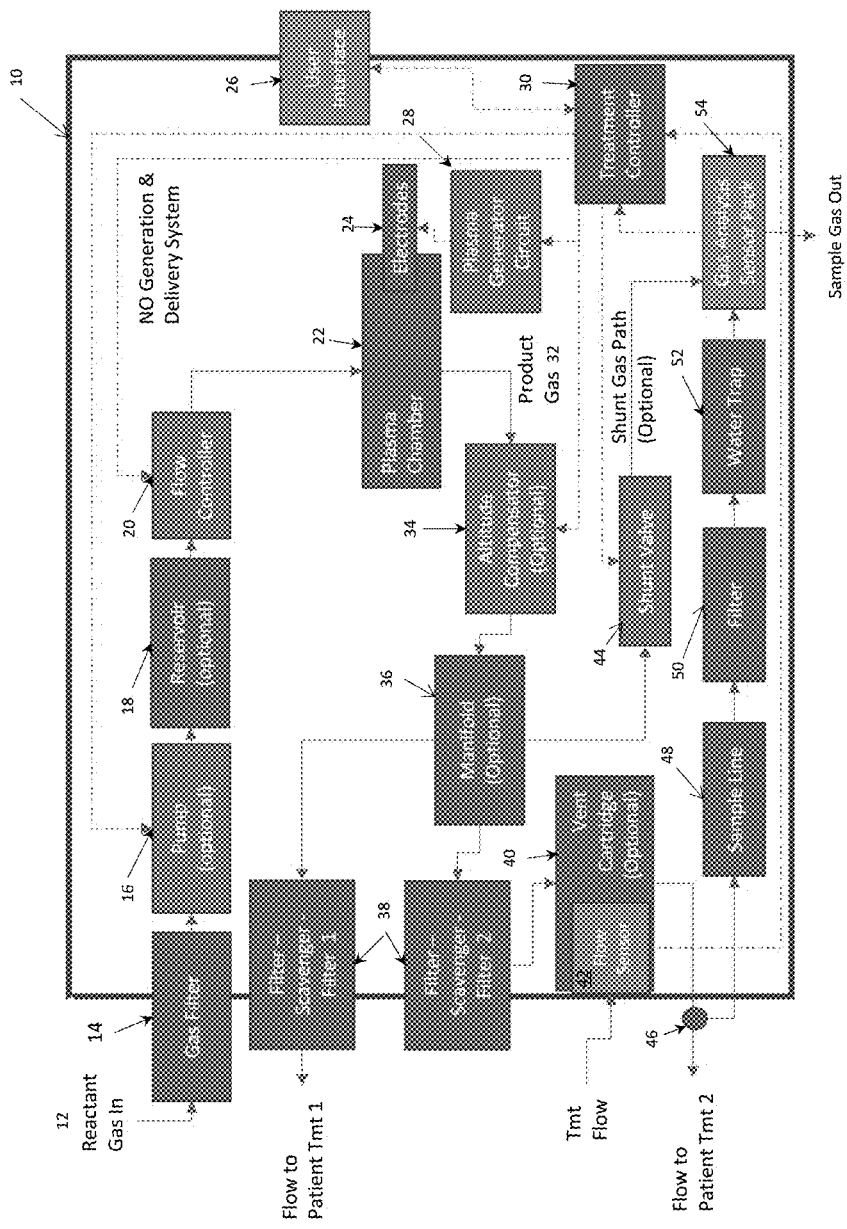
FIG. 1 is an exemplary embodiment of a system for generating an NO-enriched product gas.

FIG. 1 illustrates an exemplary embodiment of an NO generation system 10 that includes components for reactant gas intake 12 and delivery to a plasma chamber 22. The plasma chamber 22 includes one or more electrodes 24 therein that are configured to produce, with the use of a high voltage circuit 28, a product gas 32 containing a desired amount of NO from the reactant gas. The system includes a controller 30 in electrical communication with the plasma generator 28 and the electrode(s) 24 that is configured to control the concentration of NO in the product gas 32 using one or more control parameters relating to conditions within the system and/or conditions relating to a separate device for delivering the product gas to a patient and/or conditions relating to the patient receiving the product gas. In some embodiments, the plasma generator circuit is a high voltage circuit that generates a potential difference across an electrode gap. In some embodiments, the plasma generator circuit is a radio frequency (RF) power generator delivering RF power to one or more RF electrodes. In some embodiments, the RF power operates around 13.56 MHz with power in the 50-100 W range, however other power ranges can be effective depending on electrode design, production targets and reactant gas conditions. In some embodiments, RF power operates around 2.45 GHz for improved coupling and excitation of $N_2$ molecules. The controller 30 is also in communication with a user interface 26 that allows a user to interact with the system, view information about the system and NO production, and control parameters related to NO production.

In some embodiments, the NO system pneumatic path includes a pump pushing air through a manifold 36. The manifold is configured with one or more valves; three-way valves, binary valves, check valves and/or proportional orifices. The treatment controller 30 controls the flow of the pump, the power in the plasma and the direction of the gas flow post-electrical discharge. By configuring valves, the treatment controller 30 can direct gas to the manual respiration pathway, the ventilator pathway or the gas sensor chamber for direct measurement of NO, $NO_2$ and $O_2$ levels in the product gas. In some embodiments, respiratory gas (i.e. treatment flow) is directed through a ventilator cartridge that measures the flow of the respiratory gas and merges the respiratory gas with NO product gas.

The output from the NO generation system in the form of the product gas 32 enriched with the NO produced in the plasma chamber 22 can either be directed to a respiratory or other device for delivery to a patient, or can be directed to a plurality of components provided for self-test or calibration of the NO generation system. In some embodiments, the system collects gases to sample in two ways: 1) gases are collected from a patient inspiratory circuit near the patient and pass through a sample line 48, a filter 50, and a water trap 52, or 2) gases are shunted directly from the pneumatic circuit as they exit plasma chamber. In some embodiments, product gases are shunted with a shunt valve 44 to the gas sensors after being scrubbed but before dilution into a patient airstream. In some embodiments, product gases are collected from an inspiratory air stream near the device and/or within the device post-dilution. Within the gas analysis portion of the device, the product gas passes through one or more sensors to measure one or more of temperature, humidity, concentrations, pressure, and flow rate of various gasses therein.

Figure 2:
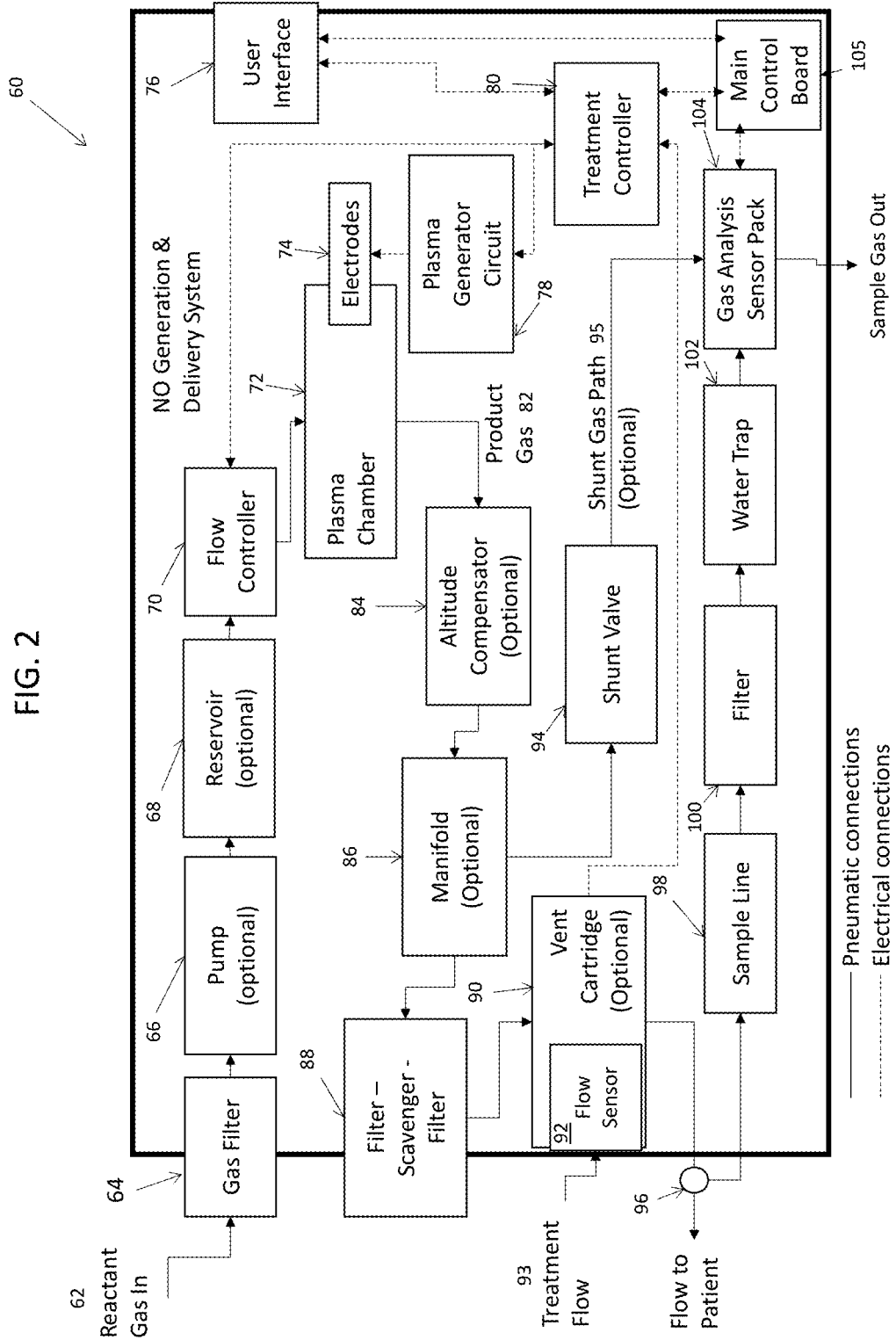
FIG. 2 is another exemplary embodiment of a system for generating an NO-enriched product gas.

FIG. 2 depicts an embodiment of a NO generation and delivery system 60. Reactant gas 62 enters the system through a gas filter 64. A pump 66 is used to propel gas through the system. Whether or not a system includes a pump can depend on the pressure of the reactant gas supply. If reactant gas is pressurized, a pump may not be required. If reactant gas is at atmospheric pressure, a pump or other means to move reactant gas through the system is required. A reservoir 68 after the pump attenuates rapid changes in pressure and/or flow from a pump. Coupled with a flow controller 70, the reservoir, when pressurized, can enable a system to provide flow rates to the plasma chamber 72 that are greater than the pump 66 flow rate. This enables the use of a smaller, lighter, quieter and more efficient pump. Electrodes 74 within the plasma chamber 72 are energized by a plasma generation circuit 78 that produces high voltage inputs based on desired treatment conditions received from a treatment controller 80. A user interface 76 receives desired treatment conditions (dose, treatment mode, etc.) from the user and communicates them to the main control board 105. The main control board 105 relays to the treatment controller 80 the target dose and monitors measured NO concentrations from the gas analysis sensor pack 104. The main control board 105 monitors the system for error conditions and generates alarms, as required. The reactant gas 62 is converted into product gas 82 when it passes through the plasma chamber 72 and is partially converted into nitric oxide and nitrogen dioxide. An altitude compensator 84, typically consisting of one or more valves (for example, proportional, binary, 3-way), is optionally used to provide a back-pressure within the plasma chamber 72 for additional controls in nitric oxide production. Product gases pass through a manifold 86, as needed, to reach a filter-scavenger-filter 88 assembly that removes nitrogen dioxide from the product gas. From the filter-scavenger-filter 88, product gas is introduced to a patient treatment flow directly, or indirectly through a vent cartridge 90. In some embodiments, the vent cartridge 90 includes a flow sensor 92 that measures the treatment flow 93. The treatment flow measurements from the flow sensor 92 serve as an input into the reactant gas flow controller 70 via the treatment controller 80. After product gas 82 is introduced to the treatment flow, it passes through inspiratory tubing. Near the patient, a fitting 96 is used to pull a fraction of inspired gas from the inspiratory flow, through a sample line 98, filter 100, water trap 102 and Nafion tubing to prepare the gas sample and convey it to gas sensors 104. Sample gas exits the gas analysis sensor pack 104 to ambient air. In some embodiments, the system 60 can optionally direct gas through a shunt valve 94 and shunt gas path 95 directly to the gas sensor pack and out of the system. In some embodiments involving the shunt valve 94, the manifold 86 includes a valve (not shown) to block flow to the filter-scavenger-filter when the shunt valve 94 is open.

Figure 3:
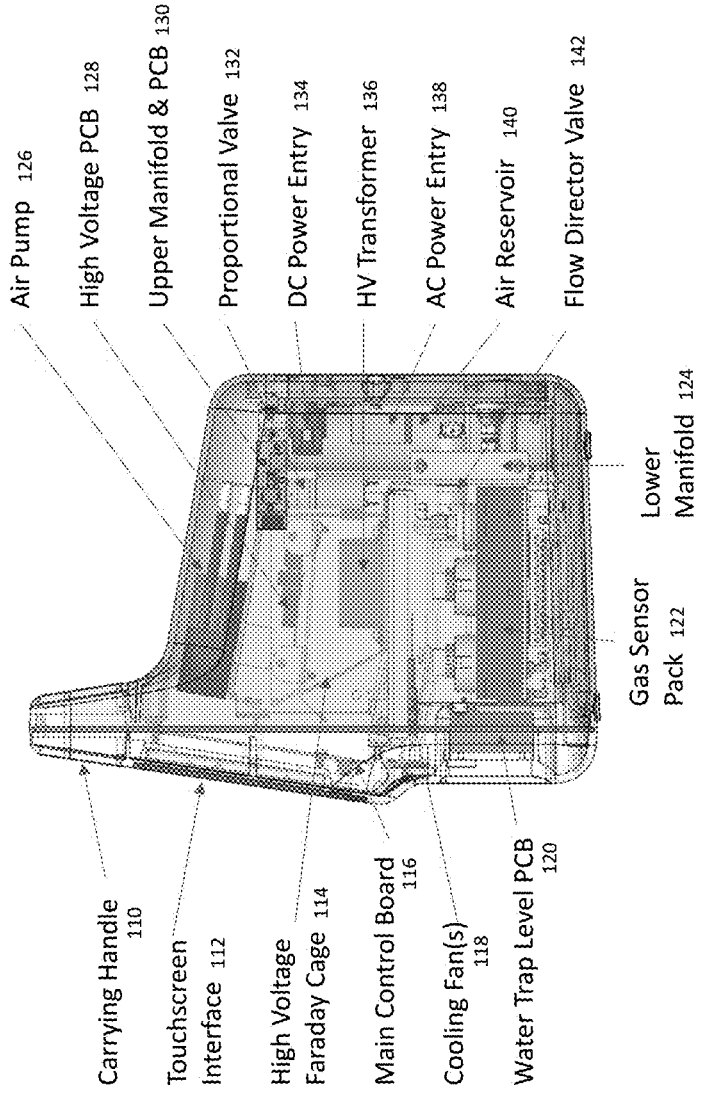
FIG. 3 is an exemplary embodiment of an NO generation system.

Another exemplary embodiment of an NO generation system is shown in FIG. 3, which includes a carrying handle 110, an interface 112, a high voltage cage 114, a control board 116, one or more cooling fans 118, and a water trap PCB 120. The system also includes a gas sensor pack 122, a lower manifold 124, an air pump 126, a high voltage PCB 128, an upper manifold 130, a proportional valve 132, a DC power entry 134, a high voltage (HV) transformer 136, an AC power entry 138, a reservoir 140, and a flow director valve 142.

Figure 4:
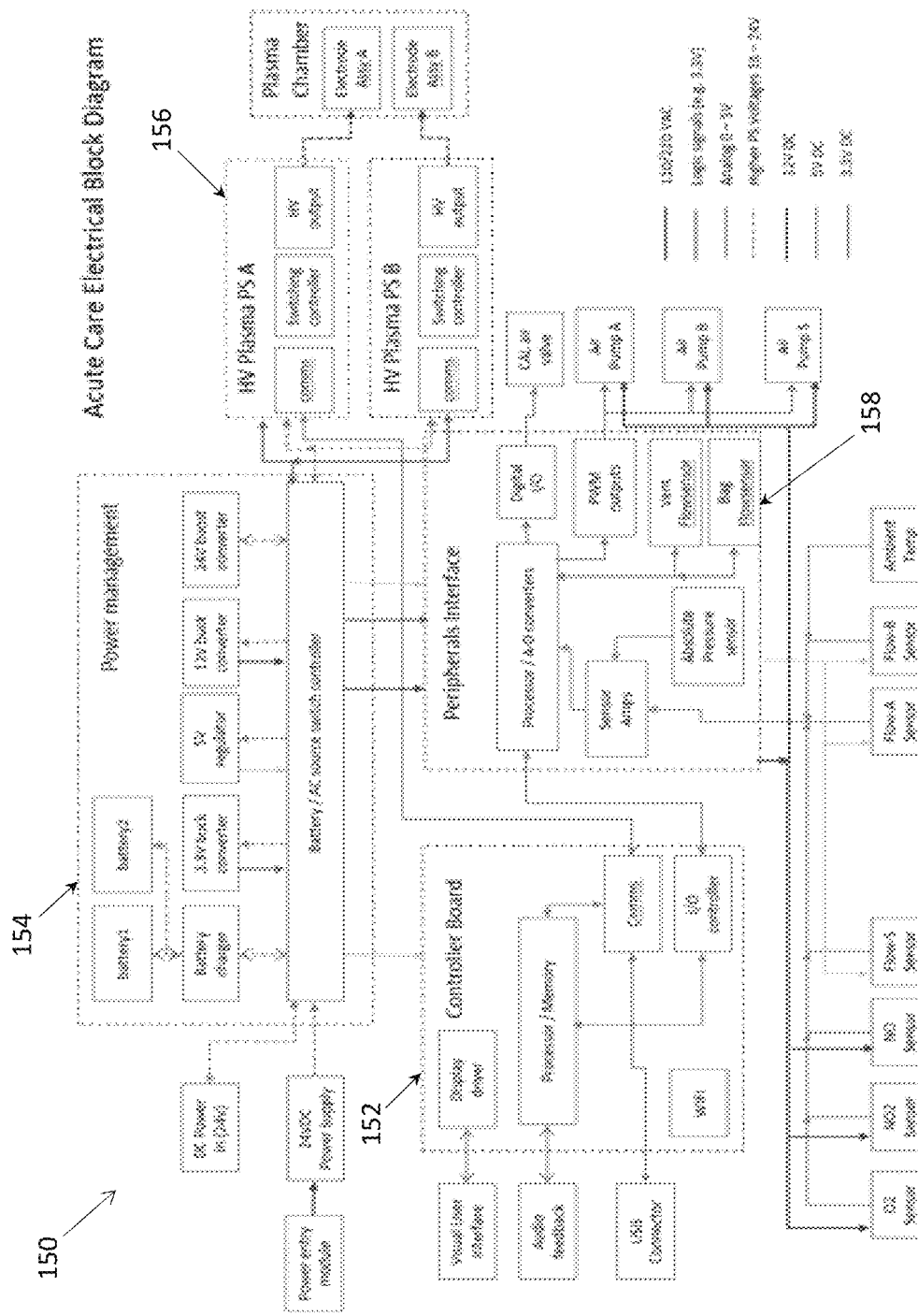
FIG. 4 illustrates an embodiment of a schematic of a controller of an NO generation system.

FIG. 4 depicts a schematic showing all the components of an embodiment of an NO device 150, including a control board 152, a power management circuit 154, one or more electrode assemblies 156, and a peripherals interface 158. A plasma chamber 22 can be part of the reusable controller or easily removed and disposable.

Figure 5:
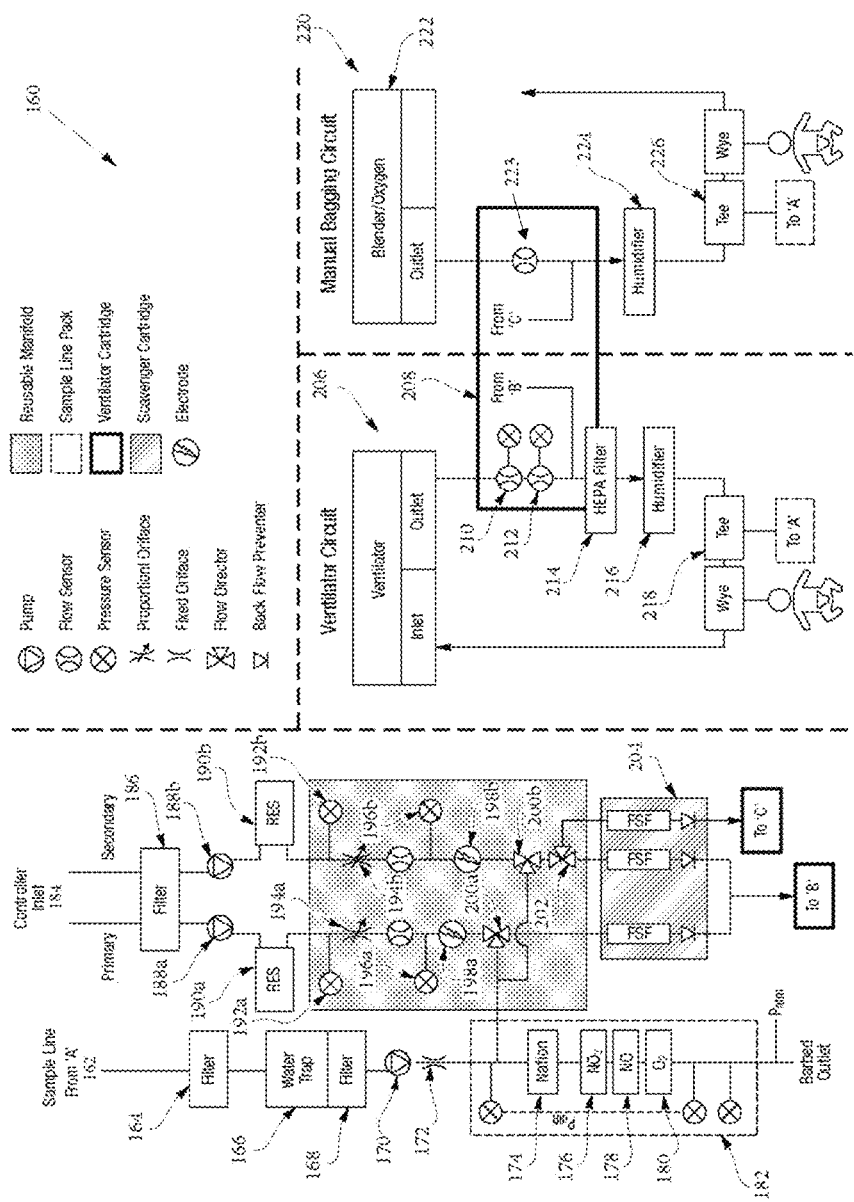
FIG. 5 is an embodiment of a pneumatic circuit.
Figure 6:
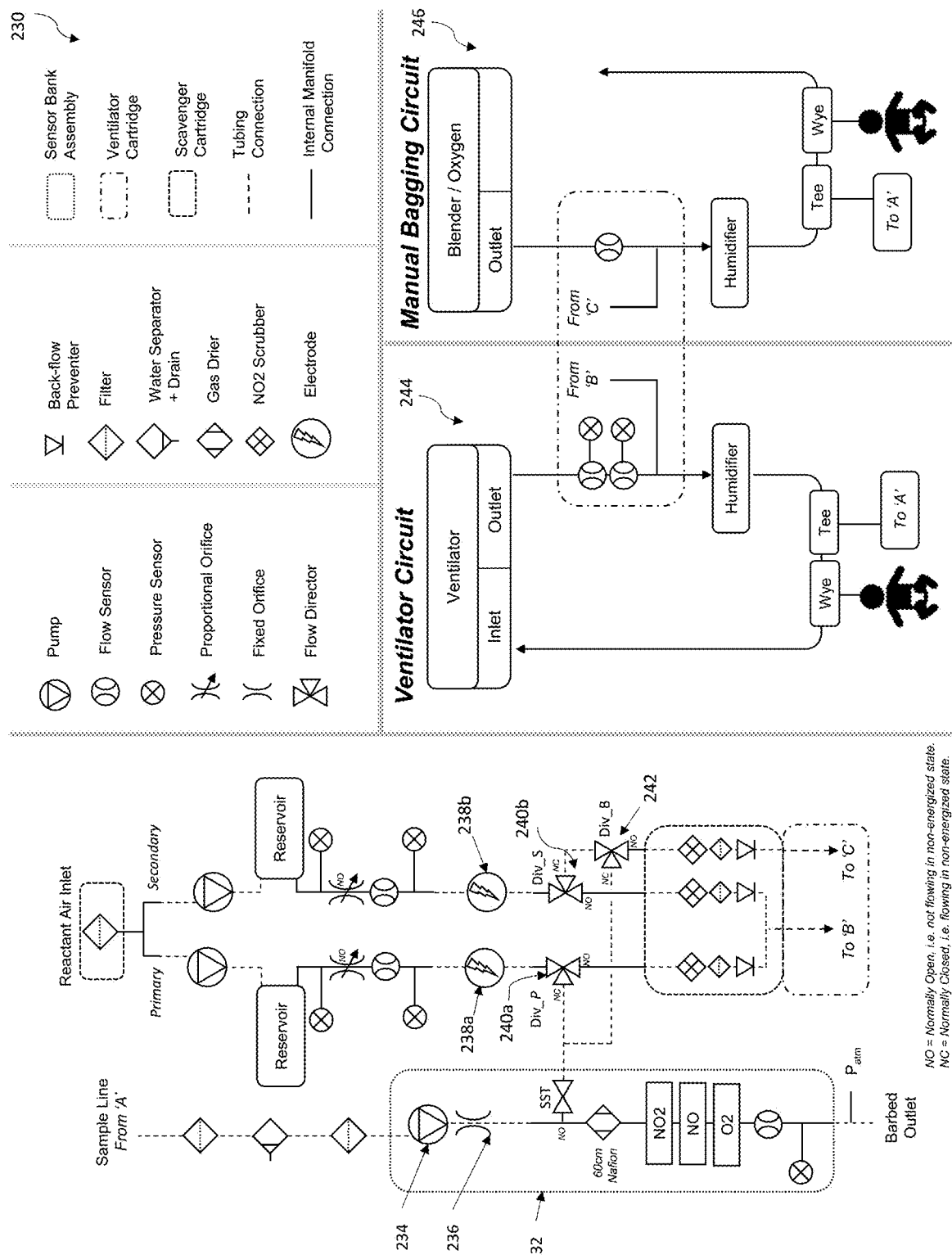
FIG. 6 is another embodiment of a pneumatic circuit.

FIG. 5 and FIG. 6 depict embodiments of NO generation and delivery systems with redundant NO generators. FIG. 5 depicts an exemplary pneumatic design 160 for an NO generation and delivery system. In the upper left of the diagram, sample gases 162 originating in the treatment circuit (lower right of FIG. 5 labeled 'A') enter the system through a hydrophilic filter 164 and travel through a water trap 166. In some embodiments, this filter 164 is disposable so that the user can replace it as needed when it clogs. An additional filter 168 after the water trap 166 protects the gas analysis sensors from contaminants. In some embodiments, the additional filter 168 is hydrophobic to prevent liquid contents from the water trap from entering the gas sensor assembly. Sample gases then flow through a pump 170 and then through a fixed orifice 172 that limits the gas flow rate through the sensors and diminishes pulsatility in the sample gas flow. Some gas sensors, electrochemical sensors for example, are sensitive to the amount of water content within the sample gas and require the gas to have roughly 50% relative humidity. Gas flows through Nafion tubing 174 to add humidity to the sample from the atmosphere in the event that sample gases are very dry as can be the case when calibration gases are used. Conversely, if the gas sample is too humid, Nafion tubing 174 removes humidity from the gas sample, driving the sample gas humidity towards ambient levels. Next, the sample gas flows through one or more gas analysis sensors. Sensors 176, 178, 180 for $NO_2$, NO and $O_2$ are shown. A differential pressure sensor shown on the left side of the sensor manifold block is used to measure the flow rate through the gas sensor manifold 182. This flow rate can be used to ensure that the sample pump is functioning and that the sample line, disc filter and water trap are not clogged or kinked. An absolute pressure sensor near the end (bottom) of the sensor manifold is used to measure atmospheric pressure. Gases exit the sensor manifold and flow through a T-fitting, where one leg is connected to atmospheric pressure and the other leg is connected to an external port in the device. The second leg is connected to atmosphere to prevent hospital vacuum from affecting the flow rate through the gas sensor manifold and potentially affecting patient treatment. The external port can be connected to hospital vacuum or just vented to atmosphere.

Moving to the right in FIG. 5, at the top of the diagram there is an inlet 184 to receive reactant gas into the system. In some embodiments, this is a 22 mm medical air connection. Incoming reactant gas flows through a filter 186 to remove particulate then bifurcates into two parallel NO generation paths. Each path consists of a pump 188a, 188b, a reservoir 190a, 190b, a reservoir pressure sensor 192a, 192b, a proportional flow valve 194a, 194b, a fixed orifice, a plasma chamber pressure sensor 196a, 196b, and a plasma chamber 198a, 198b. After the plasma chamber 198a, 198b, each flow path has a flow director 200a, 200b that can direct gases to either the gas sensor manifold 182 or towards the patient inspiratory air. These side paths to the gas sensor manifold 182 enable a system to evaluate the gas produced and/or redirect gases within the plasma chamber away from the patient. After the gas analysis side paths, one of the gas paths utilizes a flow director 202 to select whether product gases will flow to a ventilator circuit (B in the figure) or to a manual bag outlet (C in the figure). Gases then flow through one of three parallel scrubber passages in a disposable cartridge 204. The scrubber passages consist of a filter, scrubber material, a second filter and a one-way valve. The one-way valve ensures that pressures and materials outside of the system do not enter the cartridge and controller.

In the lower right corner of FIG. 5, a treatment setup is depicted. In a ventilator circuit 206, inspiratory gases exit the ventilator and enter a ventilator cartridge 208. The gases flow through two flow sensors 210, 212. In some embodiments, the flow sensors measure pressure, humidity and temperature in addition to flow. NO-containing product gas is merged with the inspiratory flow after the flow sensors. Inspiratory flow continues through a HEPA filter 214, a humidifier 216 and on to a "T" fitting 218, where sample gases are pulled, then on to the patient.

Also shown in the lower right corner of FIG. 5 is a manual bagging circuit 220. Inspiratory gases are sourced from a blender/wall outlet/cylinder 222 and enter the ventilator cartridge 208. Flow is measured within the ventilator cartridge 208 prior to adding NO-containing gas. Gases flow through an optional humidifier 224 and on to a "T" fitting 226 where sample gases are pulled and then on to the patient.

FIG. 6 illustrates a similar system to the embodiment of the system shown in FIG. 5. As explained above, FIG. 5 depicts how the filter-scrubber-filter assemblies can be grouped into a cartridge 204, and FIG. 5 also depicts how gas sensors (176, 178, 180), Nafion tubing 174, a manifold, and pressure/flow sensors can be grouped into a gas sensor assembly 182. In FIG. 6, a gas sensor assembly 232 includes a pump 234 and a flow sensor 236. FIG. 5 depicts how vent flow sensors 210, 212, a bag flow sensor 223, pressure sensors, and NO injectors can be grouped into the vent cartridge 208. A HEPA filter 214 connects to the vent cartridge 208 to keep the vent cartridge clean. In some embodiments, the HEPA filter utilizes a standard, 22 mm pneumatic connection for ease of replacement and optional use. In some embodiments, the HEPA filter connects to the vent cartridge with a proprietary connection to ensure that the system can not be used without it. FIG. 5 and FIG. 6 further differ in pneumatic design post-plasma chamber. In FIG. 5, in both NO generation channels, a first flow-director (200a, 200b) directs product gases to either the gas sensor pack 182 or the gas scrubber cartridge 204. In the secondary channel, a second flow director directs product gases to either a vent circuit (path B) or a bag circuit (path C). In FIG. 6, the pneumatic pathway differs in that a first flow director selects between vent circuit and the sensors while a second flow director selects between shunting to the sensors and bag circuit. The pneumatic design in FIG. 6 has an advantage over the flow design of FIG. 5 due to having equal flow restriction in both channels between the plasma chamber and the vent flow injector. This relates to minimizing the flow path length and having the flow restriction of the two paths be substantially identical so that they can have similar if not identical calibration settings and NO production.

In some embodiments, a scrubber cartridge can be used for demonstration purposes. The demo device can be identified by RFID, memory device, 2-d bar code, mechanical interface, optical interface, lower flow restriction or other means by a controller to enable a demonstration mode for training purposes. In some embodiments, the demonstration scrubber cartridge is non-functional for clinical purposes.

Algorithm Inputs and Controller

As explained above, the system includes a controller configured to control the concentration of NO in a product gas using one or more control parameters. The control parameters can be relating to conditions within the NO generation system, conditions relating to a separate device in fluid communication with the NO generation device for delivering the product gas to a patient, ambient conditions and/or conditions relating to a patient receiving the product gas.

Dilution Ratio

Figure 7A:
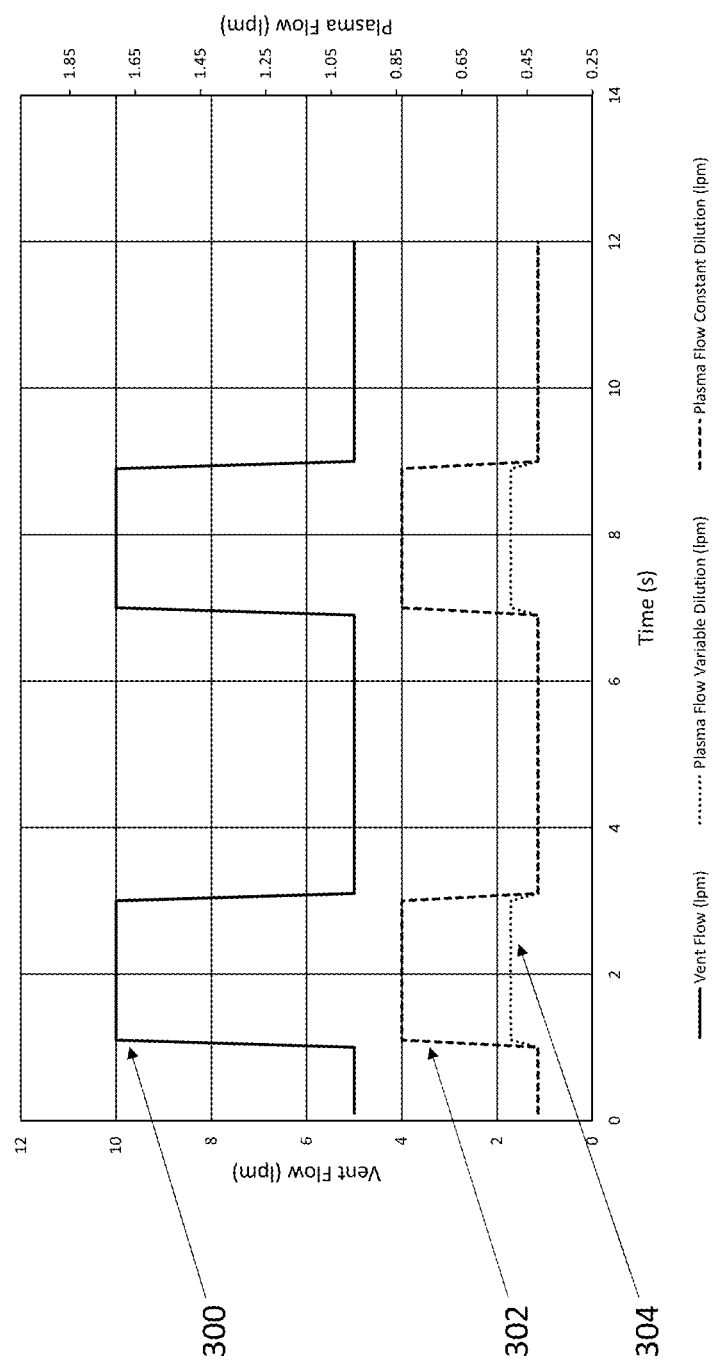
FIG. 7A illustrates an exemplary graph of ventilator flow with a constant dilution flow.

In some clinical applications, such as ventilator, anesthesia and face mask treatments, nitric oxide generators produce nitric oxide in a reactant gas prior to introducing the nitric-oxide-containing product gas to an inspiratory stream. The ratio of product gas flow rate introduced to an inspiratory stream to inspiratory flow rate is referred to as the dilution ratio. In some embodiments, the dilution ratio is held constant across all inspiratory flow rates for a given patient treatment (the product gas flow is proportional to ventilator flow). This is beneficial because the NO concentration in the product gas is constant, thereby eliminating the need to track discretized volumes of NO as they travel through the system. In some embodiments, a dilution ratio is set based on one or more of inspiratory volumetric flow, product gas concentration, inspiratory treatment mode and/or patient size. With respect to patient size, in some embodiments, smaller patients are treated with lower dilution ratios so that the volume of gas added to an inspiratory circuit is minimized, thereby minimizing the potential of over-pressurizing the lung. Dilution ratio can also be set based on a combination of one or more treatment parameters such as treatment type (constant flow, high frequency oscillation, volume-control, pressure-control, etc.), inspiratory flow parameters, such as minute volume, bias flow rate, and/or peak flow rate. In some embodiments, dilution ratio can vary with treatment type (constant flow, variable flow, high pressure, low pressure) or with inspiratory flow rate. Parameters can be entered by the user or derived from parameters sensed by the system, such as minute volume, inspiratory pressure, inspiratory flow rate, breath rate, and/or tidal volume. FIG. 7A illustrates an exemplary graph of ventilator flow (line 300) with a constant dilution flow (line 302) and with a variable dilution ratio plasma flow (line 304). As shown in FIG. 7A, variable dilution ratio plasma flow means the device can change the concentration and flow rate of product gas during a treatment. In the scenario illustrated, the system increases the concentration of NO within the product gas during the inspiratory event to decrease dilution during inspiratory flow. This is one way to work within the production capabilities of a NO generation device while minimizing dilution of the patient inspiratory flow. For example, variable dilution ratio plasma flow can mean the device adds less air flow volume during inspiratory flow.

Figure 7B:
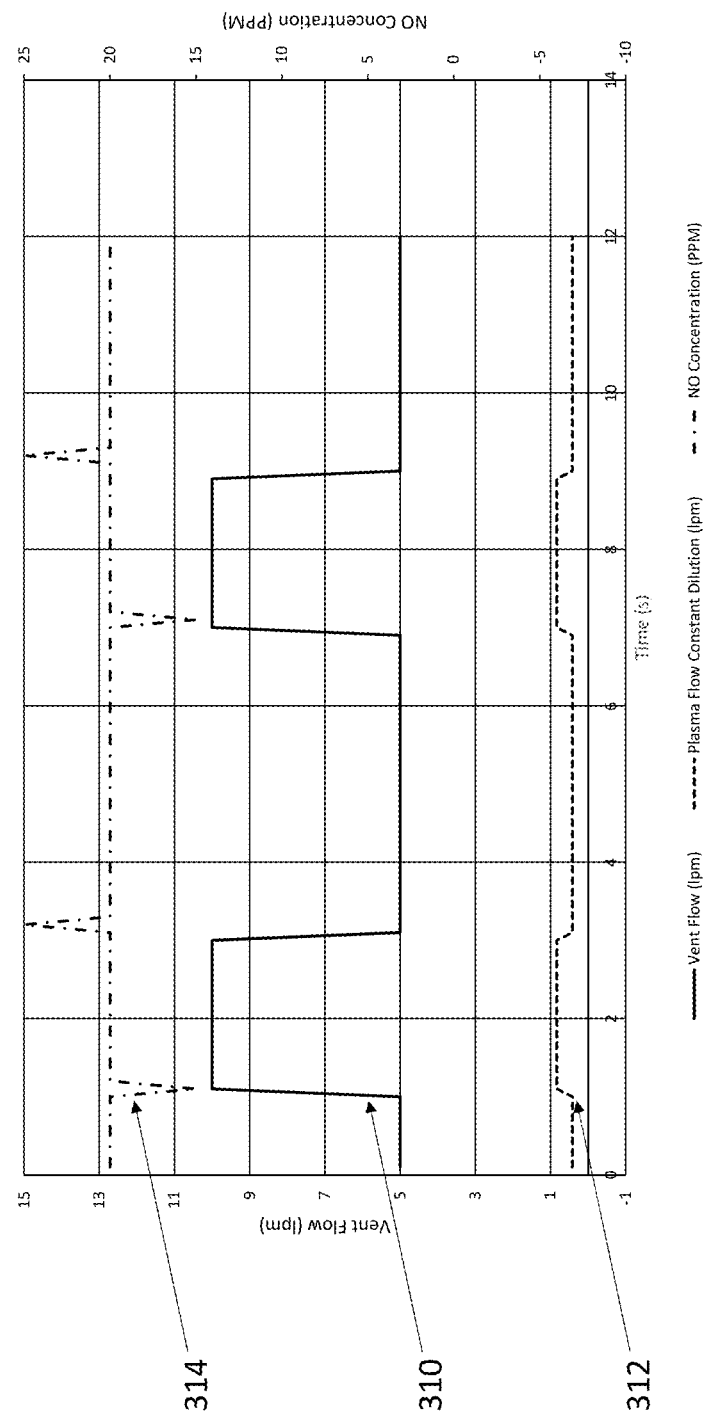
FIG. 7B illustrates an exemplary graph of ventilator flow with a variable dilution ratio plasma flow.

FIG. 7B illustrates an effect of lag on product gas delivery. FIG. 7B illustrates ventilator flow (line 310) and a constant dilution flow (line 312) Time is required for a NO generation system to do one or more of sensing the inspiratory flow, calculating a NO production level, energizing plasma activity, reacting with flow control, scrubbing product gas. Thus, product gas can be introduced to the inspiratory flow out of phase with the inspiratory flow. This can result in variance in the inspired concentration of NO (line 314), as shown in FIG. 7B. In FIG. 7B, the inspiratory flow rate increases before the product gas flow rate increases resulting in a volume of inspiratory gas being underdosed. Similarly, when the inspiratory event ends and inspiratory flow rates decrease to bias flow levels, lags in the response of product gas flow result in a volume of inspiratory gas that is over dosed. In some embodiments, a NO generation system decreases the product gas flow rate prior to the decrease in inspiratory flow rate to prevent excess NO from entering the inspiratory limb and causing a spike in NO concentrations. This can be done by controlling product gas flow at a flow controller and/or pump or by changing the position of a flow control element near the NO injector.

In some embodiments, an NO delivery device can apply a loading dose, or a dilating dose, of inhaled NO and then decrease the dose to a sustaining level based on the clinical response. The loading dose could be delivered for a certain number of breaths, for a specified amount of time, or until certain physiological changes are observed e.g. an improvement on systemic oxygenation or reduction in pulmonary vascular pressures. This can be used with any type of NO delivery device, including but not limited to devices that generate NO.

Electrochemical sensor performance can be affected by high concentrations of NO and $NO_2$. In some embodiments, an NO generation device directs products gases to the sensor bank. In order to protect the sensors from high concentration gases, the device runs the sample pump, pulling in gas through the sample line to dilute the product gas. In some embodiments, a separate NO generator produces dilution gases.

System Warming at Startup

Figure 8:
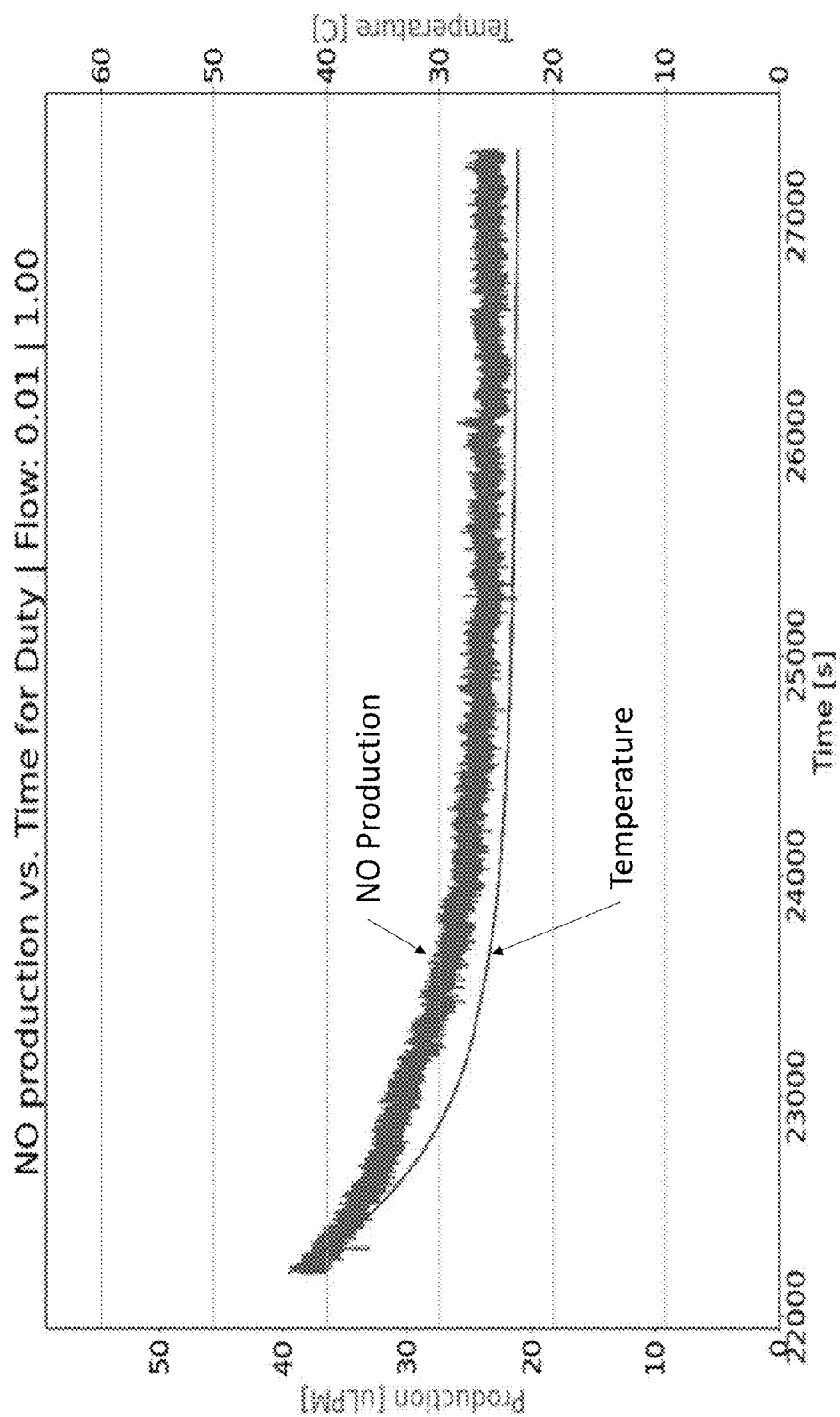
FIG. 8 illustrates an exemplary graph showing thermal stabilization time of the device and the effect on NO.

NO production can vary as a system warms up from a cold start or when settings are changed. In some embodiments, an NO generation device alters one or more NO production parameters (AC waveform shape, duty cycle, pulse frequency, reactant gas flow rate, etc.) to compensate for the plasma chamber temperature not being at steady state. FIG. 8 illustrates an exemplary graph showing thermal stabilization time of the device and the effect on NO production. In some embodiments, NO production increases as a system warms up. For example, a system can be calibrated for NO production at steady state thermal conditions. When a system is not at steady state yet, a NO generation system can alter a production parameter (AC waveform shape, NO set point, plasma frequency, plasma duty cycle, reactant gas flow rate, etc.) to achieve more accurate NO dosing. In some embodiments, a plasma chamber and/or electrodes can be warmed by the system using resistive elements, thermoelectric elements, or other means to preheat the system. In some embodiments, the temperature of the reactant gas can be altered to decrease the time to achieve steady state thermal conditions. In some embodiments, temperature can be measured on the large, flat, square face of the of the plasma chamber. An NO generation device needs to have a plasma chamber temperature measurement (or product gas temperature). In some embodiments, electrodes are energized to warm up a plasma chamber prior to use. In some embodiments, NO concentration has a 30 second moving average filter. NO concentration can reach some steady-state production value dependent on the thermal mass of the system and the competing heating and cooling forces (plasma vs. conduction and convection). In some embodiments, the electrode temperature is measured by measuring the resistance of an electrode along its length between electrical discharges. This is based on the temperature coefficient of resistance of the electrode material. In some embodiments, a NO generation system can determine the state of warm-up by monitoring electrode temperature.

As a NO generation system warms up, the resonant frequency of the high voltage circuit can change. In some embodiments, a nitric oxide generation system determines resonant frequency mid-treatment and adjusts settings accordingly to account for shifts in resonance during use, such as thermal effects.

In some embodiments, the system operates NO generators at a setting that warms up the system prior to clinical use. In some embodiments, this is a maximal setting. In some embodiments, both channels are warmed up at the same time. In some embodiments, a channel is warmed up while another channel is treating a patient.

Altitude Issues

The amount of NO generated is at least partially dependent on the quantity of $N_2$ and $O_2$ in the vicinity of the plasma. Depending on how a system prepares reactant gas, the amount of $N_2$ and $O_2$ present at the plasma can decrease with increasing elevation. In some embodiments, an NO generation system continues to deliver the same number of micrograms of NO per breath as altitude increases, rather than continue to deliver the same ppm. In some embodiments, an NO generator uses plasma chamber pressure and/or ambient pressure as an input into an algorithm that calculates plasma (duty cycle, etc.) and flow parameters to achieve a target number of micrograms per breath. In some embodiments, an NO generator uses a variable flow restriction downstream of the plasma to compensate the effects of altitude on reactant gas pressure.

Plasma Control and Current

The current through the plasma in an NO generation device is related to the amount of NO generated. In some embodiments, an NO generation system is provided that modulates the current through the plasma to vary NO production. Monitoring the plasma current can provide insight into the operation of the system and assist in the detection of degenerative changes in a system. For example, a system can use the electrical current to detect the state of electrode wear. Changes are indicative of changes in NO production.

The presence or absence of plasma in a plasma chamber can be detected by monitoring the current through the primary winding of a high voltage transformer with the secondary winding connected to one or more electrodes. In some embodiments, the presence or absence of plasma is detected from the input current to the NO generator. In some embodiments, a thermopile at or near the plasma chamber is used to detect plasma activity.

In some embodiments, an IR photo diode detects the heat of the plasma.

In some embodiments, an NO generation system uses the plasma current as a proxy for NO production. In some embodiments, an NO generation system uses closed-loop control of the plasma current (or primary circuit current as a proxy) to stabilize NO production around a target value. In some embodiments, primary current in a high voltage circuit designed to generate NO is used to control NO production. In some embodiments, plasma current is used as a proxy for NO generation measurement and can trigger an alarm if NO generation is too high or too low.

Figure 9A:
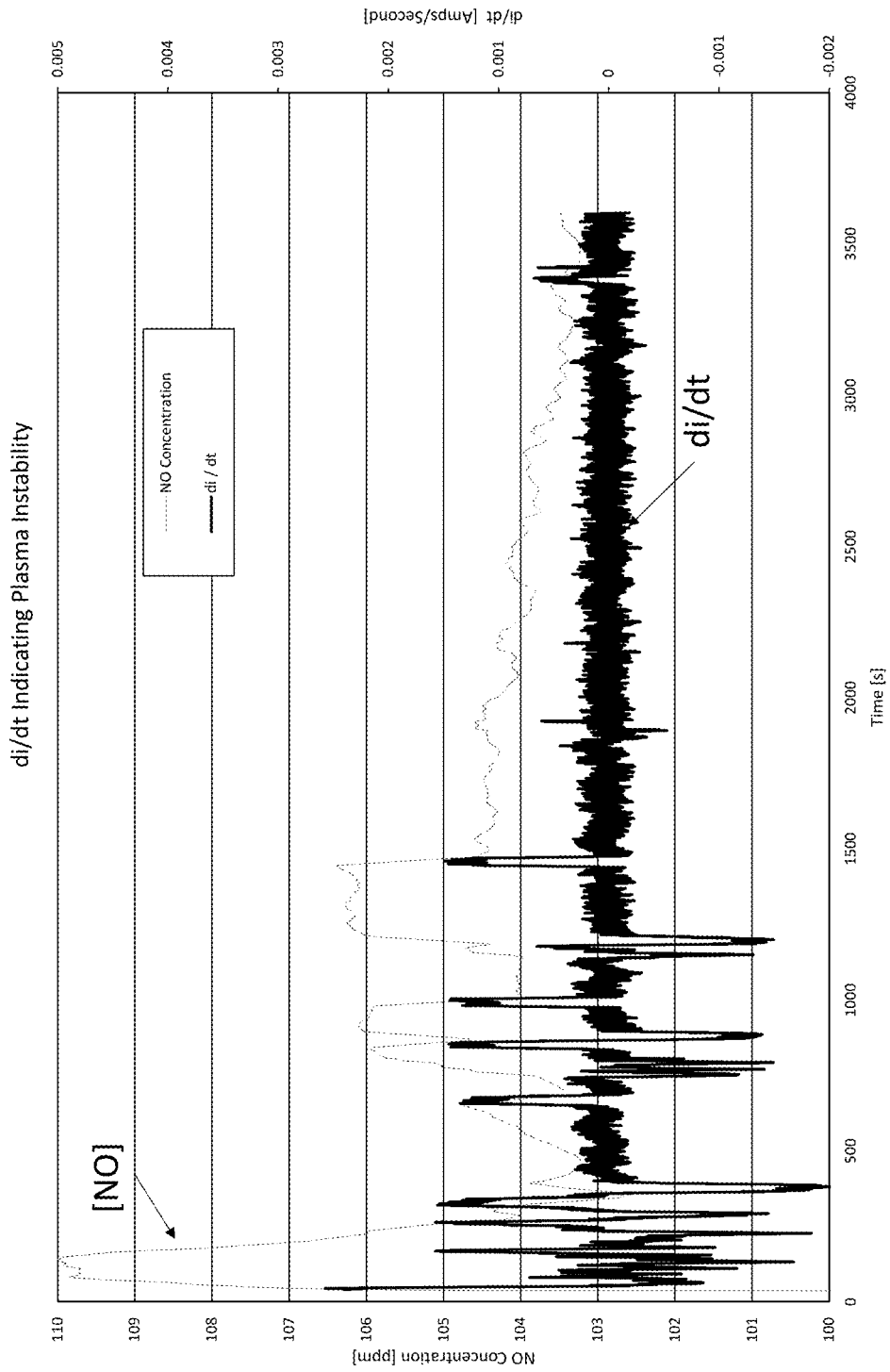
FIG. 9A shows an exemplary graph illustrating how a change in current can be indicative of plasma stability.

FIG. 9A shows an exemplary graph illustrating how a change in current (di/dt) can be indicative of plasma stability. Plasma stability is indicative of how stable NO production is. In some embodiments, a NO generation system generates an alarm to prompt electrode replacement when plasma stability exceeds a threshold. As shown in FIG. 9A, di/dt illustrates is a 5 second moving average filter applied to (30 second moving average filter of current/1 s time step). After some thermal settling effects, where di/dt rises significantly above or below, the noise corresponds with a rapid change is NO concentration. If current can be used to detect a rapid shift in NO production, a device can make a decision to alarm or switch to a back-up system in real time (versus waiting >30 s for integrated gas analyzers to detect the change).

Figure 9B:
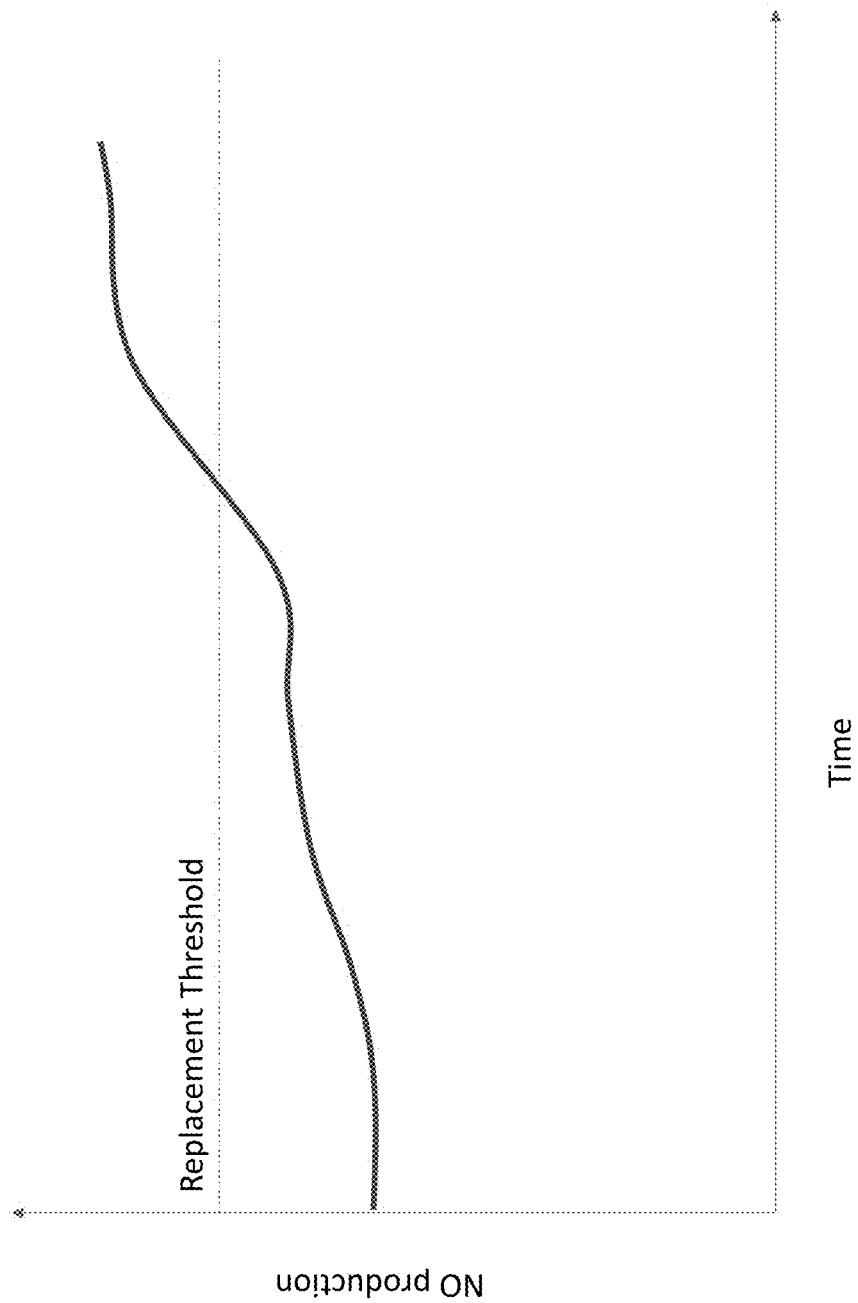
FIG. 9B shows an exemplary graph illustrating NO production increasing over time as an electrode wears.

FIG. 9B shows an exemplary graph of NO production increasing over time as an electrode wears. A system can use NO production (the mathematical product of NO concentration and reactant/product gas flow rate) as an indicator of electrode wear due to the larger gap creating a longer arc. A system can measure the amount of NO generated under standardized conditions (pulse frequency, duty cycle, voltage, current) periodically to assess the condition of the electrodes. In the embodiment shown, as electrodes wear, the gap between electrodes increases, thereby increasing NO production. NO production can be measured by measuring the concentration and flow rate of either product gas or inspired gas. A threshold for NO production at standardized settings can be utilized to trigger electrode replacement. In some embodiments, the threshold is determined based on the tolerance allowance for electrodes in the error budget for system dose accuracy. This approach can enable the electrode replacement schedule to be based more on actual electrode use instead of elapsed time.

Dose Accuracy

In an NO generation system where flow and plasma activity are controlled, the reactant gas flow rate is controlled to a target value. From time to time, the reactant gas flow rate is not accurate, which can lead to variation in NO concentration with the product gas. In some embodiments, an NO generation device selects a plasma parameter based on the actual reactant gas flow rate through the plasma chamber and the target NO production level. For example, the system can request a reactant gas flow rate from the flow controller and plasma activity can be altered, as needed, to ensure that the product gas concentration is accurate. The plasma parameter can include one or more of duty cycle, frequency, power, energy, and AC waveform.

In some embodiments, an NO generation system is designed to maintain a constant concentration of NO in the delivery tube between plasma chamber and inspiratory gas flow path. In the event that plasma flow is lower than target, plasma activity is decreased below target so that a constant concentration is maintained.

In some embodiments, a system adjusts subsequent NO production (reactant gas flow and plasma activity) up or down to account for losses or excesses from prior increments in NO production while maintaining a constant concentration, respectively. For example, if reactant gas flow was observed to be below target, a NO generation system subsequently operates with higher than nominal reactant gas flow to maintain the correct average mass flow of NO into the patient circuit.

In some embodiments, an NO generation system is characterized for reactant gas flow rate and a plasma parameter. For illustrative purposes, duty cycle has been used for the subsequent embodiments, but duty cycle could be replaced with plasma frequency, plasma energy, plasma power, or AC waveform. In order to produce a target production level of NO, the system interpolates between known duty cycles to determine the duty cycle used. In some embodiments, different combinations of reactant gas flow rate and plasma duty cycle can produce the same amount of NO. In some embodiments, the reactant gas flow rate and plasma duty cycle are selected to minimize $NO_2$ levels. In some embodiments, the reactant gas flow rate and plasma duty cycle are selected to minimize dilution of the patient inspiratory flow. In some embodiments, the reactant gas flow rate and plasma duty cycle are adjusted to optimize NO levels, dilution or a combination of the two, depending on the patient treatment (flow rate, dose level, oxygen level, etc.). In some embodiments, the reactant gas flow rate and plasma duty cycle are selected to conserve electrical power.

In the event of a problem with the reactant gas flow control, an NO generation system can shunt product gas flow and/or reactant gas flow away from the patient in order to prevent over-pressurization of a patient. In some embodiments, the gas is shunted to a sensor bank. In some embodiments, gas is released to atmosphere.

In some embodiments, in the event that the reactant gas flow sensor fails in an NO generation system, the system can use the concomitant decrease in reactant gas reservoir pressure as an indication of safe plasma flow levels.

In some embodiments, an NO generation system can use the plasma chamber pressure as a proxy for plasma flow. For example, the scrubber can act as a flow restrictor downstream from the plasma chamber such that plasma pressure will increase in proportion to flow. In some embodiments, the flow restriction within the system is well-characterized so that a calibration curve can be generated that relates plasma chamber pressure resulting from back-pressure in the system to flow rate through the system. In this embodiment, the NO production algorithm can calculate a plasma flow rate as a function of the measured back-pressure, the calibration curve, and optionally gas pathway temperature. This approach enables a NO generation device to generate accurate amounts of NO without the use of a flow sensor, which can save cost. In some embodiments, an increase in plasma chamber pressure can be indicative of a zero flow condition resulting from an obstruction downstream in the system. Obstructions could be the result of a clogged filter, kinked tube, capped vent connection, or other scenario.

Additional Algorithm Inputs

The status of a patient infection can be monitored by measuring the patient's body temperature. In some embodiments, a NO delivery system includes a temperature probe to measure the body temperature. Temperature can be measured orally, rectally, nasally, or on the skin. Temperature probes can have very slow response due to the T90 of the sensing element and the plastic enclosure. One way to achieve a faster indication of patient temperature is to utilize the rate of change of the temperature sensor reading to predict an end point based on empirical data. In some embodiments, a temperature probe is overheated and then applied to the patient. The rate of cooling of the temperature probe is used to extrapolate the body temperature. This approach offers improvements because it ensures that the probe is functioning (it got hot) and that the probe was actually applied to the patient (rate of cooling was more rapid than air cooling). In some embodiments, the NO dose is related to the patient body temperature. In some embodiments, the NO dose is increased when patient body temperature is elevated.

In some embodiments, a patient monitor device is used as part of a NO treatment system. The patient monitor measures one or more of patient pulse rate, respiration rate, $O_2$ saturation, patient motion via accelerometer (patient mobility), and body temperature. Based on data collected from these sensors, the NO device can make more informed decisions about whether or not the NO dose is appropriate. For example, if the patient is sedentary as indicated by the accelerometer and $O_2$ levels drop, this is different than $O_2$ levels dropping when the patient is active.

For determining the scrubber replacement time, the rise of measured inspiratory $NO_2$ levels over time can be used as a predictor for when the 1 ppm threshold will be reached. For example, if $NO_2$ levels are increasing 0.1 ppm per hour, the system can generate a preliminary "replace scrubber" alarm, indicating 30 minutes of remaining scrubber life, when $NO_2$ levels reach 0.3 ppm below the replacement threshold.

Algorithm for Tracking NO Production

Figure 10:
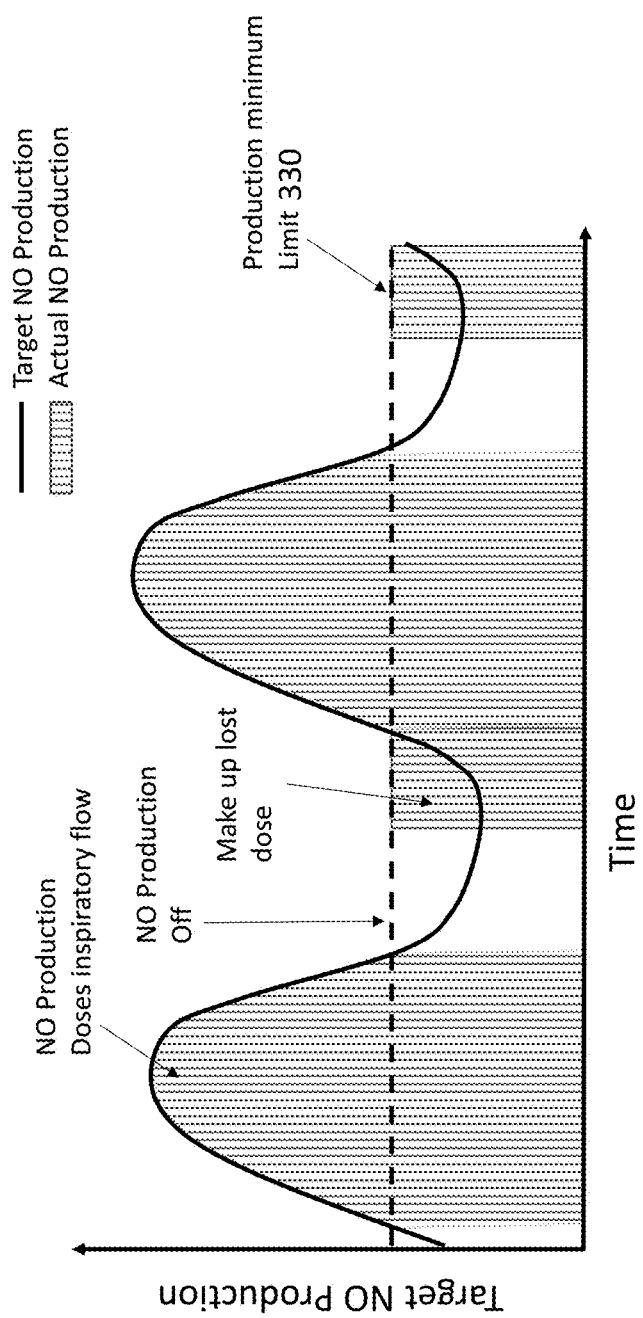
FIG. 10 shows an exemplary graph showing how the device can track NO production and keep NO production on target.

FIG. 10, FIG. 11, FIG. 12, and FIG. 13 illustrate various embodiments showing how the device can track NO production and keep NO production on target. FIG. 10 illustrates an exemplary graph of target NO production versus actual NO production using an NO generation and delivery system with a minimum NO production level (line 330) below which NO cannot be produced. When demand for NO is below the minimum production level, the system pauses production for a set time duration while continuing to track NO demand. The system then resumes NO production to make up for the NO not produced. In some embodiments, the amount of time NO production is paused is a function of the number of moles of NO not delivered. In some embodiments, the pause duration is inversely proportional to the NO production demand (i.e. very low demand requires longer pauses). As shown in FIG. 10, an NO generation system can recognize a period breathing waveform and begin NO production early to make-up for lost NO production.

Figure 11:
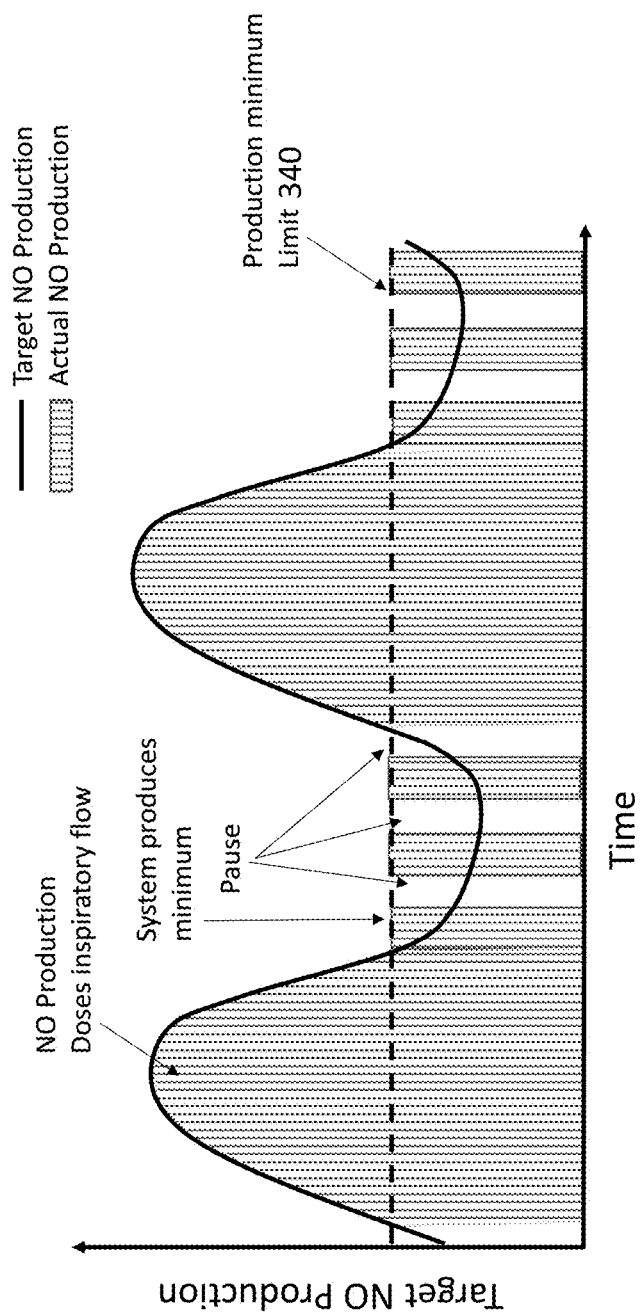
FIG. 11 shows an exemplary graph showing how the device can track NO production and keep NO production on target.

FIG. 11 illustrates an exemplary graph of target NO production versus actual NO production. An NO generation and delivery system has a minimum NO production level below which NO cannot be produced. When demand for NO goes below the minimum production level (line 340), the system continues to produce NO at the minimum level. When the delta between actual NO production and target NO production reaches a threshold, the system initiates a pause in NO production. In some embodiments, the pause is initiated when a specified number of excess moles of NO have been produced. In some embodiments, the pause is initiated after a specified amount of time. In some embodiments, the system resumes NO production when the NO moles delivered reaches the target again. As seen in FIG. 11, this can result in NO generation separated by pauses when NO production demand is low.

Figure 12:
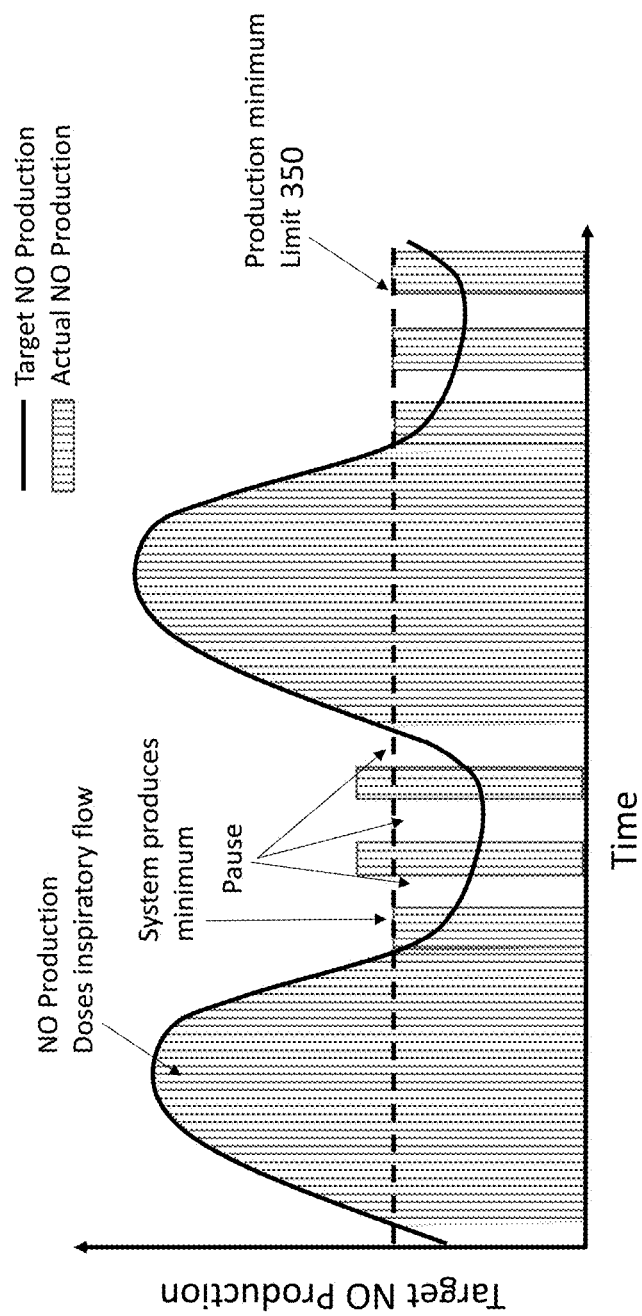
FIG. 12 shows an exemplary graph showing how the device can track NO production and keep NO production on target.

The exemplary graph shown in FIG. 12 is similar to the graph shown in FIG. 11 using similar NO generation systems, but the graph in FIG. 12 shows that the bursts of NO production during a period of low NO demand can be done at NO production levels above the minimum production level (line 350). This can allow for the system to minimize $NO_2$ generation by operating the system at a higher production level.

Figure 13:
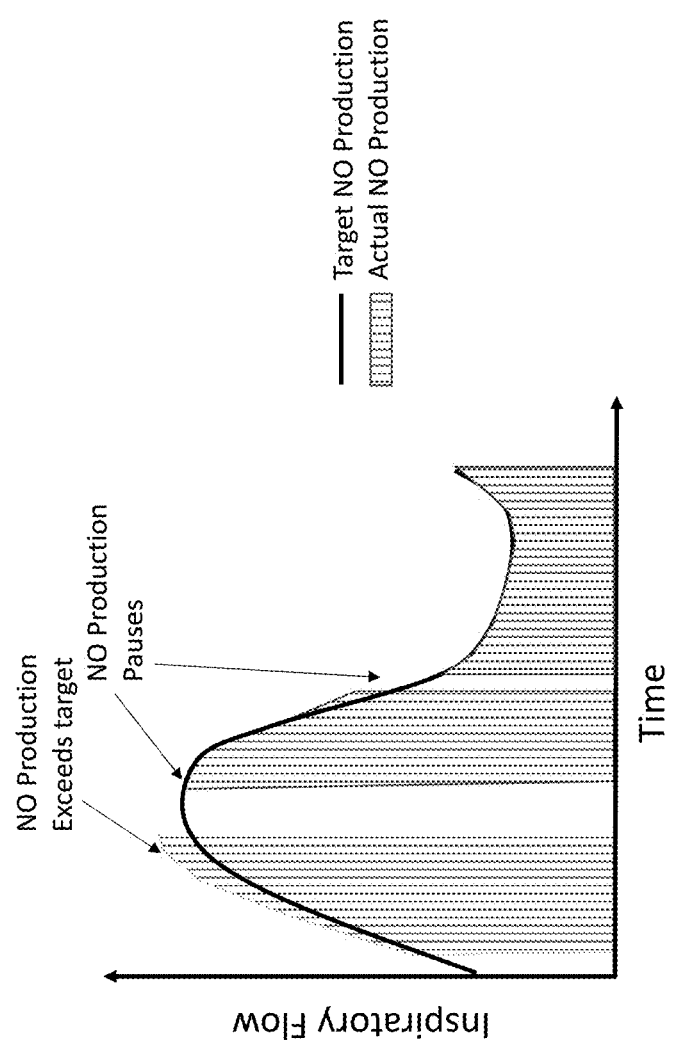
FIG. 13 shows an exemplary graph showing how the device can track NO production and keep NO production on target.

FIG. 13 illustrates an exemplary graph showing how actual NO production can vary from target NO production at NO production levels above the target NO production level. In this scenario, a similar approach is taken where the system pauses NO production in the event that NO production has exceeded a threshold. In some embodiments, the threshold is a number of moles generated in excess of demand. In some embodiments, the threshold is in units of production, whereby the system pauses production when NO production exceeds NO demand by a predetermined amount of ppm·lpm, or moles/sec, or μl/min. In some embodiments, the pause is for a set amount of time. In some embodiments, NO production resumes when cumulative NO production is equal to target cumulative NO production. In some embodiments, the system changes NO production levels to a lower production level, rather than zero in response to an over-production scenario. In some embodiments, the system changes NO production level to its minimum production level in response to an over-production scenario.

NO production can be measured and/or estimated in multiple ways within an NO generation system. In some embodiments, product gas NO concentration and reactant or product gas flow rate are measured and multiplied together. In some embodiments, NO production is calculated based on one or more input parameters including but not limited to reactant gas flow rate, reactant gas temperature, reactant gas humidity, plasma chamber temperature, Plasma current, plasma voltage, electrode gap, electrode age, and electrode type. In these embodiments, the system's sensitivity and response to input parameters is characterized and modeled. The model may take the form of, but is not limited to, regression models and/or look-up tables. Some portions of the model may be characterized as a function of the design while others may be calibrated for individual units.

Patient Controls

In some embodiments, an NO generation system can include functionality such that a user can adjust the NO dose, for example, depending on the activity level. In some embodiments, the user can adjust the dose level within a controlled range of doses. In some embodiments, the device can include a boost button. When the patient presses the boost button, the NO dose increases by a threshold percentage a threshold amount of time and then returns to baseline levels again. The system can include safeguards relating to the increased percentage and time. For example, a user could press the boost button before ascending a flight of stairs. In some embodiments, the device increases the dose by 50% for 2 minutes in response to the boost button being pressed. If the user needs additional boost, they can press the button again. In some embodiments, the device limits the number of times the boost button can be used. This can be done by limiting the number of boosts within a set time frame or by limiting the amount of NO (moles) within a time frame.

Plasma Chamber and High Voltage

The plasma chamber, as explained above, includes one or more electrodes that are configured to produce a product gas containing a desired amount of NO as determined by the controller. The NO generation system can include various features that affect the plasma chamber and the conditions therein.

In some embodiments, an NO generation device uses the $NO/NO_2$ ratio during self-test as a predictor of when to replace the electrode assembly.

In some embodiments, a voltage multiplier is used to generate the high voltage required to generate plasma. The voltage multiplier is constructed from a circuit of diodes and capacitors.

In some embodiments where a resonant high voltage generator is used, a system excites the plasma at a frequency that is near the resonant frequency but not at the resonant frequency. This is done to produce more consistent performance and/or to limit plasma current. The impedance of the resonant circuit has a significant impact on the current that flows in the plasma. Since the slope of the impedance as a function of frequency is highest at resonance, this makes a system operating at resonance particularly sensitive to small errors in frequency or to small changes in the resonant frequency.

Low Dose NO Generation

There is a finite minimum pulse width that enables repeatable plasma pulse generation and for a given plasma pulse frequency, and this can limit the minimum NO production rate. For example, in some embodiments, production rate is not reliable below 1.5% duty cycle. At low pulse frequencies, the dynamic performance of a system can be poor due to the finite number of plasma pulses that occur during the inspiratory phase of the breath, thus there is a tradeoff between dynamic accuracy and minimum dose. In some embodiments, an NO generator operates at a fixed frequency and skips scheduled plasma pulses when NO production has exceeded demand. In some embodiments, this decision is based on a calculated estimate of NO production compared to target NO production. In some embodiments, NO production is estimated based on plasma NO-time. In some embodiments, NO production is based on the current through the primary winding of a high voltage circuit. When pulses are skipped, the system essentially turns off the plasma in response to NO production tracking too high. In some embodiments, an electrical pulse within the electrode gap can be skipped by adjusting the duty cycle to 0 or near 0 in a constant frequency system. In some embodiments, the system reduces production when operating at the minimum pulse width by modulating plasma current. In some embodiments, plasma current is adjusted by changing the resonant drive voltage, wave shaping the resonant drive signal, or changing the impedance of the high voltage circuit.

Other approaches to decreasing NO production below the lower limit of a system can be one or more of the following: adjusting the frequency to 0 or near zero in a constant duty cycle system, decreasing the plasma energy so that NO production is at or near zero, changing the impedance of the high voltage circuit to reduce the current through the electrode gap thereby reducing NO production (IG), or turning the system off and back on for the duration of an electrical pulse.

Figure 14:
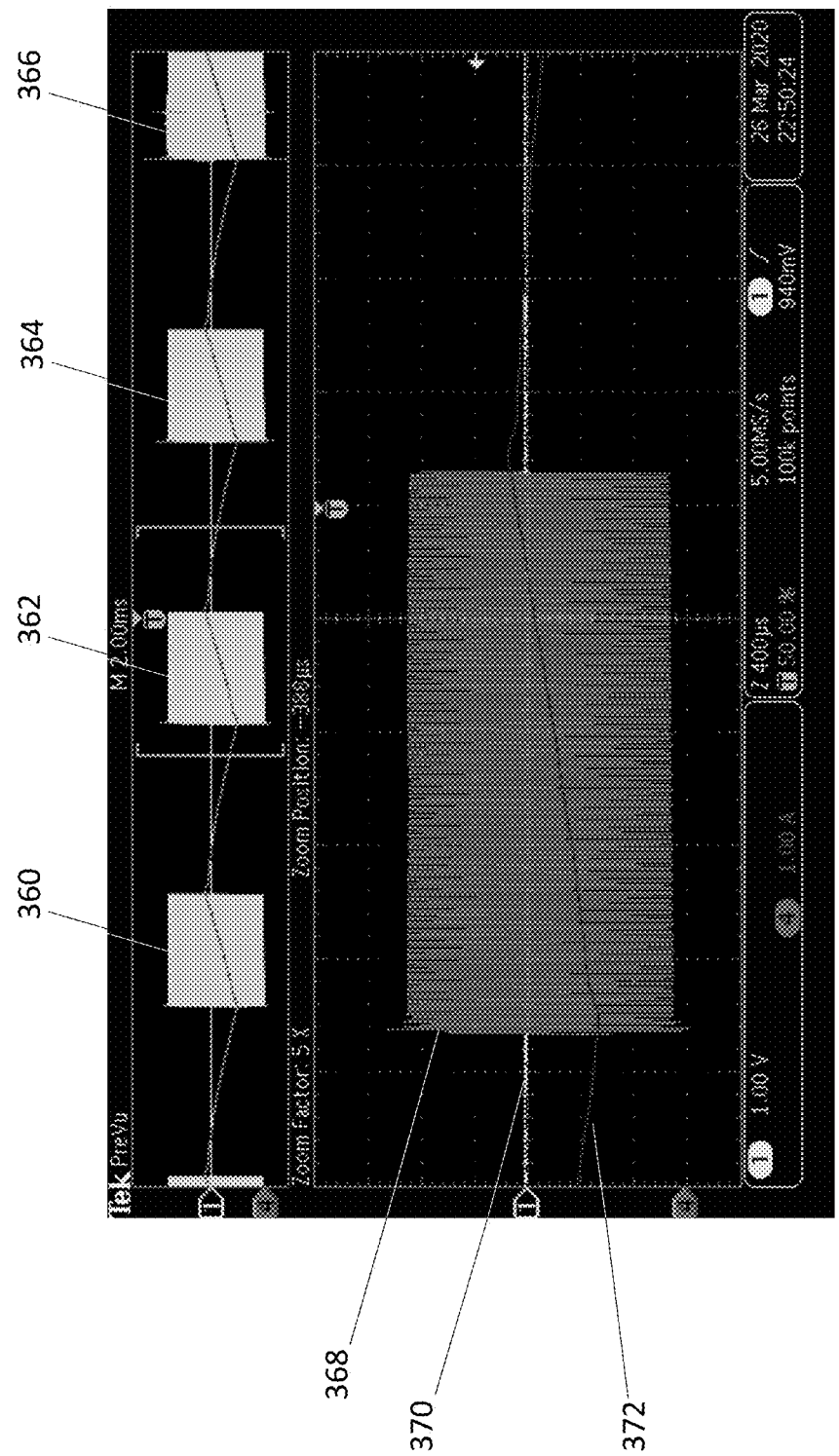
FIG. 14 shows an exemplary plot of transformer input current and transformer primary winding current.
Figure 15:
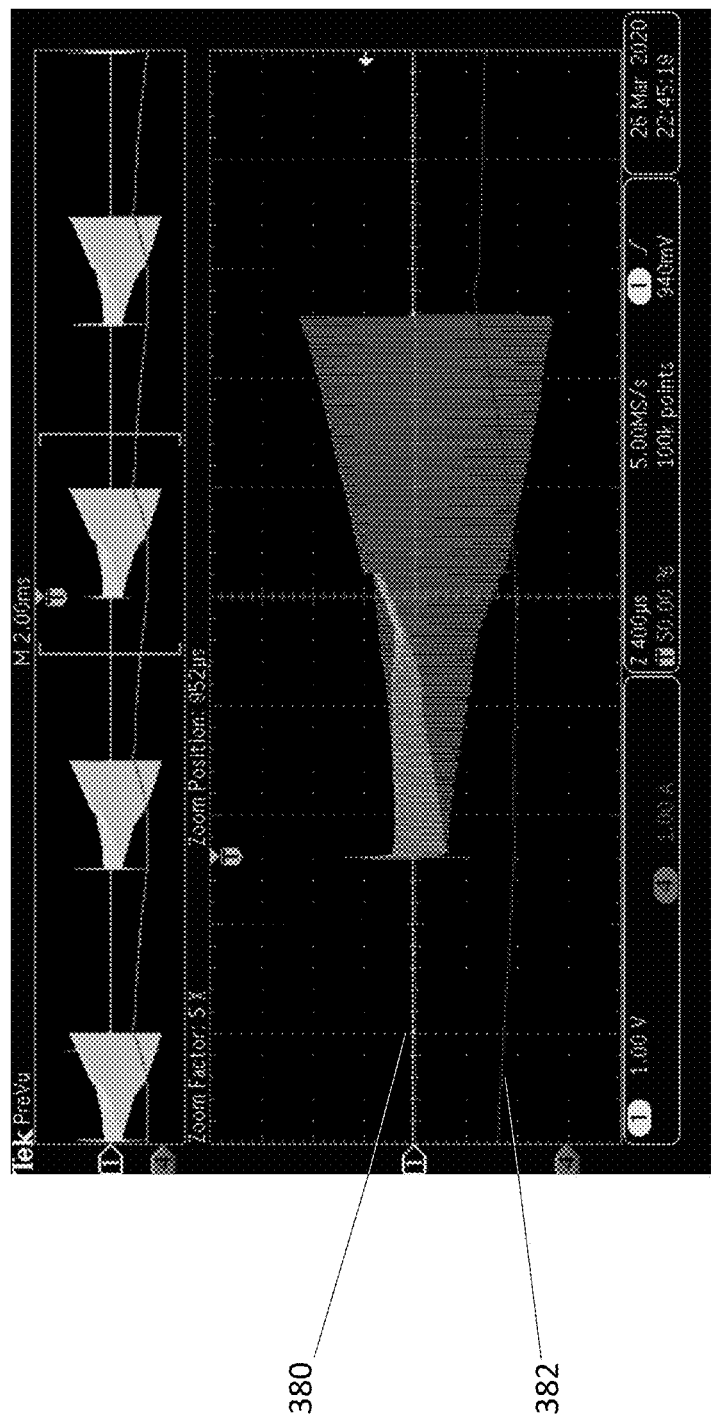
FIG. 15 shows an exemplary plot in which primary winding current scales with the elapsed time of the discharge event.

Another approach to producing NO in low amounts is to modulate the current within the electric discharge. In some embodiments, current scales linearly with duty cycle so that current is low for short duty cycles to generate low amounts of NO and current is high for long duty cycles when high NO production is required. In some embodiments, current scales with elapsed time during an electric discharge. This approach is beneficial when a gliding arc electrode or gliding torch design is used because it limits the amount of energy within the gap when the gap is small thereby decreasing electrode erosion. FIG. 14 shows an exemplary plot of transformer input current and transformer primary winding current where each discharge has a constant level of current in the primary winding. Four discharge events 360, 362, 364, 366 and a single, zoomed-in discharge event 368 is shown in FIG. 14. Primary current is plotted on line 370 using a scale of 10 A/V and is proportional to secondary current by a scale factor of 125 A/A. Resonant circuit input current is plotted on line 372. FIG. 15 depicts an exemplary plot in which primary winding current scales with the elapsed time of the discharge event. Primary current is plotted on line 380 using a scale of 10 A/V and is proportional to secondary current by a scale factor of 125 A/A. Resonant circuit input current is plotted on line 382. In the case of a gliding arc or gliding torch electrode design, the rate of current increase can be related to the rate of gap increase in the electrode and the flow rate of gas through the gas chamber to optimize the plasma energy within the gap for NO production while minimizing the potential for electrode wear. If the rate of current increase is too rapid, excessive energy is applied to the electrode gap which can accelerate electrode wear. If the rate of current increase is too slow, there is a risk that the arc will blow out before the end of the duty cycle. In some instances, an arc that extinguishes prematurely will reform at the small gap and travel along the electrode until the end of the discharge, as governed by the duty cycle. This can result in faster erosion and/or erroneous production rate of NO. In some embodiments, a NO generation system can detect premature arc failure and make up for the lost production. In some embodiments, this is done by making the subsequent electrical discharge longer.

Figure 16:
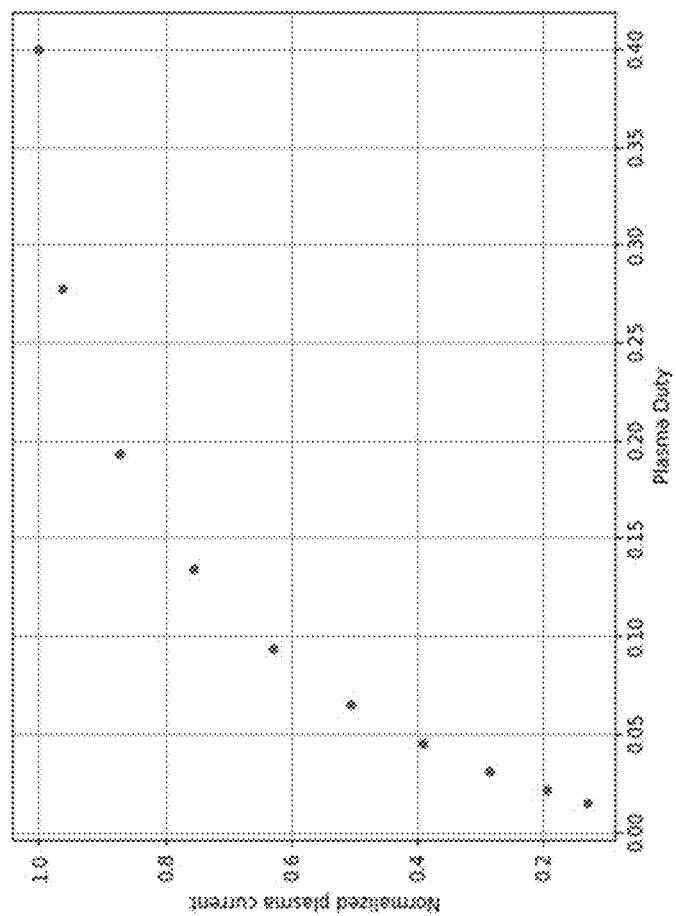
FIG. 16 shows an exemplary graph of a reduction in NO production at low duty cycles.

Gliding arc electrodes enable a broad range of NO production, owing to the variable gap. Tradeoffs occur in the design of a gliding arc electrode, however. The smaller the gap, the lower the NO production and the lower voltage required for breakdown. Shallow gliding arc electrode angle provides improved low production control but can introduce variability in high NO production control due to inconsistency in the electrode breakdown location. For high production, large gaps are required, so large gliding arc angles are utilized to transition from electrical breakdown within the gap to large gaps as quickly as possible. In some embodiments, plasma current is tied to plasma duty cycle. In some embodiments, the plasma current for a low duty cycle is lower than the plasma current for a high duty cycle. In some embodiments, the plasma current and duty cycle are directly proportional. In some embodiments, the relationship is more complex, using one or more of higher order polynomials, exponential functions or a look-up table. One example is shown in FIG. 16. This approach allows for a reduction in NO production at low duty cycles, thereby enabling lower levels of NO production, and a reduction in electrode wear during low duty cycles. However, higher current is still applied to the small gap during longer duty cycles. As an example of an embodiment, a 1.5% duty cycle is tied to 50 mA plasma current, and 50% duty cycle is tied to 200 mA, and everything in the middle is a sliding scale (i.e. 10% would be ~81 mA, 20% would be ~112 mA, etc.). In some embodiments, the relationship between duty cycle and plasma current is not linear, but instead a complex curve empirically determined during calibration of a system. In some embodiments, the mathematical relationship is determined by design, and calibration just captures the result.

Current modulation is helpful in a NO generation system because it provides an additional dimension to controlling NO production. This concept is applicable to other electrode designs, such as opposed electrodes and parallel electrodes, however it can provide the most benefit in gliding arc and gliding torch designs, where smaller gaps are utilized. With current modulation, steeper gliding arc electrode angles can be utilized for improving NO production efficiency while retaining the ability to generate low NO production levels with fine resolution. In other words, with a gliding arc electrode, it is desirable to have a low gap and a low electrode angle at the beginning of the electrical discharge so that electrical breakdown is reliable and NO production has fine resolution. If the electrode gap increases rapidly (high angle), NO production increases rapidly during the electrical discharge. Rapid increases in gap away from the short gap region ensure a more precise discharge location, the starting point of the arc travel as well as increased NO production efficiency due to spending more time arcing at high electrode gap. Having a precise arc discharge location ensures that each discharge of a given duty cycle travels over the same region of the electrode and same range of gaps. By tying the current during electrical discharges to the duty cycle, production is better controlled at all duty cycles while also enabling low production resolution with a large angle gliding arc electrode.

It should be noted that the increase in current with respect to duty cycle depends on one or more of the curvature of the electrodes, the edge of the electrode, electrode materials, initial electrode gap, and the gas flow rate through the chamber. If current does not increase fast enough, an arc can be blown out by the reactant gas flow. Contrastingly, if the current increases too rapidly, electrode erosion can be more severe.

Reactant Gas Filter

An NO generation device can be used in a location with elevated ambient $NO_2$ levels. In this case, inhaled $NO_2$ levels could be elevated due to the summation of ambient $NO_2$ and electrically generated $NO_2$. In some embodiments, an NO generation device filters incoming reactant gas with a carbon filter to scrub $NO_2$ and potential organic compounds. In some embodiments, a soda lime pre-scrubber is used for removal of $NO_2$ prior to NO generation. In some embodiments, an NO generation device filters incoming air for box cooling with carbon or another $NO_2$-reactive material. This approach scrubs ambient $NO_2$ with a $NO_2$-scrubbing filter as it circulates ambient air through the device enclosure for cooling. This removes $NO_2$ from the cooling air which protects the inner workings of the device from corrosion and removes $NO_2$ from the surroundings as the device cools itself, mitigating the potential for $NO_2$ build-up in a small room/volume.

Purity of NO generated by a NO generation device is dependent on the purity of the reactant gas. In some embodiments, an electrostatic particle collector is used to remove sub-2 micron particles from reactant gas, owing to the fact that small particles are predominantly positive charged. In some embodiments, the electrostatic particle collector is in the form of a fine filter with a negative charge that collects the small particles. In some embodiments, an electrostatic filter is located downstream of a plasma chamber, and/or scrubber to remove charged particles from the product gas as well.

Reactant Gas Preparation

In some embodiments, reactant gas can be filtered or otherwise prepared for entering an NO generation system. In some embodiments, a chemical filter on the inlet can be used to remove contaminants before the plasma. In some embodiments, the chemical filter includes activated charcoal.

In some embodiments, Gore-Tex filters prevent liquid water from entering the system.

In some embodiments, NO generation systems operate continuously, providing un-interrupted therapy to a patient. Thus, the flow of reactant gas and the filtering and/or scrubbing thereof should be continuous. It follows that in a NO generation system with multiple scrubber cartridges, it is important to ensure that incoming reactant gas is still filtered when a scrubber cartridge is removed. In some embodiments, a NO generation system changes channels to second NO generator and scrubber when a first scrubber is removed. In some embodiments, a first NO generator is able to source reactant gas from a second location when a first scrubber is removed.

Figure 17:
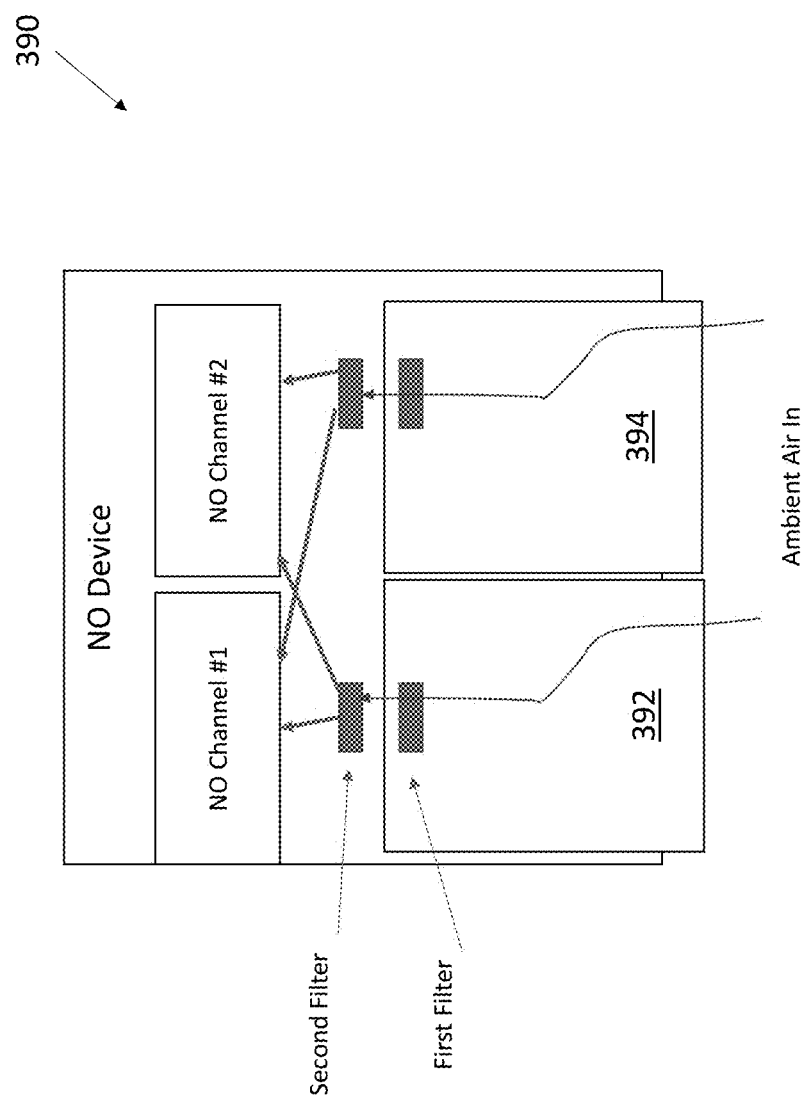
FIG. 17 shows an embodiment of an NO generation system that includes a two-channel system with two cartridges.
Figure 18:
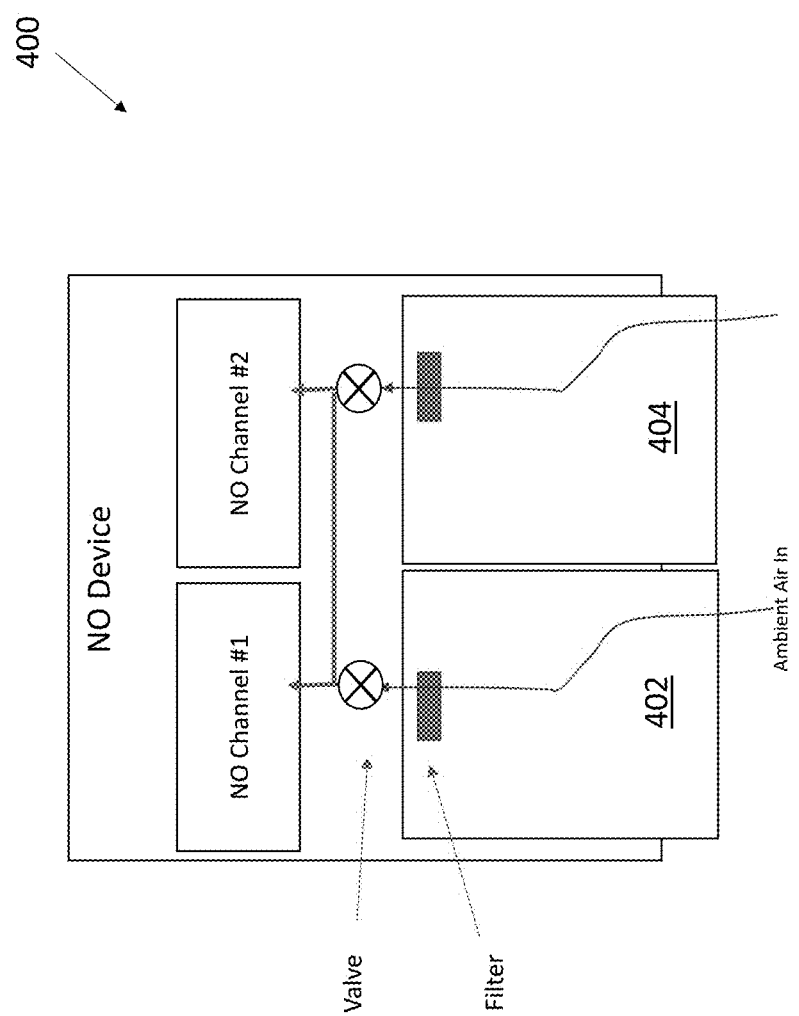
FIG. 18 shows an embodiment of an NO generation system that includes valves in the reactant gas pathway.

In some embodiments, reactant gas passes through a first filter located within a scrubber cartridge followed by a second filter located within the NO generation device. The second filter protects the system from particulates when a scrubber cartridge has been removed. In FIG. 17, a two-channel system 390 with two cartridges 392, 394 is shown. When a first cartridge 392 is removed, reactant gas can be sourced through the second cartridge 394 or through the built-in filter in the system. In some embodiments, valves are used in the reactant gas pathway to ensure that reactant gas only enters a system 400 through a filtered source, as shown in FIG. 18. When a cartridge 402 is removed, the gas flow path is blocked by closing a valve and reactant gas is sourced from the other scrubber cartridge 404.

Figure 19:
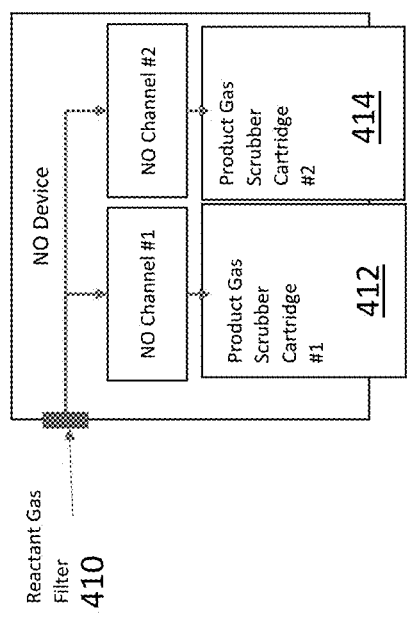
FIG. 19 shows an embodiment of an NO generation system that includes a scrubber for reactant gas and a scrubber for product gas.

In some embodiments, reactant gas is filtered and/or scrubbed by a separate reactant gas filter/scrubber 410 than the product gas filter/scrubber, as shown in FIG. 19. This enables replacement of $NO_2$ scrubber cartridges 412, 414 without an interruption to reactant gas availability.

In some embodiments, a NO generation and delivery system includes a reactant gas inlet connector for sourcing pressurized reactant gas. In some embodiments, the system can switch between sourcing reactant gas from the gas inlet connector and sourcing reactant gas from the environment via pump. In some embodiments, the system preferentially operates with reactant gas externally sourced from the system to minimize acoustic noise generated by the system which could otherwise be disruptive in a hospital setting. When the NO generation and delivery system is put in transport mode, the system automatically converts to sourcing reactant gas via pump. In some embodiments, the source of reactant gas is manually selected by the user.

Flow Control

Figure 20:
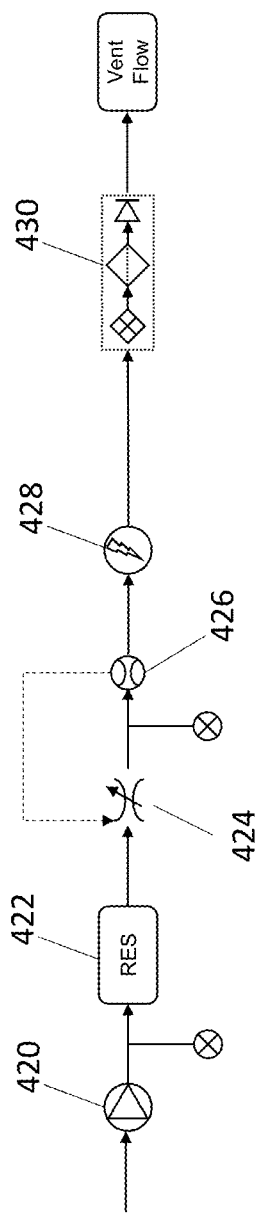
FIG. 20 illustrates an embodiment of a closed loop flow controller having a single flow control and a single plasma generator.

Flow control within an NO generator can be key to generating constant concentration NO within an inspiratory flow. Flow control can be affected by system variables, including but not limited to operating temperature, reactant gas pressure, reactant gas flow rate, flow controller age, flow controller wear, flow controller temperature, and other factors. In some embodiments, a reactant gas flow controller is controlled using a closed-loop approach using the target plasma chamber flow rate and measured plasma chamber flow rate as inputs. In some embodiments, the plasma chamber pressure is used as an input for closed loop control. In some embodiments, the product gas flow rate is used as a control loop input signal. In some embodiments, the reactant gas and/or product gas flow rate are used for partial control to trim the output of a flow controller. FIG. 20 illustrates an embodiment of a closed loop flow controller having a single flow control and a single plasma generator. In FIG. 20, reactant gas enters a pump 420 and enters a reservoir 422. A flow controller 424 (for example, a proportional valve) at the exit of the reservoir 422 controls the flow of pressurized reactant gas exiting the reservoir 422. The flow of reactant gas is measured by a flow sensor 426 prior to entering a plasma chamber 428. The measurement of reactant gas flow is used as an input to adjust the flow controller setting (dashed line). After the plasma chamber, a scrubber/filter cartridge 430 cleans the product gas prior to injection into an inspiratory flow.

Figure 21A:
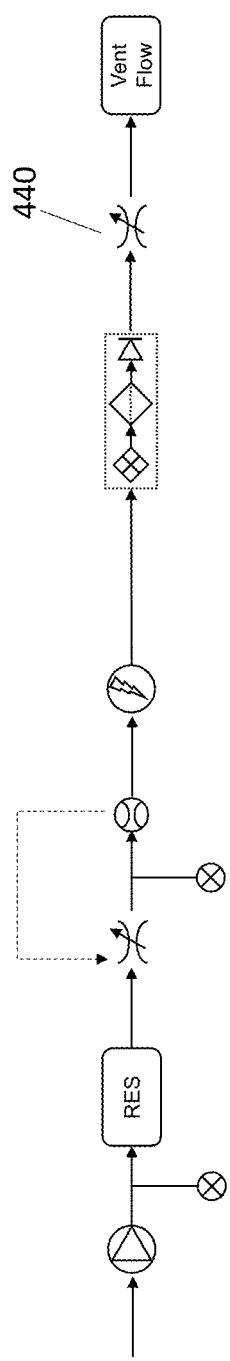
FIG. 21A illustrates an embodiment of a closed loop flow controller with an additional control of injected flow with a second proportional valve.

Multiple flow controllers can also be used. In some embodiments, there is an upstream flow controller that controls the flow of reactant gas into one or more plasma chambers and there is a downstream flow controller that controls flow of product gas into an inspiratory flow. This allows for the build-up of pressure in the product gas flow path in between patient breaths and/or when a bias flow is flowing, enabling a more rapid rise of NO flow during an inspiratory event. In addition, the downstream flow controller can be used to shut off plasma flow more quickly than an upstream flow controller if/when inspiration ends. The space between first and second flow controller is essentially a second reservoir. In some embodiments, the dead volume within a scrubber is utilized as a reservoir/accumulator for product gas. FIG. 21A illustrates an embodiment of a closed loop flow controller with an additional control of injected flow with a second flow controller (proportional valve) 440. In this embodiment, pressurized, scrubbed NO is available to the secondary flow controller 440, enabling the system to introduce NO to the variable inspiratory flow with minimal lag.

Figure 21B:
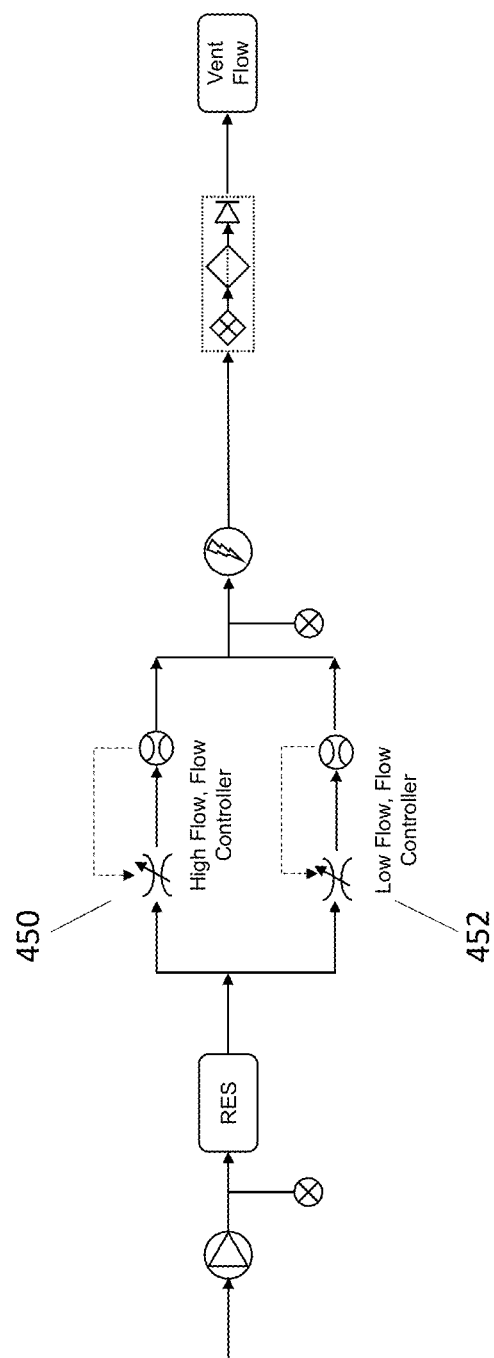
FIG. 21B illustrates an embodiment of a closed loop flow controller with a high and low flow control.

FIG. 21B illustrates an embodiment of a closed loop flow controller with a high and low flow control 450, 452. This approach provides finer resolution flow control at low flows to enable accurate dilution of low inspiratory flows with NO product gas.

In some embodiments, a proportional valve can be used to regulate the reactant gas flow. In some embodiments that provide improved flow accuracy at high and low flow rates, two or more binary valves are placed in parallel upstream of the proportional valve to provide up to 4 states of gas flow to the proportional valve: off, low, medium and high flow.

In some embodiments, two parallel flow paths each containing proportional valves and flow sensors provide high and low flow control, respectively for one or more plasma chambers. In some embodiments, a low flow controller controls gas flow rates from 0 to 1 lpm and a high flow controller controls gas flow rates from 0 to 3 lpm. In some embodiments, a low flow controller controls gas flow for the bias flow, a DC offset in flow within the inspiratory limb, while a high flow controller provides flow to dose the bolus of inspiratory flow associated in inspiration. In some embodiments, the two flow controllers are used together to dose an entire inspiratory cycle (bias flow+inspiratory flow). The combination of high and low flow controllers provides high accuracy over a large dynamic range (turn-down) in the flow rate. A high flow controller sources high flows and turns off at low flows, where it is not accurate, while a low flow controller provides fine control at low flows.

In some embodiments, a NO generation system varies the pressure in a reservoir based on the flow rates required for a particular treatment. In some embodiments, the NO generation system pressurizes a reservoir to a lower pressure for low flow treatments, requiring the proportional valve to open more to achieve higher flows, thereby actuating the proportional valve over a broader range of positions for improved fidelity. In some embodiments, an NO generation system pressurizes a reservoir to a higher pressure to enable the system to generate faster flow rates required for a treatment. In some embodiments, the pressure of the reservoir can be 2 atm.

NO Introduction to Inspiratory Flow (Injection)

The rate of NO conversion to $NO_2$ is a second-order phenomenon, i.e. $NO_2$ formation is proportional to the square of NO concentration. Thus, it can be desirable to dilute NO into an inspiratory stream as quickly as possible. In some embodiments, NO is sprayed as it is injected so that it is diluted as quickly as possible. In some embodiments, a system injects NO through one injector when the inspiratory flow has high $O_2$ levels and multiple injectors when $O_2$ levels are low, thereby minimizing the NO to $NO_2$ conversion rate.

Figure 22A:
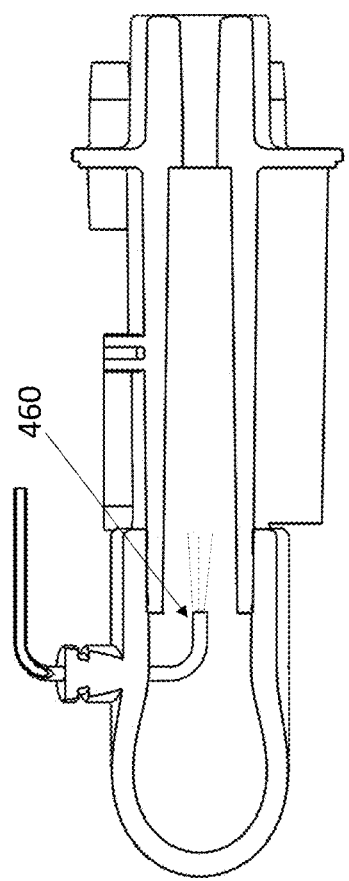
FIG. 22A illustrates an embodiment of an NO generation system where NO is introduced into an inspiratory flow with a regular NO injector.
Figure 22B:
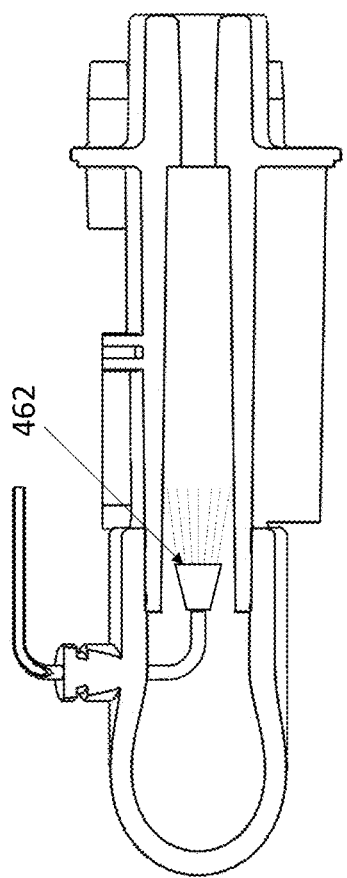
FIG. 22B illustrates an embodiment of a spray nozzle for spraying NO into the inspiratory flow to improve mixing prior to inhalation.

In some embodiments, NO is introduced to a ventilator circuit near the patient. The NO can be sprayed into the inspiratory flow to improve mixing prior to inhalation, as shown in FIG. 22B, rather than a regular NO injector 460 as shown in FIG. 22A. Thus, the NO is not introduced to potentially high $O_2$ gases until as late as possible. FIG. 22A shows introduction of NO product gas to an inspiratory flow through an injector 460 located at or near the center of the inspiratory limb. In cases of laminar flow, the product gas travels down the center of the inspiratory tube, requiring long lengths of inspiratory limb to fully mix. FIG. 22B shows an injector also located within the center of an inspiratory tube. The injector 462 is comprised of a multi-orifice injector that sprays NO product gas into the inspiratory flow (i.e. a spray nozzle injector). This approach distributes and mixes NO within the inspiratory limb faster.

Whether or not to inject NO into an inspiratory flow in a centered or sprayed way depends on the treatment configuration, inspiratory gas composition and composition of NO-containing gas being injected. For example, if the NO containing gas contains oxygen as well as NO, it can be advantageous to spray the NO, thereby diluting the NO as quickly as possible. If the inspiratory limb gas has high oxygen concentration, however, it may be beneficial to not spray the NO containing gas. If the NO containing gas has low oxygen levels, as is found in NO sourced from gas cylinders, it can be preferential to not spray the NO to slow the mixing of the NO with oxygen. Whether or not to spray NO also depends on the configuration of the therapy. If the inspiratory limb is very short, then gas transit times are brief and it can be necessary to spray NO to ensure adequate mixing prior to reaching the patient.

Other approaches to NO mixing can be effective. In some embodiments, NO-containing gas is introduced to the inspiratory flow at the side of a tube and a mixing device is used downstream of the injection point to blend the NO-containing gas and inspiratory gas. In some embodiments, NO containing gas is introduced to the center of an inspiratory flow and passes through a mixing device at or near the patient. This approach minimizes NO mixing and related oxidation for as long as possible.

Figure 23B:
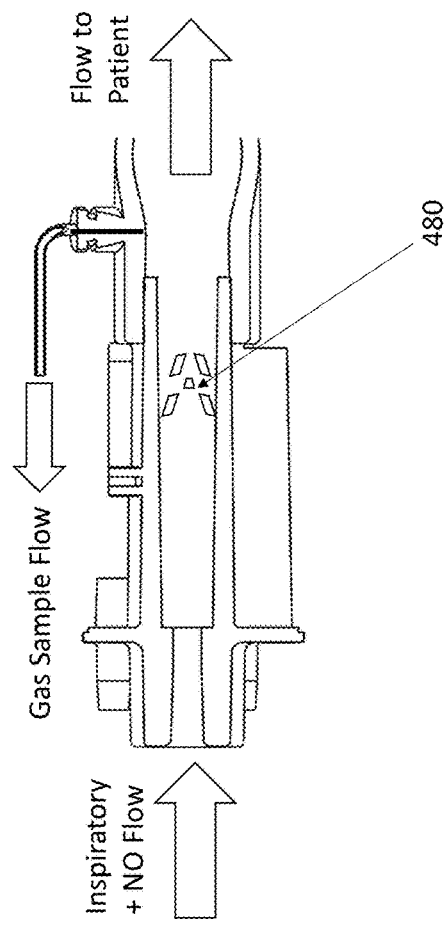
FIG. 23A and FIG. 23B illustrate an embodiment of an injector fitting configured to introduce turbulence into an inspiratory flow to improve mixing of NO into the inspiratory flow.
Figure 23A:
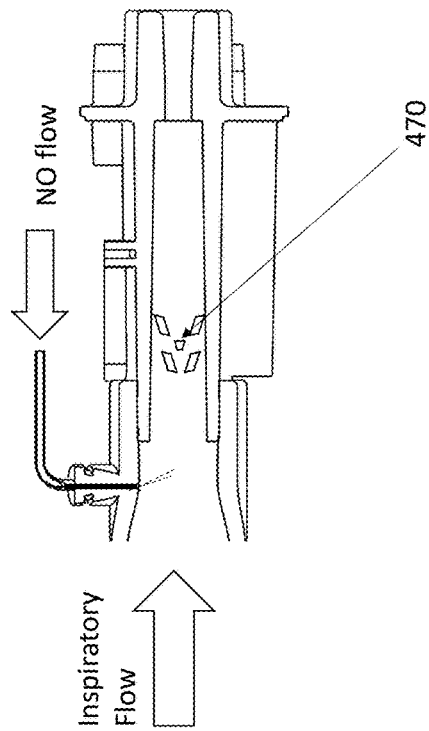

In some embodiments, the injector fitting introduces turbulence into the inspiratory flow to improve mixing of NO into the inspiratory flow, as shown in FIG. 23A. As shown in FIG. 23A, mixing vanes 470 can be used for NO mixing in a ventilator circuit post-injection. This can enable a NO generation system to inject NO closer to a patient while still ensuring well-mixed inspiratory gas. In some embodiments, as shown in FIG. 23B, a gas sample port introduces turbulence in the inspiratory gas and the NO gas prior to drawing a sample to ensure that sampled gas is fully mixed. As shown in FIG. 23B, mixing vanes 480 can be used for NO mixing in a ventilator circuit pre-gas sampling. This approach can enable also enables a NO generation system to inject NO closer to a patient, thereby decreasing transit time and NO—$O_2$ interaction. Turbulence can be added in many ways, including but not limited to mixing vanes, baffles, filters, corrugations, dimples, and tortuous paths. In some embodiments, a scrubber is utilized in the inspiratory limb of a patient. Mixing elements are utilized on the inlet of the scrubber to ensure the inspiratory gas is thoroughly mixed before it is scrubbed. This is particularly important in scrubbers constructed of sheet material, where NO-containing gas travels through multiple, independent channels through a scrubber.

In some embodiments, one or more plasma parameters (duty cycle, frequency, primary AC Waveform, voltage) are based on sensed flow beyond the scrubbing component and at or near the point of NO injection into an inspiratory gas flow. The benefit of this type of embodiment, is that it distances and isolates the plasma flow sensor from the plasma acoustic noise.

NO Generation in Use with Additional Medical Treatments and Devices

Ventilator Compatibility

Adding an NO generator to a ventilator circuit can add compressible volume. The NO generation system adds NO flow and removes sample gas flow. In some embodiments, the NO generation system varies the amount of net flow to account for the change in compressible volume, thereby eliminating the need for the ventilator to be recalibrated. In some embodiments, the NO generation system removes from the inspiratory circuit the same amount of mixed gas as was added to maintain a constant volume of gas within the inspiratory limb. This can serve as a mitigation to over-pressurizing the ventilator circuit and/or patient lungs.

Figure 24:
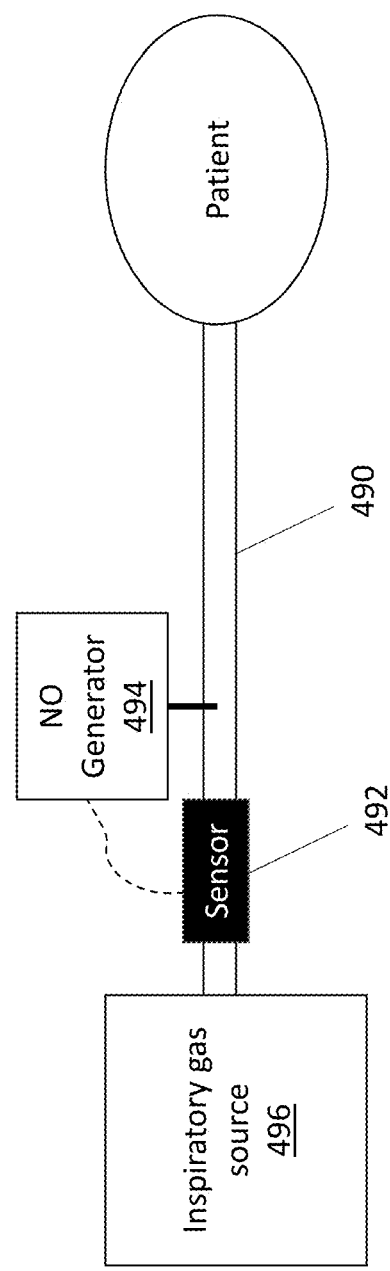
FIG. 24 illustrates an embodiment of an inspiratory tube with built-in flow sensor.

In some embodiments, an inspiratory gas sensor is located in the ventilator tube that connects between a ventilator and a NO device. The benefit of this approach is that it does not add volume to the vent tube and decreases volume in the NO device resulting less impact on compressible volume of the vent circuit. It also decreases the potential for artifact in the ventilator flow measurement that could come from vent tube diameter transitions, curvature, etc. FIG. 24 depicts an inspiratory tube 490 with built-in flow sensor 492. The inspiratory gas sensor connects to an NO device 494 with a wired or wireless connection to provide one or more of $O_2$ level, pressure, temperature, humidity and flow rate. An inspiratory gas source 496 can be a ventilator, CPAP machine, pressurized gas from a wall outlet, or other source of inspiratory gas.

Transitions from small bore ventilator tubing (10 mm and 15 mm) to a flow sensor can affect the accuracy of the vent flow measurement. In some embodiments, a screen, baffle or mesh is located immediately upstream of vent flow sensor to even out the flow and improve vent flow accuracy. The mesh can be part of the vent cartridge and/or vent tube.

Figure 25A:
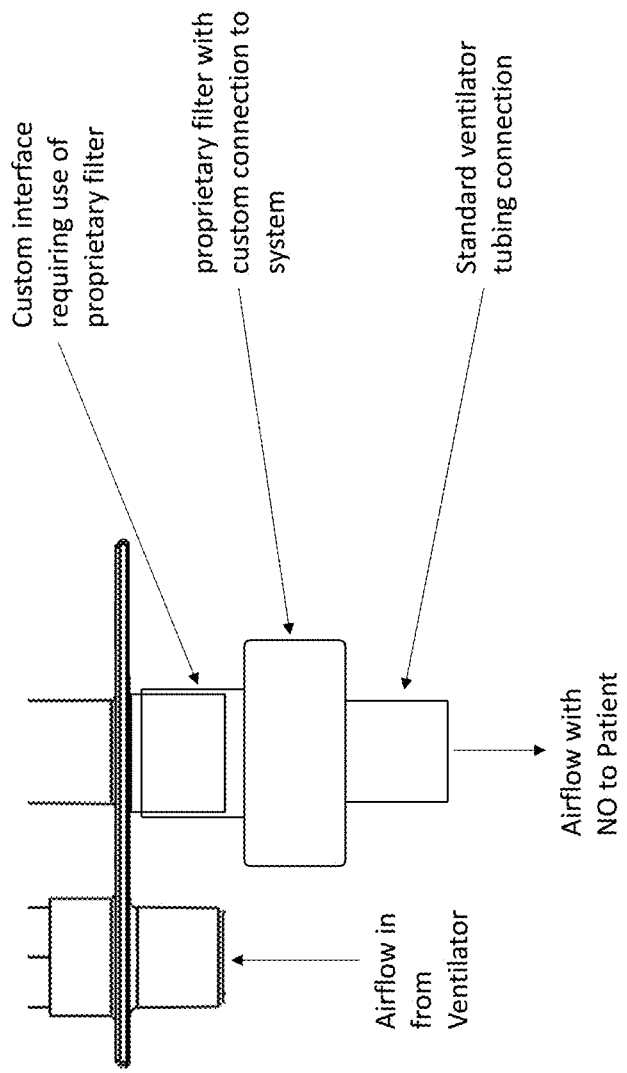
FIG. 25A and FIG. 25B illustrate embodiments of ventilator cartridges with a HEPA filter.
Figure 25B:
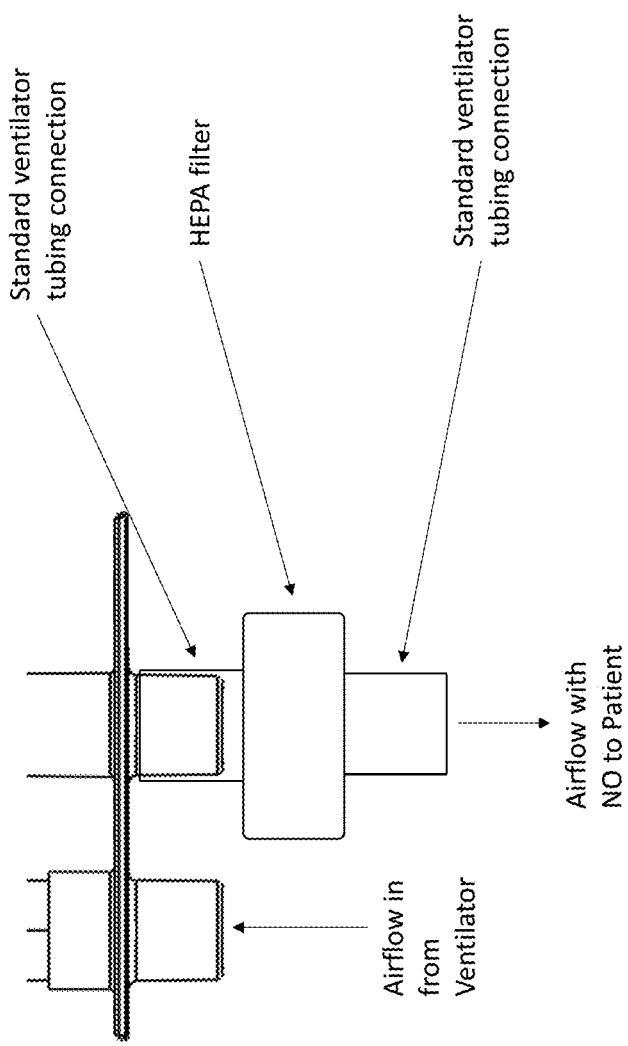
Figure 26B:
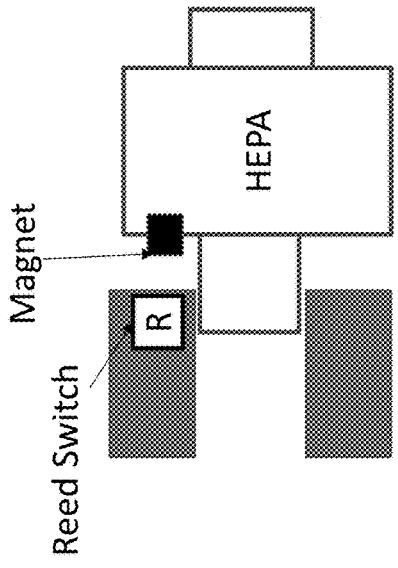
FIG. 26A, FIG. 26B, FIG. 26C, and FIG. 26D illustrate examples of pneumatic connections that can be used between the HEPA filter and ventilator cartridge and/or NO generator.
Figure 26D:
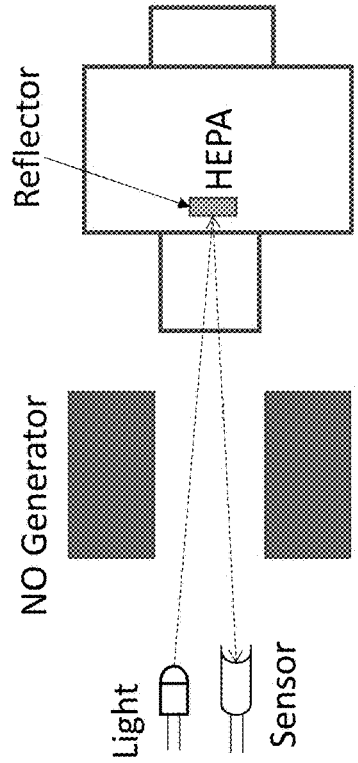
Figure 26A:
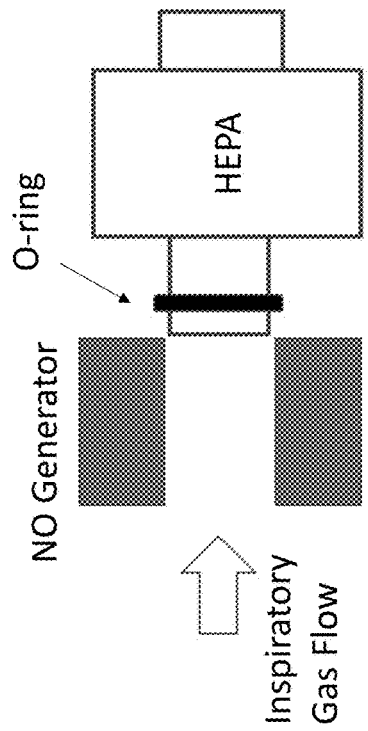

In some embodiments, a ventilator cartridge includes a HEPA filter to prevent contamination of the ventilator cartridge and/or NO generation and delivery device. In some embodiments, the HEPA filter is a removable cartridge consisting of an enclosure, HEPA filter and 22 mm vent tubing fitting. FIG. 25A and FIG. 25B illustrate embodiments of ventilator cartridges with a HEPA filter. FIG. 26A, FIG. 26B, FIG. 26C and FIG. 26D depict examples of pneumatic connections that can be used between the HEPA filter and ventilator cartridge and/or NO generator. FIG. 26A is an O-ring seal between HEPA and controller. As the HEPA is inserted, the O-ring is compressed within a bore within the controller. In some embodiments, a retention feature (not shown) is engaged that prevents the HEPA filter from pulling out without a use-step of releasing the retention feature. In some embodiments, the interface between HEPA filter and vent cartridge is comprised of a tapered tubing connection similar to standard connections but with a different diameter that prevents engagement of standard tubing sizes. FIG. 26B shows another embodiment where the HEPA filter includes a magnet. When the HEPA filter is engaged, the magnet actuates a Reed switch within the NO generator that informs the NO generator that the HEPA filter is present.

Figure 26C:
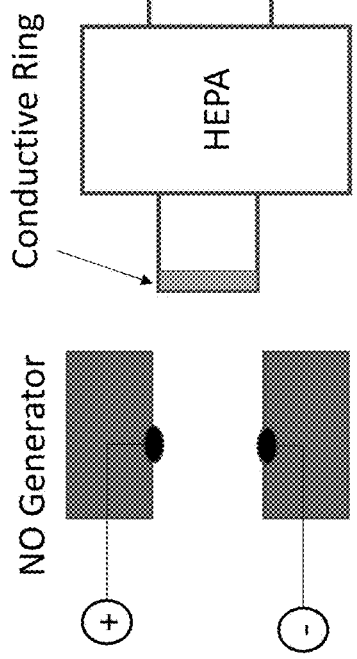

FIG. 26C depicts an embodiment where the HEPA filter includes a conductive surface that closes a circuit within the NO generator when the HEPA filter is fully inserted. FIG. 26D depicts an embodiment where the HEPA filter has a reflective feature that closes an optical circuit when the HEPA filter is fully inserted. In some embodiments, the HEPA filter engages the ventilator cartridge or NO generation device with threads.

Exhaled NO and $NO_2$ from a patient pass through the expiratory limb of a respiratory circuit and into the ambient air. In some embodiments, an $NO_2$ scrubber is placed on the exhaust of respiratory equipment to prevent $NO_2$ buildup in the hospital environment during any kind of NO treatment. In some embodiments, the scrubber is a selective $NO_2$ scrubber. In some embodiments, the scrubber is a filter that removes $NO_2$, drugs and other potential contaminants. In some embodiments, the scrubber contains activated charcoal.

Adjunct Drug Treatments

NO dilates blood vessels within the lungs, increasing blood flow and oxygen uptake. In some embodiments, NO delivery is used in combination with another drug to enhance uptake of the drug into the blood stream. In some embodiments, the other drug is an inhaled and/or nebulized pharmaceutical agent.

MRI

With the advancement of pulmonary and cardiac vascular diagnosis using MRI technology, an NO generation device can be used near or within an MRI environment.

The problem with the MM environment is three-fold. First, the influence of the strong magnetic field (for example, with the 3 Tesla MRI) can stop electromagnetic valves or motors as well as creating eddy current in the electronic and conductive pathways. This usually is solved by the distance between the core of the MM and the device. Typically, the 1 Tesla borderline is located 3 m from the MM magnet. Second, in some embodiments and situations, a medical device can interfere with the high definition imaging of the MM by creating electronic artifacts in the images due to EMI radiation. Third, the strong magnetic field of the MM can pull a medical device into the magnet, potentially injuring a patient within the magnet.

A MM-compatible NO generation and delivery system must be shielded from the outside in and from the inside out.

All MM rooms are electromagnetically shielded and therefore no WiFi, BlueTooth, GSM or any other radiofrequency can be used. Thus, there is no operator during the exam in the MRI room and the device is remotely monitored from the control room. Remote control can be achieved by wired RS 232 or ethernet with heavy shielded cables.

In some embodiments, an NO delivery system is equipped with an IR LED light source that can transmit through the wire mesh and through the shielded window of an MRI suite, enabling remote wireless control and monitoring of the therapy. In the control room, a remote display can display one or more of the following parameters: current setting, current NO level, current $NO_2$ level, current $O_2$ level, scrubber remaining life, treatment elapsed time, treatment remaining time, etc.). The remote-control panel of the NO delivery device can also provide controls for starting treatment, stopping treatment and adjusting treatment settings. In this mode, the remote control would be enabled. For certain medical devices, a total enclosure is the answer for MRI compatibility.

Figure 27A:
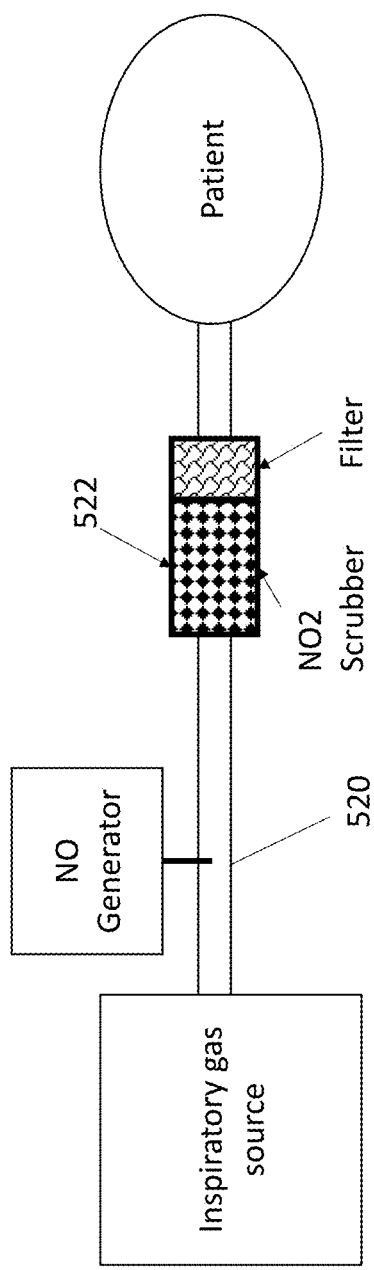
FIG. 27A and FIG. 27B illustrate embodiments of scrubber/filter assemblies.
Figure 27B:
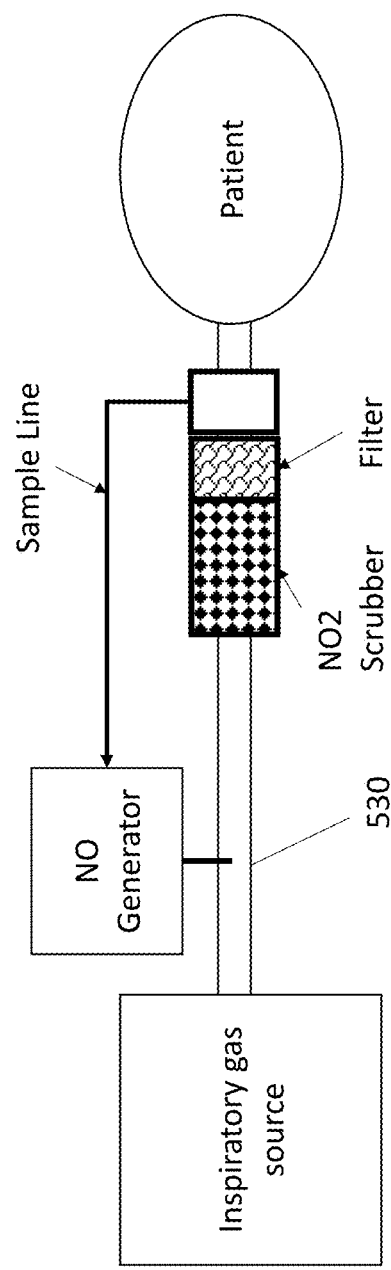

Due to the increased distance between NO source and patient when a patient undergoes an MRI scan, there is greater transit time of NO-containing gases leading to increases in inhaled $NO_2$ concentration. In some embodiments, an $NO_2$-scrubber component is located in-series with the inspiratory limb and near the patient to scrub $NO_2$ from the inspired gas before it is inhaled. In some embodiments, the $NO_2$ scrubber component is combined with a fitting for sampling inhaled gases. In some embodiments, the $NO_2$ scrubber component includes a filter downstream from the scrubbing component to remove particulate from the inspired gas prior to inhalation. This same solution is applicable to other instances, beyond MRI, where the NO generation device is far from the patient and elevated $NO_2$ levels are a concern. FIG. 27A depicts a scrubber and filter assembly 522 within the inspiratory line 520, near the patient. FIG. 27B depicts a scrubber, filter and gas sampling port within the inspiratory line 530, near the patient. The scrubber media and filter mix the NO within the inspiratory gas well, so it is beneficial to sample the inspiratory gas after scrubbing and filtering.

Purging and $NO_2$

During NO treatment with an adjunct ventilation therapy, there can be episodes of no inspiratory flow, as in the case of zero bias flow. In instances like this, NO-containing gas resides in the $NO_2$ scrubber and other parts of the pneumatic pathway and continues to oxidize, forming $NO_2$. In some embodiments, the reactant gas flow through a NO generator is controlled to be a slow, non-zero, rate during periods of zero inspiratory flow to purge the system with air. Purging is done by flowing reactant gas through the system with the plasma generation feature turned off.

In some embodiments, the system continues to flow gas through the plasma chamber at a rate equal to the gas sample flow rate during zero bias flow so that there is no net addition or loss of gas to the inspiratory gas flow path.

At the end of treatment, it is important to purge a NO generator of NO to prevent $NO_2$ formation. This prevents the device from being stored with $NO_2$ within the system, which can be corrosive. This also prevents the device from expelling a bolus of $NO_2$ the next time is used clinically. When purging a NO device, it is often insufficient to simply displace the internal volume of the system with fresh reactant gas. This is because NO and $NO_2$ absorb into the materials of a NO generator over time and require time to off-gas or extract back out of the NO generator components. In some embodiments, purge gas is passed through the NO generator for a set amount of time which has been characterized to remove a sufficient amount of NO and NO from the device materials. In some embodiments, the NO generator purges the system with a volume of reactant gas roughly equal to or greater than the internal volume of the pneumatic pathway (tubing, scrubber, injector, pump, etc.). Then, the system pauses to allow time for NO and $NO_2$ to leach out of the controller. This is followed by another replacement of the internal gas within the system and another pause. This process can be repeated multiple times until NO and $NO_2$ levels within the system are acceptable for storage. In some embodiments, a NO generation system uses an internal $NO_2$ sensor to measure the gas quality within the system to determine when purging is complete.

Another issue to consider during device purging is where to put the purged gases. In one scenario, the system introduces purge gas to an inspiratory limb at slow enough flow rates that the clinical implications are insignificant. In many clinical scenarios, however, the device may still be connected to an inspiratory limb and it may not be desirable to introduce additional gas, let alone $NO_2$-containing gas. In some embodiments, a NO generation system can purge the pneumatic pathway and/or scrubber and direct the purge gas out of the device through a pathway that is independent of the inspiratory limb. In some embodiments, purge gas is passed through the inspiratory gas sensor bench. In some embodiments, the inspiratory gas sensor bench can be utilized to measure the $NO_2$ concentration of the purge gas and determine when purging is complete. In some embodiments, purge gas is directed to house vacuum. In some embodiments, purge gas is directed to the ambient environment. In some embodiments, purge gas is directed to a scrubber prior to release into the ambient environment.

Scrubbing and Filtering

Scrubber material is consumed by the $NO_2$ reaction process over time. In some embodiments, a NO generation system uses an algorithm to estimate the remaining cartridge life. In some embodiments, the algorithm involves integrating the estimated $NO_2$ production levels over time as an estimate for scrubber life. In some embodiments, the algorithm involves integrating NO production levels over time. In some embodiments, the system estimates the quantity of $NO_2$ that has been absorbed by a scrubber based on a list of parameters including but not limited to one or more of the following: $NO_2$ concentration, NO concentration, NO production, $NO_2$ production, $NO/NO_2$ ratio, scrubber temperature, reactant gas temperature, reactant gas humidity, scrubber age, product gas temperature, product gas humidity, product gas flow rate, and reactant gas flow rate. In some embodiments, a scrubber is characterized for a quantity of $NO_2$ moles that it can safely process. In some embodiments, the quantity of $NO_2$ a scrubber has been exposed to is calculated as the integration of $NO_2$ production over time (example, $NO_2$ concentration*product gas flow rate*time). In some embodiments, the $NO_2$ exposure is calculated as the integration of NO production over time divided by the $NO:NO_2$ ratio (example, NO concentration*product gas flow rate*time/$NO:NO_2$ ratio). In some embodiments, the scrubber use is determined in units of ppm·lpm·hr. Scrubber use calculations can be calculated and updated continuously to account for variations in NO production levels over the life of the scrubber.

In some embodiments, the estimated remaining scrubber life is presented on the user interface of the device.

The scrubber is a flow restriction that can diminish the fidelity of a breath detection signal. In some embodiments, a removable scrubber cartridge design includes a port for breath detection. The port consists of a bifurcation in the product gas pathway that establishes fluid communication with a pressure sensor located in the controller, as shown in FIG. 28A and FIG. 28B. FIG. 28A depicts a scrubber module inserted into an NO generation and delivery system 542 and FIG. 28B depicts the scrubber module alone. The scrubber module consists of a chamber filled with scrubber material. The material could be loose scrubber media, soda-lime-impregnated sheet material, $NO_2$-absorbing coated materials, for example. In the embodiment shown, the chamber consists of a tubular structure with end caps. NO and $NO_2$ containing gas enters the scrubber module at the bottom of the image and passes through the scrubbing chamber. In some embodiments, the NO and $NO_2$ containing gas is filtered prior to exiting the module. The end cap at the top of the image serves to seal one end of the scrubber chamber, provide a means of retention of the scrubber module into a NO generation device and provides a conduit for fluid communication between the delivery system (for example, a cannula) and a pressure sensor within the NO generation device used to detect inspiratory events. FIG. 28A depicts a pressure sensor 544 within the NO generator that interfaces with the scrubber module with a gasket 546 between the pressure sensor 544 and scrubber module end cap. A retention feature 548 is depicted in FIG. 28A. In the embodiment shown, the retention feature 548 is part of the NO generator and slides to the left to release the scrubber module. In some embodiments, the retention feature and sliding occurs within the scrubber module. Other types of retention features can also be used, including but not limited to a detent, thumb screw, access door/panel, threaded interface between scrubber module and controller, dove-tail sliding interface, and others. In some embodiments, the scrubber module is an integral part of a cannula or other type of gas delivery component. In some embodiments, the scrubber module includes a pneumatic interface for connecting to a gas delivery component such as a barb, as depicted in FIG. 28A and FIG. 28B. In the embodiment shown in FIG. 28A and FIG. 28B, the scrubber module inserts into a pocket within the NO generation device. In some embodiments, the scrubber module attaches to the outside of a NO generation device with a mechanical connection and a pneumatic connection.

In some embodiments of a portable NO generator, $O_2$ from an external source passes through the scrubber cartridge for connection to a cannula. In some embodiments, $O_2$ from an external source passes through the controller. In some embodiments, the $O_2$ exit is located near the NO exit to facilitate connection of NO and $O_2$ to a cannula.

In some embodiments, a scrubber can be made with tea. This offers potential weight savings, reduction in potentially harmful materials (soda lime) and improved disposability of the scrubber. It also may be less expensive. In some embodiments, lithium hydroxide alone or in concert with other materials can be used to scrub $NO_2$ from product gas.

In some embodiments, product gas is passed through a fluidized bed of scrubber material, shown in FIG. 29. In some embodiments, a fluidized bed chamber 550 can be a vertically-oriented chamber with scrubber media 552 collected at the bottom of the chamber due to gravity. Gas is introduced to the chamber 550 through one or more orifices, such as a product gas inlet 554 in the bottom of the chamber and flows to an exit, such as product gas outlet 556 at the other end of the chamber. Scrubber media float in the gas, improving gas-particle interaction while minimizing flow restriction. In some embodiments, particles are uniform in size to have consistent scrubber-to-scrubber flow restriction, scrubbing performance and longevity. In some embodiments, one or more baffles 558 can be used to equalize and distribute gas flow through the media. In some embodiments, the fluidized bed chamber includes filters before and/or after the chamber to prevent particle migration during scrubber transit and/or during use.

In some embodiments, a system irradiates product gas with UV radiation with wavelengths shorter than the photodissociation energy of nitrogen dioxide (1.73 eV, equivalent to a photon with a wavelength of 390 nm). In a collision with $NO_2$, photons cause an oxygen atom to eject from the $NO_2$ molecule, thus converting $NO_2$ to NO. In this embodiment, the photons would have wavelengths longer than needed to dissociate NO (189 nM), so that NO is unaffected. Other components of the product gas such as oxygen (240 nm) and nitrogen (127 nm) require greater energy to dissociate and would thus not be affected by the reaction. Other oxides of nitrogen such as $N_2O$ (715 nm), $NO_3$ (573), and $N_2O_5$ (1254 nm) would be dissociated by UV photons, although the presence of these higher molecular weight of these molecules is low. $CO_2$, at 225 nm, requires higher than available energy, and thus would not dissociate into CO. In this embodiment, the gas would be constrained to pass through a narrow passage onto which the UV light, with wavelength shorter than 390 nm and longer than 270 nm, is focused in order to maximize the intensity of photons and thus optimize the collision cross-section for photon/$NO_2$ reactions.

In some embodiments, the UV photon source would be an array of UV light emitting diodes. In some embodiments, the UV source would be a focused laser diode. In some embodiments, the reaction chamber would be lined with a UV reflective coating in order to allow individual photons more opportunities for collisions. In some embodiments, the gas is heated to increase the average kinetic energy of the gas molecules and thus increase the probability of reactions.

Filters within the product gas path are utilized to remove particulate. Various means of filtration are effective, such as borosilicate, Porex, and Mixed Cellulose Ester. Filtration levels can be down to 10 nm particle size to remove materials from the electrodes, scrubber, and other parts of the system. In some applications, fragile filter materials require support structure to prevent tearing and/or separation from the scrubber housing. In some embodiments, a screen is placed on one or both sides of a filter membrane to protect the membrane. In some embodiments, either a spoked disk or perforated disc is placed behind the filter material. In some embodiments, an open-cell foam or amorphous material like cotton is placed on one or more sides of the filter material to support it.

Figure 30:
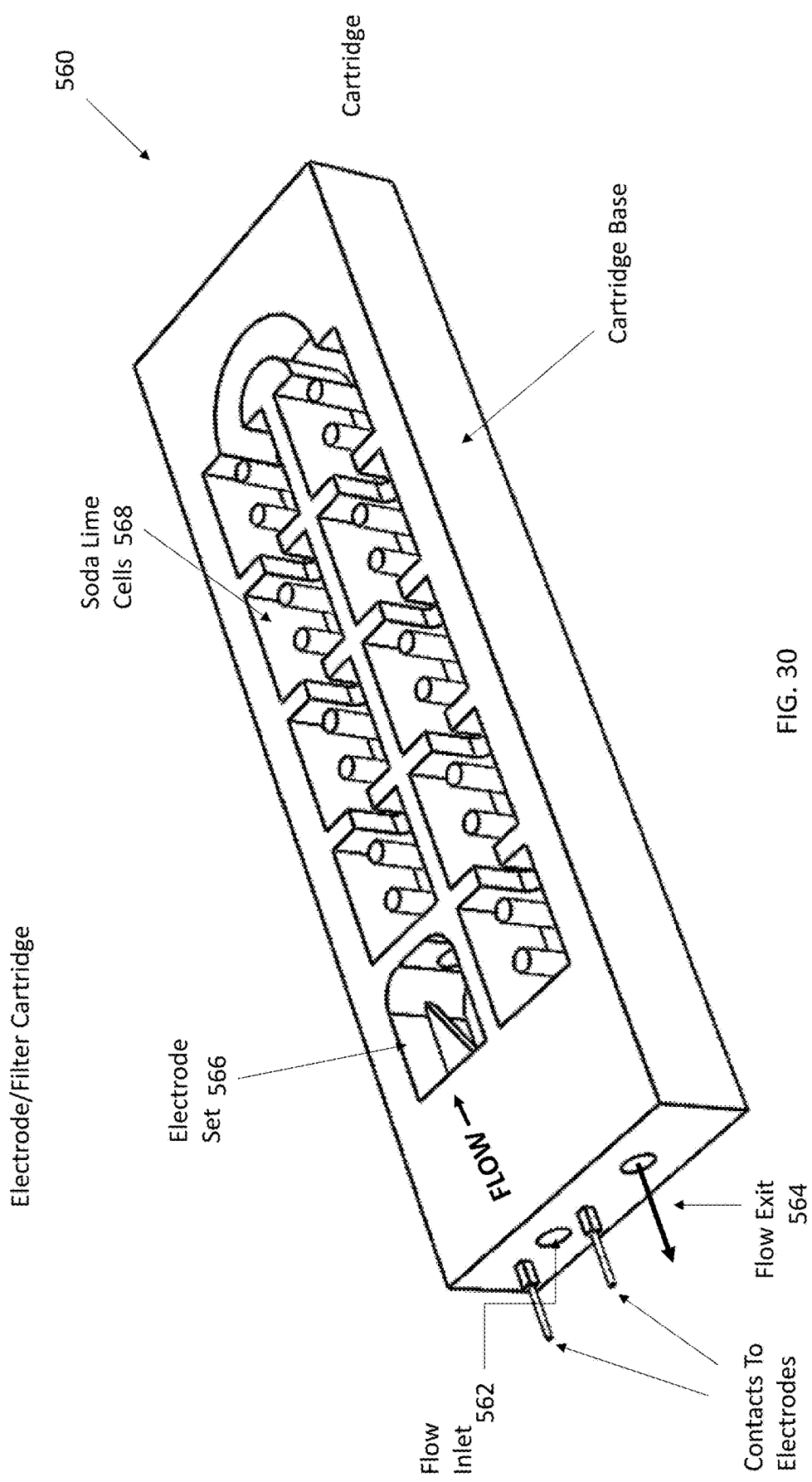
FIG. 30 illustrates an embodiment of a disposable scrubber cartridge.

In some embodiments, a disposable scrubber cartridge includes disposable electrodes. FIG. 30 depicts an embodiment of a disposable scrubber cartridge 560 with reactant gas inlet 562 and product gas outlet 564 pneumatic connections and electrical connections. Reactant gas enters the assembly and passes through a plasma chamber 566. Product gas then passes through a series of chambers 568 with scrubber media in them, for example soda lime cells. Baffles between the chambers distribute product gas and prevent migration of scrubber media. Filters between chambers can provide additional migration prevention and collect particulate from the electrodes and scrubber media. Gliding arc electrodes are shown, however this approach could be utilized with other electrode types, including but not limited to opposed electrodes, parallel electrodes, gliding torch and torch electrodes. In some embodiments, only one of the two electrodes are included in the disposable.

Figure 31:
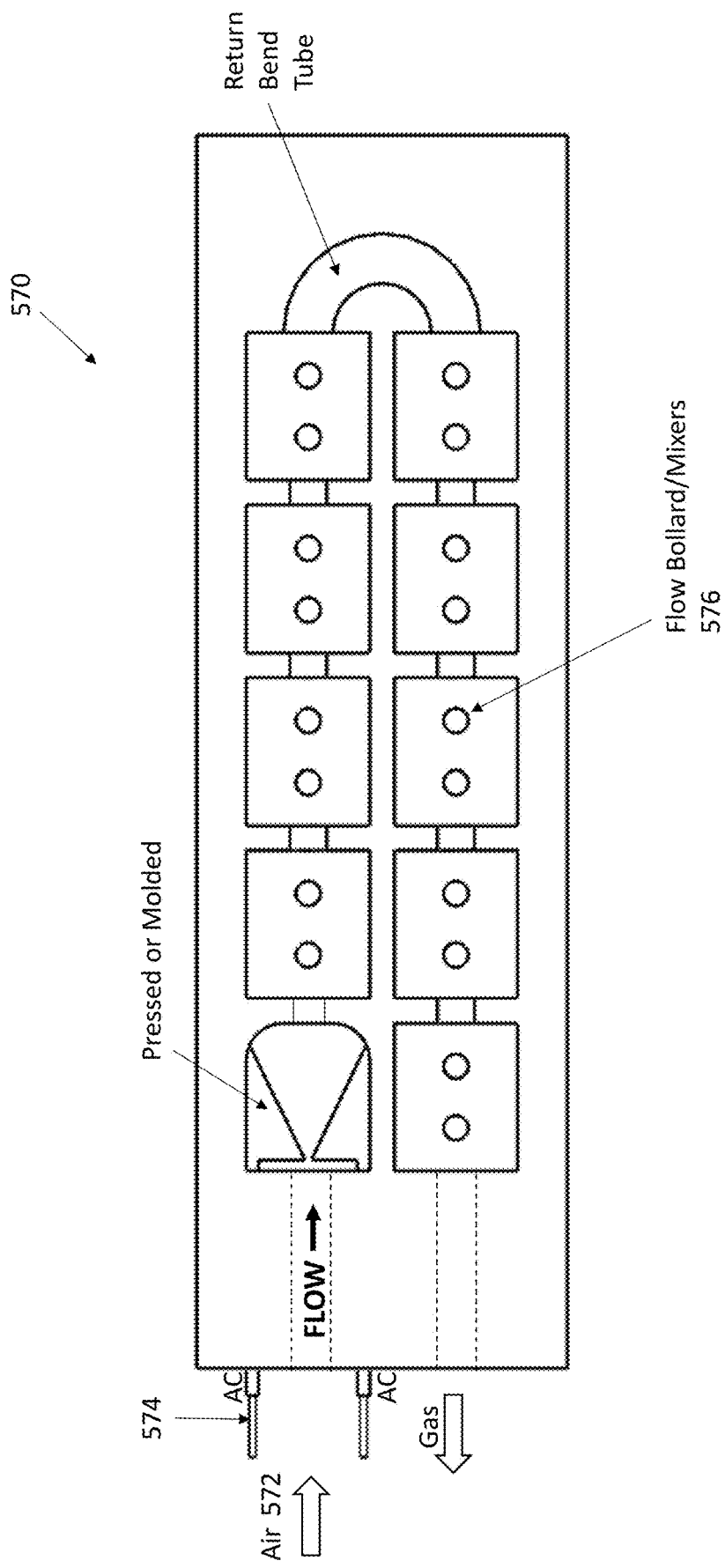
FIG. 31 illustrates an embodiment of a scrubber cartridge including electrodes.

FIG. 31 depicts a scrubber cartridge 570 with electrodes. Reactant gas enters at an inlet 572 and passes through a plasma chamber. High voltage connections 574 energize the electrodes to create NO within the reactant gas. NO-containing product gas exit the plasma chamber and passes through a series of chambers filled with scrubber media. Mixing features within each chamber ensure that product gas is distributed throughout each chamber for good gas-scrubber media interaction. In the embodiment depicted, an array of flow bollards 576 is used to increase gas turbulence.

Figure 32:
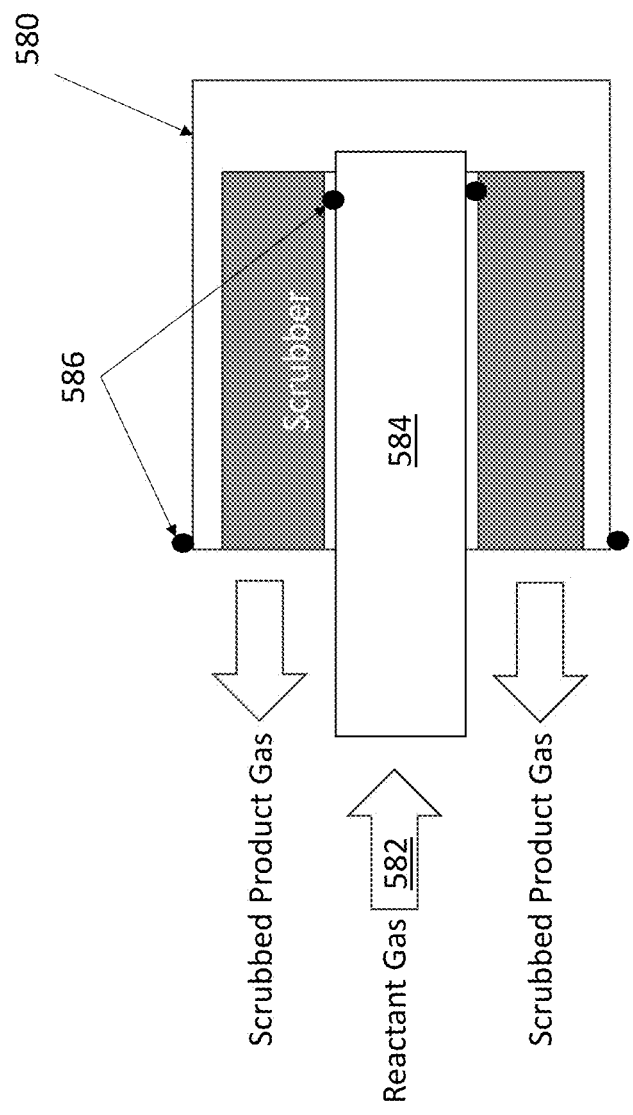
FIG. 32 illustrates an embodiment of a scrubber cartridge configured to slide over a plasma chamber.

FIG. 32 depicts a scrubber cartridge 580 that slides over a plasma chamber. High concentration NO oxides to $NO_2$ rapidly. Thus, great attention is paid to minimizing dead space within a NO generation system. In the depicted embodiment, reactant gas 582 enters a plasma chamber 584. The plasma chamber 584 is part of a larger system (not shown) that includes a high voltage supply, a treatment controller, etc. Product gases exit the plasma chamber and return through an annular space filled with scrubber material, such as soda lime granules or $NO_2$-scrubbing sheet material that has been spiral-wrapped. Filters (not shown) can be included in the scrubber cartridge to remove particulate and minimize scrubber material migration during shipping of the product. Pneumatic seals 586 prevent loss of product gas through the interfaces between the scrubber cartridge, plasma chamber 584 and rest of the system.

In some embodiments, a cylindrical scrubber is connected to a NO generator by turning the cartridge on threads until tight. In some embodiments, the scrubber is translated onto the plasma chamber until a feature engages the plasma chamber, as shown. In some embodiments, the plasma chamber is part of the disposable scrubber cartridge.

Scrubber Humidity Management

Water is an essential chemical in the chemistry of $NO_2$ absorption by some scrubber materials, such as soda lime. As soda lime dries, $NO_2$ absorption is compromised. In some embodiments, reactant gas passes through a humidification stage prior to the plasma chamber to improve $NO_2$ scrubbing. In some embodiments, NO and $NO_2$-containing product gas passes through a humidification stage prior to entering the scrubber to improve $NO_2$ scrubbing.

Humidification of gas in a NO generator can be accomplished by many ways including bubbling the gas through water, passing gas through a wetted gauze mesh, nebulizing water into the gas, passing through a wetted sponge, spraying water into the gas, passing gas through a chamber with heated water in it, passing gas through dry water or wetted silica particles or beads, and other means. In some embodiments, water is wicked from a reservoir into the gas flow path via a hydrophilic mesh. In some embodiments, an ampule of water can be used that is punctured as a scrubber cartridge is inserted. In some embodiments, humidity is added to a scrubber channel when it is not active. The addition of moisture to gas within the device can have a benefit of cooling product gases for preferred relative humidity and temperature of the soda lime. In some embodiments, temperature of some soda limes is 37 degrees C. In some embodiments, a reservoir of water can be positioned in the scrubber cartridge that is punctured by a needle upon insertion. In some embodiments, an ultrasonic pump introduces water to the flow path. In some embodiments, water is transported via wicking or capillary action to a location where it is introduced to the reactant and/or product gas. Bubbling product gas has the benefit of removing $NO_2$ while adding humidity and cooling. In some embodiments, a reservoir for bubbling product gases is located within the scrubber cartridge. In some embodiments, the system can measure the humidity of the reactant gas directly or indirectly, and the system can target a humidity level that is optimal for soda lime. In some embodiments, the system measures humidity of the incoming reactant gas and decides whether or not humidity should be added. In some embodiments, the system measures humidity of the incoming reactant gas and decides whether or not humidity should be added. In some embodiments, a bottle of water that is replaced as needed can be connected to the controller. In some embodiments, a septum is pierced by a needle when the bottle is inserted into the controller. In some embodiments, a UV light source that sterilizes water before it is introduced to the reactant gas can be used. In some embodiments, the UV of the plasma is sufficient to sterilize the plasma flow gas. In some embodiments, a water reservoir is filled by the user using a syringe, pouring water, inserting an ampule, inserting a bottle, or other means. In some embodiments, water is wicked to an open cell sponge located in the reactant gas pathway. In some embodiments, water is wicked into the scrubber housing with a mesh. In some embodiments, the mesh is cotton.

In some embodiments, a dry scrubber is rejuvenated by passing humidified gas through it so that the soda lime can regain water content. This can happen during patient treatment or when the scrubber is not otherwise active. In some embodiments, a humidification device can be positioned at the reactant gas inlet of an NO generation device. In some embodiments, a fitting, such as a 22 mm fitting, can be placed on the front of the scrubber cartridge to receive humidified gas input.

Product gases flow through Nafion tubing. High humidity on one side of the Nafion tubing drives humidity into the product gases on the other side of the Nafion tubing. Humidity can be from liquid water, humidified water, a nebulizer, etc. In some embodiments, Nafion in the scrubber can pull humidity into the treatment gas.

In some embodiments, gas is cooled before it enters the scrubber to increase relative humidity and decrease evaporation of water from the scrubber material. Gas cooling can be passive or active. One passive way is to have a metallic gas flow conduit with or without cooling fins. One active way is to use a thermo-electric cooler (e.g. Peltier device).

Scrubber Algorithm

Figure 33:
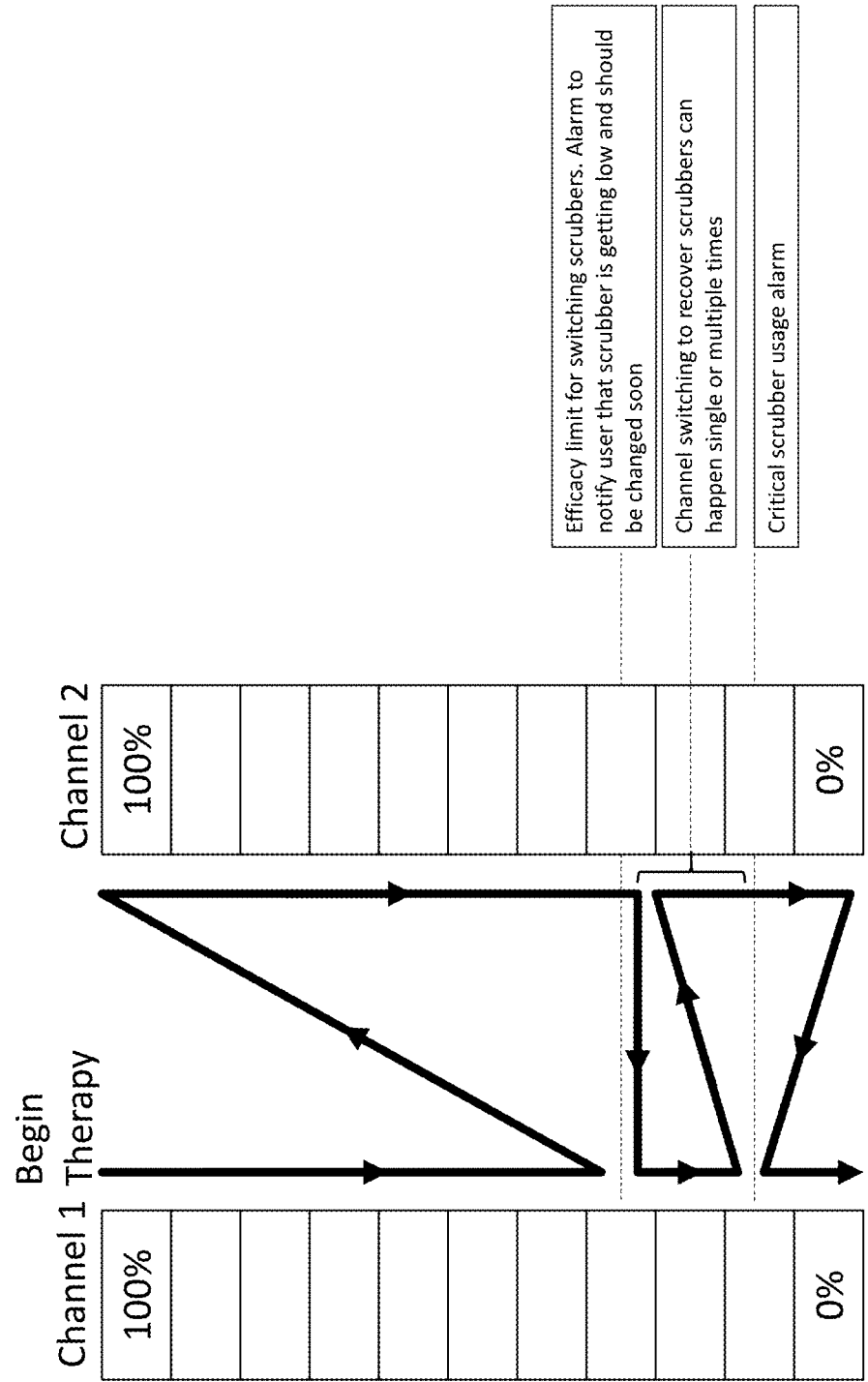
FIG. 33 illustrates an embodiment of a scrubber usage algorithm.

The system can have an algorithm to switch between two NO generating channels and their corresponding $NO_2$ scrubbers. As an $NO_2$ scrubber is used, its $NO_2$ scrubbing efficacy decreases. In some embodiments, the switching can be based on utilizing one $NO_2$ scrubber until an efficacy limit is reached. The device can run one channel to a set scrubber efficacy limit and then switch to the second channel. At this point the user can be alerted to the utilization level of the first scrubber, while having significant run time on the second channel. In some embodiments, the algorithm does not fully utilize the first channel to provide backup in case an issue arises in the second channel. Additionally, after using the second channel to a set an efficacy limit, the device can alert the user that one or more of the scrubbers need to be changed. The device can continue to operate alternating one or more times between the two channels at a shorter interval. The switching of scrubbers can provide rejuvenation of the scrubber, meaning that the $NO_2$ removal rate of a scrubber can improve after a scrubber has been inactive for a period of time. FIG. 33 illustrates an embodiment of a scrubber usage algorithm that switches between a first and second scrubber channel.

Although scrubbing efficiency of a scrubber continuously declines during use, it has been observed to partially recover between uses. In a NO generation system with two or more scrubbing channels, the system can switch between channels to provide time for a given channel to reset in scrubbing efficiency. This feature can provide the benefit of improving overall scrubbing efficiency and/or prolonging the life of a scrubber.

Channel changing frequency can be based on $NO_2$ performance or moles of $NO_2$ absorbed by an active scrubber or a set time interval, for example.

Scrubber Construction

Figure 34A:
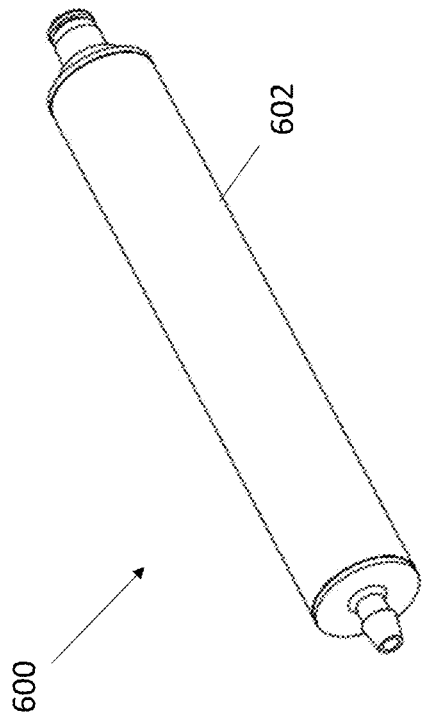
FIG. 34A illustrates a perspective view of an embodiment of a scrubber.
Figure 34B:
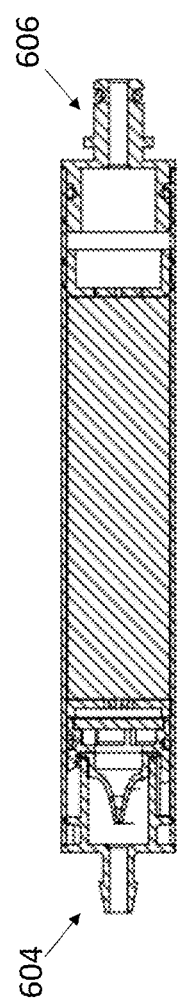
FIG. 34B illustrates a cross-sectional view of the scrubber of FIG. 34A.
Figure 34C:
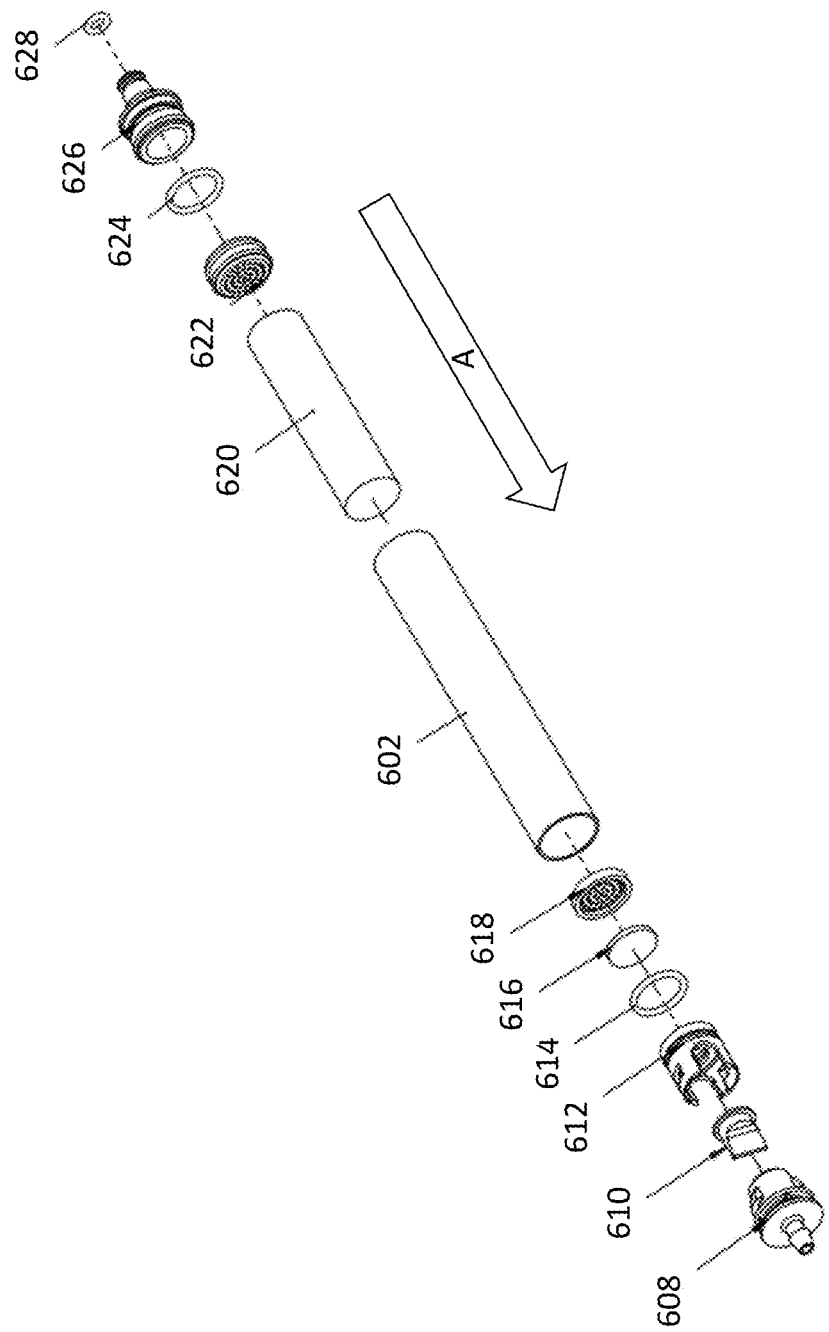
FIG. 34C illustrates an exploded perspective view of the scrubber of FIG. 34A.

FIG. 34A, FIG. 34B, and FIG. 34C illustrate an embodiment of a scrubber 600. FIG. 34A depicts a scrubber module consisting of a tubular housing 602 with end caps, and internal to the scrubber module there can be one or more scrubber materials, filters, and/or baffles. FIG. 34B shows a cross section of the scrubber module. Product gas enters the module through a fitting 604 and passes through a first filter. A first baffle maintains compression on scrubber media packed within the tube. Additional baffles can be used to prevent scrubber media migration and to redistribute gas flow through the scrubber media to prevent channeling. After passing through the scrubber media, the product gas passes through an additional baffle, a filter and a one-way valve. The filter removes particles form the scrubber media and electrodes. In some embodiments, the second filter has a pore size of 20 micron. In some embodiments, the second filter has a pore size of 10 nm. The one-way valve serves to prevent back-flow from the patient inspiratory limb into the NO generator. The use of the one-way valve depends on the treatment application and system architecture. For example, if the system includes valves downstream of the one-way valve, then inclusion of the one-way valve may not be required. Product gas exits the assembly through a second fitting 606. In the embodiment depicted, the first fitting utilizes an O-ring seal for insertion and removal into a NO generator. The second fitting is a barb-type fitting for a more permanent connection to a tube or manifold. In some embodiments, multiple scrubber modules are housed in a single cartridge to reduce use steps. In some embodiments, two scrubber modules serve a ventilator treatment channel and one scrubber module serves an auxiliary channel for manual bagging treatment.

FIG. 34C shows an exploded view of a representative scrubber module. Arrow represents the direction of product gas flow through the scrubber module. The components of the scrubber module include a barb fitting 608, one-way valve 610, connector cap 612, tube O-ring 614, a filter 616, an outlet baffle 618, tube 602, scrubber media 620, an inlet baffle 622, tube O-ring 624, connector cap 626, and connector O-ring 628. In some embodiments, each connector cap connects to the tube in two ways to mitigate against potential product gas leaks: an O-ring seal on the ID of the tube and a circumferential adhesive bond between the cap and tube on the outer surface.

Figure 35:
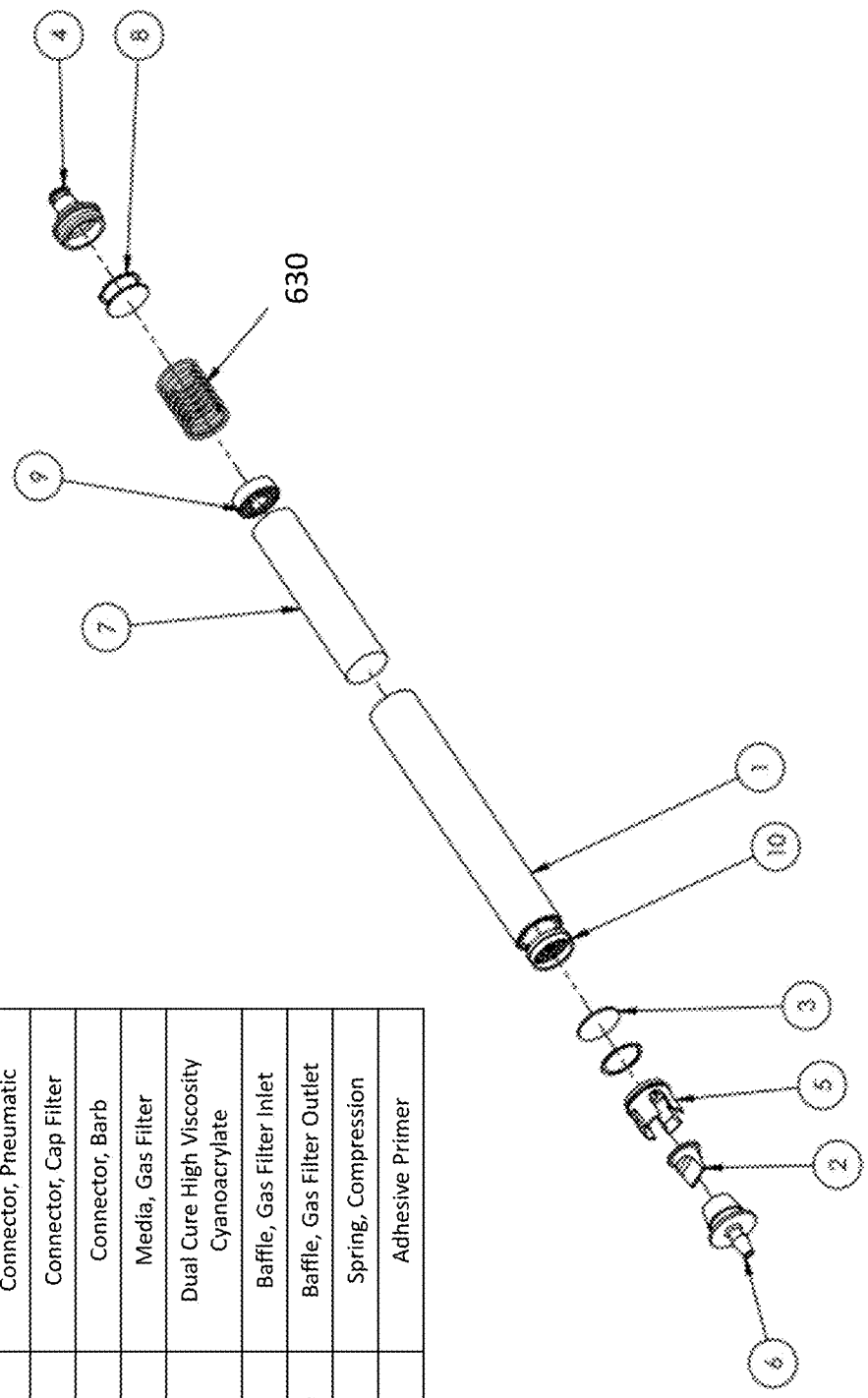
FIG. 35 shows an embodiment of a scrubber construction with a spring.

Scrubber media can settle during transit, storage and use. In some embodiments, as shown in FIG. 35, a spring 630 is used to maintain compression on scrubber media to prevent channeling. The spring can be a conventional, metallic coil spring, open cell foam, wavy washer or other means to impact compressive force on the soda lime. In some embodiments, scrubber media are compressed within a volume by using a press prior to insertion of a sliding baffle and spring to maintain compression. The scrubber media can be compressed in various ways and by various amounts. For example, in some embodiments, the scrubber media are compressed 25% of their unpacked volume as they are pressed. Compression of soda lime improves scrubbing efficiency in multiple ways, including decreasing dead volume within the scrubber, increasing scrubber surface area due to the fracturing of soda lime, and decreasing the potential for channeling, or low-flow restriction pathways through the soda lime.

In some embodiments, scrubber media, such as soda lime, is compressed between perforated baffles that diffuse gas flow across the cross-sectional area of the scrubber and maintain compression on the soda lime over time.

Compression of soda lime can leave a void within the soda lime housing that presents dead space within an NO generation system. Dead space can be detrimental to NO generation and delivery for two primary reasons: 1) It introduces a compressible volume that can cause delays in NO delivery, and 2) It increases transit time of product gas through the system, contributing to increased NO loss and corresponding $NO_2$ formation. In some embodiments, one or more spacers are placed within a void within a scrubber housing after soda lime compression. In some embodiments, spacers consist of a thick-walled tube. In some embodiments, spacers consist of additional soda lime. In some embodiments, the spacer is an open-cell foam.

In some embodiments, a scrubber can be in the form of $NO_2$-absorbing material cast into discs that are stacked in a tube. In some embodiments, the discs are perforated. In some embodiments, the discs are indexed rotationally, so that a tortuous path is created for the product gas.

In some embodiments, inspiratory gases are scrubbed near the patient. This can be done by combining the gas sample port (AKA T fitting) and an inline scrubber. By combining the T-fitting and sample port, the risk of not using a scrubber is reduced. The gas sample is pulled downstream of the scrubber to ensure that the NO and inspiratory gases have mixed and so that the efficiency of the scrubber can be monitored.

In some embodiments, a proximal scrubber includes a clip to attach to a shirt or lapel to control cannula location.

The system can characterize the flow restriction of a new scrubber cartridge (each channel) by pumping air through the scrubber and measuring plasma chamber pressure. The system can use this information to adjust the treatment algorithm. For example, the system could increase the reservoir pressure or increase pumping effort in response to a higher flow restriction scrubber, or the system can change plasma parameters to compensate for changes in pressure within the plasma chamber as a result of back pressure through the scrubber.

In some embodiments, the system uses flow restriction characterization of the scrubber cartridge to detect cartridge issues, such as leak, scrubber material settling that opens a gas path shunt (channeling), or a filter rupture.

In some embodiments, an air-tight cover can be included on the product gas connections (gas inlet and/or gas outlet) of a scrubber cartridge. This enables the user to store the NO generator with a new scrubber in it for extended periods of time. The cartridge can be inserted into the controller during storage, but the cover is removed before use. This could be an adhesive film that is adhered to the cartridge and pulled off.

Scrubber with Sheet Material

In some embodiments, a sheet material either made from an $NO_2$ absorbing material or impregnated with $NO_2$-absorbing material is used to scrub the product gas from an NO generator. This approach can provide a reduction in flow restriction over packed soda lime granules. Furthermore, this approach can reduce the flow restriction of a scrubber cartridge and decrease the amount of scrubber particulate introduced to the product gas. The sheet material can be packaged as a spiral or stacked in layers. In some embodiments, the sheet material is held in place by grooves, bosses or other features in the enclosure that surrounds the scrubber material. In some embodiments, a spacer material is placed between layers of an $NO_2$-absorbing sheet material. In some embodiments, holes in the sheet material align when the material is spiraled or layered to provide pathways for gas to pass through. In some embodiments, ridges on the sheet material hold layers apart and provide channels for product gas to pass through.

In some embodiments, rib spacing, height and width in the sheet material is optimized to achieve desired flow resistance and/or scrubbing ability.

Longer flow paths through scrubber materials provide greater residence time and improved scrubbing. In some embodiments, sheet material is wrapped in a diagonal orientation to achieve a helical (longer) flow paths. In some embodiments, ribs are molded in a sinusoidal wave pattern for increased flow path length and tortuosity. In essence, a path can be molded into the sheet material so that the resulting gas channels are longer than the actual sheet material when the sheet material is rolled into a spiral for cylindrical designs or stacked into layers for rectangular designs. Gas paths that are not straight introduce some tortuosity to the flow path that can provide additional gas-scrubber interaction and gas mixing for improved scrubber efficiency.

In some embodiments, an open-cell, sponge-like structure is constructed from an $NO_2$ absorbent material or structural material/$NO_2$ absorbent material composite. Examples of $NO_2$-absorbent materials include, but are not limited to, soda lime, lithium hydroxide, and ascorbic acid. Similar materials and approaches can be utilized for NOx scrubbers.

$NO_2$ Scrubbing

In some embodiments, the $NO/NO_2$ ratio is sufficient that there is no need for an $NO_2$ scrubber downstream of the plasma chamber. In some embodiments, a filter is still used for particulates.

In some embodiments, the volume of the scrubber is equal to the volume of the pulse to be delivered. A pulse is staged within a scrubber so that it is being scrubbed between breaths, prior to delivery.

In some embodiments, an $NO_2$ scrubber has a light pipe so that it illuminates from a light source in the controller.

In some embodiments, scrubbers are used in parallel to slow the flow of product gas and provide more than one preferred path.

In some embodiments, the system has a lock feature that only allows one scrubber to be replaced at a time to ensure that NO delivery is continuous.

Figure 36:
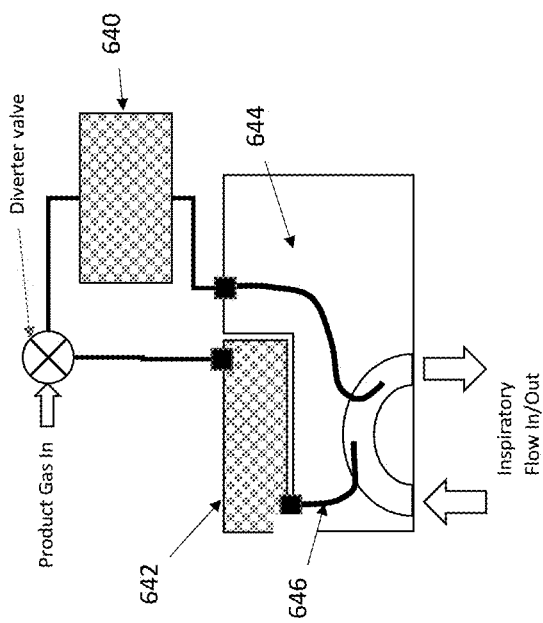
FIG. 36 shows an embodiment of a NO generation system that has the ability to bypass the primary scrubber cartridge.

When a scrubber cartridge is replaced, there can be an interruption in NO delivery. In some embodiments, product gas is not scrubbed during the brief time it takes to replace a scrubber cartridge. In some embodiments, a NO generation system directs product gas through a secondary scrubber cartridge 642 when a primary scrubber cartridge 640 has been removed, as shown in FIG. 36. In some embodiments, product gas is routed through a second scrubber located within the NO generation device. This second scrubber is replaceable, but less frequently since it is only used when the primary scrubber cartridge is not present. In some embodiments, the secondary scrubber is only replaced during annual servicing. In some embodiments, the secondary scrubber is located behind a ventilator cartridge 644. In some embodiments, the secondary product gas path has a separate injector 646. In some embodiments, flow from the secondary scrubber and the primary scrubber merge prior to a single injector. Check valves (not shown) can be used as needed, to prevent gas in the inspiratory path from leaking out when the primary scrubber is removed and/or leaking into the secondary scrubber.

In some embodiments, product gas enters one or more scrubber and exits the scrubber back into the system.

In some embodiments, the product gas enters one or more scrubber and passes into a ventilator cartridge.

In some embodiments, the product gas enters one or more scrubbers, exiting into the patient inspiratory stream directly.

Figure 37:
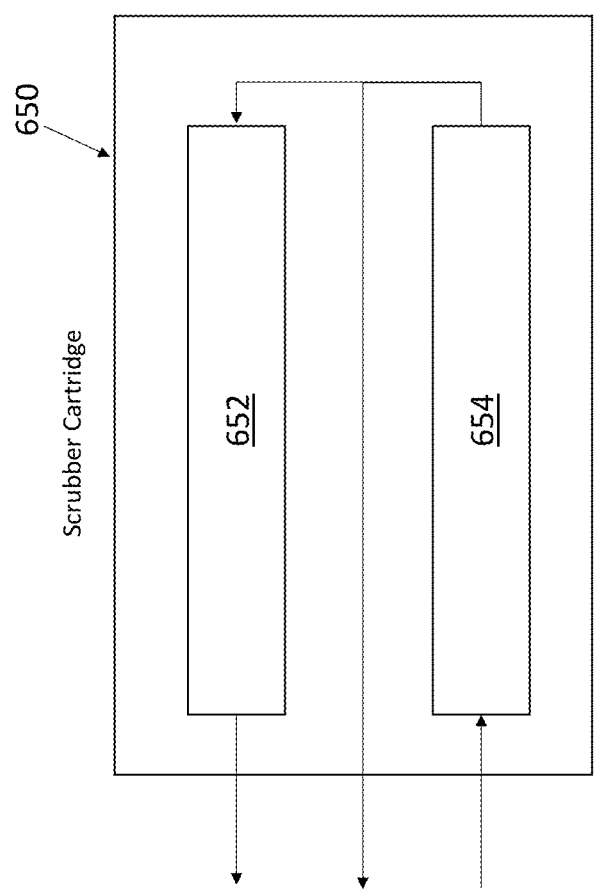
FIG. 37 shows an embodiment of a scrubber cartridge that can provide more than one level of gas scrubbing.

In some embodiments, a scrubber cartridge 650 can provide more than one level of scrubber. For example, two scrubbing modules 652, 654 can be present, as shown in FIG. 37. Flow can go through one or both modules before exiting the scrubber cartridge, as shown in FIG. 37. The actual flow path is controlled by a flow controller within the controller consisting of binary valves, proportional valves, diverter valves and/or pumps, for example.

In some embodiments, scrubber calibration information (efficiency vs. flow rate for varying levels of $NO_2$, for example) can be written to the memory device. In some embodiments, a $NO_2$ molar capacity can be written to the memory device.

In some embodiments, a $NO_2$ scrubber is comprised of sodium hydroxide. Nitrogen dioxide reacts with sodium hydroxide with the following equation to form sodium nitrite and sodium nitrate: $2NO_2+2NaOH \rightarrow NaNO_2+NaNO_3+H_2O$. FTIR analysis of soda lime scrubbers after exposure to $NO_2$ show the presence of sodium nitrite.

In some embodiments, a $NO_2$ scrubber is comprised of potassium hydroxide.

$NO_2+KOH \rightarrow KNO_3+KNO_2+H_2O$

In some embodiments, a $NO_2$ scrubber is comprised of potassium iodide.

In some embodiments, an $NO_2$ scrubber is comprised of a composition of one or more pharmaceutically acceptable substances, including but not limited to salt of ascorbic acid, ascorbic acid, a mix of salt of ascorbic acid and ascorbic acid, salt of erythorbic acid, erythorbic acid, and a mix of salt of erythorbic acid and erythorbic acid. The mixture can be used in either a dry granular form or a wet form.

In some embodiments, an $NO_2$ scrubber is comprised of a substrate or multiple substrates treated with the composition of one or more pharmaceutically acceptable substances, including but not limited to salt of ascorbic acid, ascorbic acid, a mix of salt of ascorbic acid and ascorbic acid, salt of erythorbic acid, erythorbic acid, and a mix of salt of erythorbic acid and erythorbic acid.

In some embodiments, silica granules are soaked in a solution of one or more of salt of ascorbic acid, ascorbic acid, a mix of salt of ascorbic acid and ascorbic acid, salt of erythorbic acid, erythorbic acid, and a mix of salt of erythorbic acid and erythorbic acid and dried. The granules are placed in a housing with an inlet and an outlet for scrubbing $NO_2$ from a product gas containing NO and $NO_2$.

Particulate Trap

In some embodiments, a particulate trap can be located within the gas flow path within a NO generation device. In some embodiments, a particulate trap is located upstream of a plasma chamber to remove particulate form the ambient air. In some embodiments, a particulate trap is located downstream from the plasma chamber to collect particulate from electrodes. In some embodiments, a particulate trap is downstream of the scrubber to capture particulates from the electrodes, filters and scrubber material. In some embodiments, a particulate trap can be in the form of a pocket on the outside of a tight bend in part of the plasma chamber. A particulate trap operates based on the principal that particles are heavier than gas and have inertia. Thus, when a gas is routed around a tight bend, particles do not redirect as quickly and drift into the trap. A particle trap can consist of a chamber or simply an adhesive or greasy material that can capture particles. In some embodiments, a particle trap is part of a disposable scrubber cartridge to prevent over-filling of the trap. FIG. 38A presents an embodiment of a particulate trap 660. Gas flow 662 enters and is routed around a U-turn. Heavy particles drift to the outside of the curve where they are trapped in a pocket.

A similar principal is utilized in a cascade impactor where particles impact a filter while gas flow is routed around a filter. In this embodiment, as shown in FIG. 38B, the particle trap 670 is a surface orthogonal to the direction of gas flow 672. The trap can be constructed of a filter, a tacky substance, a chamber, or other material or shape that will trap particles.

Water Trap

In some embodiments, treatment history can be written to a memory device in a water trap and/or a subcomponent of the water trap. In some embodiments, a water trap is a disposable component of a NO generation and/or delivery device. As a disposable component, information written to a water trap can include a date of manufacture, an expiration date, a water trap volume, a part number, a version number, and/or a treatment prescription. When a water trap is inserted into a controller, the controller may write to the water trap information including one or more of a date and time of insertion, a date and time of first use, a time history of water level, a history of alarms of the system, a history of water trap draining events, a patient treatment history. In some embodiments, the water trap is replaced with each patient so the water trap memory device can serve as a digital record of the patient treatment. In some embodiments, the memory device of a water trap can be removed from the water trap after use for archival purposes or for transfer of information from the water trap to a computer. In some embodiments, the water trap memory device can support a USB interface. In some embodiments, the water trap travels with a patient when a patient is transferred from one NO generation/delivery device to another. In this scenario, the patient case history including treatment settings, alarms, oxygen levels, NO settings, respiratory rate, ambient conditions, and time-histories of other collected data can be transferred from one controller to another with minimal burden to the user. In one scenario, a second NO treatment controller can begin therapy where a first NO treatment controller left off, with the same NO target concentration, alarm limits and treatment history available for review.

NO Generation and $O_2$ Removal

In some embodiments, $O_2$ is removed from the product gas using $O_2$ concentration techniques to slow the oxidation of NO. As with conventional $O_2$ concentration techniques, air is pumped into a chamber containing materials that cling to nitrogen more than oxygen (e.g. zeolite). As pressure is released from the chamber, oxygen-rich gas leaves the chamber first. Nitrogen-rich gas leaves the chamber later and can be directed out a different outlet. Tests with an oxygen concentrator demonstrate that nitric oxide exits with the nitrogen in an oxygen concentration process. This provides the opportunity to remove oxygen from nitric-oxide-containing gas, thereby reducing the oxidation rate of NO and prolonging the nitric oxide. In some embodiments, gas with high levels of $N_2$, NO and/or $NO_2$ exiting an oxygen concentrator can be passed through a NO or $NO_2$ scrubber to further-refine the gas. In some embodiments, the gas passes through ascorbic acid to remove oxygen and/or $NO_2$. In some embodiments, the gas passes through soda lime to remove $NO_2$. In some embodiments, nitric oxide is generated and passed through an oxygen concentrator. Oxygen is removed from the gas and the nitrogen/nitric oxide gas is stored prior to delivery to a patient.

Prewarmed Inhalation Air

The generation of electric NO generates heat in the plasma and in the device enclosure. Both of these forms of heat can be used for comforting the patient. Prewarmed pulsed gas for inhalation can be more comfortable than cold gas. Also, the heat from the enclosure can be used to warm the inspired gas or be used to warm the patient's body.

Safety and Testing

Drug Code

It is common within the hospital for drugs to have a 2-dimensional bar-code that can be scanned for additional information. An NO-generation device can provide similar information about NO. In some embodiments, an NO device can display a compact 2-dimensional barcode icon on the display for a clinician to scan. The 2-D bar code can contain information relating to target NO concentration, measured NO concentration, measured $NO_2$ concentration, measured $O_2$ concentration, treatment duration, device ID, scrubber age, device version, software version, treatment elapsed time, treatment start time, error codes, treatment log information, and/or other information pertinent to the patient treatment.

Combustion

Some use environments can contain volatile compounds at a concentration that could lead to combustion. In some embodiments, an NO generation device uses plasma chamber pressure to detect whether or not combustion is occurring. In the event that combustion is detected, the system can stop the reactant gas flow to starve the flame. In some embodiments, a valve down-stream of the plasma chamber can prevent flammable gas from entering the plasma chamber from downstream. In some embodiments, the valve is a passive check valve that permits product gas to pass to the patient but does not permit inspiratory gases to enter the system.

Power-on Self-Test (POST)

In some embodiments, the system performs a pneumatic test during POST to test for leaks. In some embodiments, a valve can be closed downstream of the plasma chamber so that the pneumatic pathway from a reactant gas source to a closed valve can be tested for leaks. In some embodiments, the system includes a reactant gas pump that can be used to pressurize the system during POST.

In some embodiments, a NO generation system can evaluate the response of onboard gas sensors by subjecting them to a step increase in NO concentration and tracking their t90 time. Electrode chemical sensors, for example, can fail by drying out. This effect manifests itself as increases in t90 time, making sensor drying detectible.

In some embodiments, there can be a plasma current check. The plasma flow/pressure are within limits when the pump is on (and off), resonance frequency is within expected limits, and 12V and "input voltage" are within range.

IOT

In some embodiments, cloud computing is used to monitor the operation and use of an NO generator. Examples of the types of information transferred through the internet cloud are: NO assessment information, weaning schedule, treatment protocol, treatment strategy, advice for treatment with NO, device use information (run time, NO moles generated, number of scrubbers consumed, gas sensor drift, NO levels, $NO_2$ levels, $O_2$ levels). These types of information can be used to process automatic reordering of consumables, remote diagnostics, pre-emptive diagnostics, automatic billing, generate safety alerts, ensure patient compliance with their prescription. In some embodiments, a user can download a weaning protocol from the cloud. In some embodiments, the user training schedule is managed through the cloud. In some embodiments, the actual user training procedure is conducted through the NO generation device by a remote person through the cloud using one or more of audio, text and video communication. In some embodiments, a NO generation and/or delivery device can be remotely controlled or disabled through the medical internet of things (MIOT).

Ambulatory Devices

There can also be systems and methods for portable and compact nitric oxide (NO) generation that can be embedded into other therapeutic devices or used alone. The portable NO generation device enables the generation and delivery of NO to a patient in any location or setting as the device is small enough to be mobile and used anywhere, including in a home of a patient or during travel. The size and portability of the ambulatory NO generation system allows a patient to use the system on-the-go outside a hospital and to have the benefit of NO delivery through a respiratory gas delivery device without having to be in a hospital, clinic or other medical setting. In some embodiments, an ambulatory NO generation system can be comprised of a controller and disposable cartridge. The cartridge can contain filters and scavengers for preparing the gas used for NO generation and for scrubbing output gases prior to patient inhalation.

Ambulatory Device Design

Figure 39:
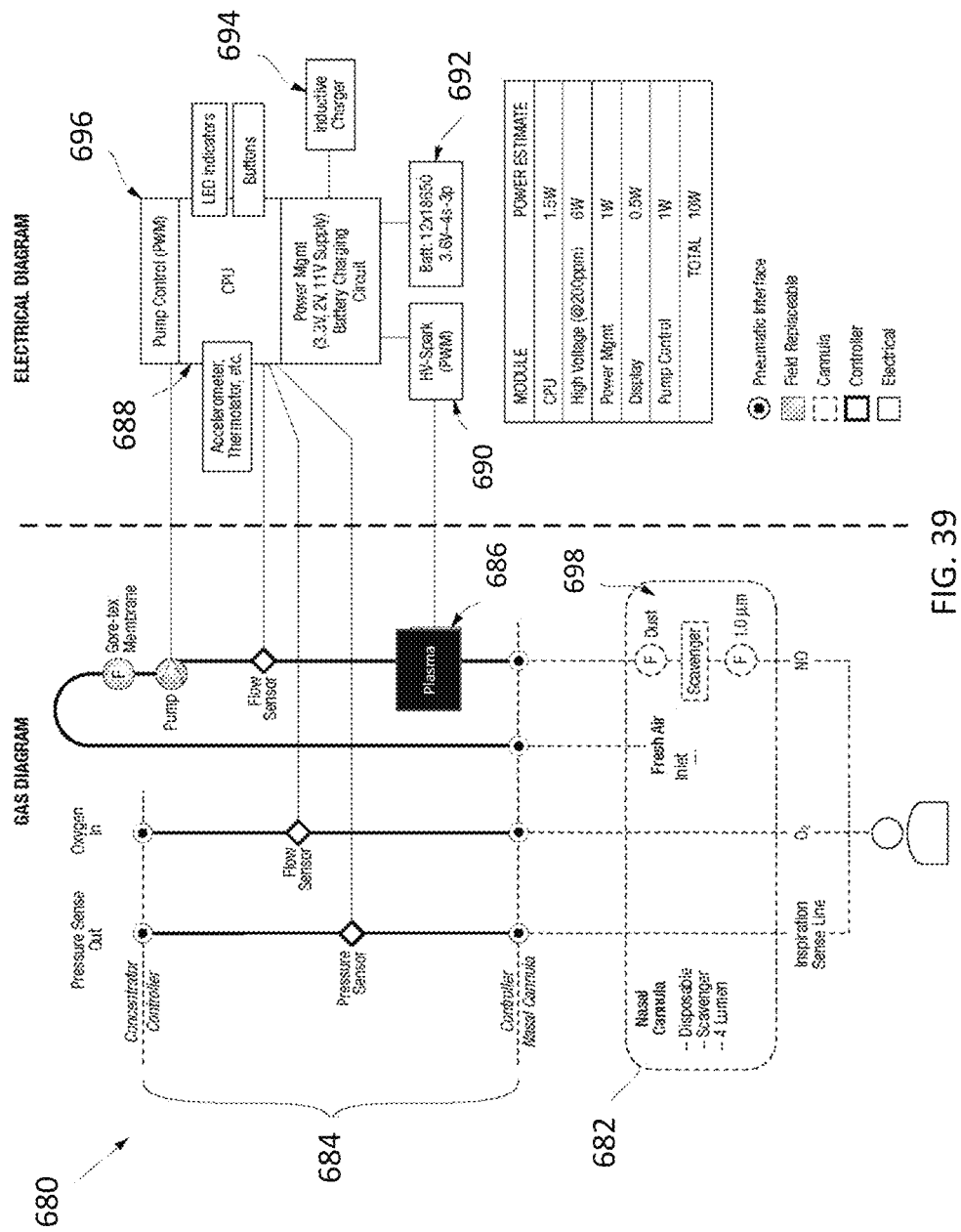
FIG. 39 is an embodiment of a portable, or ambulatory, NO generation system.

FIG. 39 illustrates an embodiment of a portable ambulatory NO generation system 680 that includes a delivery device, such as a cannula 682, for delivering a product gas containing NO to a patient, that includes a filter/scavenger 698. A controller 684 is configured to control the production of NO by a plasma chamber 686 using a variety of sensors. The controller 684 includes a CPU 688 with LEDs and buttons for communication therewith by a user, a high voltage circuit 690, a power source 692, an inductive charger 694, and a pump controller 696.

The cannula has a dedicated lumen for breath detection, a lumen for delivery of $O_2$, a lumen for sourcing ambient air and a lumen for delivery of NO. $O_2$ flow rate is measured by the controller 684. This information can be used to document compliance to $O_2$ therapy, to ensure that total flow to the nose is tolerable, to mark breath detection events, or other purposes. NO generation gas is sourced from a lumen in the cannula. This enables a NO generation device to be located in a confined space, such as a hand-bag, and still source air for NO generation. In some embodiments, the ambient air is sourced near the patient's neck.

Figure 40:
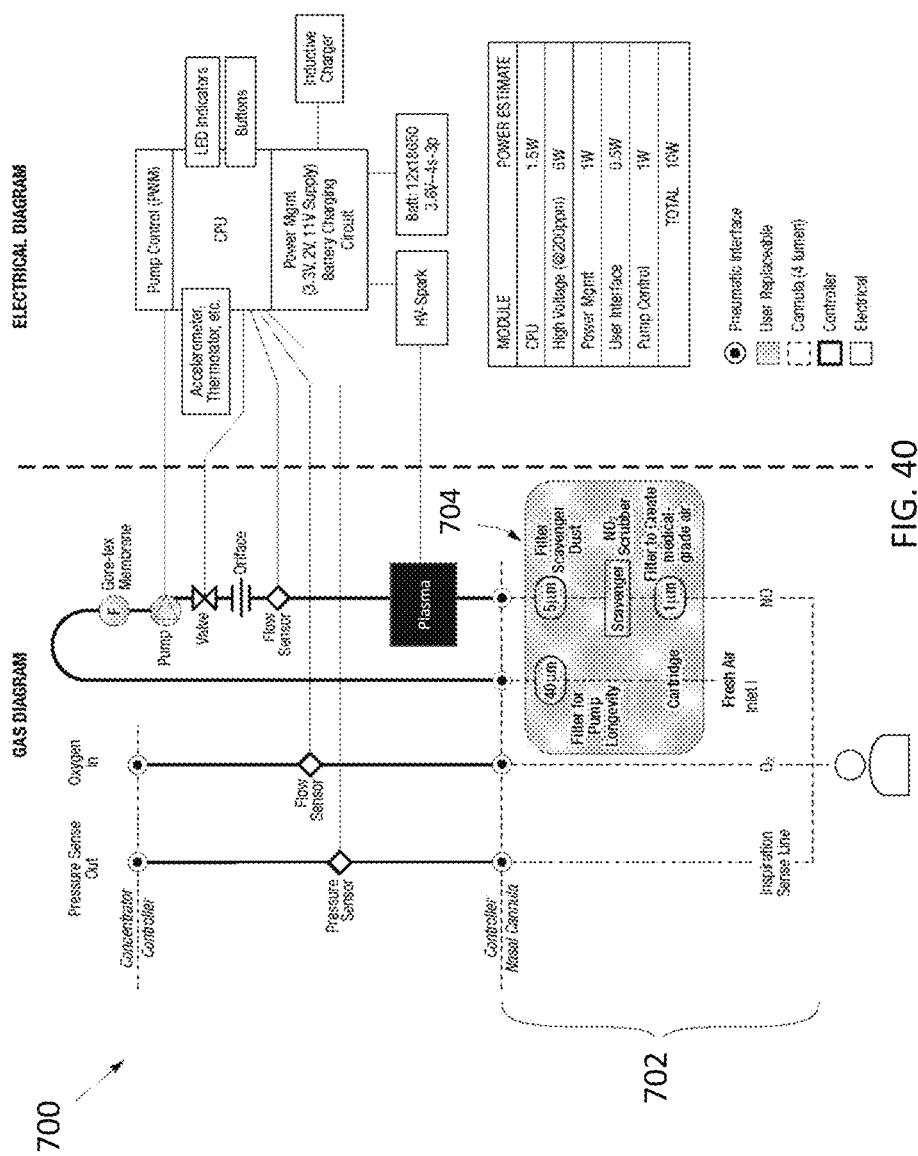
FIG. 40 is an embodiment of a portable, or ambulatory, NO generation system.

FIG. 40 illustrates an embodiment of a portable ambulatory NO generation system 700 that includes a delivery device, such as a cannula 702, and a disposable replaceable cartridge 704 that includes a scavenger therein. In this embodiment, the replaceable cartridge includes a filter for incoming reactant gas, a pre-scrubber filter, scrubber material and a post-scrubber filter. In some embodiments, reactant gas is filtered to 20 microns prior to entering the controller.

Figure 41:
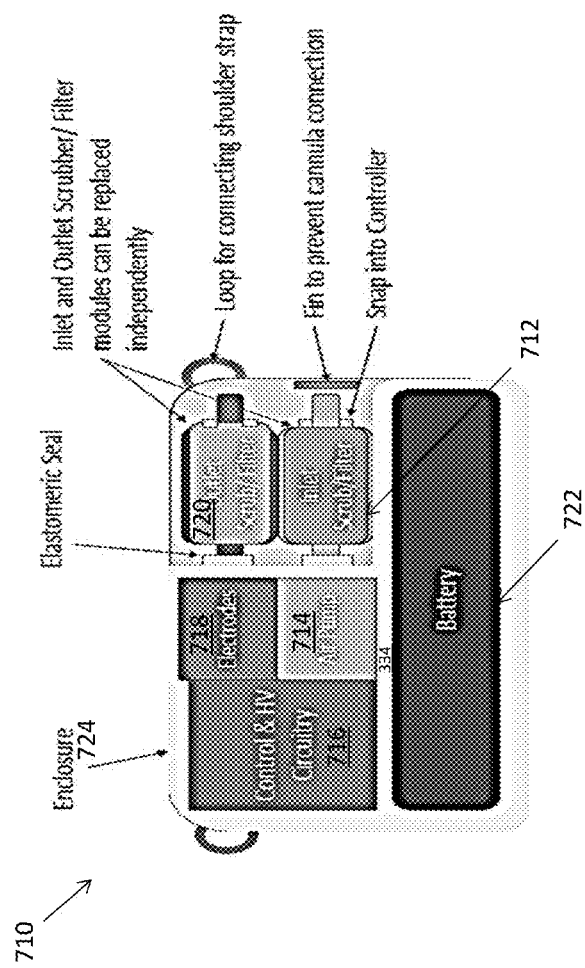
FIG. 41 is an embodiment of a wearable NO generation system.

FIG. 41 illustrates an embodiment of a wearable NO generator 710 with an inlet scrubber/filter combination 712, an air pump 714, control and high voltage circuitry 716, one or more electrodes 718, an outlet scrubber/filter 720, a battery 722, and an enclosure 724. The inlet and outlet scrubber/filters can be replaced independently. The scrubber/filters have a tapered or barbed end that is pressed into an elastomeric ring for retention and sealing. The opposite end of the scrubber filter is retained by one or more spring clips that grasp the outer surfaces of the scrubber filters. The user inserts one end of the scrubber/filter into the elastomeric seal and rotates the body of the scrubber/filter towards the controller enclosure so it "snaps" into position with the one or more spring clips holding it in place, or simply presses the scrubber filter into the device so that it locks into place, and then presses down in order to release it. The scrubber filters can optionally be covered with a cover to protect them from being dislodged during use.

A cartridge for use with an ambulatory NO generation system can include various features and designs. The system can utilize various different types of cartridges that can be used for different applications. For example, cartridges can vary in size of scavenger depending on the expected duration of use and required NO levels. Cartridges could have one or more pneumatic connections, depending on the application. In some embodiments, a single pneumatic connection can be for a single-lumen nasal cannula connection to the device. In some embodiments, two pneumatic connections can be used for a device that adds NO to an existing gas flow. A first pneumatic connection can be for gas flow into the system, and a second pneumatic connection can be for NO+gas output. In some embodiments, three pneumatic connections can be used for a device that measures the flow of an incoming gas flow, but does not add NO to the gas flow. A first pneumatic connection can be for the incoming gas. A second pneumatic connection can be for outgoing gas to the patient. A third pneumatic connection is for NO-containing gas to the patient. The device can source ambient air through a pneumatic opening in the cartridge or through a wall of the controller enclosure.

Figure 42:
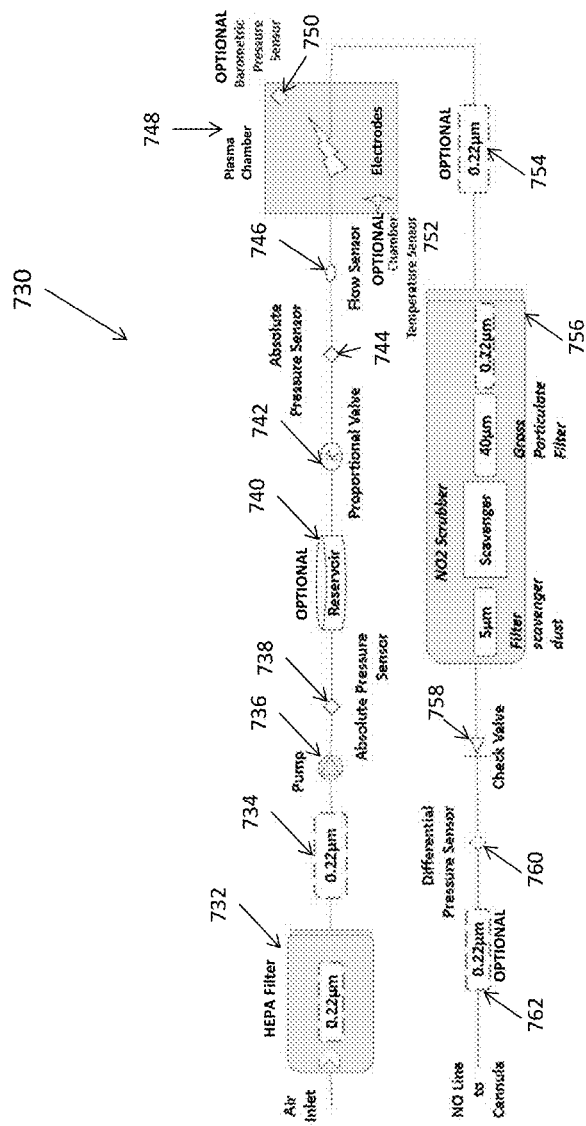
FIG. 42 illustrates an embodiment of a pneumatic pathway within a portable NO generation device.

FIG. 42 depicts an exemplary pneumatic pathway 730 within a portable NO generation device. Shaded portions are removable and disposable. In some embodiments, the removable/disposable elements are located in a single disposable cartridge. In the embodiment depicted, ambient air or other reactant gas is drawn through a disposable filter 732 and then through a permanent filter 734 within the device. The air then flows to a pump 736. The pressure distal to the pump is measured by an absolute pressure sensor 738. This pressure is used to confirm pump activity and measure reservoir pressure when a reservoir 740 is used. The reservoir 740 serves as an accumulator that can provide rapid flow of high pressure air. In some embodiments, the pump alone can sufficiently deliver air flow to the treatment, rendering the reservoir unnecessary. In some embodiments, the air pump pumps against an orifice or one or more valves. A pressure sensor 744 beyond the proportional valve 742 shown is used to measure pressure within the plasma chamber. A flow sensor 746 prior to the plasma chamber 748 is used for closed-loop control to ensure accurate air flow through the plasma chamber. The closed-loop control can be used as input to one or more of the following: pumping effort/speed, valve position, reservoir pressure. The plasma chamber 748 houses one or more electrodes used to create plasma in the air. Optional barometric pressure, humidity and temperature sensors 750, 752 can be connected to the plasma chamber, as shown, or be located up or downstream of the plasma chamber to provide additional input to the control algorithm. An optional third filter 754 within the air flow is located within the controller to provide further protection from contaminates entering the controller. Nitric oxide and air then flow through an $NO_2$ scrubber 756 that includes one or more filters, an $NO_2$-absorptive scrubber and another filter. The NO plus air then flows through a check valve 758, a pressure sensor 760 used for breath detection, another optional filter 762 and a connection to the delivery tube (e.g. a nasal cannula, catheter, or other tube).

Figure 43:
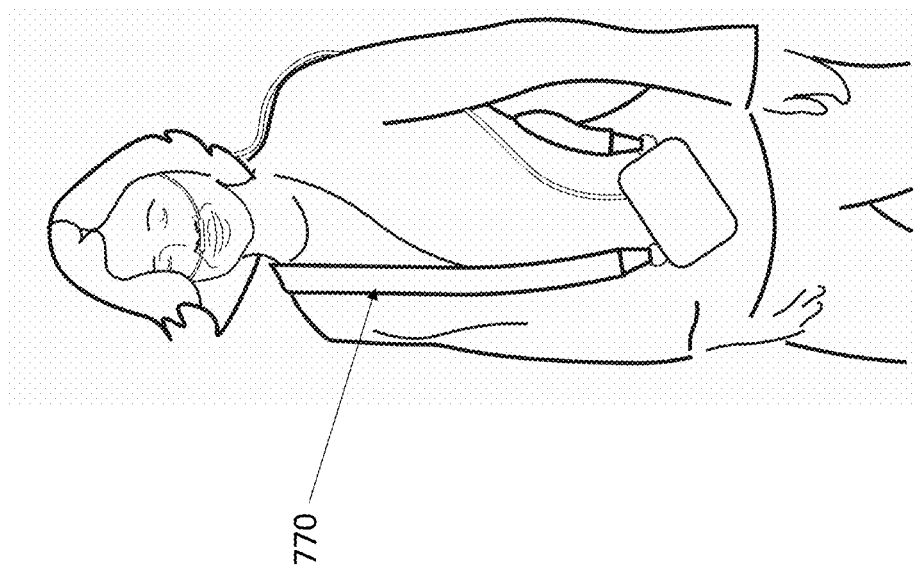
FIG. 43 illustrates an embodiment of a portable NO device that can be worn on a shoulder strap.
Figure 44:
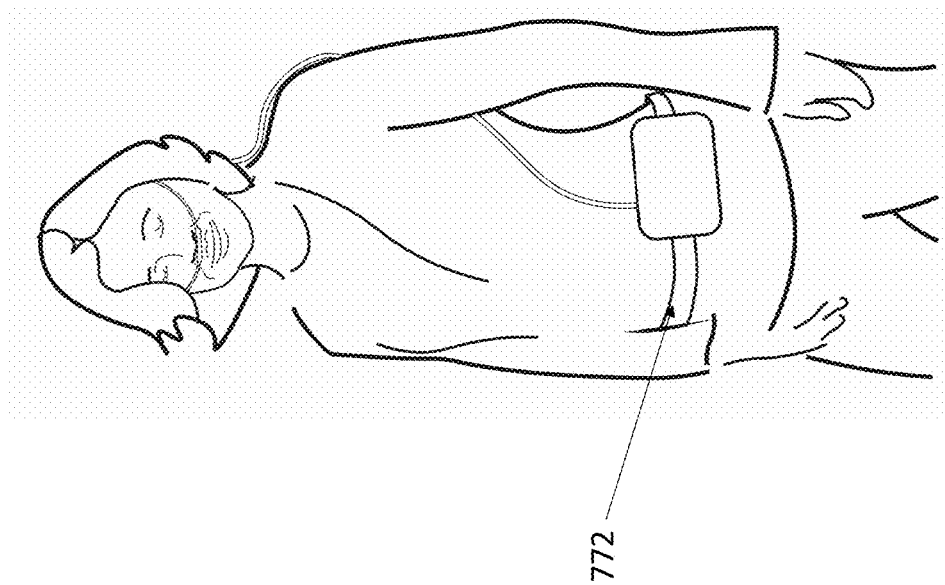
FIG. 44 illustrates an embodiment of a portable NO device that can be worn on a waist belt.
Figure 45:
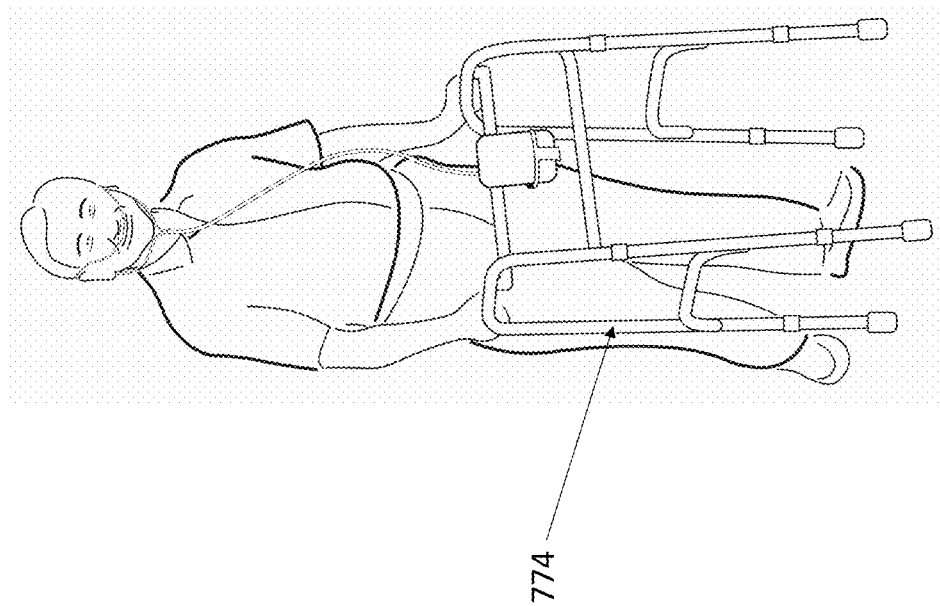
FIG. 45 illustrates an embodiment of a portable NO device that can be worn on a walker.

In some embodiments, a portable NO device can be worn by the patient. As shown in FIG. 43, FIG. 44, and FIG. 45, a portable NO device can be worn on a shoulder strap 770, on a waist belt 772, or on a walker 774. It will be understood that a portable NO device can be worn or carried by a patient in any way that allows the patient to transport the portable NO device.

Figure 46:
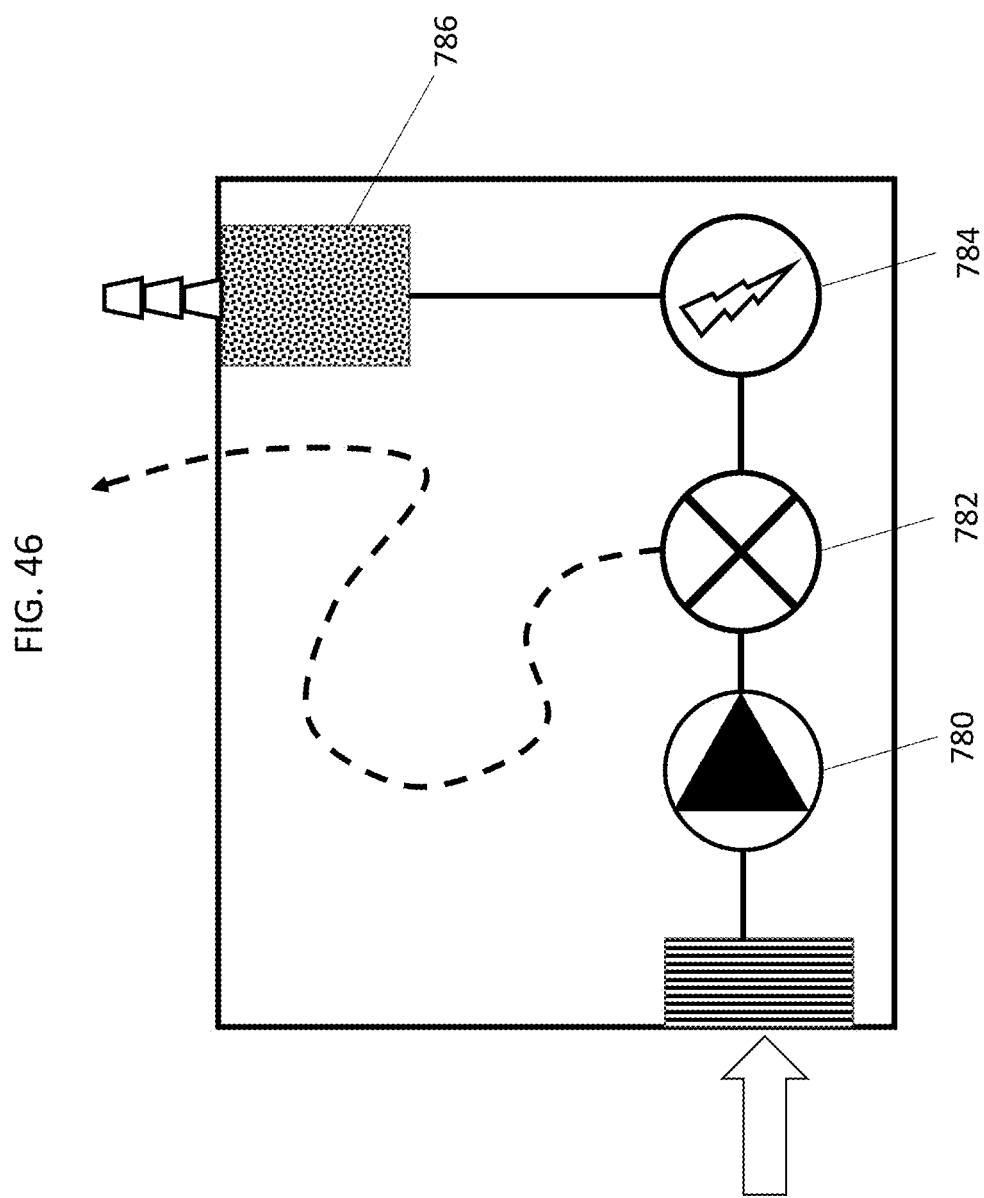
FIG. 46 is an embodiment of an NO generation device that is used to deliver reactant gas to plasma chamber and to push gas for cooling the system.
Figure 47:
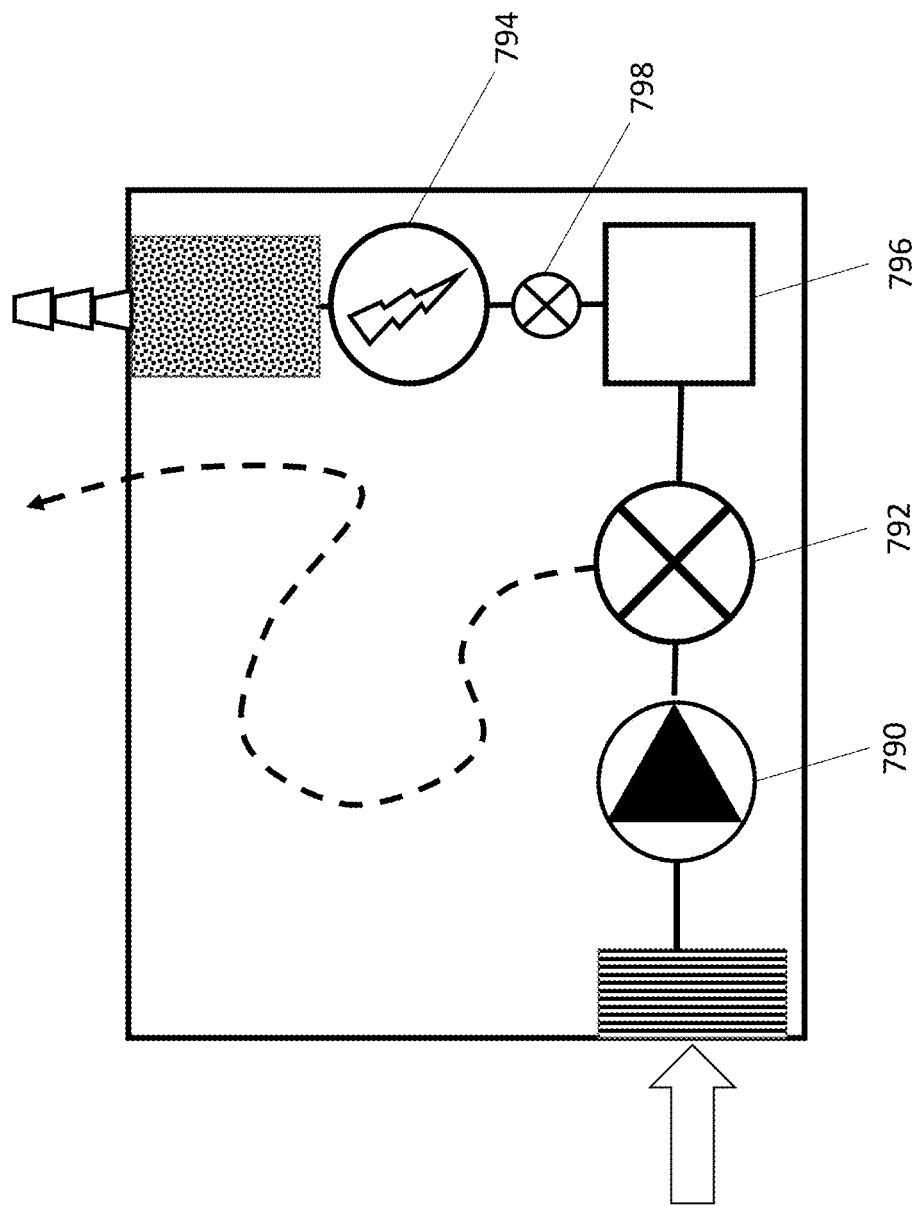
FIG. 47 is an embodiment of an NO generation device that is used to deliver reactant gas to plasma chamber and to push gas for cooling the system using a reservoir.

Pulsed delivery of NO can require rapid changes in reactant gas flow rate. NO generation also generates heat. In some embodiments, a pump within a NO generation device is used to deliver reactant gas to plasma chamber and to push gas for cooling the system. In some embodiments, the pump runs continuously and a diverter valve directs reactant gas to a plasma chamber when a pulse of NO is to be delivered but otherwise delivers gas to the device enclosure for cooling (FIG. 46). FIG. 46 depicts ambient air entering the system through a filter. A pump 780 directs reactant gas to a diverter valve 782, where gas either enters the enclosure for cooling or continues to the plasma chamber 784. Reactant gas is converted to NO-containing product gas in the plasma chamber prior to going through a filter/scrubber assembly 786 and leaves the enclosure through a cannula connection. In some embodiments as shown in FIG. 47, a pump 790 directs reactant gas to a diverter valve 792. As shown, there is a reservoir 796 with another valve 798 prior to a plasma chamber 794 so that the reservoir 796 can be pressurized between breaths. This reservoir embodiment enables a system to use a smaller pump since it does not have to deliver the entire pulse flow rate (FIG. 47).

The number of moles of NO delivered within a pulse of gas is a function of the pulse concentration, pulse flow rate and pulse duration. In some embodiments, a system detects an inspiratory event as quickly as possible. It then holds the flow rate and duration of a pulse constant and only varies the concentration of the NO pulse. Concentration of the NO pulse is controlled by altering plasma parameters, one or more of plasma frequency, plasma duty cycle, plasma power, primary circuit AC waveform shape, burst count, a burst period, voltage, and a burst duty cycle. In some embodiments, the NO pulse duration is based on respiratory rate, shortening as respiratory rate increases and increasing the concentration correspondingly to ensure constant moles of NO per breath. In some embodiments, an NO generator adjusts the NO dose in moles per breath in proportion to patient activity level. In some embodiments, the number of moles per breath is altered in order to maintain a prescribed run rate of NO delivery. In some embodiments, the prescribed run rate is specified in moles of NO per minute, or mg per hour. In some embodiments, patient activity level is measured with a three-axis accelerometer.

In some embodiments, the concentration of NO within an inspiratory pulse is varied within the NO pulse. This approach, as well as varying pulse timing with respect to breath initiation, can provide an ability to deliver specific concentrations of NO to specific regions of the lung. In some embodiments, the NO concentration is maximized at the beginning of the NO pulse and ramped down as the breath continues (a sawtooth shape with a very steep onset). This approach provides variable dosing within the lung with the highest dose going the deepest within the lung. In some embodiments, the concentration of a NO pulse is proportional to the inspiratory flow rate, beginning at a low concentration, increasing to a high concentration and then decreasing to a low concentration. This approach enables an NO generation and delivery device to create a constant concentration within the inspired gas of a breath. A constant concentration of NO within a breath can be beneficial when dosing otherwise healthy lung to treat infections, for example. Exemplary embodiments are shown in FIG. 48A, FIG. 48B, FIG. 48C, and FIG. 48D. FIG. 48A depicts a constant concentration pulse 800 delivered to the patient at constant flow rate during the initial portion of inspiration. FIG. 48B depicts an NO pulse at or near the beginning of an inspiratory event where the pulse flow rate changes (increases) throughout the duration of the pulse 802 and NO concentration remains constant. FIG. 48C depicts an NO pulse 804 lasting the duration of an inspiratory event with constant concentration NO. FIG. 48D depicts a constant flow NO pulse 806 of varying concentration. By increasing the NO pulse concentration as inspiratory flow rate increases, the inhaled concentration can be controlled. In some embodiments, the NO pulse flow and concentration are controlled to achieve a constant NO concentration in the dosed regions of the lung. In some embodiments, NO concentration and flow rate are both varied to deliver NO concentrations within the lung to desired levels.

In some embodiments, the flow rate of a NO pulse is varied in proportion to the velocity of a patient's inspiratory flow rate. In some embodiments, a patient's inspiratory flow rate is detected by a dedicated lumen for measuring pressure within the nares. Vacuum pressure within the lumen is a proxy for inspiratory flow rate. In some embodiments, the flow rate of the NO pulse is varied in proportion to the inspiratory flow rate of the patient to provide an even dose of NO within the breath.

In some embodiments, the plasma and flow settings are set to optimize for battery life and the pulse duration adjusts to provide the correct dose.

In some embodiments, an ambulatory NO generation system doses the breath of a patient while tracking a target dose to be delivered per unit of time (for example, mg/hour). As patient respiratory rate varies, the NO generation system varies the concentration of NO gas pulses in each breath to maintain a dosing run rate equal to the target dose per unit of time. In some embodiments, an NO generation system skips a breath by not delivering a gas pulse in order to maintain the dosing run rate equal to the target dose per unit of time. In some embodiments, an NO generation system delivers a gas pulse with no NO (for example, concentration at or near 0 ppm, i.e. air) in order to maintain the dosing run rate equal to the target dose per unit of time.

In some embodiments, a pulsed NO delivery system can make the pulse longer, as needed, to keep production levels at an acceptable level while still delivering the target moles of NO. A pulsed delivery NO device can vary pulse duration, pulse concentration and/or pulse flow rate to control the dose of NO to the patient. In some embodiments, the pulse duration and pulse flow rate are held constant and only the pulse concentration is varied with each breath. The pulse duration can be a fixed time duration or can be a fixed percentage of the respiratory period. In some embodiments, as pulse duration shortens due to decreasing inspiratory time and the flow remains the same, the concentration of the pulse increases to maintain a dosing target. In some embodiments, as respiratory rate increases, (decreasing respiratory period) and the flow rate remains the same, the concentration of the pulse decreases to maintain a dosing target because there are more breaths/pulses per minute. There can be limitations to the amount of NO concentration that a device can produce. Thus, in some embodiments, a pulsed NO delivery system prevents further decreases in pulse duration when the system reaches a maximum NO production limit during a pulse. In some embodiments, a pulsed NO delivery system increases the pulse flow rate when maximum NO production limits are reached in order to provide target NO dosing. In some embodiments, a pulsed NO delivery system adjusts both the pulse duration and pulse flow rate in the event that NO production demand exceeds NO production limits.

In some embodiments, a light source within a controller illuminates a portion of the disposable scrubber to display status. In some embodiments, a portion of the disposable functions as a light pipe and glows to show status. For example, the outer surface or edge of a scrubber could flash red when it needs to be replaced.

In some embodiments, a light shines inside a scrubber cartridge to make the interior of the cartridge glow as an indication of scrubber status.

In some embodiments, a groove is provided on a side of an ambulatory device to help manage an oxygen delivery tube. This way $O_2$ can be routed to the back of the device with close management.

In some embodiments, a reactant gas pump runs continuously, and diverter valve is used to direct gas towards the patient or away from patient. In some embodiments, gas directed away from the patient is released into the device enclosure to assist in device cooling (FIG. 46).

In some embodiments, an ambulatory system can run continuously, treating a patient night and day. Thus, in some embodiments it is not desirable for an ambulatory system to be easily shut down by the user. However, an emergency shut off feature can be used in the event of a malfunction. In some embodiments, a feature on a cannula can be used as an input signal to the system to shut down. In some embodiments, a key feature on a cannula can be used to deactivate a controller. This key feature can be inserted into the ambulatory device enclosure in a way that shuts down the system. In some embodiments, the key depresses a contact switch within the controller that shuts the system down. In some embodiments, a magnet on a key feature opens a reed switch when inserted, thereby shutting down the system. In some embodiments, two recessed buttons on either side of the system can be pressed simultaneously to shut the system down.

Cannula

The generated NO in the form of the NO-enriched product gas can be delivered to the patient in a variety of ways. In some embodiments, the NO is delivered through a nasal cannula. Patients report discomfort with cannula flow rates of 15-20 lpm and beyond. If $O_2$ and NO are delivered in a pulsatile fashion simultaneously, the net flow rate could exceed the comfort threshold of the patient. In some embodiments, the pulse from an NO generation device is much longer than that of a pulsed oxygen delivery device. In some embodiments, the flow rate of the NO pulse is much lower in flow rate so that the summation of the $O_2$ and NO pulses are not uncomfortable. In some embodiments, the NO device generates NO within the $O_2$ pulse of an $O_2$ concentrator. In some embodiments, NO is generated in the ambient air before entering an $O_2$ concentrator. In some embodiments, an $O_2$ concentrator is programmed to deliver slower flow rate, longer pulses so that NO can be delivered simultaneously or earlier with respect to the inspiratory event. In some embodiments, the NO pulse is delivered after the $O_2$ concentrator pulse so that nasal cannula flow rates do not exceed patient comfort thresholds. In some embodiments, NO pulse generation is triggered to begin by the end of the $O_2$ pulse to prevent overlap.

$NO_2$ formation from NO occurs as a function of exposure time to oxygen-containing gas. Decreasing the volume of a gas pathway between NO generator and patient can reduce the exposure time and thus reduce inhaled $NO_2$ levels. In some embodiments, the gas pathway volume can be reduced by inserting one or more objects into the NO delivery lumen of a nasal cannula to decrease the volume of the pathway inside the nasal cannula and thereby decrease transit time of the product gas. In some embodiments, a filament is inserted into the NO delivery lumen of a nasal cannula, leaving sufficient cross-sectional area for NO flow. In some embodiments, the filament is made with a selective $NO_2$-absorptive material. In some embodiments, a cannula lumen is filled with soda lime pellets to scrub NO-containing gas and reduce transit time. A filter is located between the scrubber material and patient to control particulates. It will be understood that any suitable material can be inserted into a cannula to decrease the volume therein.

Figure 49A:
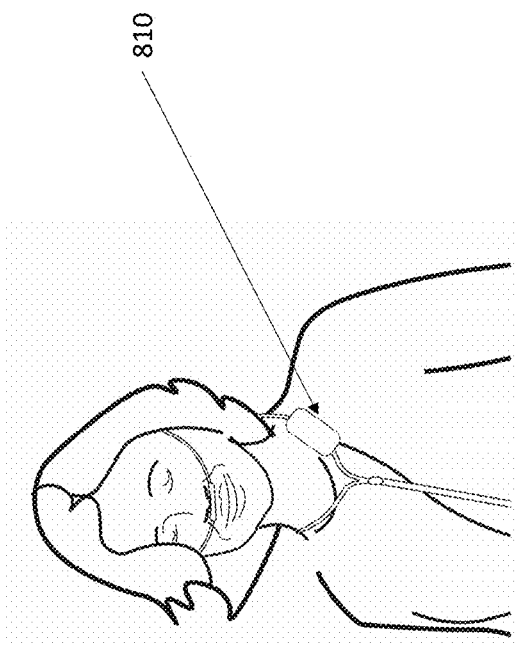
FIG. 49A is an embodiment of a portable NO generation system with a proximal scrubber.

In some embodiments, a proximal scrubber 810, as shown in FIG. 49A, can be used to decrease $NO_2$ levels within an NO pulse. Use of a proximal scrubber can inhibit the propagation of pressure waves through a delivery device (cannula) that could be used to detect patient inspiratory events. In some embodiments, a dual lumen cannula is used where the proximal scrubber is in the NO delivery lumen and the $O_2$ delivery lumen is patent (open). The NO delivery system senses inspiratory events through the $O_2$ lumen. In some embodiments, a proximal scrubber includes a proximal filter to prevent scrubber materials and other types of particulate from reaching the patient.

In some embodiments of an ambulatory or portable NO generation system, a cannula can have a proximal scrubber and a distal scrubber. The distal scrubber can connect to a NO generator. The NO generator does not include a scrubber. In this way, all the disposable components are in one assembly. It also enables the controller to be lighter. In some embodiments, the distal scrubber (controller end) includes one or more filters for filtering incoming air for cooling the controller and/or reactant gas.

In some embodiments, characteristics of the back pressure from the cannula as NO is delivered is used as an indicator that the correct cannula is being used. In some embodiments, one or more back pressure characteristics are used to confirm whether or not a cannula is connected. In some embodiments, one or more back pressure characteristics are used to detect leaks in a cannula or cannula connection. In some embodiments, one or more back pressure characteristics are used to detect whether or not there are kinks in the cannula. Back pressure characteristics that can be used for this purpose can include one or more of back pressure magnitude, peak pressure timing with respect to pulse delivery, pressure pulse rise rate, and pressure pulse decay rate. In some embodiments, cannula back pressure is detected by a pressure sensor within the controller. In some embodiments, cannula back pressure is detected by the breath detection sensor.

Figure 49B:
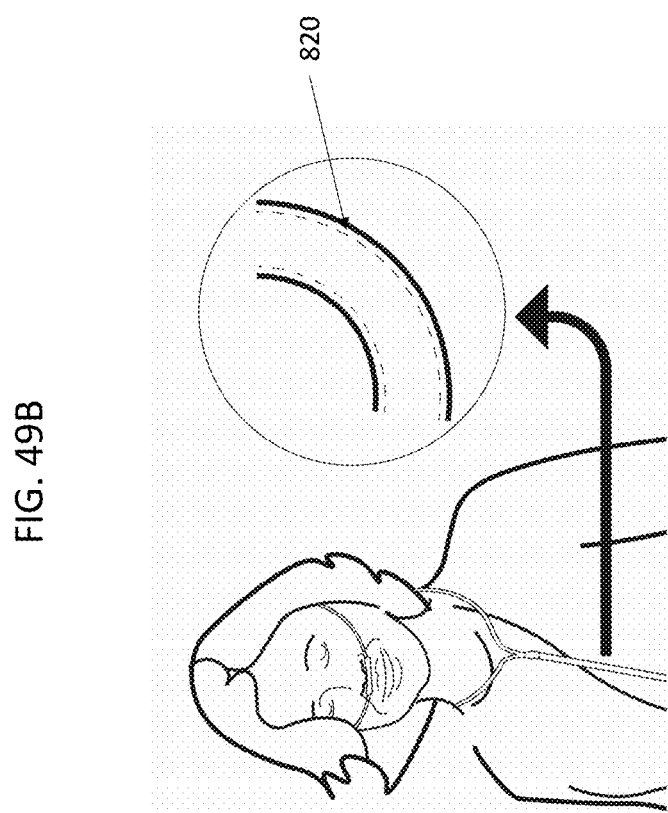
FIG. 49B is an embodiment of a portable NO generation system with a scrubber-lined delivery device.

In some embodiments, a cannula can be constructed from a composite material extrusion containing soda lime or another $NO_2$-scrubbing material. The outer surface of the extrusion can be coated with a biocompatible material since it is skin-contacting. FIG. 49B illustrates an embodiment of a cannula 820 lined with an $NO_2$-absorbent material. In some embodiments, a filter is located at the proximal (patient) end of the cannula to prevent scrubber material from migrating from the cannula to the patient.

Figure 50:
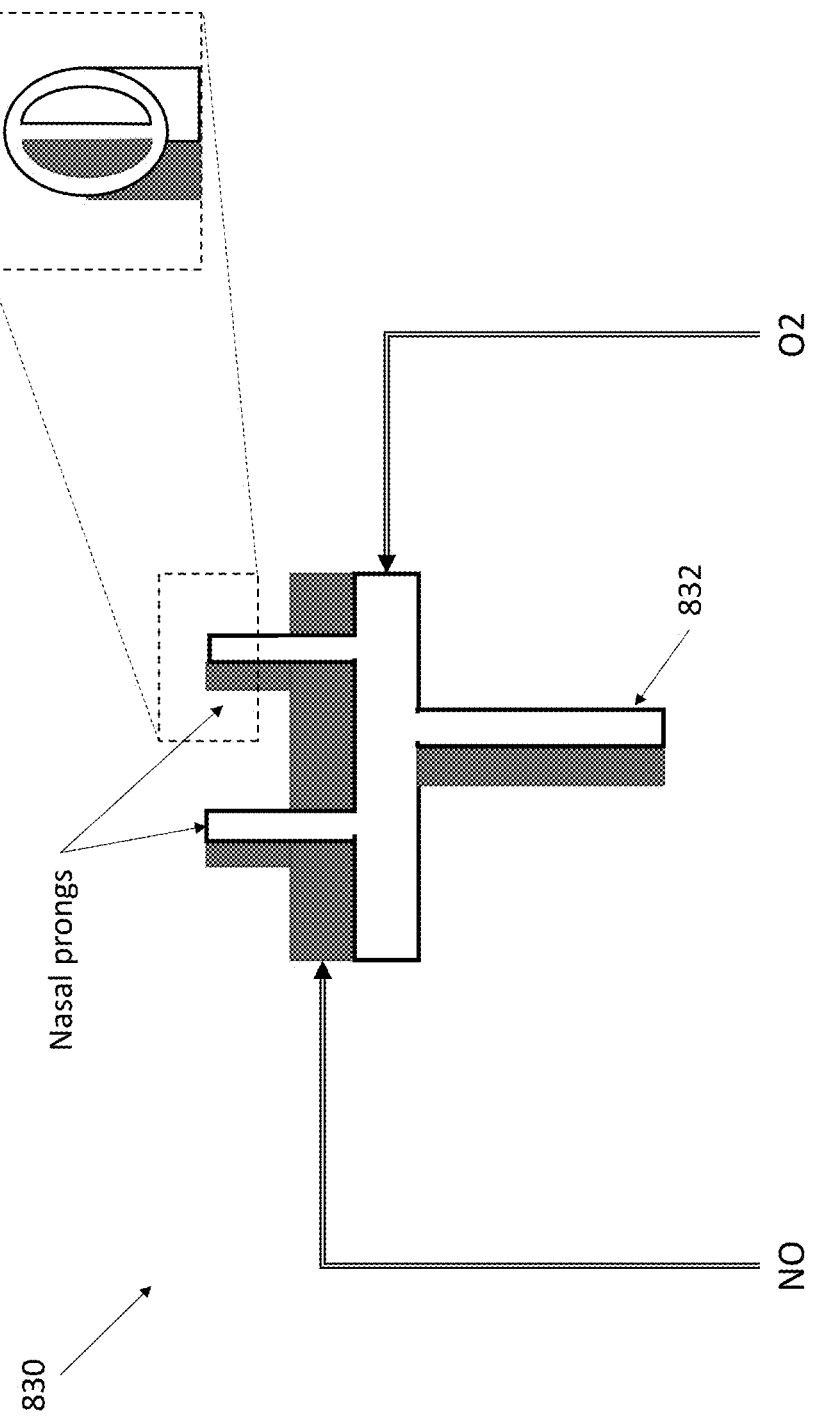
FIG. 50 is an embodiment of a triple lumen cannula for delivering product gas to a patient.

In some embodiments, a nasal cannula 830 for combined $O_2$ and NO delivery can include a mouth piece or prong 832 for patients that tend to breathe through their mouth (FIG. 50). In some embodiments, NO and $O_2$ are separated by a septum in each of the prongs and only mix after ejection from the cannula. In some embodiments, the mouth lumen is fully independent from the nasal lumen(s) and can be used to detect mouth breathing via pressure sensor or microphone to detect changes in pressure.

In some embodiments, breath is detected by measuring $CO_2$ levels near the patient. In some embodiments, capnography is used to measure $CO_2$. As the patient exhales, high levels of $CO_2$ are measured. As $CO_2$ levels reach atmospheric levels, the end of exhalation occurs. This can serve as a trigger point for an NO generator to begin production and/or delivery of NO for the next breath.

In some embodiments, there is a lumen in the cannula to pull NO back into the controller. NO travels in a circuit down the cannula and back, like a ventilator circuit. When the patient inhales, a valve closes at the controller so that flow enters the patient. In some embodiments, recirculated NO gas is scrubbed a second time as it passes through either the controller or scrubber cartridge. In some embodiments, NO gas is scrubbed near the patient, after exiting the recirculation loop but prior to injection into the patient. Recirculation of NO product gas in this way keeps the NO scrubbed of $NO_2$ while enabling the device to be very responsive to detected breaths because there is NO available near the patient's nose. In some embodiments, recirculation mode could flow at a faster flow rate than NO delivery. In some embodiments, a system stages a NO pulse at the patient end of the cannula with a rapid recirculation flow rate. In some embodiments, this can be done in response to sensing the breath. This enables the system to transport the pulse at a flow rate that exceeds the comfort level and reduces transport and storage time.

Figure 51:
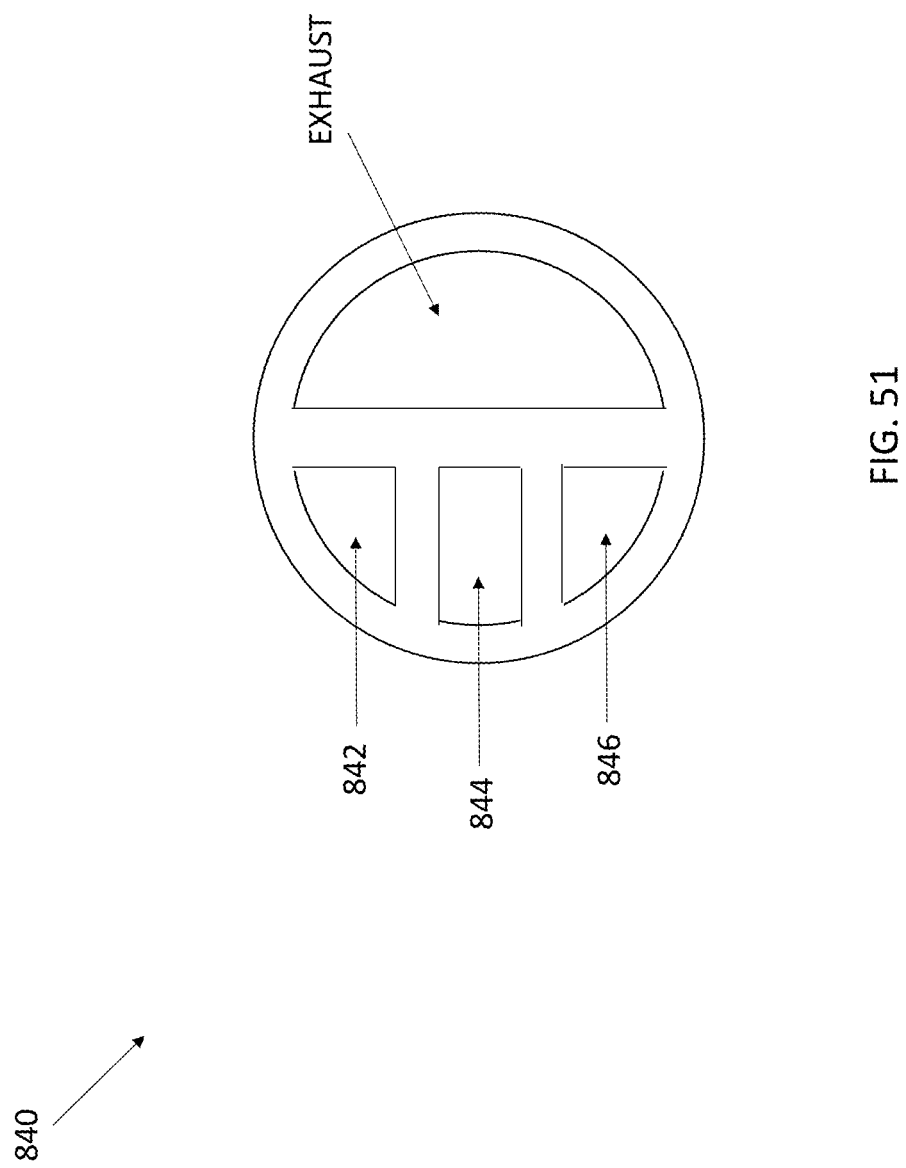
FIG. 51 shows an embodiment of a cannula with a return path with a large cross section.

In some embodiments, the return path within a cannula 840 has a large cross section to be at low pressure, as shown in FIG. 51. The larger cross-section decreases the flow resistance for the NO controller, decreasing pump energy and conserving energy. As shown in FIG. 51, a cannula can have a lumen 844 for NO and a lumen 846 for $O_2$. Having a separate lumen 842 for breath detection improves the signal strength of the inspiration event which can result in improvements in breath detection sensitivity and reliability, enabling faster breath detection. In some embodiments, the product gas that returns to the controller is scrubbed for NOx and released to atmosphere. In some embodiments, the returning product gas is scrubbed for $NO_2$ and passed back through the plasma chamber as reactant gas.

In some embodiments, $O_2$ and NO lumens can be different diameters within the cannula. The NO lumen can be smaller to decrease transit time.

In some embodiments, a cannula has three lumens. A first lumen is for NO delivery to a chamber located at or near the nasal prongs. A second lumen delivers $O_2$ to a separate chamber at or near the nasal prongs. A third lumen pulls gas from the NO chamber located at or near the nasal prongs. In some embodiments, the third lumen is additionally used for breath detection and for priming the cannula. Priming the cannula involves pushing NO gas through the NO lumen while simultaneously pulling NO from the patient end of the cannula at a same or higher flow rate back to the controller.

Priming gas can be of variable concentration and is disposed of in most cases, rather than using it to treat the patient. The NO device can pass the priming gas through an $NO_2$ or NOx scrubber prior to releasing to atmosphere. In some embodiments, the $NO_2$ or NOx scrubber is part of the controller. In some embodiments, the $NO_2$ or NOx scrubber for priming is part of the cannula.

In some embodiments, $SpO_2$ can be measured between the prongs of a nasal cannula through the nasal septum. Optical fiber runs up the cannula lumen. In some embodiments, the cannula is used as a light pipe for making $SpO_2$ measurements.

In some embodiments, the cannula has a memory device that includes the device prescription.

In some embodiments, the system can detect what kind of delivery device is connected to the system (example: mask, cannula). Detection can be made by optical, mechanical, electrical, wired, wireless, RFID, Bluetooth, WiFi, or other means.

In some embodiments, a color indicator changes color in the presence of $CO_2$ from exhalation. Optical fiber conducts color information along the cannula to the controller. An optical sensor or video chip is used to detect the color. The cannula can act as a light pipe.

Figure 52:
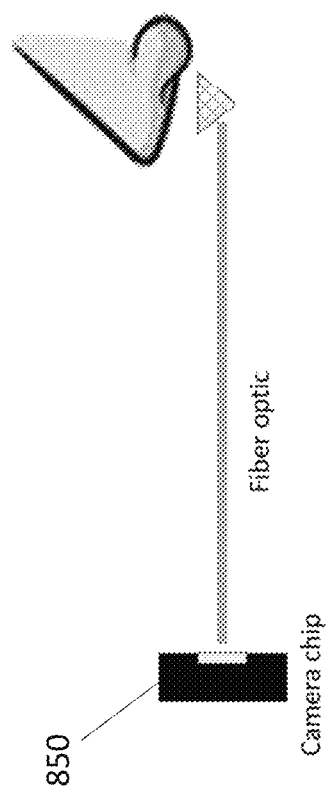
FIG. 52 illustrates an embodiment of a camera chip used for breath detection in an NO generation system.

In some embodiments, a camera chip 850 is used for breath detection, as shown in FIG. 52. In some embodiments, the camera chip is located in a NO generation and delivery device. In some embodiments, the camera chip is located in a delivery device (e.g. cannula, gas canister delivery device). Optical information is communicated to the camera chip through one or more optical fibers. Breath detection is accomplished by visualizing changes in the nostril by means of one or more of the following indicators: fogging of the optics due to humidity of exhaled gases, motion of nasal tissue, motion of nasal hairs, changes in color to a chemical sensor (e.g. litmus) that changes color in the presence of $CO_2$ during exhalation, changes in color to a sensor that changes color based on temperature (e.g., thermochromic liquid crystal).

In some embodiments, a thermopile is located near the patient nose or mouth and used for breath detection by detecting the temperature difference between inhaled and exhaled gas. In some embodiments, the thermopile and associated wires are integrated into a nasal cannula.

Pulsed Delivery

Pulsed delivery from a portable NO generator requires a triggering event. In some embodiments, pressure fluctuations within a lumen of the cannula are used to detect an inspiratory event.

In some embodiments, a NO pulse is generated and delivered based on a patient breath signal, where the breath signal could be one or more of the following inputs: patient chest wall strain, chest band strain, chest impedance, bioimpedance, chest sounds, temperature change in gas near the patient's nose/mouth, $CO_2$ concentration change in gas near the patient's nose/mouth, $O_2$ concentration change, or diaphragm EMG signal.

A breath begins by diaphragm muscle contraction. Thus, an NO generation system can use diaphragm activity as a control parameter to control the generation of NO. In some embodiments of an NO generation and delivery system, the system senses diaphragm activity using an EMG signal using an EMG sensor 860 for breath detection, as shown in FIG. 53. This triggers an NO generation system to begin delivering a NO pulse earlier than a cannula pressure detection approach (typical breath detection). This enables the nasal cavity to be primed with NO before actual inspiratory flow begins. In addition, the use of diaphragm activity as an indicator of patient breathing can detect shallow breaths as can occur during sleeping more accurately. In some embodiments, an NO generator generates and delivers a pulse of NO containing gas to a nasal cavity before nasal cavity air flow begins, thereby enabling the NO to travel deeper into the patient lungs. Improved detection of an inspiratory event enables a system to dose more breaths, thereby decreasing the NO concentration per breath which in turn decreases the delivered $NO_2$ concentration.

Leaving NO within a nasal cannula or other delivery device between breaths can result in increases in $NO_2$ concentration in the inspired gas due to oxidation of the NO. It can be possible to purge a delivery device, such as a cannula, with air or other gases to remove NO and/or $NO_2$ and prevent aging of the delivery device. For example, an eNO device can purge a cannula with air after NO delivery to prevent NO from stagnating within the delivery lumens and converting to $NO_2$. Purging timing can vary. For example, a purge can be done after each NO pulse (every breath), after treatment is shut down, or both. In some embodiments, the cannula is purged with air during patient exhalation. In some embodiments, a pulsed NO delivery system stages a NO pulse within the nasal cannula prior to patient inhalation. Based on desired pulse timing, the contents of the cannula are delivered to the patient by pushing the staged NO gas through the cannula by displacing it with additional gas. If the desired pulse volume is larger than the volume of the cannula, then the plasma is turned on at the beginning of pulse delivery to generate additional NO in the reactant gas flow as the pulse is delivered. Once the target volume/dose/moles of NO have been generated, the plasma is turned off while the reactant gas continues to flow to the end of the cannula, thereby leaving the cannula filled with air. The system pauses gas flow until a moment in time before inspiration begins to prime the cannula again with NO to repeat the process. In some embodiments, cannula priming occurs when a diaphragm EMG signal is detected. In some embodiments, the timing of cannula NO priming is based on analysis of the timing of prior breaths. In some embodiments, cannula priming is complete prior to the expected time of breath detection so that there is a cleaner signal for breath detection within the cannula. FIG. 54A and FIG. 54B illustrate a method of priming and purging a cannula. FIG. 54A represents the length of the cannula oriented vertically. The cannula begins this sequence empty and then fills with NO gas, depicted in black. FIG. 54B, aligned in time with FIG. 54A, begins at the beginning of patient exhalation. Part-way through exhalation, the reactant gas flow and plasma are turned on to prime the cannula with NO gas. Once the cannula is filled, the reactant gas flow and plasma generation are turned off. The device waits for the breath detection event 870. When breath detection occurs, reactant gas flow and plasma activity are resumed. Plasma activity turns off once the target amount of NO per pulse has been generated while gas flow continues until the entire pulse has been delivered and the cannula is devoid of NO gas again. In some cases, the cannula volume is larger than the target pulse so that a sufficient bolus of NO exists in the cannula from priming and plasma generation does not turn on during patient inspiration.

Pulse Generation

Figure 55A:
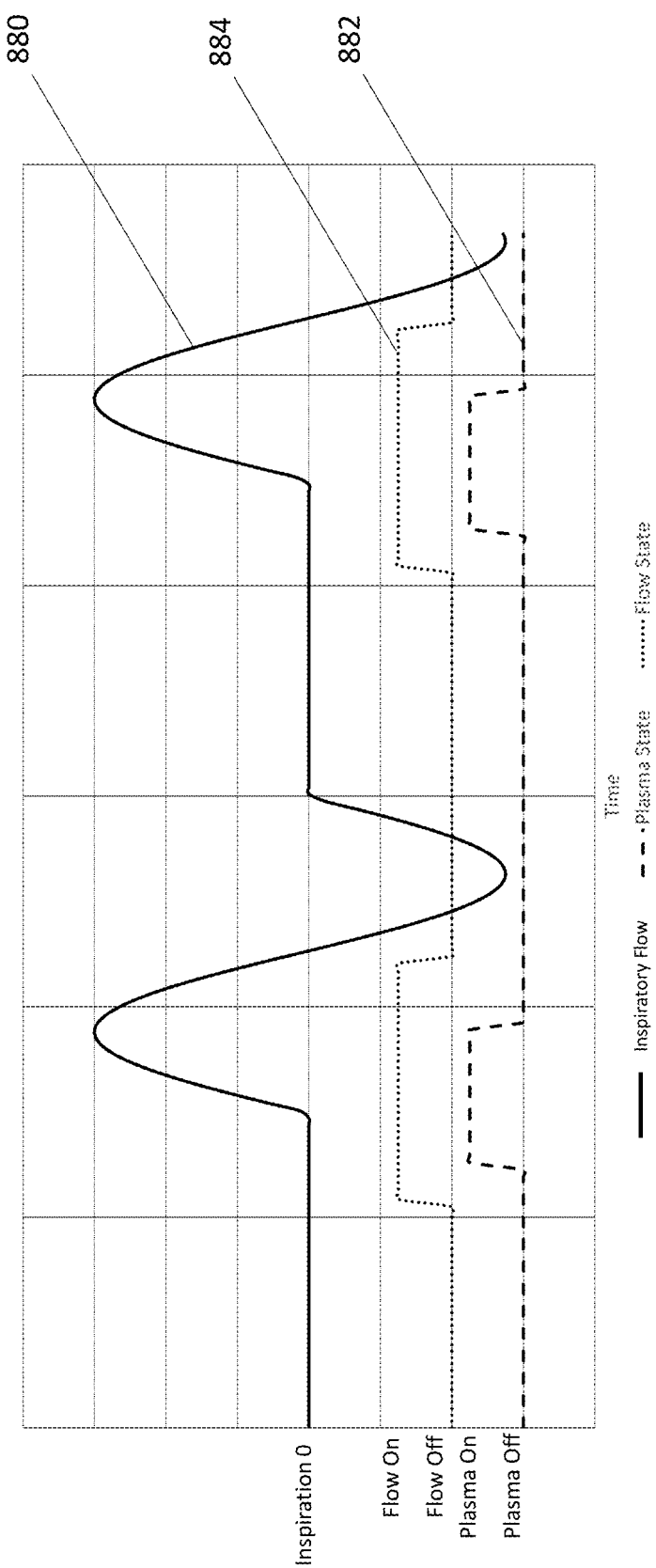
Figure 55B:
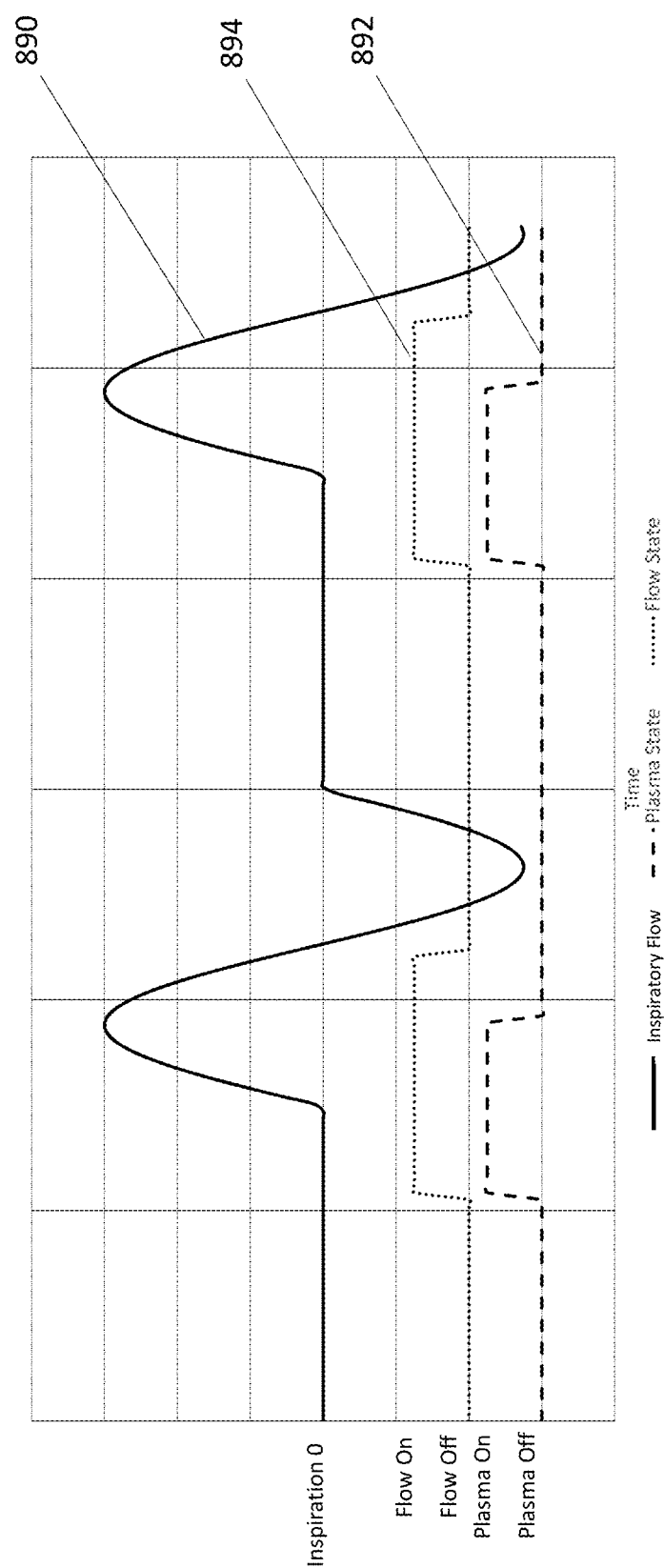

It can take time to increase the speed of a pump from zero to a target rotational rate. In a pulsed-NO delivery system, the pump can be turned on before the breath is detected to provide additional time to reach a target speed. Plasma can be turned on at the same time as the pump or be delayed. In some embodiments, plasma is initiated when breath is detected. FIG. 55A and FIG. 55B illustrate exemplary embodiments of timing a pump ahead of a pulse. In FIG. 55A, a pump is turned on ahead of plasma to provide time for gas flow to come up to speed. Plasma is activated prior to the inspiratory event, based on the timing of prior breaths. Once the target amount of NO has been generated in a bolus, plasma activity ceases. The pump can stay on longer than plasma to purge all NO through the scrubber and cannula. By keeping the cannula filled with air between breaths, there is no $NO_2$ formation from stagnant NO residing in the cannula. The inspiratory flow 880, plasma state 882, and flow state 884 over time are shown in FIG. 55A.

In FIG. 55B, pump onset coincides with NO generation (pre-breath detection) such that a pump can be turned on at the same time as plasma. The pump stays on longer than plasma to purge all NO through cannula. The inspiratory flow 890, plasma state 892, and flow state 894 over time are shown in FIG. 55B.

In some embodiments, an NO generation device includes an independent lumen in the delivery device for breath detection. Delivery devices include but are not limited to nasal cannulas, masks (CPAP, face, nasal CPAP), endotracheal tubes, and tracheal catheters.

In some embodiments, reactant gas flow is on all the time, and can produce a graph such as the one shown in FIG. 55C. Plasma is activated in anticipation of the inspiratory event to provide time for the NO pulse to travel the length of the cannula to the patient and arrive at the patient at or near the onset of inspiration. In some embodiments, the concentration of the product gas from the NO device is the same for all pulses. In some embodiments, the concentration of the pulse varies with the duration of the pulse, respiratory rate and/or the target dose of NO for the patient. The plasma turns off after the desired amount of NO has been generated for a given NO bolus. The pump continues pushing reactant gas through the system, delivering the NO bolus to the patient. The inspiratory flow 900, plasma state 902, and flow state 904 over time are shown in FIG. 55C. This approach provides the advantage of generating NO on demand, avoiding $NO_2$ formation associated with stagnant air+NO within a cannula between breaths. In some cases, this approach has the potential to improve oxygenation by flushing out the nasal sinus with atmospheric levels of oxygen between breaths.

Figure 55D:
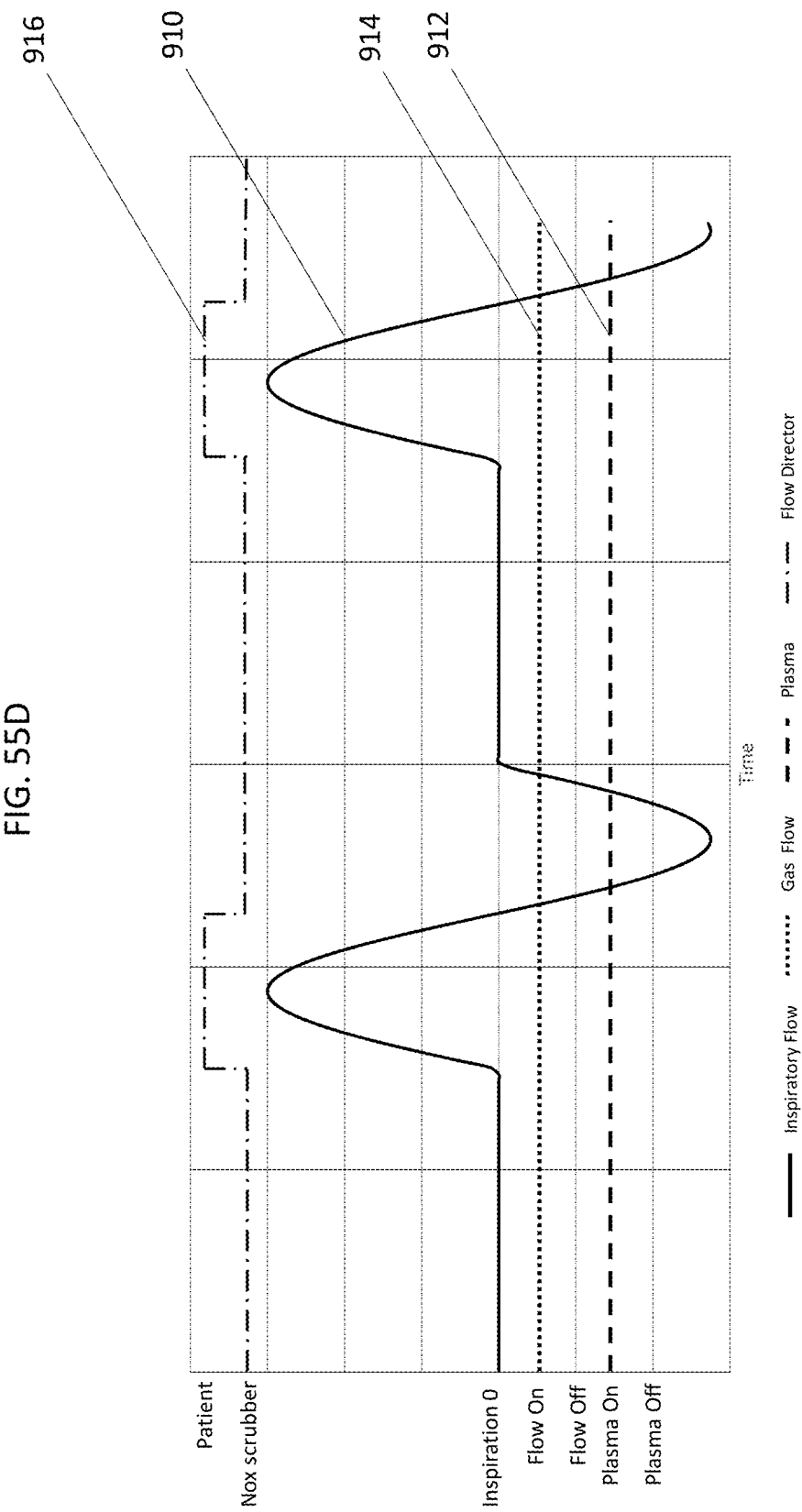

In some embodiments, reactant gas flow and plasma activity are on all the time. Product gases, i.e. gases containing NO, are directed with a flow director valve either towards the patient or towards a NOx filter. FIG. 55D presents a graph showing the position of the flow director either toward the patient or toward the NOx scrubber. In some embodiments, the NOx filter is an activated charcoal filter. This embodiment involves leaving air+NO within the cannula between breaths. In some embodiments, a proximal scrubber or scrubbing cannula is required to reduce $NO_2$ levels to acceptable levels prior to inhalation. The inspiratory flow 910, plasma state 912, flow state 914, and the position of the flow director 916 over time are shown in FIG. 55D.

In some embodiments, the system component that moves the gas, such as a pump, turbine, diaphragm, or pressurized cylinder, is on all the time. The system can have two states during treatment: 1) flow directed towards patient with plasma on, and 2) flow directed towards atmosphere with plasma off.

In some embodiments, the pump is on all the time. Reactant gas is flowed either to the patient or to the internals of the device enclosure for cooling based on the position of a flow director.

In some embodiments of a portable NO generation and delivery device, a charging base station measures environmental $NO_2$ and communicates with the generation and delivery device to change NO production parameters and/or alarm when environmental $NO_2$ levels are too high. The alarm can be generated by the charging base or the NO generation device.

Service

In some embodiments, the wearable pump components are easily replaceable for the user. In some embodiments, the diaphragm of a diaphragm pump is part of a scrubber cartridge. In some embodiments, permanent binary valves are used to control gas flow into and out of the pump chamber. In some embodiments, check valves to control gas flow into and out of the pump chamber are also included in the scrubber cartridge and disposable. In some embodiments, the check valves are one of more of the following types: ball & cage valve, flapper valve, duck bill valve.

Face Mask Design

In some embodiments, a scrubber in or at the face mask can act as a secondary scrubber for high dose NO delivered to a patient. In some embodiments, the face mask has an outlet port that connects to a tube that connects to the ventilator or other gas source. In some embodiments, a face mask has a scrubber on the outlet port to remove $NO_2$ and/or NOx. This facilitates the use of a bias flow and enables scrubbing of the exhaled gas and treatment gas before release into the environment.

Vibration

In some embodiments, a pump has inertia and can apply a torque to a portable NO generator when the motor starts. This sort of twisting of an NO device could be distracting and/or uncomfortable for a user wearing the device. In some embodiments, the speed of the pump motor is ramped to prevent a sudden rotation of the NO generation device when the pump starts. In some embodiments, the motor runs all of the time at varying speeds so that it is not starting from a stand-still, thereby requiring less torque.

In some embodiments, a pump runs continuously with its speed selected so that it can fill a reservoir to a target pressure prior to the next inspirational pulse. This approach minimizes pump noise and vibration and can save energy.

Breath Detection

In some embodiments, an accelerometer on either the chest wall or abdomen is used to detect respiration. In some embodiments, the device uses a breath detection sensor to detect pulsations associated with snoring. In some embodiments, a nitric oxide generation system delivers a pulse during the snoring noise (inhalation). Snoring detection can be detected by various devices, including but not limited to a microphone, accelerometer, pressure sensor and other means.

Various inputs can be used related to breath detection to alter control parameters to adjust the generation of NO. In some embodiments, the sensitivity of breath detection can be adjusted based on time of day (for example, during sleep). In some embodiments, the sensitivity can be adjusted based on activity level. While activity level can be detected using various techniques, in some embodiments, activity level can be sensed by an accelerometer. In some embodiments, breath detect sensitivity can be adjusted based on ambient noise. In some embodiments, a NO generator measures ambient noise levels with a microphone and increases the breath detect threshold as ambient noise levels increase to decrease the potential for a false breath detect event.

In some embodiments, exhalation can be detected by detecting elevated levels of $CO_2$ gas over ambient. A corollary is that low level, near-atmospheric levels of $CO_2$ can be used for inspiration detection.

Inline NO Generator

Figure 56:
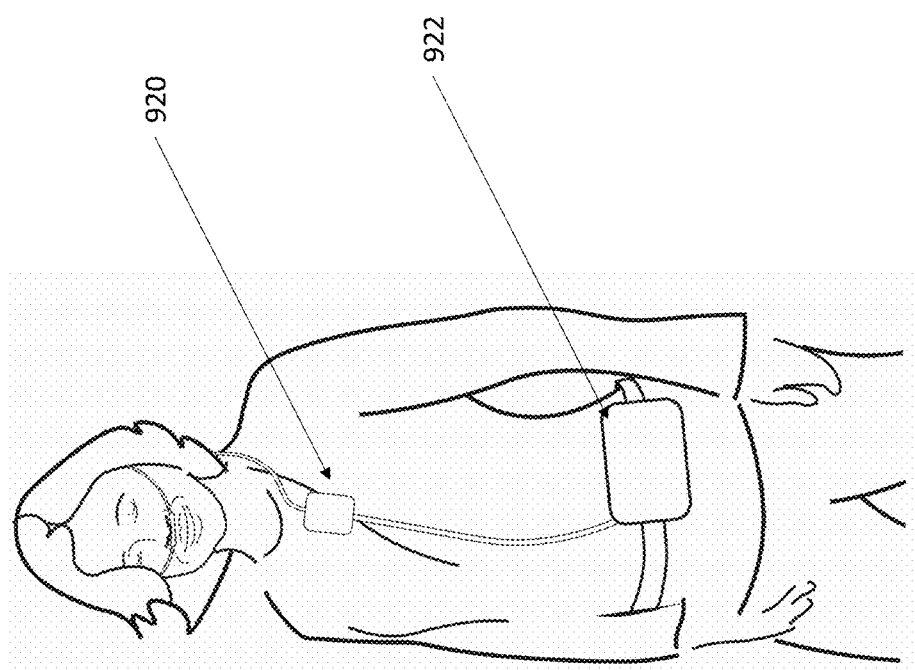
FIG. 56 illustrates an embodiment of an NO generator inline of a cannula and closer to the head of the patient.

In some embodiments, a proximal NO generator is located in between an inspiratory gas source and patient's mouth/nose. FIG. 56 illustrates an embodiment of an NO generator 920 inline of a cannula and closer to the head of the patient, with a battery pack 922, user interface, and controller being configured to be worn on the waist of a patient. The inspiratory gas source may be a portable ventilator, CPAP machine, $O_2$ concentrator, compressed cylinder, house compressed air, or manual bag device, for example. In some embodiments, the NO generator is housed within the inspiratory gas source for ease of use and shared components. In some embodiments, the NO generator is a separate component from the gas source. The NO generator may be part of a cannula, for example. The benefit of building a NO generator into a cannula is that the transit time of NO to the patient and volume of residual gas in the cannula between breaths is minimized, thereby minimizing $NO_2$ levels in the inhaled gas. In some embodiments, the wearable NO generation component is disposable. The NO generation component can contain one or more of a transformer, electrodes, nozzle, plasma chamber, scrubber and filters, EMI enclosure, breath detection sensor(s), pneumatic connections and electrical connections. The breath detection signal can be stronger when the sensor is closer to the patient enabling a proximal NO generation device to more accurately and reliably detect inspiratory events. In some embodiments, the NO generator sources its own air. In some embodiments, oxygen flowing from an $O_2$ concentrator creates a venturi effect in an inline NO generator, pulling reactant gas through a plasma chamber and into the oxygen pulse. In some embodiments, the inline NO generator receives reactant gas from an external source, such as a wall outlet or wearable pump or compressor.

In some embodiments, the inline NO generator includes a transformer so that there are low voltage wires extending from the controller to the generator. In some embodiments, the low voltage wires are embedded within a cannula. In some embodiments, electrical and pneumatic connections between the cannula and controller are made with a single connector and action. In some embodiments, the inline NO generator includes batteries for one or more of powering NO generation, communicating with the treatment controller, detecting breath, and managing dose control.

Calibration Device

In some embodiments, a device can be provided that includes a plasma chamber that is controlled by a CPU or other computing device to create a defined gas mixture of $NO/NO_2$ for the purpose of verification and/or calibration of a gas monitoring device that measures NO and $NO_2$. The ratio can be set by the controller to, for example, 50 ppm NO and 5 ppm of $NO_2$. In some embodiments, the calibration device is tankless and plasma can be generated on demand with NO and $NO_2$ for calibration gas generation. An algorithm can be used to precisely control the $NO/NO_2$ ratio, and can also control performance to compensate for altitude (pressure) and weather variations (pressure, temperature, humidity). In some embodiments, the device can use a simple blower pump with a low power requirement, and a simple user interface. In some embodiments, wireless communications (RFID, WiFi, GSM, Bluetooth, etc.) can be used to support data exchange and integration into a larger system, such as a hospital quality system. In some embodiments, the calibration device can be portable such that it is compact and handheld. By providing two types of calibration gas at multiple concentrations, this single device can improve the logistics and handling associated with calibration gas cylinders.

In some embodiments, a tankless calibration device utilizes the plasma technology that will create defined NO and $NO_2$ molecules from ambient air. A pump can suck in air through a filter and push the air through a plasma chamber. In the plasma chamber an electronical controlled arc can dissociate the $N_2$ molecule and some N atoms can oxidize and produce NO and $NO_2$ molecules in enough quantity to produce a desired ratio, such as a 50 ppm NO and 5 ppm $NO_2$ concentration. In some embodiments, a critical orifice is used to ensure that the gas flow rate through the plasma chamber is consistent.

An ambient pressure sensor can provide the input to a controller to adjust the pump speed and spark frequency to create the desired calibration gas concentration independent from the weather and altitude air pressure variation. A temperature sensor and a humidity sensor can measure the ambient and/or reactant gas properties to serve as an input into a control algorithm. In some embodiments, the flow from an external gas source can be adjusted to greater than 12 lpm by the controller with a simple flow meter comprised of a known orifice and a pressure transducer. The standard sampling tube from the gas monitor can be connected to the outlet of the handheld calibration unit.

With the built-in one-way bleeder valve, it is assured that the gas monitoring sampling line will never be over pressured and will not draw in ambient air and dilute the concentration of the calibration gas.

To accommodate the simplistic calibration procedure, an 100% oxygen supply line from the wall can optionally be attached to the device to accommodate the need for HI $O_2$ calibration. A built pneumatic 3-way switch will select $O_2$ or NO/$NO_2$ calibration gas.

In some embodiments, the device is battery operated and has a simple use interface with on/off and an indicator for power, calibration gas delivery and other functions.

In some embodiments, a calibration gas generator can generate NO gas with low concentrations of $NO_2$ by use of a $NO_2$ scrubber. In some embodiments, a calibration gas generator can provide known levels of $NO_2$ by thoroughly oxidizing product gas so there is no remaining NO. In some embodiments, product gas is thoroughly oxidized by blending with an appropriate amount of pure oxygen and allowing sufficient time to fully oxidize the NO. Although the accuracy of this approach does not represent the highest accuracy of calibration gas, it can provide sufficient accuracy in some cases. For example, gas analysis benches for NO therapy are permitted to have an accuracy of 0.5 ppm+20% for NO concentrations up to 20 ppm. This provides a generous tolerance for calibration error if the NO sensor in the NO generation and delivery device is adequately stable and repeatable.

Figure 57:
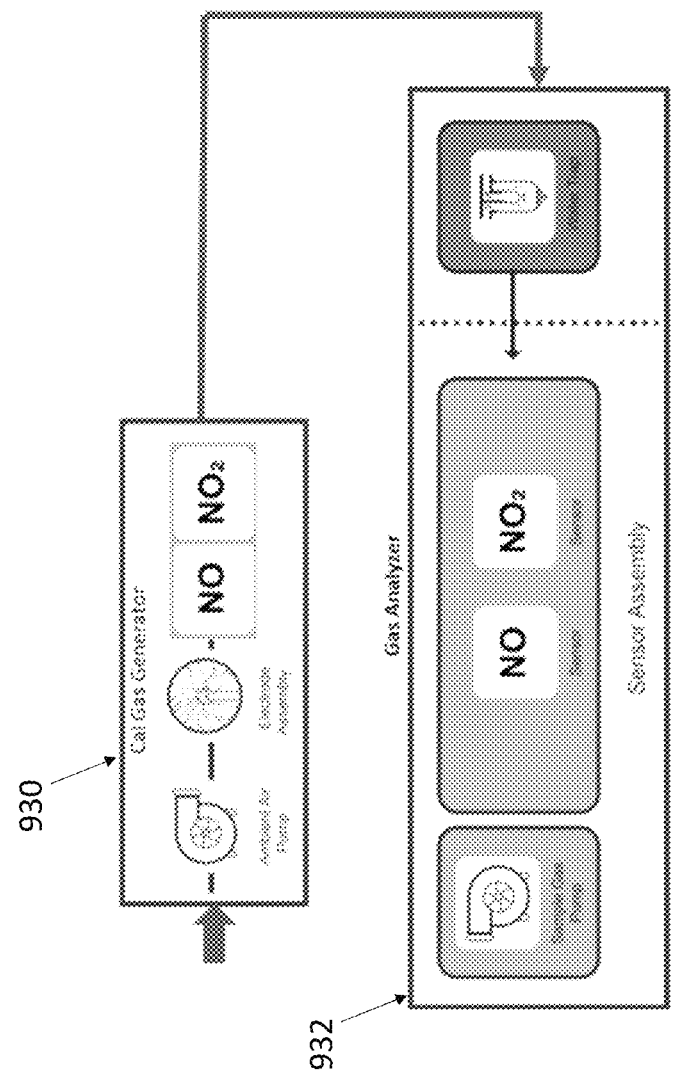
FIG. 57 is an embodiment of a calibration device configured to calibrate an NO generation device.

In some embodiments, a portable generation box can be used that makes electric NO and $NO_2$ for calibration purposes, using an electrode specifically designed for consistent NO and $NO_2$ production. In some embodiments, the electrode is in the form of a pair of spheres to ensure consistent NO generation over time, as this is the shape the electrodes approach with wear. FIG. 57 illustrates an embodiment of a device used to generate NO and/or $NO_2$ gas for calibration purposes. As shown in FIG. 57, a calibration gas generator 930 includes a reactant gas flow source and plasma chamber at a minimum. The calibration gas generator 930 outputs a product gas with known levels of NO and $NO_2$ to a gas analyzer 932. In some embodiments, the NO calibration device includes calibrated NO and/or $NO_2$ gas sensors to indicate the actual NO and $NO_2$ levels produced by the device, as shown in FIG. 59A. A production adjustment feature on the system can enable a user to tune NO/$NO_2$ gas production to a specified level prior to using the gas for calibrating an external system. In some embodiments, the production adjustment feature consists of one or more trim knobs that can be turned to adjust NO and/or $NO_2$ concentrations.

In some embodiments, additional sensors for one or more of plasma chamber pressure, ambient pressure, ambient humidity, ambient temperature, plasma chamber temperature, electrode temperature, reactant gas flow rate, and product gas flow rate, can also be included. This calibration gas is passed to a gas analyzer for calibration of internal sensors. The gas analyzer can be a stand-alone gas analyzer or an internal gas analyzer, as found in some NO generation and delivery devices.

In some embodiments, the NO to $NO_2$ ratio favors producing higher $NO_2$ levels for a high reference level. In some embodiments, this is accomplished by having more than one pair of electrodes that differ by material and or geometry so that the NO to $NO_2$ ratio is different in the product gas generated by each electrode pair. In some embodiments, the calibration gas generator relies on the NO analyzer to pull sample gas through the calibration gas generator. This has the benefit of simplifying the NO generator while also ensuring that the analyzer under calibration receives gas sample at the flow rate and pressure that it requires. In some embodiments, the calibration gas generator includes a variable pressure relive valve and/or variable reactant gas flow control so that calibration gas is presented to the analyzer under test with the appropriate flow rate and pressure.

Figure 58:
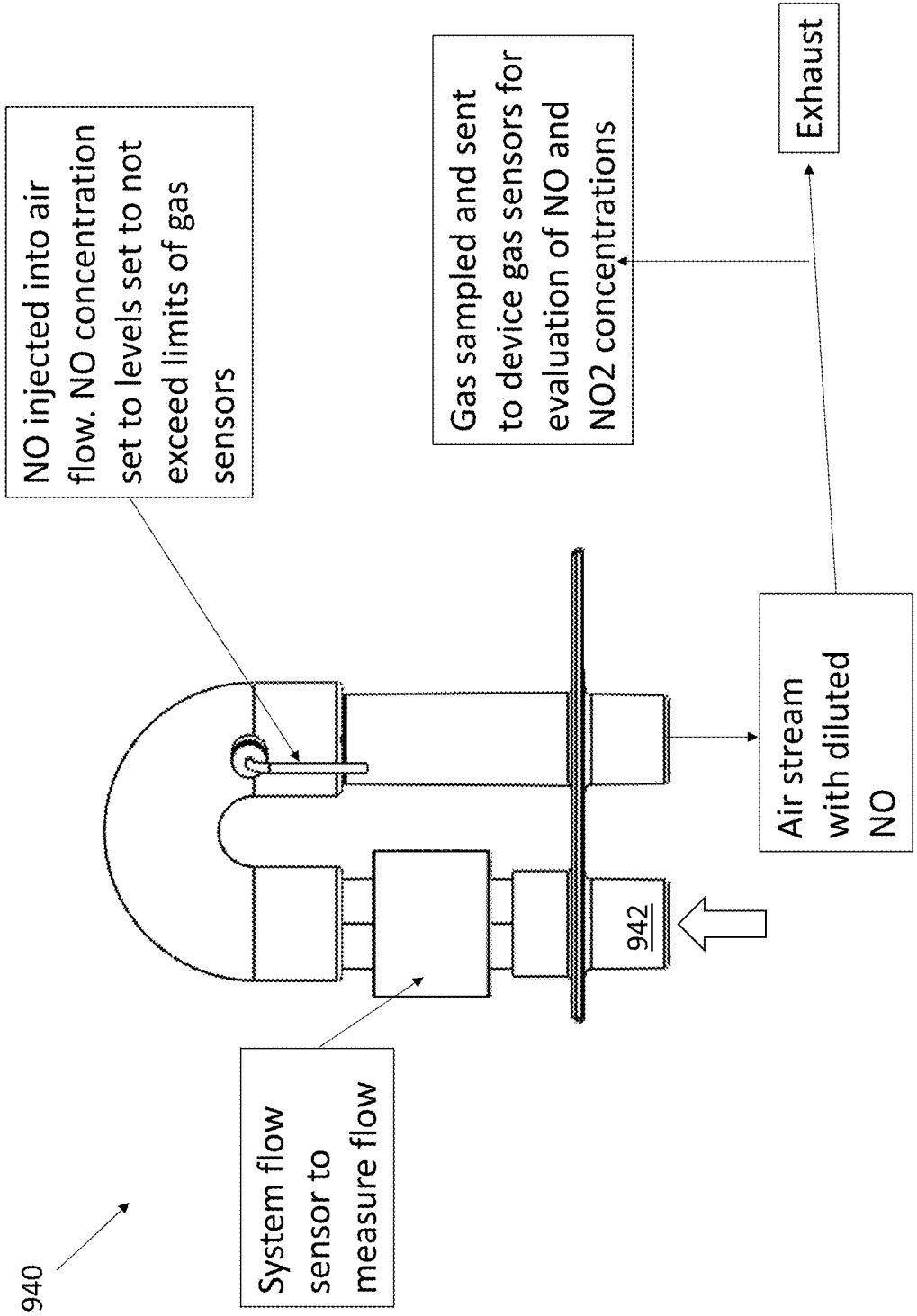
FIG. 58 is an embodiment of a calibration device used to reduce the concentration of calibration gas.

FIG. 58 illustrates a portion of an embodiment of a calibration device 940 used to reduce the concentration of calibration gas. For example, a pseudo-ventilator flow can be used to dilute gases. The same concept is also applicable to a NO generation and delivery system with onboard gas analyzer, making its own gas sensor calibration gas. In some embodiments, a constant flow of dilution gas (air, $N_2$, $CO_2$) can be introduced to an inlet 942. The constant flow can be provided from a pressurized source, a pump or other means to propel gas. In some embodiments (not shown), the calibration device includes a pump with a critical orifice to provide a constant and known amount of dilution flow. A flow sensor measures the flow of the introduced gas. NO/$NO_2$-containing gas is introduced to the dilution gas at known quantities. Diluted NO/$NO_2$-containing gas flows through tubing to a sample collection point where a sample gas stream flows to gas analysis sensors to be calibrated. By providing the gas analysis sensors with one or more known concentrations of NO and/or $NO_2$, the correct gain and offset of the sensors can be derived for accurate gas measurements. Excess diluted sample gas is exhausted to the environment or vacuum. In some embodiments, the excess diluted sample gas is passed through an $NO_2$ or NOx scrubber prior to release.

FIG. 59A illustrates an embodiment of an NO/$NO_2$ calibration device 950. Ambient air 952 enters the system and passes through a filter 954. As shown in FIG. 59A, ambient air is drawn into the system through the filter 954 by a pump 956. The air is pushed through a plasma chamber 958 where the gas is ionized by plasma to generate NO and $NO_2$. An optional check valve after the plasma chamber ensures forward flow through the system. When present in the system, the check valve prevents oxygen flow from flowing upstream into the plasma chamber. A pressure sensor 960 downstream from the plasma chamber serves as a proxy for a reactant gas flow rate measurement. In some embodiments, a flow sensor can be used to measure reactant gas flow. In some embodiments, a critical orifice is used to ensure the same gas flow rate at all times. A flow selection valve 962 permits either oxygen flow or NO-containing gas flow to advance to the gas sensors. An optional pop-off valve 964 releases excessive pressure in the system to protect the gas analysis sensors from over-pressurization. A sample line 966 provides fluid communication between the calibration device and the gas sensors being calibrated. The calibration device is powered by external power (AC or DC), battery, or both. A controller element within the calibration device controls pump activity, plasma activity and the flow selection valve. In some embodiments, the flow selection valve is manual. In some embodiments, the controller can read the position of the manual flow selection valve and direct the generation of NO, as needed. The controller receives inputs from an absolute pressure sensor and product gas pressure sensor. In some embodiments, the controller also receives a target calibration gas concentration from an input from a user. The input can be a switch position, touch screen entry, dial position, or other means of inputting a level indication. In some embodiments, a single calibration device is used to generate a single concentration of NO or $NO_2$.

Figure 59B:
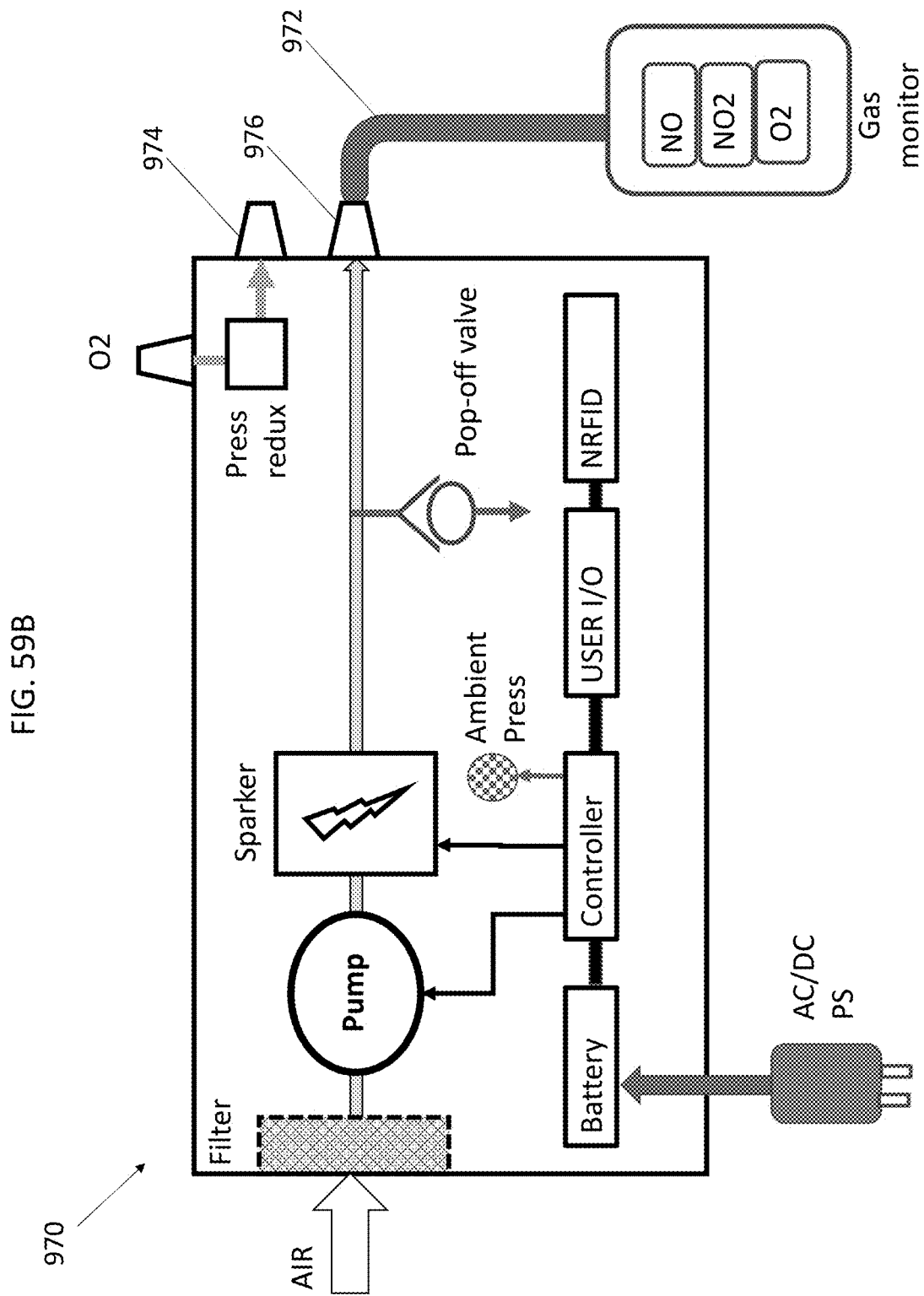
FIG. 59B illustrates an embodiment of an $NO/NO_2$ calibration device with an independent oxygen line.

FIG. 59B illustrates an embodiment of an $NO/NO_2$ calibration device 970 with independent oxygen line. FIG. 59B depicts a system that is similar to that in FIG. 59A, however oxygen flow is kept independent of NO-containing gas flow. Oxygen enters the system and flows through a pressure regulator to reduce the oxygen pressure to a level that is compatible with the gas sensors to be calibrated. A pressure pop-off valve is used to prevent over-pressurization of the gas sensors. As shown in FIG. 59B, a sample line 972 is connected to either an oxygen outlet 974 or a $NO/NO_2$ gas outlet 976 for calibration purposes. In high altitudes (or elevations), the absolute pressure sensor indicates less atmospheric pressure. The controller can respond to low atmospheric pressure by increasing plasma activity (pulse frequency or pulse duty cycle or plasma energy) to increase NO levels to achieve the target NO concentration for calibration of the gas sensors. In some embodiments, a scrubber (not shown) is placed at the exit of the gas analysis sensors under calibration to remove $NO_2$ and/or NOx from the calibration gas before it enters the ambient environment.

Figure 60:
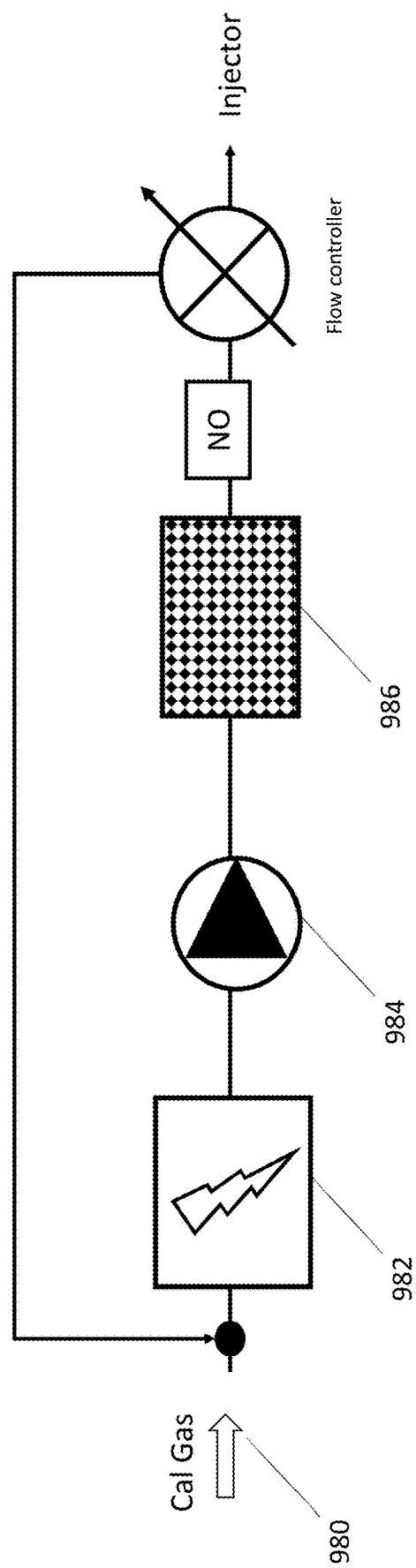
FIG. 60 illustrates an embodiment of a gas sensor calibration recirculation architecture.

Gas sensors can be calibrated using recirculation architectures. In some embodiments as shown in FIG. 60, an external source of NO calibration gas 980 is introduced to the system through the reactant gas inlet and exits out the flow path through a plasma chamber 982, pump 984, and scrubber 986 to the patient. In some embodiments, a calibration scrubber is used that does not include scrubber media to mitigate the potential of altering the calibration gas. In some embodiments, the scrubber is bypassed during calibration by configuring valves within the pneumatic pathway. In this embodiment, the pump 984 operates to drive calibration gas through the system. In pumpless NO generators, where reactant gas is driven by the pressure of an external gas source, pressurized calibration gas passes through the system passively.

Figure 61:
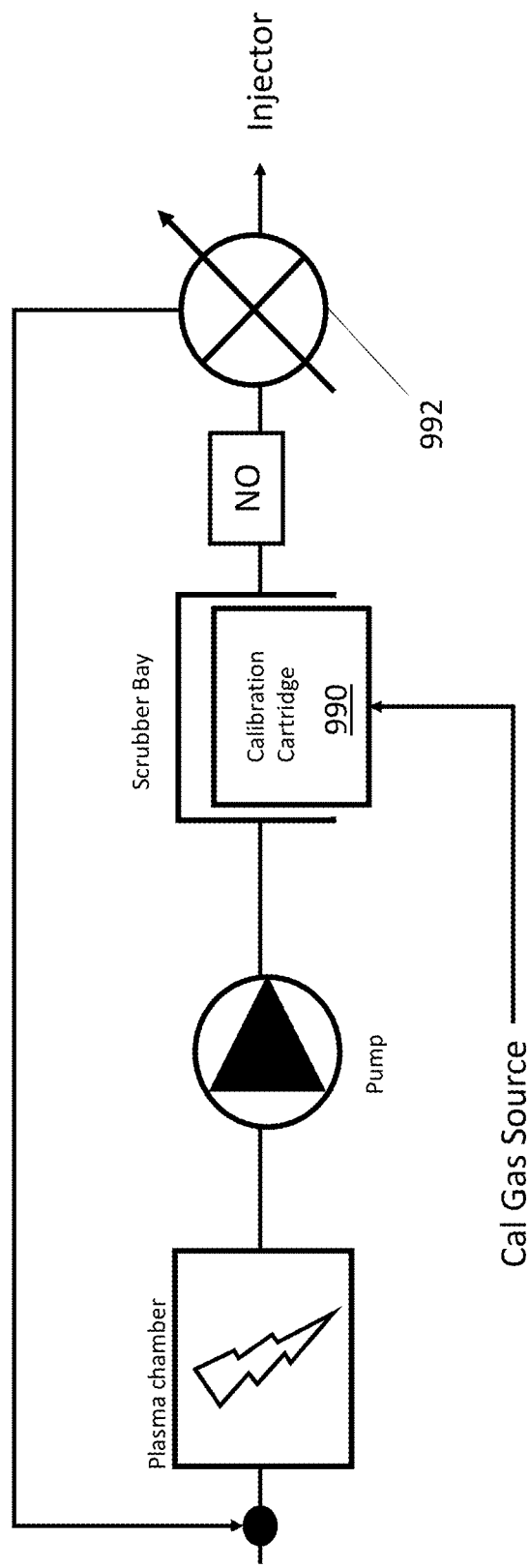
FIG. 61 illustrates an embodiment of a gas sensor calibration recirculation architecture.

As shown in FIG. 61, in some embodiments, a calibration cartridge 990 is inserted into the system in place of the scrubber. NO or $NO_2$ calibration gas is introduced into the system. In some embodiments, a flow diverter (or flow controller) 992 prevents flow through to the injector creating a closed volume filled with calibration gas. In some embodiments, the flow diverter regulates a flow of calibration gas from the cartridge to the injector past the NO gas sensor. In some embodiments, the flow regulator permits a volume of calibration gas to pass through the system prior to stopping flow so that the volume in fluid communication with the gas sensor has been primed. In some embodiments, the calibration cartridge is a compact gas cylinder that inserts into the NO generation system. In some embodiments, the calibration cartridge is an adaptor connecting gas from a larger gas cylinder or house supply to the NO generator.

Figure 62:
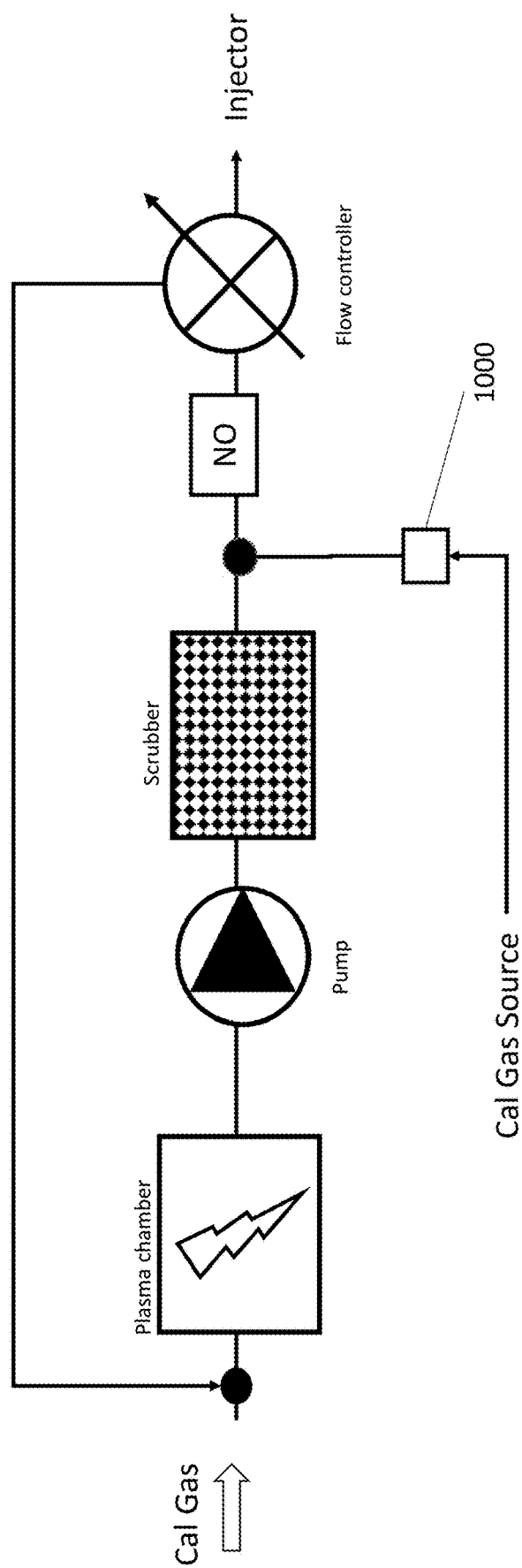
FIG. 62 illustrates an embodiment of a gas sensor calibration recirculation architecture.
Figure 63:
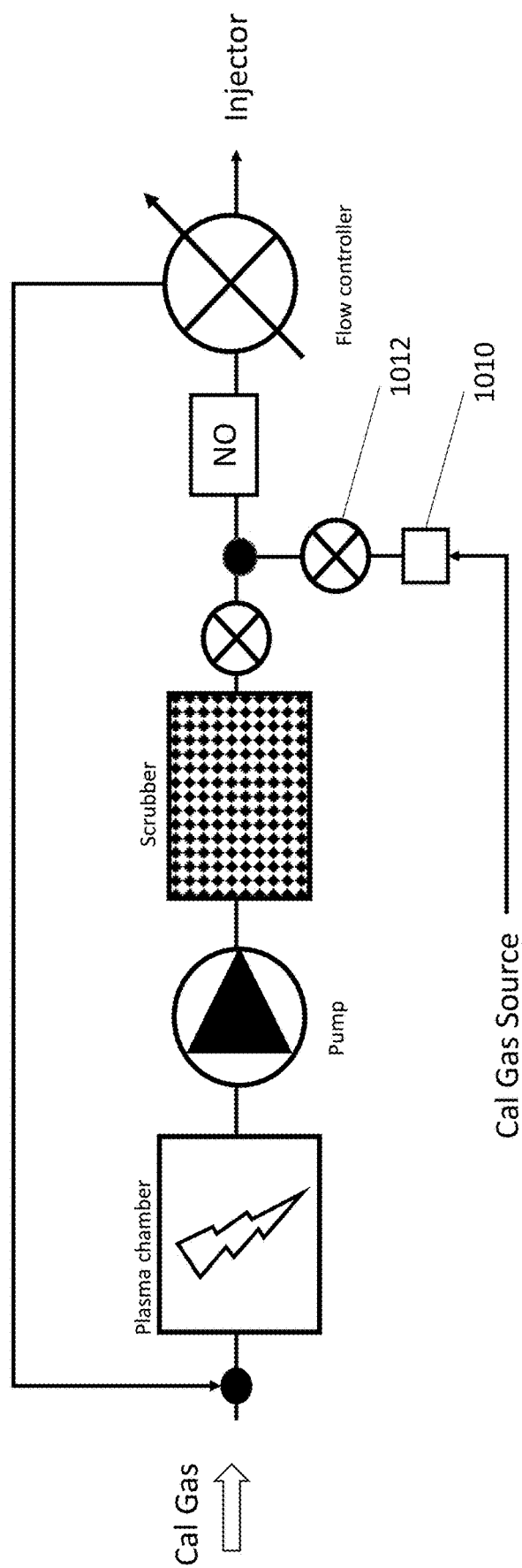
FIG. 63 illustrates an embodiment of a gas sensor calibration recirculation architecture.

FIG. 62 depicts calibration of a NO generation device by passing calibration gas through a dedicated calibration gas port 1000. When the system is not being calibrated, the port is capped to prevent loss of product gas from the system during clinical operation. FIG. 63 shows a binary valve 1012 upstream of the calibration gas port 1010 to prevent dilution of the calibration gases from the scrubber. In this embodiment, a valve in the calibration gas port path prevents loss of product gas during clinical operation.

Figure 64:
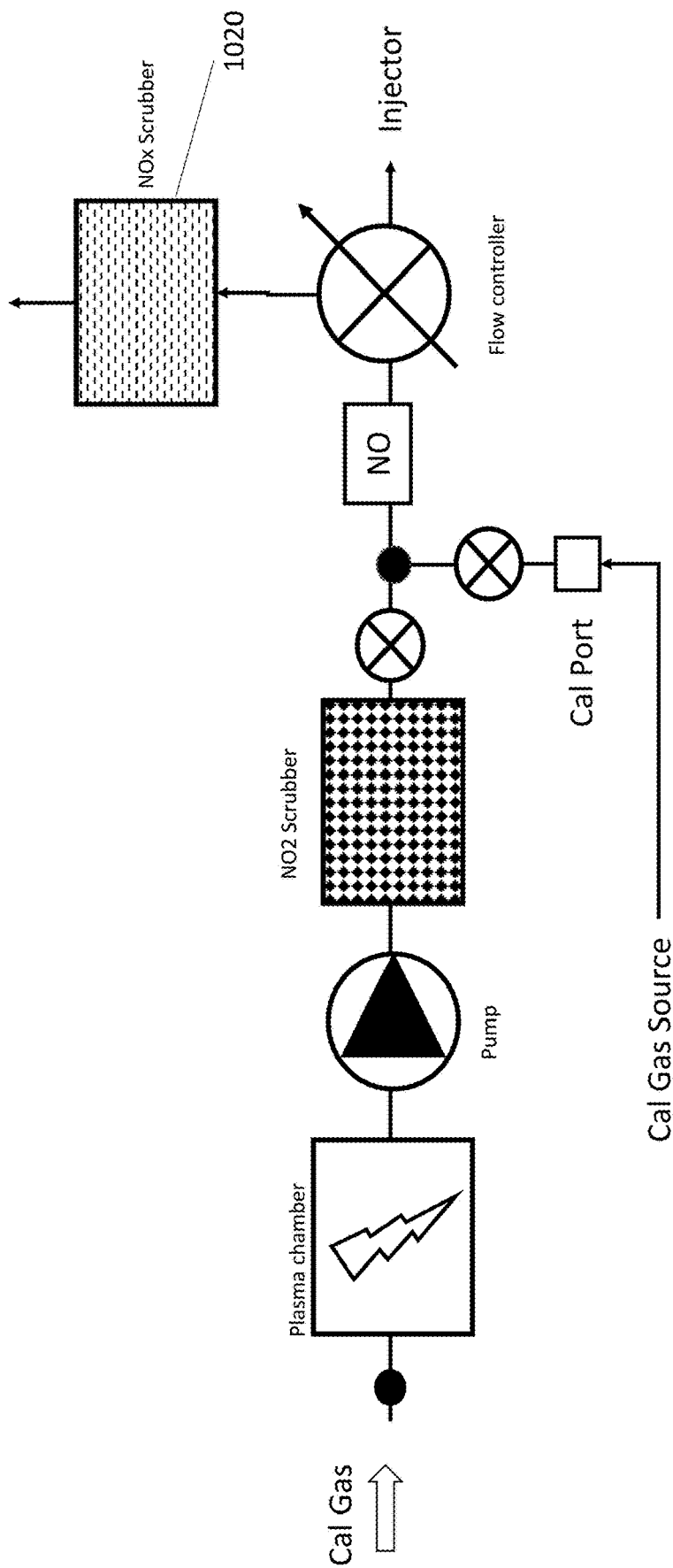
FIG. 64 illustrates an embodiment of a gas sensor calibration recirculation architecture.

FIG. 64 depicts an open pneumatic architecture with an NOx scrubber 1020. In this embodiment, calibration gas is passed by the NO and/or $NO_2$ product gas sensor and is routed to the NOx scrubber 1020. This approach does not send calibration gas out the injector which could be connected to a patient.

Figure 65:
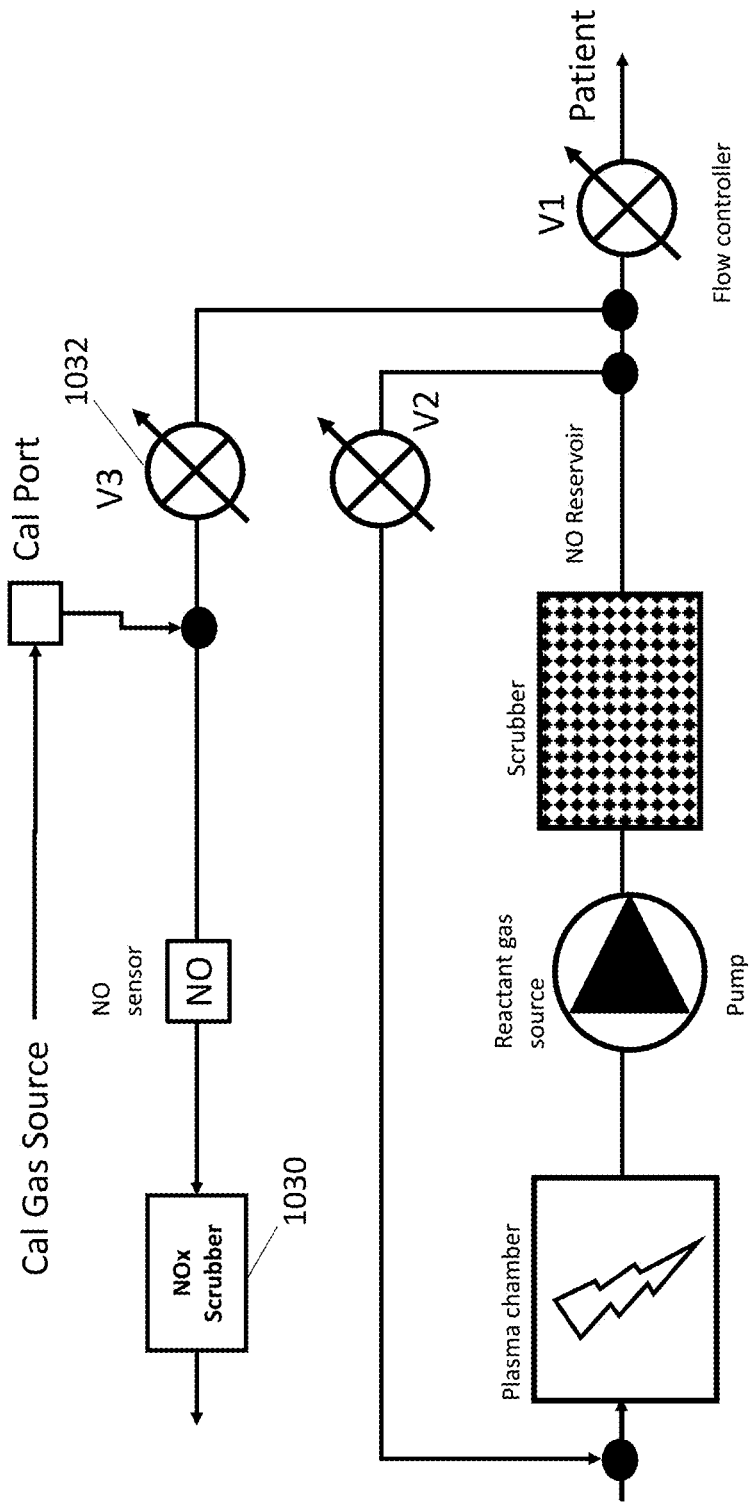
FIG. 65 illustrates an embodiment of a gas sensor calibration recirculation architecture.

FIG. 65 depicts an architecture where product gas is sampled from the system and passed through a NOx scrubber 1030. In some embodiments, a valve 1032 is closed during calibration and calibration gas is introduced to the system through a calibration port. When not in use, the calibration port is capped or closed off by a valve (not shown) to prevent errors in the product gas measurements.

An external calibration device requires a known flow rate for generating calibration gas. This can be done with a pump and a critical orifice. Alternatively, the sample pump of the device being calibrated can be used to generate air flow through the plasma chamber with the calibration device measuring the flow and generating plasma according to target NO levels and reactant gas flow rate.

In some embodiments, the portable calibration device includes one or more compressed gas reservoirs for providing reactant gas flow to the plasma chamber. The compressed gas reservoir can be filled by an internal or external pump. Compressed gas reservoirs can be filled with nitrogen, oxygen, a nitrogen/oxygen mix, air, or dry air.

In some embodiments, the NO calibration device delivers one or more set NO levels.

In some embodiments, the calibration device uses electrodes at a sub-breakdown voltage to generate corona thereby generating ozone. The ozone can be used for calibration of an ozone analyzer. In some embodiments, the calibration device generates ozone and then generates NO to mix with the ozone to generate $NO_2$. When this process is done with controlled methods, the output $NO_2$-containing gas can be used for calibration purposes. In some embodiments, ozone and NO generation are alternated in rapid succession to enable good interaction and mixing of the ozone and NO gases.

Calibration

In some embodiments, NO production of an NO generation system is calibrated with the following method: 1) Connect an external reference NO source; 2) Flow NO from the external source through the sensor bank of the NO generation system; 3) Record the sensor reading for the external source; 4) Generate NO using the NO generator and flow it through the sensor bank; and 5) Tune NO production parameters until the sensor reading indicates that NO production has been matched to the calibration gas level. In some embodiments, production parameters are adjusted to minimize $NO_2$ levels as well. Production parameters adjusted can contain one or more of the following: plasma frequency, plasma duty cycle, reactant gas flow rate, plasma energy, and primary AC waveform. This approach can be done in conjunction with or independently of calibration of onboard NO and $NO_2$ gas sensors.

In some embodiments, a calibration method can include the use of pseudo-vent flow to dilute gases for checking NO generator operation.

Calibration and RFID

It should be understood that the use of the term "RFID" in this section is a general term for any wireless or wired means to communicate information in the memory of one device to another device. In some embodiments, a near field identification device (NRFID) can communicate the state of a calibration device, such as information relating to the last calibration, calibration values, operation life, error codes, serial number, SW, hospital owner ID (for loss prevention), etc., to a standard computing device such as a laptop or smart phone. The RFID function can be used by the gas monitor to store device information in its calibration record (for example, which serial number and device model was used for calibration) as part of a hospital quality system.

RFID on the calibration device can be used for a variety of purposes. In some embodiments, RFID can be used to identify the calibration device to the gas monitoring device. The RFID on the calibration device can be loaded with identification information, such as a serial number, last calibration date, concentration of calibration gas provided, and/or owner information. The gas monitoring device to be calibrated reads the calibration device RFID for its calibration records. In some embodiments, RFID can be used for loss prevention. A calibration device with an RFID reader can be programmed to only work with a specific list of devices to calibrate so that it will not work at other institutions or with other devices. Similarly, the calibration device can read the RFID of an authorized user's badge to permit them to use the calibration device.

NO Generation and Delivery Device Calibration

Pressurized calibration gas can be used as a reference for calibrating gas analysis sensors in a nitric oxide generation and/or delivery device. In some embodiments, an NO delivery system can also provide a gas monitoring sub system that is configured to monitor the inspired gas concentration by sampling the gas close to the Y piece to determine the concentration of NO and $NO_2$ and $O_2$. The reason for measuring these gas parameters is to assure that the target clinically relevant NO gas concentration is actually provided and that no malfunction or leakage occurs. In some embodiments, the range for the potential delivery system is 1-80 ppm of NO. In some embodiments, the gas monitor system also measures the presence of $NO_2$. $NO_2$ is created as NO molecules are exposed to the oxygen as they travel through the NO generation and delivery device and within the inspiratory track. $NO_2$ in the presence of water (for example, in the moist air in the inspiration limb and in the lung) can create an acid fluid that can harm the patient upper airway tissue and in the lung tissue itself. Therefore, the gas measurement cell in the delivery system can be periodically checked with calibration gas and recalibrated if needed.

In some embodiments, an adapter tube connects to a pressurized calibration gas source on one end to a gas sensor on the other end. In some embodiments, one end of the adapter tube is shaped like a water trap and is inserted into the NO generation device. The NO device can identify the calibration adapter tube using various techniques, including but not limited to reading an RFID chip in the connector, reading a memory device, by measuring a unique value from the water level sensor, by reading a bar code, by reading a 2D bar code, by optical detection of the presence or absence of a feature detected by optical sensor, or by physical contact switch. Alternatively, a user can identify the type of calibration gas through the device user interface. In some embodiments, when the calibration adapter tube is connected, the NO generation system can automatically enter a calibration mode. In some embodiments, the calibration mode is fully automated where the system pulls gas samples through the gas analysis sensors and makes the necessary adjustments. In some embodiments, reference gas for zeroing the sensors is drawn through the NO generation system from the fresh air intake. In some embodiments, gas pulled from the environment for zeroing is passed through a filter and scrubber (NO, $NO_2$, NOx, VOC, for example) prior to flowing past the gas sensors to remove impurities. In some embodiments, the NO generator device can detect what kind of calibration gas is connected to the device by the identifying features listed above in the adapter tube connector.

Electronics

In some embodiments, a software-based controller is used. In some embodiments, the operation is simple enough that it could be handled with a hardware-only solution (electronic control circuit). For example, a system which operates at constant production rates could utilize a resonant high voltage generator excited by a self-oscillating or fixed frequency driver and pulse modulated at a fixed or adjustable frequency and duty cycle.

In some embodiments, a variable resistor (e.g. potentiometer) is in series with the electrode gap. For a given voltage in the high voltage circuit, the resistance is varied to apply variable voltage to the electrode gap thereby modulating NO production. In some embodiments, power to the high voltage circuit is applied continuously (i.e. not pulsed) and a variable resistance is adjusted to modulate NO production.

Power Measurement

Production of NO is related to the amount of power within the electrode gap. In some applications, power within the plasma is used as a proxy for NO production levels. By knowing the power within the plasma, a system knows the level of NO production rate and can tune the production accordingly to achieve target production levels.

Measurement of power within the electrode gap is challenging, however. A high voltage probe can be utilized to measure power in the secondary/high voltage circuit, however this can shift the resonant frequency, making a circuit perform differently. Thus, it is preferable to build the current and voltage measurement circuit into the high voltage circuit of a NO generator. In this way, a device is calibrated with the effects of the measurements accounted for, thus not affecting system performance while measurements are taken.

Construction of a built-in high voltage probe can be complex. There can be issues with electrical isolation and prevention of EMI interference. Furthermore, data must be sampled at high frequency to capture rapid events. In some embodiments, the high voltage power measurement circuit samples at 1 MS/s.

In some embodiments, a transformer can include a circuit connected to the primary (low voltage) side to measure current and voltage and compute power. This enables the low voltage components to report the power in the plasma pulse. In some embodiments, the transformer can include a circuit connected to the secondary (high voltage) side to measure current and voltage and compute power. Measurement in the secondary circuit is closer to the plasma, eliminating errors from transformer inefficiencies and phase shifts between power in the low voltage side and the high voltage side. This enables the low voltage components to measure current and voltage to compute the power in the plasma pulse and the timing of breakdown. Information can be gained about the integrity of the electrode over time based on breakdown timing and breakdown voltage.

Measurement of secondary circuit voltage and current provides insight into the "health" of an NO generation system. Current, voltage, and impedance measurements (breakdown, current signal slope, voltage slope, current levels), when calibrated, can be used as a baseline to detect NO generation drift and errors during use of the device. As these values drift, a system can compensate for them with adjustments in voltage, current and timing. Ultimately, a system can prompt replacement of components or re-calibration based on these measurements.

Breakdown voltage level and plasma voltage after breakdown both correlate to the gap size. This can provide a NO generation system information on the status of electrode wear and indicate a need for electrode replacement. This information can also be used to determine the size of the plasma arc for improved estimates of NO production. This approach is applicable to a multitude of electrode designs, including but not limited to gliding arc, opposed electrodes, coaxial, parallel and torch designs. Furthermore, discontinuity in the plasma power consumption, voltage and/or current levels and their rate of change during NO generation can indicate electrode decay over the life of the electrode. Rate of change of voltage and current can indicate the position of arcing on the electrode. Plotting the voltage-current curve (during current modulation and/or changing input voltage) can be used as a proxy for plasma gas temperature (negative or positive plasma impedance).

Figure 70:
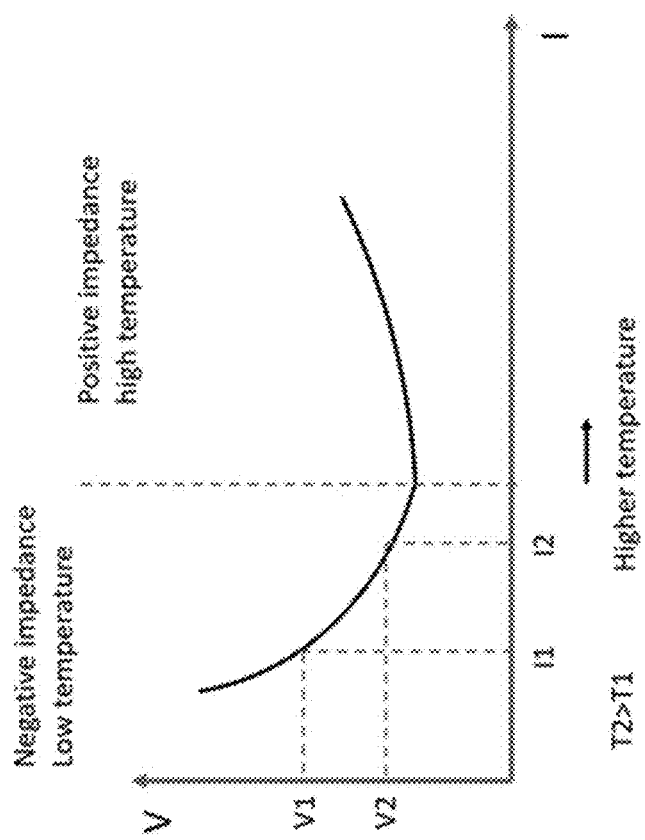
FIG. 70 shows an exemplary graph of plasma impedance.

When voltage is plotted against current, as shown in FIG. 70, the slope of the plot is equal to the plasma impedance. In arc discharges, the impedance of the plasma can be positive or negative, depending on the plasma temperature. A NO generator can utilize the voltage/current relationship to identify the current plasma regime (cold plasma vs. hot plasma). In some embodiments, the NO generator sweeps through a range of input voltages to determine whether current is increasing with voltage or decreasing with voltage. In some embodiments, the NO generator sweeps through a range of plasma current to determine whether voltage is increasing with current or decreasing with current. Cold plasma is associated with lower temperatures and less electrode erosion. For the given level of plasma power, a NO generator can determine the plasma temperature (high vs. low) and adjust the current and voltage to maintain the plasma in the low temperature regime.

In some embodiments, a DC HV system reverses polarity of the electrodes periodically to even electrode wear.

Flow Measurement

Figures 66A, 66B:
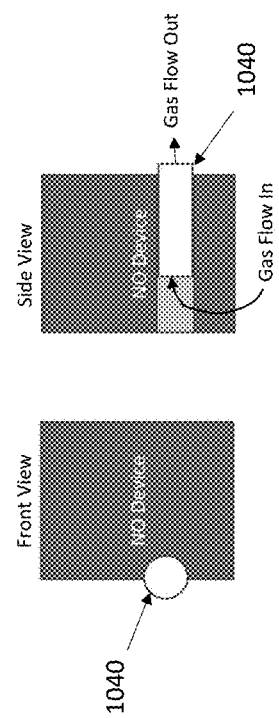
FIG. 66A and FIG. 66B show an embodiment of an NO generation system that includes a patient inspiratory flow sensor.

In some embodiments, a patient inspiratory flow sensor snaps into the side of a controller to enable straight-through flow which facilitates cleanability. In some embodiments, patient inspiratory flow enters a flow sensor 1040 at the back of the NO device and flows towards the front of the NO device, as shown in FIG. 66A and FIG. 66B. In some embodiments, NO is added to the inspiratory flow within the flow sensor module, but typically after the flow sensing components.

In some embodiments, the system can detect reverse flow within the ventilator circuit of sufficient magnitude and duration to potentially contaminate the ventilator cartridge and alerts the user. In some embodiments, the inspiratory flow magnitude and duration are used to calculate a volume of gas and compared with the volume of the inspiratory limb. If the volume of reverse inspiratory flow is greater than the volume of the inspiratory limb, there is a risk of contamination of the NO generation system.

Under certain conditions, such as relaxing compliance in the ventilator tubing at the end of inspiration, air flow through the ventilator cartridge can flow in reverse. Under some circumstances this could result in air getting dosed twice, resulting in inaccurate dose levels delivered to the patient. In some embodiments, the system measures the volume of air that flowed in reverse and suspends injection of additional NO until forward flow cancels the reverse flow.

Acoustic Noise

In some embodiments, electrical discharges in the plasma chamber create an acoustic noise signal that interferes with plasma flow and pressure measurements. In some embodiments, the acoustic noise is dampened with a muffler, chamber, length of tube, scrubber, filter housing, or elastomeric membrane. In some embodiments, an active noise cancellation method is used to eliminate the noise.

In some embodiments, a NO generation system employs flow sensors which do not develop significant offset errors in the presence of acoustic noise. The system uses an analog to digital converter or other sample-and-hold circuit to sample the sensor or sensors synchronously with the plasma pulsation. This forms a digital filter at the pulse frequency and its harmonics (i.e. all harmonics are aliased to 0 Hz).

In some embodiments, the flow sensor signal acquisition time is significantly shorter than the pulse period. The acquisition time is phase-locked to the pulse frequency. The phase is set equal to the zero-crossing of the noise waveform (i.e. where the instantaneous value is equal to the mean). This method rejects non-linearities in the noise signal that can average to produce a DC offset. It also produces shorter phase lag (group delay) in the flow signal than a filter that averages the entire pulse period. Because the flow signal is used for feedback in the flow controller, this can provide superior control loop response.

In some embodiments, samples are acquired and digitally filtered over an integer number of pulse periods, effectively producing an FIR filter with full rejection of the pulse frequency and its harmonics. The filtering rejects inaccuracies that would arise in the phase-locked single sample scheme if the phase of the zero crossing changes. It also has a lower noise bandwidth than the phase-locked embodiment.

Pump pulsatility can also produce variations in pressure and flow rate within the plasma chamber. This can contribute to variations in NO production. In some embodiments, discharge pulses are synchronized with pump pulsations so that each NO production event occurs at the same point in the pressure/flow cycle. In some embodiments, the NO generator measures plasma chamber pressure and adjusts NO production settings in real time to account for pressure levels within the chamber. In some embodiments, a flow restriction or critical orifice located between the pump and plasma chamber is used to smooth out pressure and flow variations in the reactant gas flow rate to improve NO production consistency. These approaches improve consistency in NO production.

Plasma Noise

The intense heat of plasma generation in an NO device can generate a pressure wave within the pneumatic pathways leading to and from a plasma chamber. In some embodiments, these pressure waves can interfere with measurements made before and after the plasma chamber, such as pressure and/or flow rate measurements. In some embodiments, noise cancellation pressure waves are generated to prevent plasma pressure waves from affecting sensor measurements of pressure and flow.

Figure 67C:
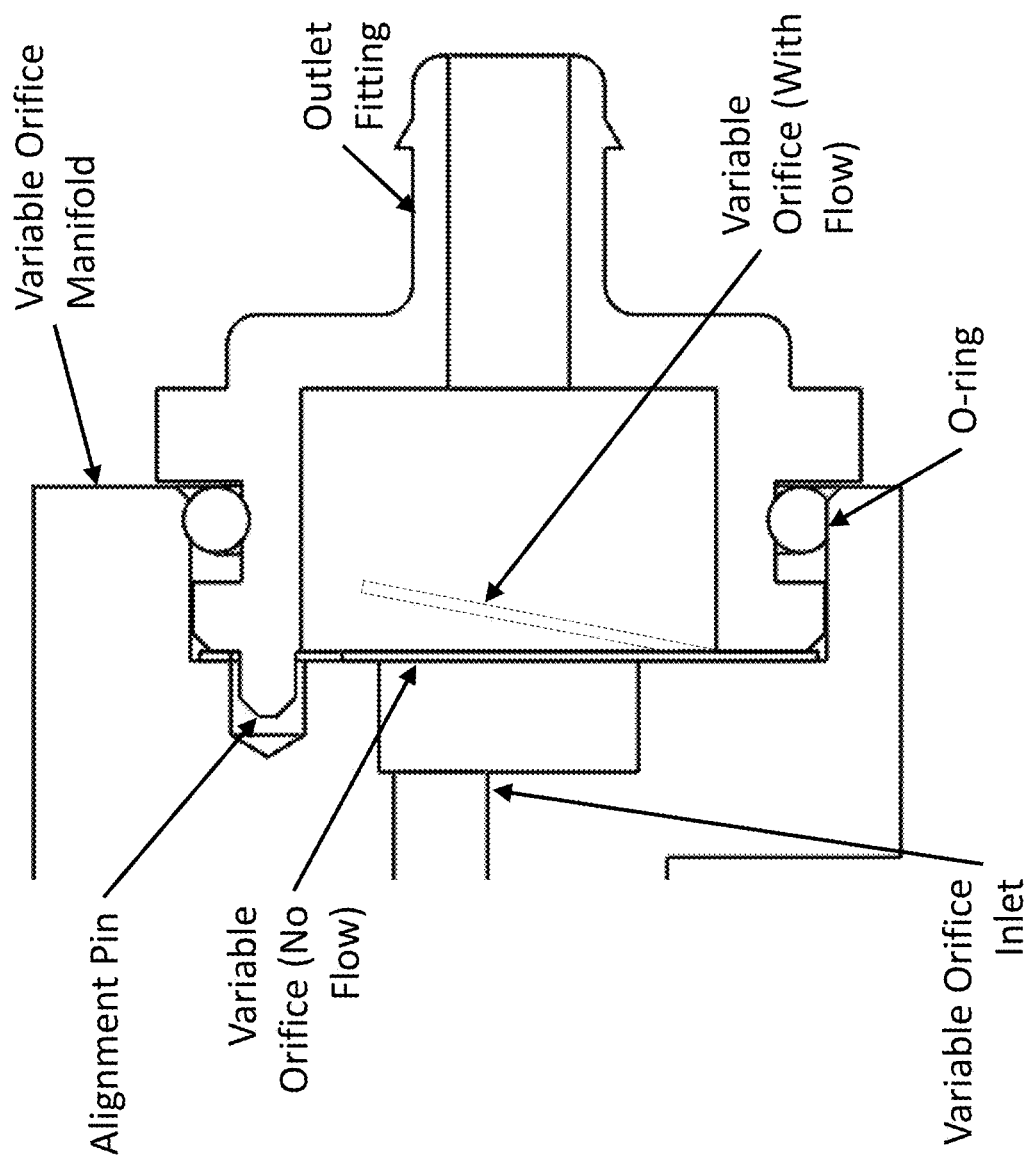
Figure 67D:
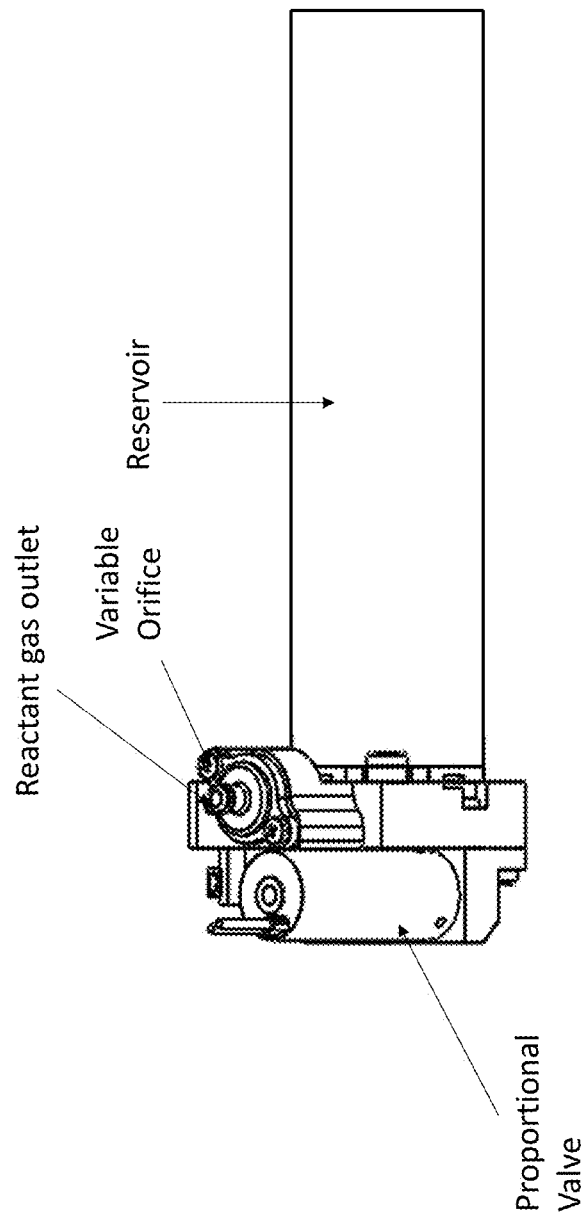
Figure 67E:
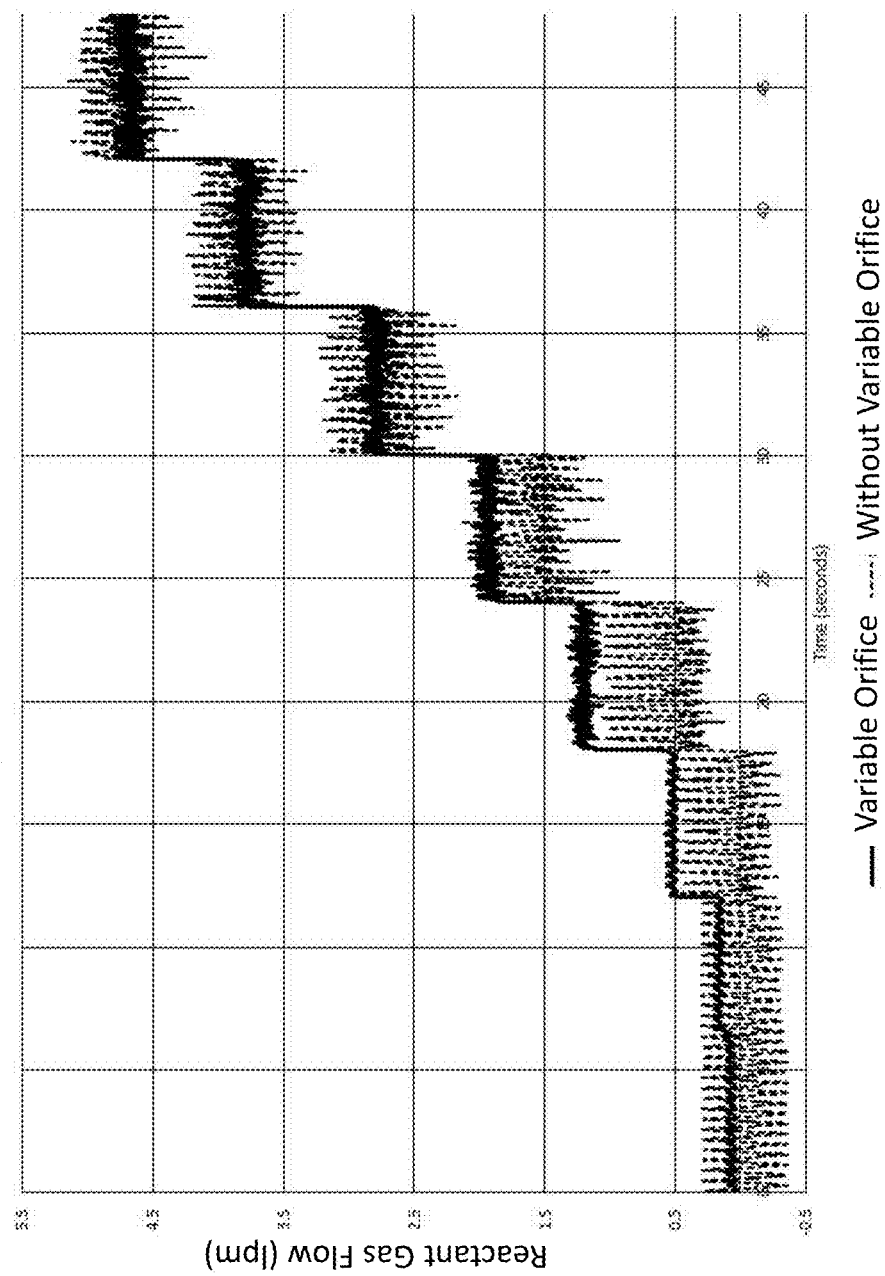
FIG. 67E shows an exemplary graph of variable orifice plasma noise reduction.

In some embodiments, the subject measurements are sampled at sufficient frequency that their signal can be filtered in software to remove artifact from the plasma events. In some embodiments, reactant gas flow rate is sampled at up to 100 kHz and digitally filtered to support a flow controller operating at 1 kHz. In some embodiments, reactant gas flow is sampled at 100 kHz, moving-average-filtered to 200 Hz and used to control a flow controller at 200 Hz. In some embodiments, electrical hardware and/or software are used to remove plasma pressure wave artifact from sensor readings. In some embodiments, acoustic baffling, similar to a muffler is used to suppress plasma pressure waves. In some embodiments, sensors are sampled at a frequency that is not harmonic with plasma frequency to minimize artifact. In some embodiments, sensors reject periodic error signals produced by the plasma by sampling at the zero crossing of the error signal. In some embodiments, sensors reject periodic error signals produced by the plasma by using an FIR filter (including moving average) over an integer number of periods of the error signal. In some embodiments, reactant gas flow and/or pressure measurements are made in-between plasma events when there is an absence of plasma acoustic noise. In some embodiments, a passive variable orifice is used to suppress plasma acoustic waves. FIG. 67A, FIG. 67B, FIG. 67C, and FIG. 67D illustrate an embodiment of a variable orifice flow controller 1050 to prevent plasma noise. The variable orifice plate can be constructed from metal, polymer, composite, wood, or another suitably stiff material. FIG. 67E shows an exemplary graph of variable orifice plasma noise reduction. In the experimental setup, reactant gas flowed through a flow sensor and an active plasma chamber. Time is plotted along the X axis and reactant gas flow rate as measured by a flow sensor on the Y axis. During the experiment, the flow rate through the plasma chamber is increased step-wise from 0 lpm to roughly 4.6 lpm. The initial curve, labeled "without variable orifice", is plotted as dashed lines and shows large amounts of noise corresponding to the pressure wave from electrical discharges in the plasma chamber. The amplitude of the noise is up to +/−0.25 lpm and the mean reading is low in most cases. The second curve was generated by placing a variable orifice between the flow sensor and the plasma chamber, as shown in solid black. The variable orifice reduces fluctuations in the flow signal and enables the flow sensor to read the mean flow rate with improved accuracy. Without the variable orifice, the signal to noise ratio is worst at low flows.

In some embodiments, physical features within the reactant gas flow path such as sound-absorbing materials and/or sound reflective surfaces are used to suppress and/or cancel plasma acoustic noise.

In some embodiments, the plasma flow sensor is located as far from the plasma source as possible to minimize the effects of plasma noise. In some embodiments, the plasma flow sensor is located post-scrubber so that plasma acoustic noise has less of an impact. Architecturally, the sensor can be located within the ventilator cartridge.

Plasma Generation

In some embodiments, plasma is generated with radio frequency energy. In some embodiments, NO generation can be modulated by adjusting one or more of the following parameters: RF Frequency, wave guide spacing, electrode gap, flow, pressure, temperature, etc. as variables in production.

In some embodiments, a NO generation system energizes $N_2$ and $O_2$ molecules with UV light to generate NO. In some embodiments, UV light is utilized to convert $NO_2$ to NO prior to injection of NO into an inspiratory stream.

In some embodiments, one or more lasers are focused to a point in space. The energy density in that space is high enough for gas to turn to the plasma state such that one or more lasers can be used to generate NO. When coupled with a reactant gas flow, NO is generated in the reactant gas as it flows through the laser-generated plasma. This can provide improved control of energy and temperature while eliminating the wear of electrodes and contamination from particulates. In some embodiments, the laser(s) are focused using a lens. In some embodiments, a single laser is split and then directed to intersect at a point in space.

In some embodiments, a NO generator generates electricity for NO generation from a compressed gas supply. In some embodiments, compressed gas from an external source passes through a turbine that rotates a generator, thereby generating electricity for the system. Regulation of pressure and flow can be done internally or externally to the NO generation device. The device may have an internal battery or capacitor to provide peak power requirements during NO generation. The internal battery and/or capacitor can be charged from the electricity generated from compressed air. In some embodiments, the compressed gas is air and is also used as the source of reactant gas.

Control Algorithms

Acute Control Algorithm

In some embodiments, plasma intensity is modulated based on target (set point) flow through the plasma chamber, producing more accurate average production. In some embodiments, plasma intensity is modulated based on measured (actual) flow through the plasma chamber, producing more accurate product gas concentration.

In some embodiments, the control circuit and/or controller detects plasma formation and adjust its excitation frequency and/or duty cycle after plasma formation. Plasma formation may be detected by high dv/dt or high di/dt signals or by measuring a change in the resonant frequency. In some embodiments, the plasma is left on for a target duration of time after electrical breakdown occurs, thereby eliminating production errors from variance in break-down time. One complicating factor with this approach is that AC current has a frequency that could be at any point in its cycle when breakdown is detected. This can result in varying levels of NO production based on what point during the AC sine wave, break down occurred and how long the pulse is. To mitigate against this type of phase shift, a NO generation system can reset the AC sine wave with each new pulse or when breakdown is detected to ensure consistent NO production for a given duration of arcing. This approach to NO production can eliminate NO product variance attributed to changes in breakdown time attributed to component drift and reactant gas properties (pressure, temperature, humidity). It also enables fine resolution modulation of the electrical discharge pulse width. In some embodiments, electrical discharge pulse width is controlled with a resolution between 0.1 and 1 microseconds.

In some embodiments, NO production is modulated by modulating plasma intensity and/or pulsing the plasma on/off.

The AC, resonant operation of the circuit produces quantization of energy which may produce large step changes in NO production rate. In some embodiments, there is a minimum required on-time of the pulse to guarantee that electrical breakdown occurs and to ensure that the plasma duration after breakdown is repeatable. This approach, however, may result in excess NO production at high operating frequencies. Low pulse frequencies improve effective resolution but introduce a different kind of quantization due to a finite number of pulses per breath. In some embodiments, a NO generation system achieves fine control of production rates between discrete duty cycles by dithering between discrete duty cycles to produce an average production rate that is between the discrete production rates of each duty cycle.

To dither between duty cycles, in some embodiments the system first identifies the discrete duty cycles that result in production immediately above and below the target production. The system then uses an integrator to track the desired number of moles of NO produced and the actual number of moles produced, based on historical pulse widths and expected production at those pulse widths. At the start of each pulse, if the desired production exceeds the actual production, the system operates at the higher pulse width. If the actual production exceeds the target production, the system operates at the lower pulse width. The accumulated error in desired production will result in the system spending more time at one duty cycle or the other such that the average production is correct. Production rates below the minimum production are also achievable by using a special case of this control scheme where the lower duty cycle is zero, during which time production is also zero. In some embodiments, the system varies duty cycle between two levels on alternating pulses to achieve production levels in between that of the two levels. This is interpolating in a way. In some embodiments, duty cycle can be varied from 0 to 100%. In some embodiments, operating at a constant frequency, the system tracks the NO production and will vary the duty cycle as needed to match production demand. In some embodiments, operating frequency varies from 101 Hz to 100 kHz. In some embodiments, the system pre-calculates the production variation caused by the sinusoidal plasma currents and uses the model to modulate pulse width with a finer resolution than one resonant cycle.

In some embodiments, a NO production algorithm can be used that adjusts (for example, increases) production levels in anticipation of losses within the system downstream of the plasma chamber. Losses can be from leaks, NO oxidation, and absorption of NO from the system. Absorption of NO from the system can be during initial use or throughout the treatment duration. Losses from oxidation can occur within the internal volume of the system, including the tubing and the scrubber.

Pressure within a NO generation system can result in decreased NO production. As reactant gas flow rates through an NO generation system increase, back pressure downstream of the plasma chamber creates increases in the plasma chamber pressure. Since air is an insulator, higher voltage is required to create an electrical discharge and generate NO, resulting in delayed electrical breakdown and reduced NO production for a given plasma generation setting. In some embodiments, a control algorithm uses plasma chamber pressure as an input to a calculation of NO production and/or plasma settings. In some embodiments, the plasma duty cycle is increased when increases in plasma chamber pressure are sensed to ensure NO generation is accurate. In some embodiments, the relationship of reactant gas flow rate to plasma chamber pressure and/or back pressure is characterized so that reactant gas flow rate is used as a proxy for plasma chamber pressure.

In some embodiments, an NO dose algorithm can use patient ideal body weight, height, disease state, gender or other physiologic parameters as an algorithm input. For example, a patient's height can be indicative of lung size and tidal volume. The patient's disease state can affect whether or not NO delivery should be pulsed, as is the case for chronic lung disease where it is desirable to dose only the healthy/first-recruited parts of the lung. Viral or bacterial infection presents an alternative disease state where is preferred to fill the entire lung with bactericidal and/or viricidal doses of NO.

There is a concern that over the course of inhaled NO therapy, a patient may slow their endogenous NO production and become dependent on exogenous NO. Thus, it is desirable to minimize the amount of NO delivered to the patient, only delivering the therapeutic minimum. In some embodiments, the NO dose is increased and decreased based on sensed activity level. Activity level can be detected by accelerations measured at the device, accelerations measured at the patient, breath rate, and/or heart rate. For example, a patient that is resting with a breath rate of 10 breaths per minute would get a NO dose of 2 mg/hour. If that patient stands up, climbs stairs and increases their breath rate to 30 bpm, the NO dose increases to 6 mg/hr.

In some embodiments, the system uses temperature of the plasma chamber as an input to NO production. In some embodiments, NO set point is set higher than target when the system is cold. In some embodiments, a NO generation system uses one or more of the following parameters as an input to the NO generation control algorithm: reactant gas temperature, product gas temperature, electrode temperature, plasma chamber temperature, high voltage cable temperature.

In some embodiments, if plasma is not detected at the plasma chamber, the system can perform a resonance sweep, and/or operate at a different frequency.

In some embodiments for acute inhalation treatments, product gas NO concentration varies from 5 ppm to 5000 ppm pre-injection, depending on the patient target dose and the dilution ratio.

Dilution

Oxygen is diluted when the NO plus air are added to a ventilator system. High concentration NO results in lower volumes of product gas to achieve a target NO concentration in the inspired gas. In some embodiments, a NO generation and delivery system maintains a constant dilution ratio. This allows the system to generate a constant concentration of NO within the system so that the system does not have to track gas as it travels through the system because all gas is at the same concentration. In some embodiments, a constant dilution ratio of 20:1 is used. In some embodiments, the dilution ratio is varied as a function of target patient dose. In some embodiments, dilution ratio is adjusted from a ratio of 10:1 (ventilator: NO+air flow) to 30:1. Dilution ratio can vary from 1:1 to 100:1, however.

Weaning

In some embodiments, the system permits customization of weaning schedule to match hospital protocol.

Ambulatory Control Algorithm

In some embodiments, NO gas pulse duration changes based on breath period. The system can use average of prior breath durations to select the duration of the next pulse. In some embodiments, a target fraction of the duration of inspiration is targeted. In some embodiments, the pulse duration is a set duration of time, (e.g. 50 msec). In some embodiments, the pulse duration is a fraction of the inspiratory duration, based on the prior n number of inspiratory events (e.g. 25%). In some embodiments, the duration method (% vs. time duration) is selected based on the breath rate. This is particularly applicable as breath rate increases and a system operating in a percent-based approach is unable to deliver sufficient NO in an ever-shortening portion of the inspiratory event. Therefore, a NO delivery system changes to a set time duration when the respiratory rate reaches a level at which the percent-based approach is no longer sufficiently accurate.

In some embodiments, a patient can be treated with a dose with mg/hr. This can be independent of ideal body weight.

In some embodiments, an NO delivery system can generate NO on demand, meaning that a pulse of NO is generated when an inspiratory event is detected.

In some embodiments, the device can purge the cannula of $NO_2$ during patient exhalation. In some embodiments, the cannula is purged with reactant gas.

In some embodiments, electric NO systems can vary the concentration of NO within an inspiratory pulse, tailoring the delivered NO concentration delivered to various depths of the patient anatomy.

In some embodiments, the lengths of NO boluses that can be generated range from 20 msec to seconds.

Constant NO Generation

In some embodiments, a portable NO generator generates and delivers NO at a constant concentration and flow rate. This approach has advantages in simplicity and the constant flow rate minimizes transit time for the NO gas from the plasma chamber to the patient. This approach presents a risk of NO and $NO_2$ concentrations increasing to unsafe levels in a poorly ventilated room. In some embodiments, a base station, recharging station, or entirely separate system/device flows ambient gas through a NOx scrubber to minimize $NO_2$ build-up in a room. In some embodiments, the NOx scrubber is activated charcoal.

$O_2$ Concentrator

An $O_2$ concentrator is a device that begins with an oxygen and nitrogen mixture, typically air, and separates oxygen from the mixture for delivery to a patient. In many cases, concomitant use of NO therapy with $O_2$ therapy improves a patient's oxygen uptake over the use of either treatment individually. Based on how an oxygen concentrator works, there are opportunities to combine a nitric oxide generator and oxygen concentrator into a single device. In some embodiments, an oxygen concentrator concentrates $O_2$ to 50% then passes gas through plasma for optimal NO production. This is advantageous because NO production is highest at the stoichiometric ratio of 50% $O_2$ and 50% $N_2$.

In some embodiments, a bypass $N_2$ stream from an $O_2$ concentrator is introduced to the reactant gas flow prior to the plasma to limit $O_2$ fraction in plasma chamber, thereby reducing NO production and limiting $NO_2$ formation. This can enable an NO generation system to produce low levels of NO.

In some embodiments, a bypass $N_2$ stream from an $O_2$ concentrator is introduced to the product gas after plasma to dilute $O_2$ levels, thereby decreasing $NO_2$ formation.

In some embodiments, NO production increases as oxygen content in the reactant gas increases, with maximum NO production occurring at the stoichiometric ratio of 50% $O_2$ and 50% $N_2$. In some embodiments, oxygen levels are increased by compressing reactant gas in the presence of zeolite within the plasma chamber. Gas is compressed within the plasma chamber such that $N_2$ molecules enter the zeolite, leaving a gas with higher concentration $O_2$ in the plasma chamber. In some embodiments, plasma is generated in the reactant gas as it is compressed in the presence of zeolite thereby increasing NO production. In some embodiments, NO and $N_2$ within the zeolite are exhausted independently of the high oxygen concentration gas. In some embodiments, the NO lumen of the cannula is filled with NO in $N_2$ that exit an oxygen concentrator with plasma chamber, thereby slowing the NO oxidation process. In some embodiments, NO in $N_2$ gas exiting the plasma chamber of an oxygen concentrator is scrubbed for $NO_2$ prior to entering a cannula. In some embodiments, NO in $N_2$ gas passes through a $NO_2$ scrubber that is part of the cannula assembly.

In some embodiments, reactant gas is depressurized after the plasma event so that $N_2$ can re-enter the reactant gas, thereby reducing $O_2$ levels again and decreasing the rate of $NO_2$ formation. In some embodiment, reactant gas is released from a chamber with elevated $O_2$ levels and subsequently exposed to a plasma. Nitrogen within the zeolite is released in a subsequent step after release of the reactant gas.

In some embodiments, a NO generator uses zeolite to separate $N_2$ and $O_2$. Excess $O_2$ is diverted upstream to mix with reactant gas and improve the $N_2$ to $O_2$ ratio. In some embodiments, the zeolite is located within a plasma chamber. In some embodiments, the zeolite is located in separate chamber from the plasma chamber. ratio during plasma formation. As the chamber is depressurized, high concentration $O_2$ is diverted upstream to mix with the reactant gas, thereby increasing the $O_2$ content in the reactant gas. The benefit of this approach is that less pressure is required within the plasma chamber.

Gas Sensors

NO Measurement

In some embodiments, a conductive ink is used to print a specific gas sensor (for example, NO, $NO_2$ or $O_2$) onto a substrate and using a small Bluetooth microcontroller to send sensor values in a Bluetooth data beacon. In some embodiments, the ink is printed on a filter material (ex. Porex) and wire-bound or heat-staked to a flexible PC board with a coin-cell battery. The filter can be located in the gas pathway in a proximal scrubber. In some embodiments, a conductive ink contains one or more of the following chemicals: tin sulfide, graphine. Data transport is not limited to Bluetooth protocols. Ant+, Zigbee, 802.14.4, proprietary protocols and the like may be used in addition or instead.

Some gas sensors are affected by sample pressure. In some embodiments, the pressure of the gas sample is controlled to improve gas sensor accuracy. One way of doing this is by modulating the flow rate of the sample pump based on feedback from a gas sensor pressure sensor.

In some embodiments, zero (i.e. gas for low calibration, or zeroing the gas sensors) can be sourced from ambient air or from an external source. In some embodiments, the ambient air is passed through a scrubber to remove NO and/or $NO_2$ to improve the accuracy of zero calibration. In some embodiments, the zero scrubber is part of the gas sensor assembly.

If a gas sensor has a typical exponential settling time, its frequency response can be modeled as a first order system (1 Pole), i.e. its transfer function is $k/(s+p)$. In some embodiments, the signal from the gas sensor is "filtered" with the inverse transfer function, i.e. a zero at the same corner frequency, to get a uniform gain of 1 at all frequencies. In practice this can amplify noise, so another pole is added in the gas sensor signal filter at a higher frequency than the original so it can respond more quickly.

Nitrogen Measurement

Atmospheric oxygen is typically 21% and atmospheric nitrogen is typically 78%. In some embodiments, a NO generation system measures nitrogen instead of oxygen levels. This measurement could be of the reactant gas, the product gas or the inspired gas. Since the level of NO production is dependent on the ratio of $O_2$ to $N_2$ in the reactant gas, an $N_2$ measurement can be used as an input to a control system for compensating the $O_2$ to $N_2$ ratio. In some embodiments, $N_2$ levels in the inspired gas path can serve as an indication of $O_2$ levels since they practically sum to 100%.

Calibration

Calibration of a NO delivery system can be cumbersome of the user. In some embodiments, the NO delivery system includes an onboard gas cylinder/cartridge of calibration gas. It releases said gas through the gas sensors to self-calibrate. The onboard calibration gas cartridge can be replaced during periodic servicing of the device.

Gas Sampling

An NO generation and delivery system uses sensors to monitor NO and $NO_2$ levels in one or more of the product gas (immediately post-plasma), scrubbed gas or inspired gas. Gas sensors can drift over time, requiring re-zeroing. In some embodiments, a NO generation device sources ambient air to flow across the gas sensors so that drift of the sensors can be quantified and/or the measurement offset can be re-zeroed as needed.

Polymeric tubing can absorb $NO_2$ molecules when exposed to $NO_2$ and release $NO_2$ molecules after the source of $NO_2$ ceases. In some embodiments, an NO generation and delivery system uses metallic tubing such as stainless steel so that $NO_2$-free gas can be sourced from ambient air for sensor zeroing purposes. This allows the system to be flushed using ambient air.

User Interface

In some embodiments, the system permits customization of default alarm limits for user-selected NO target ranges to match hospital protocol. In some embodiments, alarms are fully customizable for audio on/off, alarm on/off. In some embodiments, alarm silence duration is customizable. In some embodiments, alarm lights are controlled by a safety manager. Some or all of the LEDs are controlled by the safety manager. This ensures an illuminated alarm in the event of a GUI failure.

In some embodiments, the device communicates device health, servicing records, maintenance records, usage data. In some embodiments, these data are sent up to the cloud for record keeping and device diagnostics. Data can be used for optimization of device operation.

A user interface associated with the NO generation system can include a variety of features. In some embodiments, an NO delivery system has a user interface that includes an animated manual respiration bag on screen to indicate that bag mode is active. In some embodiments, a lung animation is synchronized with respirations detected by the system. In some embodiments, respirations are detected with a flow sensor within the inspiratory pathway. In some embodiments, a lung animation changes colors to show drug inhaling and exhaling.

In some embodiments, a light pipe from the plasma chamber to the front panel conveys light from the plasma to the user for evidence that the plasma is working.

In some embodiments, an NO generation and delivery system includes a shoe insole that detects footsteps. In some embodiments, footstep information is transferred to a NO generation and delivery device. Information can be recorded and/or used to adapt the NO delivery algorithm based on patient activity. The shoe insole could derive energy for its operation from the kinetic energy of the foot step (compression of piezo electric crystals, for example).

In some embodiments, an NO delivery and generation system interfaces with a wristwatch that measures one or more of heart rate, $SpO_2$, activity, respiration rate, skin temperature, methemoglobin and arterial pressure. One or more of these values can be used as input into the NO generation algorithm. In some embodiments, patient data are uploaded for a physician review and adjustment of patient NO dosing, as required.

In some embodiments, product gas is actively warmed and/or kept warm (due to heat from plasma) prior to delivery to the patient to increase patient comfort. In some embodiments, product gas is at or near 37° C. at the point of inhalation. In some embodiments, oxygen is warmed to at or near 37° C. at the point of inhalation.

In some embodiments, a cannula includes a heating capability to maintain product gas temperature prior to injection. In some embodiments, a cannula is insulated to maintain product gas temperature prior to injection.

Additional System Features

Reusable Component Sterilization

NO and $NO_2$ are toxic gases that have antimicrobial properties. In some embodiments, a portion of the NO generation and delivery system is reused between patients. To prevent cross-contamination between patients, a NO generator can use NO generated by the system to disinfect portions of the system. In some embodiments, a ventilator cartridge is capped between uses and the device fills the ventilator cartridge with NO to disinfect the internal surfaces. In some embodiments, the NO within the ventilator cartridge is pumped out of the ventilator cartridge through a NOx filter and/or soda lime prior to exhausting the gas after use. In some embodiments, a ventilator cartridge cap includes a valve and/or NOx or $NO_2$ scrubbing element. In some embodiments, NO-rich gas exits the ventilator cartridge and passes through gas sensors within the NO generation device to confirm adequate NO concentration for disinfection. A similar approach to sterilization can be utilized for other components of an NO delivery system, such as a inspiratory flow sensor, inspiratory tube, humidifier, and gas sampling components. In some embodiments, NO with a concentration of 150 to 600 ppm is utilized to sterilize components, although even higher concentrations can be utilized in some applications.

In some embodiments, an electric NO generation device is used to generate high concentration NO to sterilize equipment. In some embodiments, medical equipment (e.g. an endoscope) is placed within a chamber for sterilization. A NO generation device delivers NO gas to the chamber. In some embodiments, the NO flow rate through the chamber is sufficient to minimize $NO_2$ formation within the chamber, which could be damaging to hospital equipment. NO gas exiting the chamber can either pass through a NOx scrubber and be vented to atmosphere or be directed to house vacuum.

Self-Test

In some embodiments, the device generates one or more electrical discharges during a self-test and confirms that operating parameters are within range. Operating parameters can include one or more of the following: peak voltage, breakdown time, maximum current, RMS breakdown voltage, peak plasma voltage, plasma current, phase shift between plasma voltage and plasma current, RMS plasma voltage.

Mounting Solution

In some embodiments, a docking station is provided that establishes gas connections to house air and power when the controller is connected.

Figure 68:
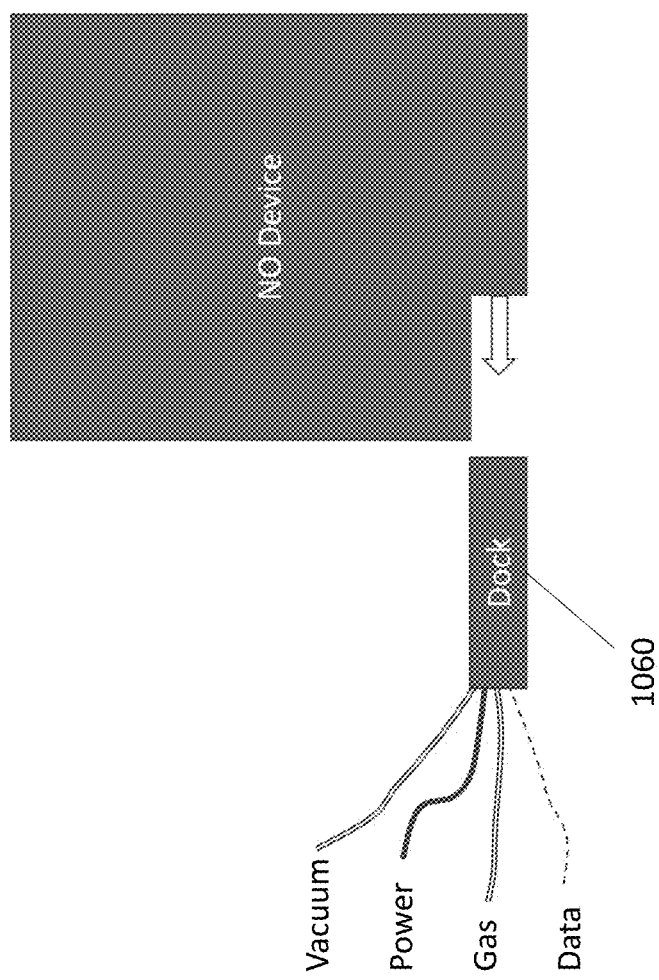
FIG. 68 shows an embodiment of a NO generation system with a docking station.

In some embodiments of an NO generation and delivery system, a docking station 1060, as shown in FIG. 68, can be included and can be connected to one or more of a hospital gas supply, house vacuum, hospital data (e.g. ethernet) as well as to AC mains. The reactant gas supply can be sourced from either the docking station 1060 or the controller pump to direct reactant gas to the plasma chamber. Since the product gas can be directed to either the ventilator or bag circuit within the controller, this would eliminate the need to connect the wall air supply to the front of the unit for the bag circuit, thereby eliminating a use step. When docked and connected to the wall air supply, the NO device runs without the noise of pumps, which may be favorable to prevent disturbing the patient's sleep. This approach can also provide advantages to flow accuracy as the upstream pressure can be held constant (the pressure within a reactant gas reservoir typically drops during an inspiratory event causing variation in pressure head). For transport, the unit would simply be unlatched from the docking station, via a mechanical interface that may be attached to a stand, wall mount or bed rail mount, and would automatically switch to run from batteries and source reactant gas with the pump. The expectation for noise control during transport may not be as rigorous as that for overnight conditions at the NICU. Thus, operating pumps to source reactant gas during transport is acceptable.

In some embodiments, the docking station itself can be configured to be placed on a surface, permanently mounted to a wall, or serve as an interface to a mobile stand.

Once placed on a docking station, one or more of the following connections are established: reactant gas, power, exhaust gas vacuum, and data. The NO generation device senses the docking station by many ways including, but not limited to: an electrical connection, mechanical connection, a magnet-Reed switch interaction, optical connection, and/or sensing the reactant gas pressure. The NO generation system can automatically begin sourcing reactant gas from the docking station upon sensing the presence of a docking station.

In some embodiments, the docking station provides power for charging the batteries of a NO generation and delivery device.

In some embodiments, the docking station provides an electrical connection to the hospital nurse-call system.

In some embodiments, the docking station provides an electrical connection to the hospital data network (Ethernet, etc.)

In some embodiments, the docking stand could include RS232, CAN, I2C or other digital communication protocols.

In some embodiments, exhaust gas from the NO generator and/or gas sampling system are passed through the docking station. In some embodiments, the docking station provides fluid communication to house vacuum to remove exhaust gases. In some embodiments, a docking station includes an $NO_2$ and/or NOx scrubber to clean exhaust gas prior to releasing it to the environment. In some embodiments, software within the NO generation and delivery device can detect connection with the docking station and automatically initiate external communications.

In some embodiments of a NO generation and delivery system, features that are not essential during transport are located in the docking station in order to make the portable portions of an NO generation and delivery system as light, simple and power-efficient as possible. In some embodiments, the docking station includes one or more of a graphical user interface, AC power transformer, and gas analyzer for one or more of $O_2$, NO, and $NO_2$.

Placement of a portable NO generation and delivery system near a patient should be as versatile and simple as possible. In some embodiments, the bottom of a NO generation and delivery system has a geometry that enables it to latch to a mounting assembly. In some embodiments, a mounting plate is removably attached to the bottom of the NO generation device and mechanically engages a mounting assembly. The mounting assembly provides a common mechanical interface to the NO generator. Mounting assemblies provide an interface between the No generator and other objects within the patient treatment area, such as a bed rail, mounting arm, rolling stand, a standard rails, or a pole. In some embodiments, the latching mechanism between mounting assembly and NO generator engages the NO generator passively as the weight of the NO generator is applied to the mechanism. Release of the mechanism to detach the NO generator from the mounting solution can be done by turning a knob, squeezing a handle, or pressing a foot pedal, for example.

In some embodiments, a NO generation and delivery system includes hangers for hanging the system off a bed rail. In some embodiments, the hangers on the back of the device are hinged so that they can be stowed within the back of the device. In some embodiments, the hangers are spring-loaded so that that they rotate out from a stowed position to a hanger position when a release button is pressed. This can facilitate and shorten the process of mounting the NO generation and delivery device when beginning administration of a new treatment.

Remote Gas Measurement

In some embodiments, a gas analyzer is a separate device from a NO generator. In some embodiments, the gas analyzer measures sample gas from a gas source and does one or more of the following: communicates wired or wirelessly with a NO generator, generates alarms, presents gas reading information. Exposure of the gas analyzer to the subject gas can be passively or actively sourced. In some embodiments, the gas analyzer consists of a module that can be inserted in series or parallel with an inspiratory flow stream. In some embodiments, this approach eliminates the need for sample lines, water traps. In some embodiments, a gas analyzer has one or more sensors for NO, $NO_2$ and $O_2$ that are in fluid communication with the gas within an inspiratory limb. One advantage to this approach is that it reduces the delay of gas sensors by eliminating the transit time of sample gas from an inspiratory limb to a remote gas sensor bench. Another benefit is that it improves gas sensor accuracy because the shorter transit time results in less $NO_2$ formation.

In some embodiments, the gas analyzer is compact, light-weight and intended for single patient use. Each of the gas sensors is printed on a PCB and powered by a battery. In the simplest of forms, the sensor measures gas measurements and wirelessly communicates the measurements to a NO generator, ventilator, CPAP machine, hospital data system, hand-held device or other device that can utilize the information. In some embodiments, the device receiving data from the gas analyzer can also generate alarms based on the gas measurements.

Figure 69:
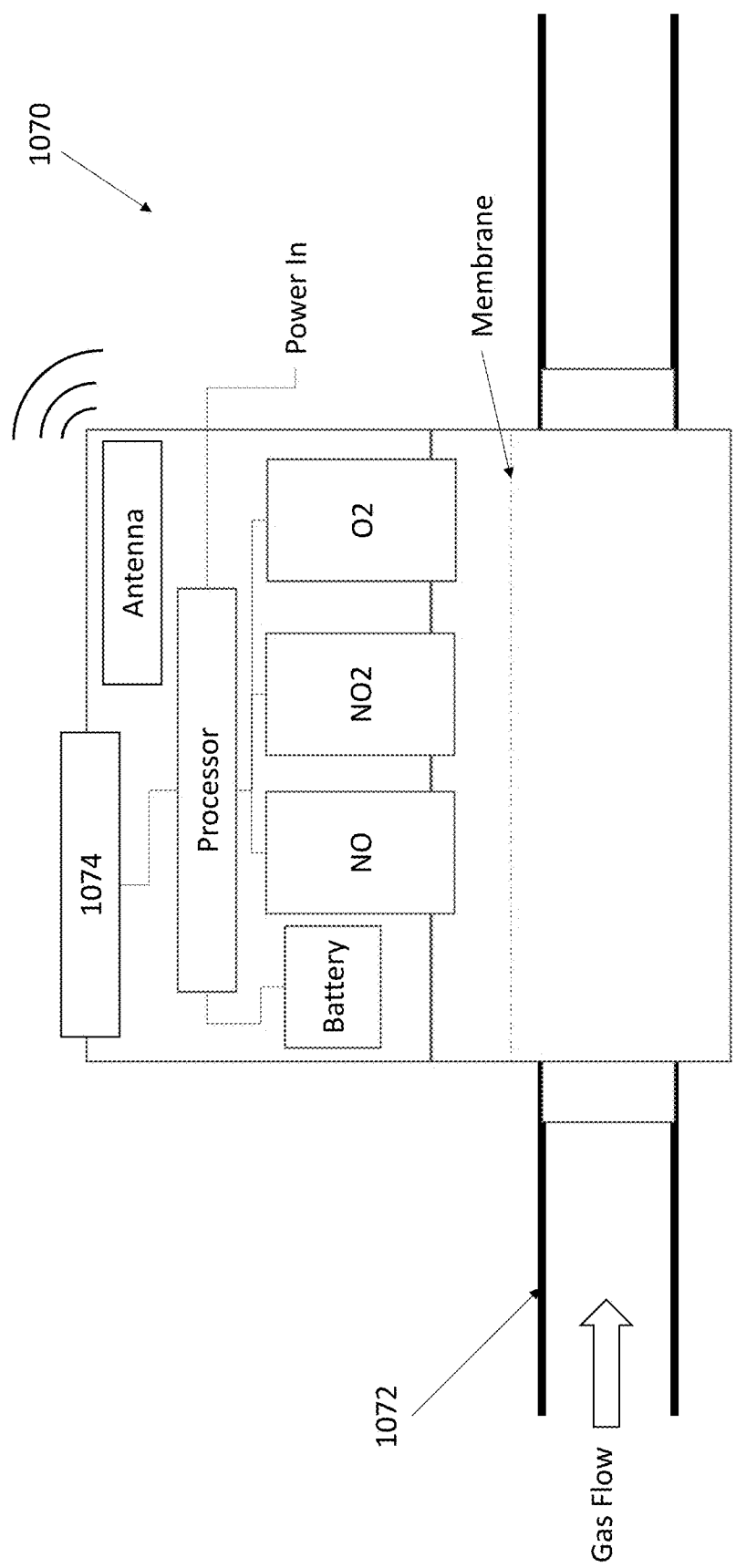
FIG. 69 illustrates an embodiment of a remote gas measurement device.

FIG. 69 depicts a remote gas measurement device 1070. It features connectors to be integrated into an inspiratory limb 1072. The device receives power from either an external source, internal batteries, or both. The embodiment shown communicates wirelessly with other treatment devices, such as a NO generator, medical gas blender, NO delivery system, and/or ventilator. In some embodiments, the inspiratory flow rate is also measured. A user interface 1074 can provide real time measurements of gas concentrations. The device can enable users to set high and low alarm thresholds for each gas.

The device in FIG. 69 shows an optional membrane between the gas sensors and the inspiratory gas. The membrane can protect gas sensors from direct exposure to patient exhaled gases. The membrane can also prevent liquid water from contact the gas sensors. In some embodiments, the gas sensors are mounted above the inspiratory limb, as shown to prevent liquid water from contacting the sensors. In some embodiments, the sensor chamber is warmed to prevent water condensation on the sensors. In some embodiments, the sensor chamber is warmed to 37 degrees C. In some embodiments, sensors are calibrated at the temperature that they are warmed to. In some embodiments, gas sensor outputs are temperature compensated based on the temperature of either the gas sensor chamber, the gas sensor or both.

Continuing with FIG. 69, in some embodiments, the gas sensor housing can be separated from a lower housing. The lower housing consists of input and output inspiratory flow connectors, a housing, a connector to the gas sensor module and an anti-microbial membrane. The anti-microbial membrane permits active and/or passive exchange of inspiratory gases within an inspiratory flow stream and the gas sensors of a gas analyzer. The lower housing is single-patient-use while the upper, gas sensor module can be used for multiple patients. In some embodiments, pressurized gas within the patient inspiratory stream passively passes by gas sensors within a gas analyzer before being released to the ambient environment. In some embodiments, the sampled gas is scrubbed for NO and/or $NO_2$ prior to release into the environment.

Clinical Applications

Various therapies can be used with an NO generation device. In some embodiments, an NO generation and delivery device can be combined with a humidifier.

In some embodiments, an NO generation and delivery device is in the form of an ET tube. In some embodiments, the ET tube generates NO continuously with NO-containing gas entering and exiting the patient. In some embodiments, the system only generates NO as inspiratory gas enters the patient. The system can use a flow sensor to measure inspired gas and generate plasma accordingly. In some embodiments, the device pulses plasma constantly at an adjustable frequency and or duty cycle. The user can increase plasma activity to vary the dose.

In some clinical applications in home and/or in hospital, it can be advantageous to inhale NO for short intervals, periodically. In some embodiments, a patient inhales NO concentrations in excess of 80 ppm for several minutes, multiple times a day to treat or prevent pulmonary infection. In some embodiments, the range of inhaled NO concentration to prevent infection can be 100 to 300 ppm. NO delivery means for periodic dosing include but are not limited to an inhaler, an ambulatory device, a ventilator, an oxygen concentrator, and a NO tank. Treatments at high NO concentration can be based on elapsed time or clinical parameters, such as methemoglobin level. In some embodiments, a NO delivery system measures and/or receives methemoglobin readings and terminates a treatment when methemoglobin levels reach a threshold. In some embodiments, a NO delivery system can resume NO delivery when methemoglobin levels fall below a threshold.

In some clinical applications, a patient inhales NO on an as-needed basis. For example, after a short walk, ascending a flight of stairs, when their $SpO_2$ is low, when $O_2$ needs are high. In some embodiments, a NO delivery device permits the patient to select a dose within a pre-determined range. In some embodiments, a NO delivery device limits the amount of NO a patient can inhale over a period of time.

There are also a variety of clinical applications of inhaled NO in a hospital/clinical setting. Clinical applications include but are not limited to respiratory failure of prematurity, bronchopulmonary dysplasia (infants), serious lung infection, respiratory failure in the intensive care unit (PCU) or pediatric intensive care unit (PICU), heart surgery, acute iNO testing in pulmonary hypertension (PH) or chronic pulmonary hypertension (e.g. PAH), cardiac surgery in the USA, acute respiratory distress syndrome, cardiopulmonary resuscitation, cardiopulmonary bypass prevention of renal injury, acute stroke and traumatic brain injury, and acute ST-Elevation myocardial infarction (STEMI).

In some embodiments, a clinical application can include the prevention and/or treatment of ventilator associated pneumonia. NO is an anti-infective agent currently being explored in cystic fibrosis (CF) for mycobacterial infections and bacterial infections, e.g. *Pseudomonas*. It can be used with prolonged ventilated patients to reduce ventilator associated pneumonia.

In some embodiments, a clinical application can include periodically dosing a patient with NO to prevent ventilator associated pneumonia. In some embodiments, a ventilator that generates NO periodically doses a patient to prevent ventilator associated pneumonia.

In some embodiments, a clinical application can include Acute Right Heart Failure (diverse etiology) including pulmonary embolism. In this application, NO decreasing the pulmonary resistance, thereby offloading the right heart.

In some embodiments, a clinical application can include administration with hemoglobin oxygen carriers and stored blood. Hemoglobin-based oxygen carriers (HBOCs) or hemoglobin based oxygen carrying solutions (HBOCs) can cause scavenging of NO and systemic and pulmonary vasoconstriction inhibited by iNO. Hemolyzed blood scavenges NO leading to systemic and pulmonary vasoconstriction.

There are also a variety of clinical applications of inhaled NO in an Ambulatory setting, including the following:

WHO Group 1 PAH—Potential to subtype e.g. idiopathic, familial etc., pediatric PAH, and PAH during pregnancy (avoids toxicity from PAH drugs)

WHO group 2 PAH—Selected well-controlled patients with left heart failure (risk of pulmonary edema, and LVAD recipients with right heart disease (RHD) and pulmonary hypertension (PH) (Orphan)

WHO group 3 PH—PH-ILD or subtype ILD e.g. IPF, CT-related ILD, cHP, etc., PH-COPD, and Combined pulmonary fibrosis emphysema (CPFE)

WHO group 4 Chronic Thromboembolic PH (CTEPH)— Improve right heart disease (RHD)

Sarcoidosis

Right heart dysfunction, diverse etiology—Afterload reduction even in absence of pulmonary hypertension (PH), and Etiologies include ischemic heart disease, valvular disease etc.

Infectious diseases, such as cystic fibrosis e.g. *Pseudomonas, B. cepacia*, NTM, Multiple Drug-resistant tuberculosis, Non-tuberculous mycobacterial infection (NTM), and Bronchiectasis Bridge to lung and/or heart transplant—Addresses pulmonary hypertension (PH), oxygenation, RVD etc Post lung and/or heart transplant—Reduces pulmonary vascular resistance and contributes to the prevention of bacterial infections High altitude medicine—To address mountain sickness, High altitude pulmonary edema (HAPE), and reduce hypoxic pulmonary vasoconstriction Military field applications, such as inhalation injury, cardiopulmonary resuscitation/shock, and High-altitude sickness including during flight Cardiopulmonary Resuscitation—reverses acute PH due to pulmonary vasoconstriction increasing cardiac output (compressions)

With stored blood or hemoglobin oxygen carriers to prevent complications

During cardiopulmonary bypass to prevent complications

With ECMO to reduce the use of heparin

All publications, patent applications and patents mentioned herein are hereby incorporated by reference in their entirety as if each individual publication or patent was specifically and individually indicated to be incorporated by reference. Reference is made to U.S. application Ser. No. 15/907,241, filed Feb. 27, 2018, U.S. application Ser. No. 16/388,464, filed Apr. 18, 2019, U.S. application Ser. No. 16/697,498, filed Nov. 27, 2019, U.S. application Ser. No. 15/907,258, filed on Feb. 27, 2018, U.S. application Ser. No. 16/363,505, filed Mar. 25, 2019 and U.S. application Ser. No. 16/724,233, filed Dec. 21, 2019 which are hereby incorporated by reference in their entireties.

It will be appreciated that several of the above-disclosed and other features and functions, or alternatives thereof, may be desirably combined into many other different systems or applications. Various presently unforeseen or unanticipated alternatives, modifications, variations, or improvements therein may be subsequently made by those skilled in the art which are also intended to be encompassed by the following claims.

What is claimed is:

1. A nitric oxide (NO) generation system comprising:
   at least one pair of electrodes configured to generate a product gas containing NO from a flow of a reactant gas; and
   a controller configured to regulate the amount of nitric oxide in the product gas produced by the at least one pair of electrodes by varying current to the electrodes with respect to time during a plasma pulse associated with the electrodes,
   the controller being configured to control a high voltage circuit to vary the current during a time period in which the plasma pulse is between a single pair of the at least one pair of electrodes such that the current is an initial current at a start of an electrical discharge and increases throughout the electrical discharge.

2. The NO generation system of claim 1, wherein the current variation is tied to a duty cycle of the plasma pulse.

3. The NO generation system of claim 1, wherein a longer duty cycle results in a higher current at the end of the duty cycle.

4. The NO generation system of claim 1, wherein a lower current is configured to be associated with a small gap between the electrodes to protect the electrodes from erosion in a small gap region.

5. The NO generation system of claim 1, wherein the current is configured to increase over time to increase production at a large electrode gap between the pairs of electrodes.

* * * * *